US012673958B2

(12) United States Patent
Mizuki et al.

(10) Patent No.: US 12,673,958 B2
(45) Date of Patent: Jul. 7, 2026

(54) POLYCYCLIC COMPOUND, AND AN ORGANIC ELECTROLUMINESCENCE DEVICE COMPRISING THE POLYCYCLIC COMPOUND

(71) Applicant: Idemitsu Kosan Co., Ltd., Chiyoda-ku (JP)

(72) Inventors: Yumiko Mizuki, Basel (CH); Michelle Groarke, Binningen (CH); Pierre Boufflet, Basel (CH); Natalia Chebotareva, Hagenthal le Bas (FR); Francois Rime, Delemont (CH)

(73) Assignee: Idemitsu Kosan Co., Ltd., Chiyoda-ku (JP)

( * ) Notice: Subject to any disclaimer, the term of this patent is extended or adjusted under 35 U.S.C. 154(b) by 807 days.

(21) Appl. No.: 17/271,871

(22) PCT Filed: Aug. 29, 2019

(86) PCT No.: PCT/IB2019/057267
§ 371 (c)(1),
(2) Date: Feb. 26, 2021

(87) PCT Pub. No.: WO2020/044270
PCT Pub. Date: Mar. 5, 2020

(65) Prior Publication Data
US 2022/0109115 A1 Apr. 7, 2022

(30) Foreign Application Priority Data
Aug. 31, 2018 (EP) .................................... 18192010

(51) Int. Cl.
*C07D 493/04* (2006.01)
*C09K 11/06* (2006.01)
(Continued)

(52) U.S. Cl.
CPC ............ *C07D 493/04* (2013.01); *C09K 11/06* (2013.01); *H10K 85/654* (2023.02);
(Continued)

(58) Field of Classification Search
CPC ........ H10K 50/11; H10K 50/16; H10K 50/18; H10K 85/654; H10K 85/6574;
(Continued)

(56) References Cited

U.S. PATENT DOCUMENTS

2002/0121860 A1* 9/2002 Seo .............................. 313/506
2010/0295444 A1 11/2010 Kuma et al.
(Continued)

FOREIGN PATENT DOCUMENTS

CN 110294703 A 10/2019
EP 2 298 774 A1 3/2011
(Continued)

OTHER PUBLICATIONS

English translation of KR 2017/0086277 and the original KR 2017/0086277, Eun Youl Jung, Jul. 26, 2017 (Year: 2017).*
(Continued)

*Primary Examiner* — Seokmin Jeon
(74) *Attorney, Agent, or Firm* — Oblon, McClelland, Maier & Neustadt, L.L.P.

(57) ABSTRACT

Specific polycyclic compounds of the general formula (I) and a process for their preparation, a material for an organic electroluminescence device comprising said compound, an organic electroluminescence device comprising said compound, an electronic equipment comprising said organic electroluminescence device, and the use of compounds according to general formula (I) in an organic electroluminescence device.

3 Claims, 1 Drawing Sheet

(51) Int. Cl.

| | |
|---|---|
| ***H10K 50/11*** | (2023.01) |
| ***H10K 50/16*** | (2023.01) |
| ***H10K 50/18*** | (2023.01) |
| ***H10K 85/60*** | (2023.01) |
| ***H10K 101/10*** | (2023.01) |

(52) U.S. Cl.
CPC ..... *H10K 85/6574* (2023.02); *H10K 85/6576* (2023.02); *C09K 2211/1018* (2013.01); *H10K 50/11* (2023.02); *H10K 50/16* (2023.02); *H10K 50/18* (2023.02); *H10K 2101/10* (2023.02)

(58) Field of Classification Search
CPC ............ H10K 85/6576; H10K 2101/10; H01L 51/5012; H01L 51/5072; H01L 51/5096; H01L 51/0067; H01L 51/0073; H01L 51/0074; H01L 51/5016; C07D 493/04; C07D 495/04; C07D 251/00; C07D 251/02; C07D 251/24; C09K 11/06; C09K 2211/1018; C09K 2211/1059; C09K 2211/1088; C09K 2211/1092
See application file for complete search history.

(56) References Cited

U.S. PATENT DOCUMENTS

| | | | |
|---|---|---|---|
| 2014/0158992 A1 | 6/2014 | Xia et al. | |
| 2016/0060251 A1 | 3/2016 | Xia et al. | |
| 2017/0186965 A1* | 6/2017 | Parham | H01L 51/0067 |
| 2017/0222160 A1 | 8/2017 | Lee et al. | |
| 2017/0237014 A1 | 8/2017 | Xia et al. | |
| 2019/0140185 A1 | 5/2019 | Xia et al. | |
| 2019/0152985 A1* | 5/2019 | Suh | C07D 493/14 |

FOREIGN PATENT DOCUMENTS

| | | | |
|---|---|---|---|
| EP | 2 301 926 | A1 | 3/2011 |
| KR | 1020100105099 | A | 9/2010 |
| KR | 10-2016-0028524 | A | 3/2016 |
| KR | 10-2017-0086211 | A | 7/2017 |
| KR | 10-2017-0086243 | A | 7/2017 |
| KR | 10-2017-0086277 | A | 7/2017 |
| KR | 1020190010500 | A | 1/2019 |
| KR | 10-2019-0110775 | A | 10/2019 |
| WO | WO 2010/134350 | A1 | 11/2010 |

OTHER PUBLICATIONS

Jae-Wook Kang et al. "Silane- and triazine-containing hole and exciton blocking material for high-efficiency phosphorescent organic light emitting diodes", J. Mater. Chem. 2007, vol. 17, 3714-3719 (Year: 2007).*

Huiqing Pang et al. "A full-color, low-power, wearable display for mobile applications", SPIE, Mar. 29, 2012 (Year: 2012).*

English translation of JP 2010045281 A and the original JP 2010045281 A, Tatsuo Tanaka (Year: 2010).*

English translation of KR 2017/0086211 A and the original KR 2017/0086211 A, Se-jin Lee, Jul. 26, 2017 (Year: 2017).*

English translation of KR 2012/0120886 A, and the original KR 2012/0120886 A, Bokyoung Kim, Nov. 2, 2012 (Year: 2012).*

Jae-Wook Kang et al. "Silane- and triazine-containing hole and exciton blocking material for high-efficiency phosphorescent organic light emitting diodes", J. Mater. Chem. 2007, vol. 17, p. 3714-3719 (Year: 2007).*

Xiao-Ke Liu et al. "Novel bipolar host materials based on 1,3,5-triazine derivatives for highly efficient phosphorescent OLEDs with extremely low efficiency roll-off", Phys. Chem. Chem. Phys. 2012, vol. 14, p. 14255-14261 (Year: 2012).*

The English translation of KR 2018/0051354 A and the original KR 2018/0051354 A, Cha et al., May 16, 2018 (Year: 2018).*

The English translation of CN 108047235 A and the original CN 108047235 A, Jun et al, May 16, 2018 (Year: 2018).*

International Search Report issued on Oct. 18, 2019 in PCT/IB2019/057267 filed on Aug. 29, 2019.

* cited by examiner

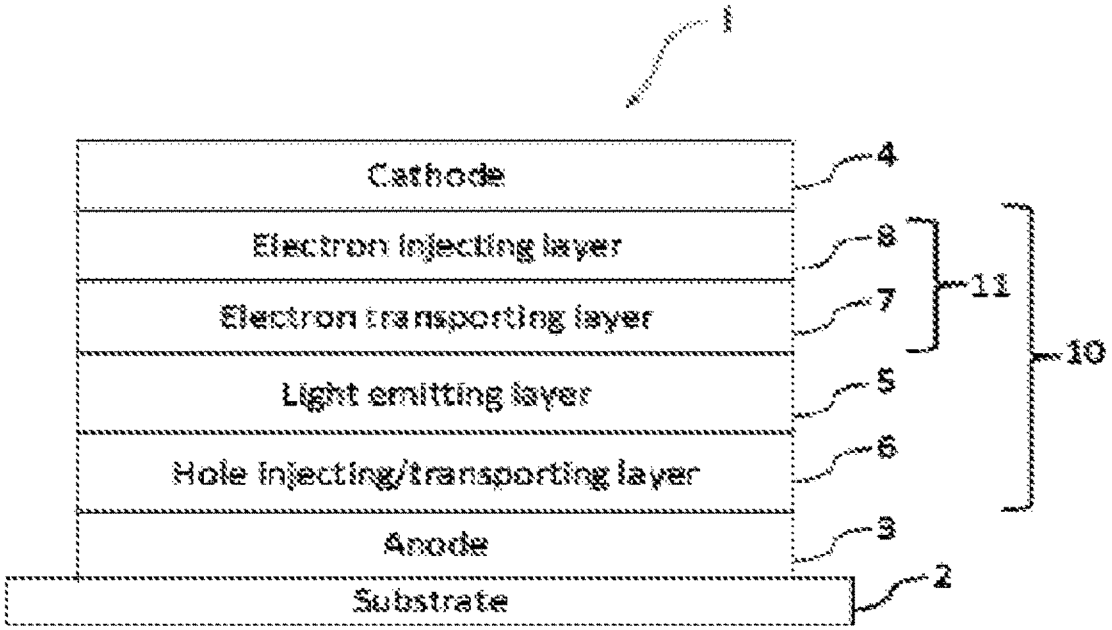
1
Cathode
4
Electron injecting layer
8
Electron transporting layer
7
11
10
Light emitting layer
5
Hole injecting/transporting layer
6
Anode
3
Substrate
2

POLYCYCLIC COMPOUND, AND AN ORGANIC ELECTROLUMINESCENCE DEVICE COMPRISING THE POLYCYCLIC COMPOUND

The present invention relates to specific polycyclic compounds, and to organic electroluminescence devices comprising the same.

US 2017/222160 discloses an organic light emitting device including a first electrode, a second electrode opposite to the first electrode, and at least one organic layer interposed between the first and second electrodes wherein the organic layer includes first and second compounds represented by Formulae A and B, respectively:

(A)

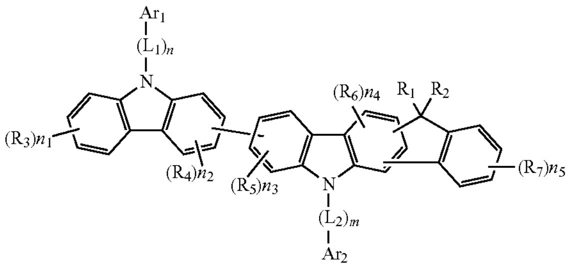

(B)

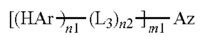

The group HAr in formula B may under numerous structures be represented by the following structure:

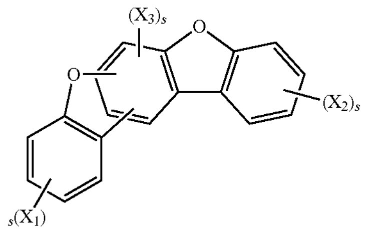

EP 2 301 926 A1 discloses a polycyclic compound represented by the following formula (1) or (2):

(1)

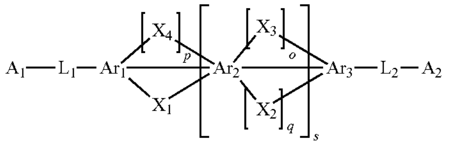

(2)

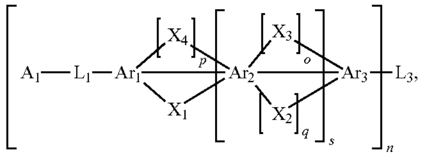

and an organic EL device having one or more organic thin film layers including a light emitting layer between a cathode and an anode in which at least one layer of the organic thin film layers contains a polycyclic compound represented by formulae (1) or (2). Further, the polycyclic compound represented by formulae (1) or (2) is effective also as a material for an organic electron device such as an organic solar cell, organic semiconductor laser, a sensor using organic matter, or an organic TFT.

In EP 2 301 926 A1 the following compounds are for example disclosed under numerous compounds:

No. 131

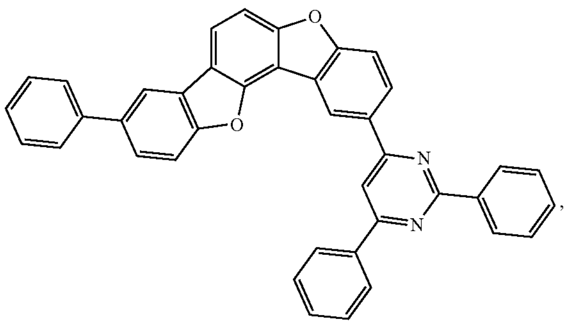

No. 589

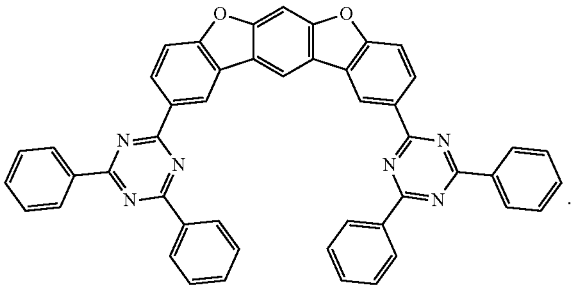

EP 2 298 774 A1 discloses a polycyclic compound represented by the following formulae (1) or (2):

(1)

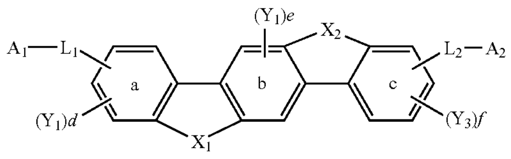

(2)

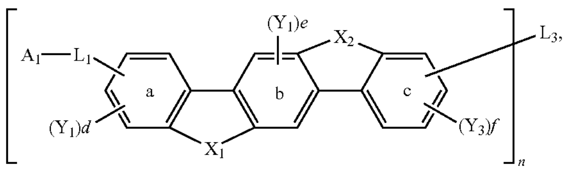

and an organic EL device having one or more organic thin film layers including a light emitting layer between a cathode and an anode in which at least one layer of the organic thin film layers contains a polycyclic compound represented by formulae (1) or (2). Further, the polycyclic compound represented by formulae (1) or (2) is effective also as a material for an organic electron device such as an organic solar cell, organic semiconductor laser, a sensor using organic matter, or an organic TFT.

In EP 2 298 774 A1 the following compounds are for example disclosed under numerous compounds:

No. 26

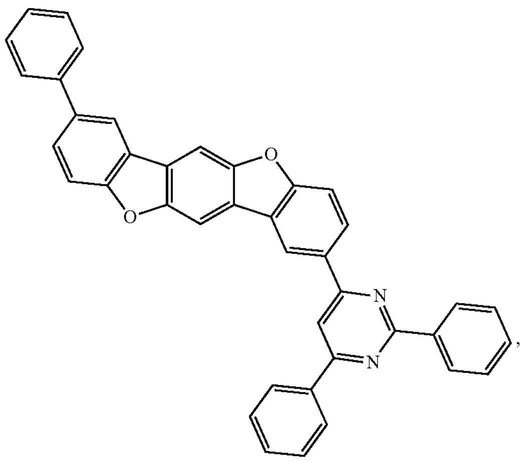

,

No. 33

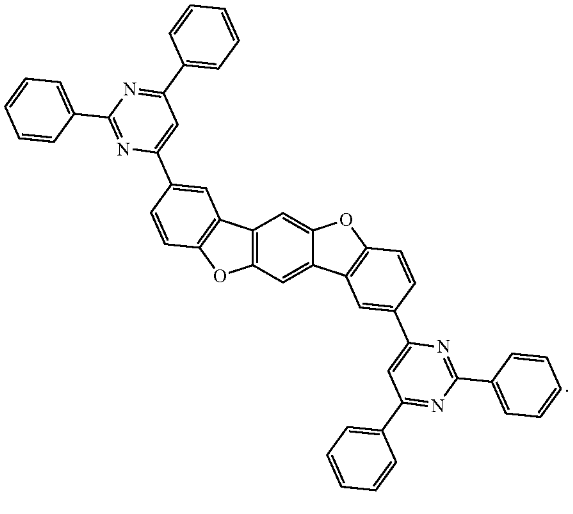

.

KR 2017-0086277 as well as KR 2017-0086243 disclose an organic electroluminescent device comprising a first compound represented by the following formula (1) and a second compound represented by the following formula (2) in an organic layer interposed between a first electrode and a second electrode opposite to each other. The organic light emitting device according to KR 2017-0086277 can be utilized in various display and lighting industries.

The compounds according to formulae (1) and (2) in KR 2017-0086277 are:

(1)

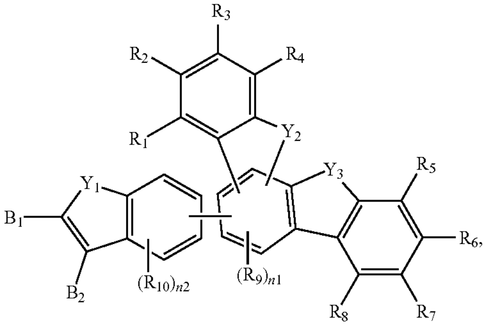

(2)

$$[(HAr)_{n3}-(L)_{n4}]_{m1}-Az$$

The compounds according to formulae (1) and (2) in as KR 2017-0086243 are:

(1)

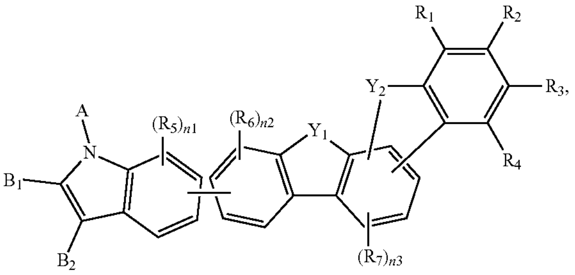

(2)

$$[(HAr)_{n4}-(L)_{n5}]_{m1}-Az$$

In KR 2017-0086277 and KR 2017-0086243 the following compounds (in each case corresponding to the compounds of formula (2)) are for example disclosed under numerous compounds:

(E26)

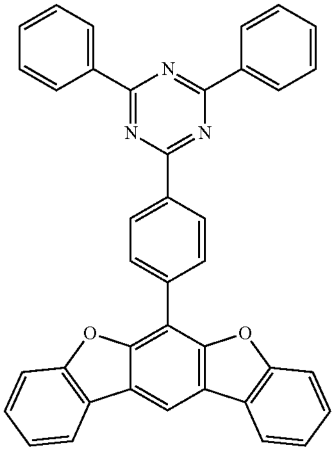

,

-continued (E30)

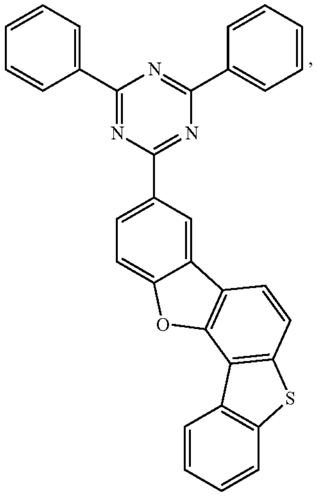

(E50)

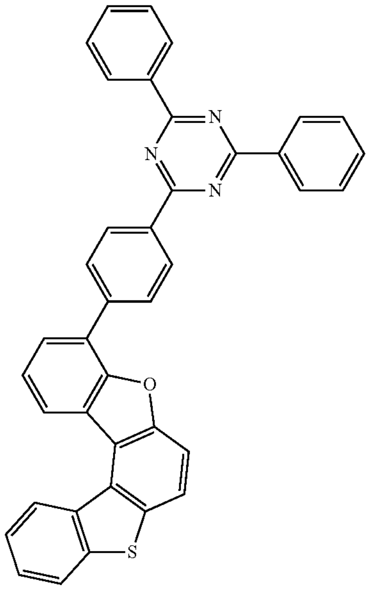

KR 2017-0086211 also discloses an organic electroluminescent device comprising a first compound represented by the following formula (1) and a second compound represented by the following formula (2) in an organic layer interposed between a first electrode and a second electrode opposite to each other. The organic light emitting device according to KR 2017-0086211 can be utilized in various display and lighting industries.

$$HAr_1 - (L)_n - HAr_2 \quad (I)$$

$$[(HAr)_{n1} - (L_1)_{n2}]_{m1} - Az \quad (2)$$

In KR 2017-0086211 the following compounds are for example disclosed under numerous compounds:

(E58)

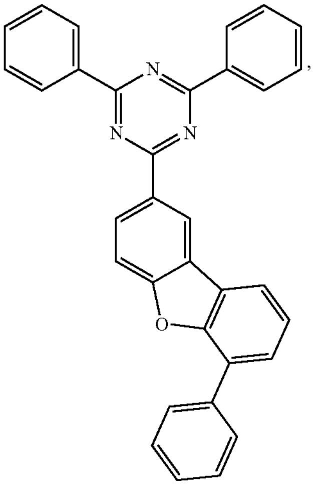

(E79)

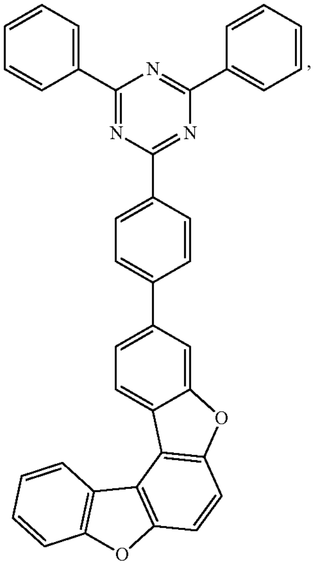

KR 2017-0139443 discloses compounds of the following formula and an organic electroluminescent device comprising said compound:

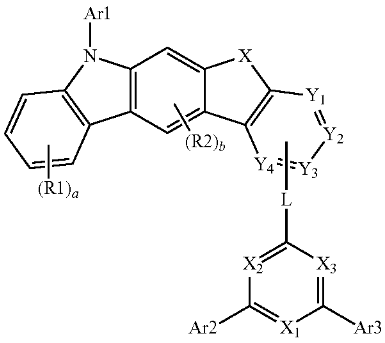

However, the specific structure and substitution pattern of polycyclic compounds has a significant impact on the performance of the polycyclic compounds in organic electronic devices.

Therefore, notwithstanding the developments described above, there remains a need for organic electroluminescence devices comprising new materials, especially host (=matrix) materials, charge blocker materials, e.g. hole blocker materials and/or charge transport materials, e.g. electron transport materials, to provide improved performance of electroluminescent devices.

Accordingly, it is an object of the present invention, with respect to the aforementioned related art, to provide further materials suitable for use in organic electroluminescence devices and further applications in organic electronics. More particularly, it should be possible to provide charge transport materials, e.g. electron transport materials, and/or charge blocker materials, e.g. hole blocker materials, and/or host (=matrix) materials for use in organic electroluminescence devices. The materials should be suitable especially for organic electroluminescence devices which comprise at least one emitter, which is a phosphorescence emitter and/or a fluorescence emitter, preferably a phosphorescence emitter, for example at least one green emitter—or—in a further embodiment—preferably a fluorescent emitter, for example at least one blue emitter Furthermore, the materials should be suitable for providing organic electroluminescence devices which ensure good performance of the organic electroluminescence devices, especially a long lifetime and/or low driving voltage.

Said object is solved by a compound of formula (I)

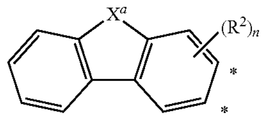

(I)

wherein each * is a bonding site to a group of formula (II)

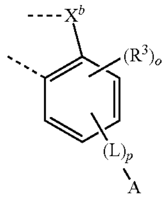

(II)

the dotted lines in the group of formula (II) are bonding sites to the * in the compound of formula (I);

$X^a$ and $X^b$ are each independently O or S;

L represents a direct bond, divalent unsubstituted or substituted phenyl, divalent unsubstituted or substituted biphenyl, divalent unsubstituted or substituted terphenyl group, divalent unsubstituted or substituted naphthyl, divalent unsubstituted or substituted dibenzothiophenyl or divalent unsubstituted or substituted dibenzofuranyl;

p is 1, 2 or 3;

$R^2$ and $R^3$ each independently represents hydrogen, a halogen atom, a substituted or unsubstituted alkyl group having 1 to 25 carbon atoms, a substituted or unsubstituted alkenyl group having 2 to 25 carbon atoms, a substituted or unsubstituted alkynyl group having 2 to 25 carbon atoms, a substituted or unsubstituted cycloalkyl group having 3 to 25 carbon atoms, a substituted or unsubstituted alkoxy group having 1 to 25 carbon atoms, a substituted or unsubstituted aryl group having 6 to 24 carbon atoms, a substituted or unsubstituted heterocyclic group having 4 to 30 carbon atoms, a substituted or unsubstituted aryloxy group having 6 to 24 carbon atoms, a substituted or unsubstituted alkylthio group having 1 to 25 carbon atoms, a substituted or unsubstituted arylthio group having 6 to 24 carbon atoms, an alkyl and/or aryl substituted silyl group, an alkyl or aryl substituted carbonyl group, or a substituted phosphoryl group;

n is 0, 1 or 2;

o is 0, 1, 2 or 3;

A is a group of formula (III)

(III)

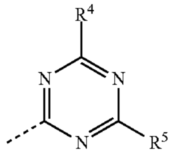

$R^4$ and $R^5$ each independently represents hydrogen, a halogen atom, a substituted or unsubstituted alkyl group having 1 to 25 carbon atoms, a substituted or unsubstituted alkenyl group having 2 to 25 carbon atoms, a substituted or unsubstituted alkynyl group having 2 to 25 carbon atoms, a substituted or unsubstituted cycloalkyl group having 3 to 25 carbon atoms, a substituted or unsubstituted alkoxy group having 1 to 25 carbon atoms, a substituted or unsubstituted aryl group having 6 to 24 ring carbon atoms, a substituted or unsubstituted heterocyclic group having 4 to 30 carbon atoms, a substituted or unsubstituted aryloxy group having 6 to 24 carbon atoms, a substituted or unsubstituted alkylthio group having 1 to 25 carbon atoms, a substituted or unsubstituted arylthio group having 6 to 24 carbon atoms, an alkyl and/or aryl substituted silyl group, an alkyl or aryl substituted carbonyl group, or a substituted phosphoryl group; and the dotted line in the group of formula (III) is a bonding site.

The specific polycyclic compound of the present invention according to formula (I) substituted by a triazine group may be used as a material, especially host, charge transport or charge blocking material, that is highly suitable in organic electroluminescence devices. Moreover, a balanced charge transport and/or charge blocking in devices is achieved, especially resulting in low driving voltages and long lifetimes.

The compounds of the present invention may also be used in further organic electronic devices than organic electroluminescence devices such as electrophotographic photoreceptors, photoelectric converters, organic solar cells (organic photovoltaics), switching elements, such as organic transistors, for example, organic FETs and organic TFTs, organic light emitting field effect transistors (OLEFETs), image sensors and dye lasers.

Accordingly, a further subject of the present invention is directed to an organic electronic device, comprising a compound according to the present invention. The organic electronic device is preferably an organic electroluminescence device (EL device). The term organic EL device (organic electroluminescence device) is used interchangeable with the term organic light-emitting diode (OLED) in the present application.

The compounds of formula (I) can in principal be used in any layer of an EL device, but are preferably used as host, charge transport, especially electron transport, and/or charge blocking, especially hole blocking, material. Particularly, the compounds of formula (I) are used as host material, hole blocking material and/or electron transport material for phosphorescence or fluorescence emitters. More preferably, the compounds of formula (I) are used as host material for phosphorescence or fluorescence emitters. Most preferably, the compounds of formula (I) are used as host material for phosphorescence emitters.

Hence, a further subject of the present invention is directed to a material for an organic electroluminescence device comprising at least one compound of formula (I) according to the present invention.

A further subject of the present invention is directed to an organic electroluminescence device which comprises an organic thin film layer between a cathode and an anode, wherein the organic thin film layer comprises one or more layers and comprises a light emitting layer, and at least one layer of the organic thin film layer comprises at least one compound of formula (I) according to the present invention.

A further subject of the present invention is directed to an electronic equipment comprising the organic electroluminescence device according the present invention.

A further subject of the present invention is directed to the use of a compound of formula (I) according to the present invention in an organic electroluminescence device.

A further subject of the present invention is directed to an emitting layer, comprising a compound of formula (I) according to the present invention. In said embodiment a compound of formula (I) is preferably used as host material or as co-host material together with one or more, preferably one, further host materials. More preferably, a combination of a compound of formula (I) as host material or as co-host material together with a phosphorescent emitter is used.

A further subject of the present invention is directed to an electron transporting layer comprising a compound of formula (I) according to the present invention. Preferably, the electron transporting layer is provided between the cathode and the light emitting layer of an EL device such as an OLED.

A further subject of the present invention is directed to a hole blocking layer comprising a compound of formula (I) according to the present invention. Preferably, the hole blocking layer is provided between the electron transporting layer and the light emitting layer of an EL device such as an OLED.

The terms aromatic hydrocarbon group having 6 to 30 ring carbon atoms, aryl group having 6 to 24 carbon atoms, heterocyclic group having 4 to 30 carbon atoms, alkyl group having 1 to 25 carbon atoms, alkenyl group having 1 to 25 carbon atoms, alkynyl group having 1 to 25 carbon atoms, cycloalkyl group having 3 to 25 carbon atoms, aralkyl group having 7 to 24 carbon atoms, alkylene group having 1 to 30 carbon atoms, cycloalkylene group having a ring structure formed of 3 to 20 carbon atoms, alkyl and/or aryl substituted silyl group, divalent aromatic hydrocarbon group having a ring structure formed of 6 to 30 carbon atoms, divalent heterocyclic group 4 to 30 carbon atoms, silyl group, halogen atom, alkoxy group having 1 to 20 carbon atoms, haloalkyl group having 1 to 20 carbon atoms, haloalkoxy group having 1 to 20 carbon atoms, aryloxy group having 6 to 24 ring carbon atoms, alkylthio group having 1 to 20 carbon atoms, arylthio group having 6 to 24 ring carbon atoms, substituted phosphoryl group, alkylamino group having 1 to 25 carbon atoms, arylamino group having 6 to 24 carbon atoms, alkyl or aryl substituted carbonyl group, carboxyalkyl group having 1 to 25 carbon atoms, carboxamidalkyl group having 1 to 25 carbon atoms, carboxyaryl group having 6 to 24 carbon atoms, carboxamidaryl group having 6 to 24 carbon atoms are known in the art and generally have the following meaning, if said groups are not further specified in specific embodiments mentioned below:

The aromatic hydrocarbon group having 6 to 30 ring carbon atoms, preferably 6 to 24 ring carbon atoms or the substituted or unsubstituted aryl group having 6 to 24 carbon atoms, may be a non-condensed aromatic hydrocarbon group or a condensed aromatic hydrocarbon group, preferably, the aromatic hydrocarbon group having 6 to 24 ring carbon atoms is an aryl group having 6 to 24 carbon atoms. Specific examples thereof include phenyl group, naphthyl group, phenanthryl group, biphenyl group, terphenyl group, quaterphenyl group, fluoranthenyl group, triphenylenyl group, phenanthrenyl group, fluorenyl group, anthracenyl, chrysenyl, spirofluorenyl group, 9,9-diphenylfluorenyl group, 9,9'-spirobi[9H-fluorene]-2-yl group, 9,9-dimethylfluorenyl group, benzo[c]phenanthrenyl group, benzo[a]triphenylenyl group, naphtho[1,2-c]phenanthrenyl group, naphtho[1,2-a]triphenylenyl group, dibenzo[a,c]triphenylenyl group, benzo[a]fluoranthenyl group, benzo[j]fluoranthenyl group, benzo[k]fluoranthenyl group and benzo[b]fluoranthenyl group, with phenyl group, naphthyl group, biphenyl group, terphenyl group, phenanthryl group, triphenylenyl group, fluorenyl group, spirobifluorenyl group, and fluoranthenyl group being preferred, and phenyl group, 1-naphthyl group, 2-naphthyl group, biphenyl-2-yl group, biphenyl-3-yl group, biphenyl-4-yl group, phenanthrene-9-yl group, phenanthrene-3-yl group, phenanthrene-2-yl group, triphenylene-2-yl group, 9,9-dimethylfluorene-2-yl group, fluoranthene-3-yl group, fluoranthene-2-yl group, fluoranthene-8-yl group being more preferred.

The heterocyclic group having 4 to 30 carbon atoms, preferably 4 to 18 carbon atoms, may be a non-condensed heterocyclic group or a condensed heterocyclic group. Specific examples thereof include the residues of pyrrole ring, isoindole ring, benzofuran ring, isobenzofuran ring, benzothiophene, dibenzothiophene ring, isoquinoline ring, quinoxaline ring, quinazoline, phenanthridine ring, phenanthroline ring, pyridine ring, pyrazine ring, pyrimidine ring, pyridazine ring, indole ring, quinoline ring, acridine ring, pyrrolidine ring, dioxane ring, piperidine ring, morpholine ring, piperazine ring, carbazole ring, furan ring, thiophene ring, benzoxazole ring, benzothiazole ring, benzimidazole ring, pyran ring, dibenzofuran ring and benzo[c]dibenzofuran ring, with the residues of dibenzofuran ring, carbazole ring, and dibenzothiophene ring being preferred, and the residues of dibenzofuran-1-yl group, dibenzofuran-3-yl group, dibenzofuran-2-yl group, dibenzofuran-4-yl group, 9-phenylcarbazole-3-yl group, 9-phenylcarbazole-2-yl group, 9-phenylcarbazole-4-yl group, dibenzothiophene-2-yl group, and dibenzothiophene-4-yl, dibenzothiophene-1-yl group, and dibenzothiophene-3-yl group being more preferred.

Examples of the alkyl group having 1 to 25 carbon atoms include methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, with methyl group, ethyl group, n-propyl group, isopropyl group, n-butyl group, s-butyl group, isobutyl group, t-butyl group being preferred.

Examples of the alkenyl group having 2 to 25 carbon atoms include those disclosed as alkyl groups having 2 to 25 carbon atoms but comprising at least one double bond, preferably one, or where possible, two or three double bonds.

Examples of the alkynyl group having 2 to 25 carbon atoms include those disclosed as alkyl groups having 2 to 25 carbon atoms but comprising at least one triple bond, preferably one, or where possible, two or three triple bonds.

Examples of the cycloalkyl group having 3 to 25 carbon atoms include cyclopropyl group, cyclobutyl group, cyclopentyl group, cyclohexyl group, cyclooctyl group, and adamantyl group, with cyclopentyl group, and cyclohexyl group being preferred.

Examples of an aralkyl group having 7 to 24 carbon atoms, preferably 7 to 20 carbon atoms, include benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenyl isopropyl group, and 1-chloro-2-phenylisopropyl group.

Examples of the alkylene group (i.e. alkane-diyl group) having 1 to 30 carbon atoms represented include methylene group, ethylene group, n-propylene group, isopropylene group, n-butylene group, s-butylene group, isobutylene group, t-butylene group, n-pentylene group, n-hexylene group, n-heptylene group, n-octylene group, n-nonylene group, n-decylene group, n-undecylene group, n-dodecylene group, n-tridecylene group, n-tetradecylene group, n-pentadecylene group, n-hexadecylene group, n-heptadecylene group, n-octadecylene group, neopentylene group, 1-methylpentylene group, with methylene group, ethylene group, n-propylene group, isopropylene group, n-butylene group, s-butylene group, isobutylene group, t-butylene group being preferred.

Examples of the cycloalkylene group (i.e. cycloalkane-diyl group) having 3 to 20 carbon atoms include cyclopropylene group, cyclobutylene group, cyclopentylene group, cyclohexylene group, cyclooctylene group, and adamantylene group, with cyclopentylene group, and cyclohexylene group being preferred.

Examples of the substituted divalent silyl group having 2 to 30 carbon atoms include divalent dimethylsilyl group, divalent diethylsilyl group, divalent dibutylsilyl group, divalent methylethylsilyl group, divalent t-butylmethylsilyl group, divalent vinylmethylsilyl group, divalent propylmethylsilyl group, divalent methylisopropylsilyl group, divalent methylpropylsilyl group, divalent methylbutylsilyl group, divalent methyltertiarybutylsilyl group, divalent ethylisopropylsilyl group, divalent phenylmethylsilyl group, divalent phenylmethylsilyl group, divalent phenyltertiarybutylsilyl group, and divalent diphenylsilyl group, with divalent dimethylsilyl group, divalent diethylsilyl group, divalent t-butylmethylsilyl group, divalent vinylmethylsilyl group, and divalent propylmethylsilyl group being preferred.

The divalent aromatic hydrocarbon group having 6 to 30 ring carbon atoms may be a non-condensed divalent aromatic hydrocarbon group or a condensed divalent aromatic hydrocarbon group. Specific examples thereof include phenylene group, naphthylene group, phenanthrylene group, biphenyl-diyl group, terphenyl-diyl group, quaterphenyl-diyl group, fluoranthen-diyl group, triphenylenylene-diyl group, phenanthrene-diyl group, fluorene-diyl group, spirofluorene-diyl group, 9,9-diphenylfluorene-diyl group, 9,9'-spirobi[9H-fluorene]-2-diyl group, 9,9-dimethylfluorene-diyl group, benzo[c]phenanthrene-diyl group, benzo[a]triphenylene-diyl group, naphtho[1,2-c]phenanthrene-diyl group, naphtho[1,2-a]triphenylenylene-diyl group, dibenzo[a,c]triphenylenylene-diyl group, benzo[a]fluoranthene-diyl group, benzo[j]fluoranthene-diyl group, benzo[k]fluoranthene-diyl group, and benzo[b]fluoranthene-diyl group, with phenylene group, naphthylene group, biphenyl-diyl group, terphenyl-diyl group, phenanthryl-diyl group, triphenylenylen-diyl group, fluorene-diyl group, spirobifluorene-diyl group, and fluoranthene-diyl group being preferred, and 1,2-phenylene group, 1,3-phenylene group, 1,4-phenylene group, 1,4-naphthylene group, 1,8-naphthylene group, 2,6-naphthylene group, 2,7-naphthylene group, biphenyl-2,2'-diyl group, biphenyl-2,3'-diyl group, biphenyl-2,4'-diyl group, biphenyl-2,5'-diyl group, biphenyl-2,6'-diyl group, biphenyl-3,3'-diyl group, biphenyl-3,4'-diyl group, biphenyl-3,5'-diyl group, biphenyl-3,6'-diyl group, biphenyl-4,4'-diyl group, biphenyl-4,5'-diyl group, biphenyl-4,6'-diyl group, biphenyl-5,5'-diyl group, biphenyl-5,6'-diyl group, biphenyl-6,6'-diyl group, phenanthrene-9,10-diyl group, phenanthrene-2,3-diyl group, phenanthrene-2,7-diyl group, phenanthrene-2,8-diyl group, phenanthrene-2,6-diyl group, phenanthrene-2,9-diyl group, phenanthrene-2,10-diyl group, phenanthrene-3,9-diyl group, phenanthrene-3,10-diyl group, triphenylene-2,3-diyl group, triphenylene-2,5-diyl group, triphenylene-2,6-diyl group, triphenylene-2,7-diyl group, triphenylene-2,8-diyl group, 9,9-dimethylfluorene-2,7-diyl group, 9,9-dimethylfluorene-3,7-diyl group, 9,9-dimethylfluorene-1,4-diyl group, fluoranthene-3,9-diyl group, fluoranthene-3,8-diyl group, fluoranthene-3,4-diyl group, fluoranthene-3,5-diyl group, fluoranthene-3,6-diyl group, fluoranthene-2,9-diyl group, fluoranthene-2,8-diyl group, fluoranthene-2,4-diyl group, fluoranthene-2,5-diyl group, fluoranthene-2,6-diyl group, fluoranthene-1,9-diyl group, fluoranthene-1,8-diylgroup, fluoranthene-1,4-diyl group, fluoranthene-1,5-diyl group, fluoranthene-1,6-diyl group being more preferred.

The divalent heterocyclic group having 4 to 30 carbon atoms may be a non-condensed heterocyclic group or a condensed heterocyclic group. Specific examples thereof include the divalent residues of pyrrole ring, isoindole ring, benzofuran ring, isobenzofuran ring, dibenzothiophene ring, isoquinoline ring, quinoxaline ring, quinazoline ring, phenanthridine ring, phenanthroline ring, pyridine ring, pyrazine ring, pyrimidine ring, pyridazine ring, indole ring, quinoline ring, acridine ring, pyrrolidine ring, dioxane ring, piperidine ring, morpholine ring, piperazine ring, carbazole ring, furan ring, thiophene ring, benzoxazole ring, benzothiazole ring, benzimidazole ring, pyran ring, dibenzofuran ring, and benzo[c]dibenzofuran ring, with the divalent residues of dibenzofuran ring, carbazole ring, dibenzothiophene ring being preferred, and the dibenzofuran-diyl group, 9-phenylcarbazole-diyl group and dibenzothiophene-diyl group being more preferred.

Examples of silyl groups are aryl and/or alkyl substituted silyl groups including alkylsilyl groups having 1 to 10 carbon atoms, preferably 1 to 5 carbon atoms, including trimethylsilyl group, triethylsilyl group, tributylsilyl group, dimethylethylsilyl group, t-butyldimethylsilyl group, vinyldimethylsilyl group, propyldimethylsilyl group, dimethylisopropylsilyl group, dimethylpropylsilyl group, dimethylbutylsilyl group, dimethyltertiarybutylsilyl group, diethylisopropylsilyl group, and arylsilyl groups having 6 to 30 carbon atoms, preferably 6 to 18 carbon atoms, including phenyldimethylsilyl group, diphenylmethylsilyl group, diphenyltertiarybutylsilyl group, and triphenylsilyl group, with trimethylsilyl group, triethylsilyl group, t-butyldimethylsilyl group, vinyldimethylsilyl group, and propyldimethylsilyl group being preferred.

Examples of halogen atoms include fluorine, chlorine, bromine, and iodine, with fluorine being preferred.

Examples of an alkoxy group having 1 to 20 carbon atoms include those having an alkyl portion selected from the alkyl groups mentioned above.

Examples of a haloalkyl group having 1 to 25 carbon atoms include the alkyl groups mentioned above wherein the hydrogen atoms thereof are partly or entirely substituted by halogen atoms.

Examples of a haloalkoxy group having 1 to 25 carbon atoms include the alkoxyl group mentioned above wherein the hydrogen atoms thereof are partly or entirely substituted by halogen atoms.

Examples of an aryloxy group having 6 to 24 ring carbon atoms include those having an aryl portion selected from the aromatic hydrocarbon groups mentioned above.

Examples of an alkylthio group having 1 to 25 carbon atoms include those having an alkyl portion selected from the alkyl groups mentioned above.

Examples of an arylthio group having 6 to 24 ring carbon atoms include those having an aryl portion selected from the aromatic hydrocarbon groups mentioned above.

Examples of an alkylamino group having 1 to 25 ring carbon atoms include those having an alkyl portion selected from the alkyl groups mentioned above.

Examples of an arylamino group having 6 to 24 ring carbon atoms include those having an aryl portion selected from the aromatic hydrocarbon groups mentioned above.

Examples of a carboxyalkyl group having 1 to 25 carbon atoms, preferably 1 to 5 carbon atoms, include those having an alkyl portion selected from the alkyl groups mentioned above.

Examples of a carboxamidalkyl group having 1 to 25 carbon atoms, preferably 1 to 5 carbon atom include those having an alkyl portion selected from the alkyl groups mentioned above.

Examples of a carboxyaryl group having 6 to 24 carbon atoms, preferably 6 to 18 carbon atoms, include those having an aryl portion selected from the aromatic hydrocarbon groups mentioned above.

Examples of a carboxamidaryl group having 6 to 24 carbon atoms, preferably 6 to 18 carbon atoms, include those having an aryl portion selected from the aromatic hydrocarbon groups mentioned above.

Examples of substituted phosphoryl groups are di-substituted phosphoryl groups having a substituent selected from the group consisting of a substituted or unsubstituted alkyl group having 1 to 25 carbon atoms and a substituted or unsubstituted aromatic hydrocarbon group having 6 to 24 ring carbon atoms. A preferred phosphoryl group is a diphenylphosphine oxide group.

Examples of alkyl or aryl substituted carbonyl groups include those having an alkyl portion selected from the alkyl groups mentioned above and/or having an aryl portion selected from the aromatic hydrocarbon groups mentioned above.

Examples of the optional substituent(s) indicated by "substituted or unsubstituted" and "may be substituted" referred to above or hereinafter include a halogen atom (fluorine, chlorine, bromine, iodine), a cyano group, an alkyl group having 1 to 25, preferably 1 to 6 carbon atoms, a cycloalkyl group having 3 to 25, preferably 5 to 12 carbon atoms, an alkoxyl group having 1 to 25, preferably 1 to 5 carbon atoms, a haloalkyl group having 1 to 25, preferably 1 to 5 carbon atoms, a haloalkoxyl group having 1 to 25, preferably 1 to 5 carbon atoms, an alkylamino group having 1 to 25 carbon atoms, preferably 1 to 5 carbon atoms, a carboxyalkyl group having 1 to 25 carbon atoms, preferably 1 to 5 carbon atoms, a carboxamidalkyl group having 1 to 20 carbon atoms, preferably 1 to 5 carbon atoms, a silyl group, an aromatic hydrocarbon group having 6 to 24 ring carbon atoms, preferably 6 to 18 ring carbon atoms, an aryloxy group having 6 to 24, preferably 6 to 18 ring carbon atoms, an aralkyl group having 7 to 24, preferably 7 to 20 carbon atoms, an alkylthio group having 1 to 25, preferably 1 to 5 carbon atoms, an arylthio group having 6 to 24, preferably 6 to 18 ring carbon atoms, an arylamino group having 6 to 30 carbon atoms, preferably 6 to 18 carbon atoms, a carboxyaryl group having 6 to 24 carbon atoms, preferably 6 to 18 carbon atoms, a carboxamidaryl group having 6 to 24 carbon atoms, preferably 6 to 18 carbon atoms, and a heterocyclic group having 5 to 24 ring atoms, preferably 5 to 18 ring atoms.

The optional substituent is preferably a fluorine atom, a cyano group, an alkyl group having 1 to 25 carbon atoms, an aromatic hydrocarbon group having 6 to 24 ring carbon atoms, preferably 6 to 18 ring carbon atoms, and an heterocyclic group having 4 to 30 carbon atoms, preferably 5 to 18 ring atoms; more preferably a fluorine atom, a phenyl group, a naphthyl group, a biphenyl group, a terphenyl group, a phenanthryl group, a triphenylenyl group, a fluorenyl group, a spirobifluorenyl group, a fluoranthenyl group, a residue based on a dibenzofuran ring, a residue based on a carbazole ring, and a residue based on a dibenzothiophene ring, a methyl group, an ethyl group, an n-propyl group, an isopropyl group, an n-butyl group, an s-butyl group, an isobutyl group, a t-butyl group, a cyclopentyl group, and a cyclohexyl group.

The optional substituent mentioned above may be further substituted by one or more of the optional substituents mentioned above.

The number of the optional substituents depends on the group which is substituted by said substituent(s). Preferred are 1, 2, 3 or 4 optional substituents, more preferred are 1, 2 or 3 optional substituents, most preferred are 1 or 2 optional substituents. In a further preferred embodiment, the groups mentioned above are unsubstituted.

The "carbon number of a to b" in the expression of "substituted or unsubstituted X group having a to b carbon atoms" is the carbon number of the unsubstituted X group and does not include the carbon atom(s) of an optional substituent.

The hydrogen atom referred to herein includes isotopes different from neutron numbers, i.e., light hydrogen (protium), heavy hydrogen (deuterium) and tritium.

The term "unsubstituted" referred to by "unsubstituted or substituted" means that a hydrogen atom is not substituted by one the groups mentioned above.

An index of 0 in the definition in any formula mentioned above and below means that a hydrogen atom is present at the position defined by said index.

The Compound of Formula (I)

The present invention relates to a compound of formula (I)

(I)

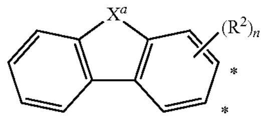

wherein each * is a bonding site to a group of formula (II)

(II)

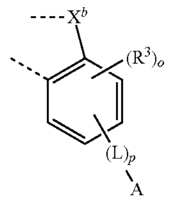

the dotted lines in the group of formula (II) are bonding sites to the * in the compound of formula (I);

$X^a$ and $X^b$ are each independently O or S, preferably, at least one of $X^a$ and $X^b$ is O, more preferably, $X^a$ and $X^b$ are O.

$R^2$, $R^3$, n, o, L, p and A in the compound of formulae (I) and (II) are described above and below.

The compound of formula (I) is preferably represented by a compound of formula (Ia) or (Ib)

(Ia)

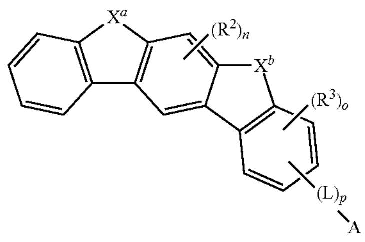

or (Ib)

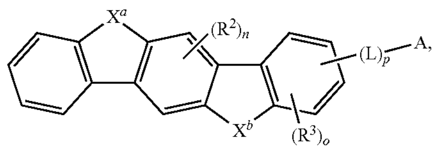

wherein $X^a$, $X^b$, $R^2$, $R^3$, L, A, n, o and p are defined above and below.

More preferably, the compound of formula (Ia) is represented by a compound of formula (Iaa) and the compound of formula (Ib) is represented by a compound of formula (Iba)

(Iaa)

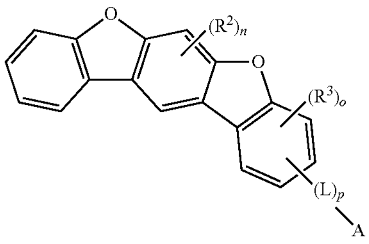

(Iba)

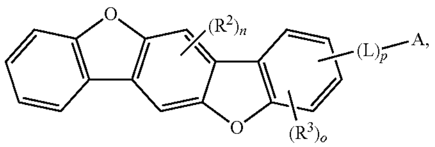

wherein $R^2$, $R^3$, L, A, n, o and p are defined above and below.

$R^2$ and $R^3$ $R^2$ and $R^3$ each independently represents hydrogen, a halogen atom, a substituted or unsubstituted alkyl group having 1 to 25 carbon atoms, a substituted or unsubstituted alkenyl group having 2 to 25 carbon atoms, a substituted or unsubstituted alkynyl group having 2 to 25 carbon atoms, a substituted or unsubstituted cycloalkyl group having 3 to 25 carbon atoms, a substituted or unsubstituted alkoxy group having 1 to 25 carbon atoms, a substituted or unsubstituted aryl group having 6 to 24 carbon atoms, a substituted or unsubstituted heterocyclic group having 4 to 30 carbon atoms, a substituted or unsubstituted aryloxy group having 6 to 24 carbon atoms, a substituted or unsubstituted alkylthio group having 1 to 25 carbon atoms, a substituted or unsubstituted arylthio group having 6 to 24 carbon atoms, an alkyl and/or aryl substituted silyl group, an alkyl or aryl substituted carbonyl group, or a substituted phosphoryl group, or CN.

Preferably, $R^2$ and $R^3$ each independently represents hydrogen, a substituted or unsubstituted alkyl group having 1 to 25 carbon atoms, a substituted or unsubstituted cycloalkyl group having 3 to 25 carbon atoms, or a substituted or unsubstituted aryl group having 6 to 24 carbon atoms, or a substituted or unsubstituted heterocyclic group having 4 to 30 carbon atoms, or CN.

More preferably, $R^2$ and $R^3$ each independently represents hydrogen, a methyl group, an ethyl group, a n-propyl group, an isopropyl group, a n-butyl group, a s-butyl group, an isobutyl group, a t-butyl group, a cyclohexyl group, or a phenyl group, wherein the groups mentioned before are unsubstituted or substituted, preferably unsubstituted. Suitable substituents are mentioned above.

Most preferably, $R^2$ and $R^3$ are hydrogen.

n is 0, 1 or 2, preferably 0.

o is 0, 1, 2 or 3, preferably 0.

Most preferred compounds of formulae (Iaa) and (Iba) are therefore represented by the following formulae:

(Iaaa)

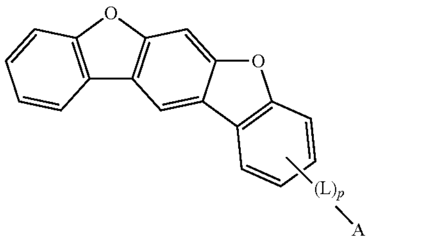

(Ibaa)

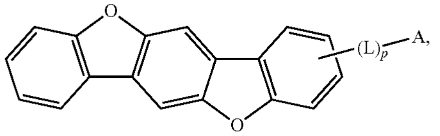

wherein L, A and p are defined above and below.

The Group -$(L)_p$-A

L represents a direct bond, a divalent phenyl group, a divalent biphenyl group, a divalent terphenyl group, a divalent naphthyl group, a divalent dibenzofuranyl group or a divalent dibenzothiophenyl group, wherein the groups mentioned before are unsubstituted or substituted, preferably unsubstituted. Suitable substituents are mentioned above.

p is 1, 2 or 3; in the case that p is 2 or 3, L is the same or different in each occurrence, preferably p is 1 or 2, in the case that p is 2, L is the same or different in each occurrence.

A is a group of formula (III)

(III)

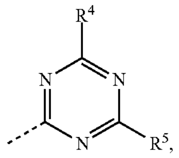

wherein $R^4$ and $R^5$ each independently represents hydrogen, a halogen atom, a substituted or unsubstituted alkyl group having 1 to 25 carbon atoms, a substituted or unsubstituted alkenyl group having 2 to 25 carbon atoms, a substituted or unsubstituted alkynyl group having 2 to 25 carbon atoms, a substituted or unsubstituted cycloalkyl group having 3 to 25 carbon atoms, a substituted or unsubstituted alkoxy group having 1 to 25 carbon atoms, a substituted or unsubstituted aryl group having 6 to 24 ring carbon atoms, a substituted or unsubstituted heterocyclic group having 4 to 30 carbon atoms, a substituted or unsubstituted aryloxy group having 6 to 24 carbon atoms, a substituted or unsubstituted alkylthio group having 1 to 25 carbon atoms, a substituted or unsubstituted arylthio group having 6 to 24 carbon atoms, an alkyl and/or aryl substituted silyl group, an alkyl or aryl substituted carbonyl group, or a substituted phosphoryl group; and the dotted line in the group of formula (III) is a bonding site.

Preferably, $R^4$ and $R^5$ each independently represents a substituted or unsubstituted alkyl group having 1 to 25 carbon atoms, a substituted or unsubstituted cycloalkyl group having 3 to 25 carbon atoms, a substituted or unsubstituted aryl group having 6 to 24 carbon atoms, a substituted or unsubstituted heterocyclic group having 4 to 30 carbon atoms.

More preferably, $R^4$ and $R^5$ each independently represents a substituted or unsubstituted aryl group having 6 to 24 ring carbon atoms, preferably phenyl, biphenyl, terphenyl, naphthyl, anthryl, phenanthryl, pyrenyl, benzophenanthryl, fluorenyl, spirobifluorenyl, more preferably phenyl, biphenyl or terphenyl; or a substituted or unsubstituted heterocyclic group having 4 to 30 carbon atoms, preferably pyridyl, pyrimidyl, dibenzofuranyl, dibenzothiophenyl, or carbazolyl, more preferably dibenzofuranyl, dibenzothiophenyl, benzofurodibenzofuranyl, benzofurodibenzothienyl, benzothienodibenzothienyl or carbazolyl, wherein the groups mentioned before are unsubstituted or substituted, preferably unsubstituted. Suitable substituents are mentioned above.

Most preferably, $R^4$ and $R^5$ each independently represents phenyl, biphenyl, terphenyl, naphthyl, dibenzofuranyl, dibenzothiophenyl, benzofurodibenzofuranyl, benzofurodibenzothienyl, benzothienodibenzothienyl or carbazolyl, wherein the groups mentioned before are unsubstituted or substituted, preferably unsubstituted. Suitable substituents are mentioned above.

Further most preferably, $R^4$ and $R^5$ each independently represents phenyl, biphenyl, terphenyl, naphthyl, dibenzofuranyl or dibenzothiophenyl, wherein the groups mentioned before are unsubstituted or substituted, preferably unsubstituted. Suitable substituents are mentioned above.

Examples for groups -$(L)_p$-A are

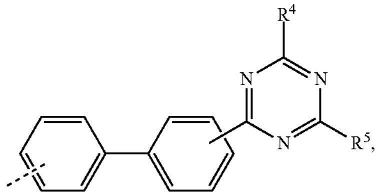

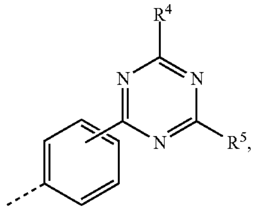

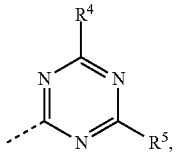

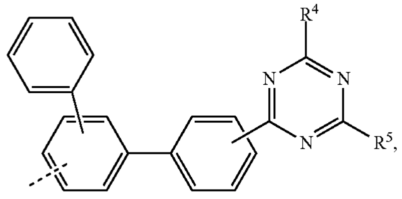

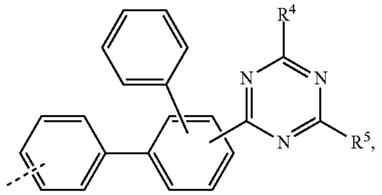

-continued

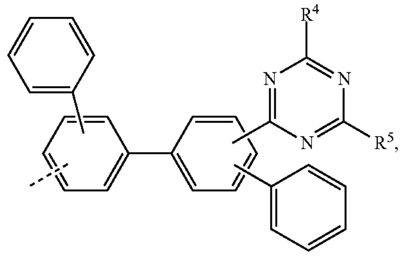

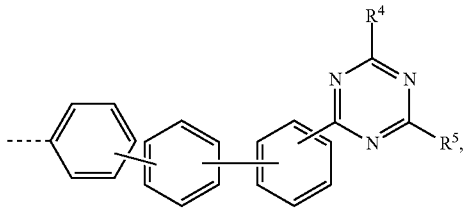

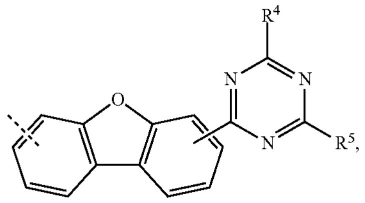

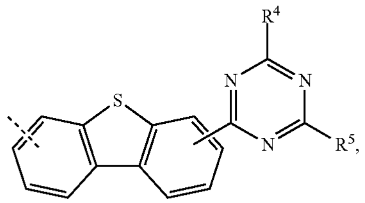

-continued

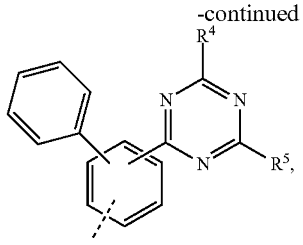

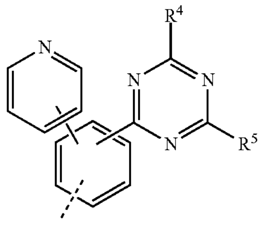

wherein $R^4$ and $R^5$ each independently represents phenyl, biphenyl, terphenyl, naphthyl, anthryl, phenanthryl, pyrenyl, benzophenanthryl, fluorenyl, spirobifluorenyl, pyridyl, pyrimidyl, dibenzofuranyl, dibenzothiophenyl, benzofurodibenzofuranyl, benzofurodibenzothienyl, benzothienodibenzothienyl or carbazolyl; preferably phenyl, biphenyl, terphenyl, dibenzofuranyl, dibenzothiophenyl, or carbazolyl, wherein the groups mentioned before are unsubstituted or substituted, preferably unsubstituted; preferably, $R^4$ and $R^5$ each independently represents phenyl, biphenyl, terphenyl, naphthyl, anthryl, phenanthryl, pyrenyl, benzophenanthryl, fluorenyl, spirobifluorenyl, pyridyl, dibenzofuranyl or dibenzothiophenyl; more preferably phenyl, biphenyl, terphenyl, naphthyl, dibenzofuranyl or dibenzothiophenyl, wherein the groups mentioned before are unsubstituted or substituted, preferably unsubstituted. Suitable substituents are mentioned above.

The compounds of formula (I) as well as preferred residues, groups and indices of the compounds of formula (I) have been described above.

Below, examples for compounds of formula (I) are given:

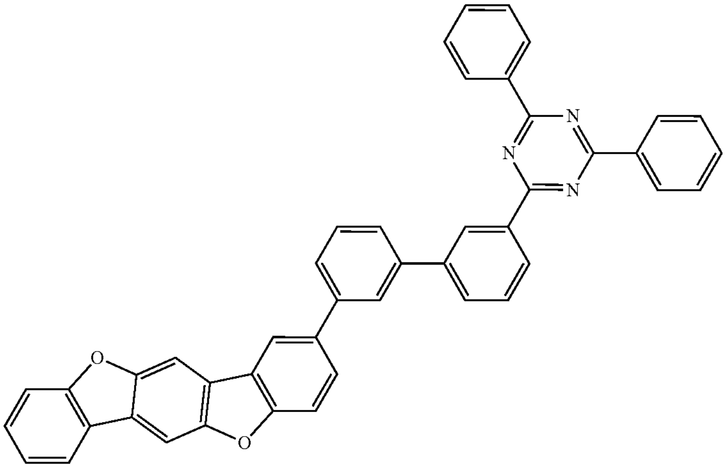

-continued
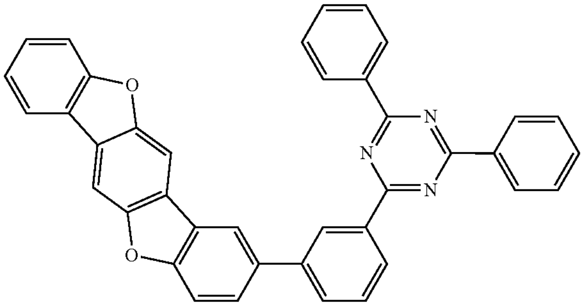
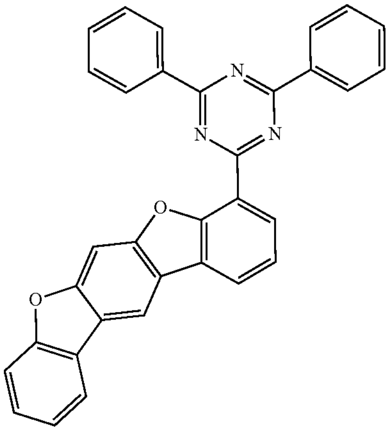
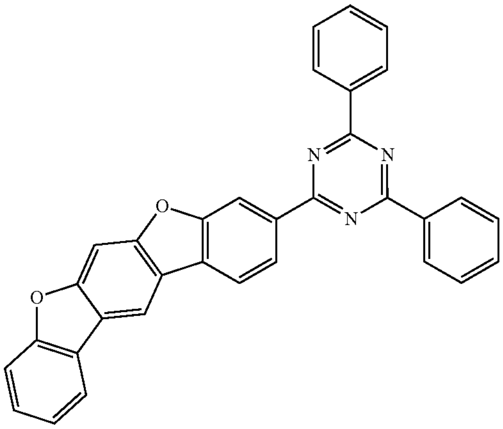
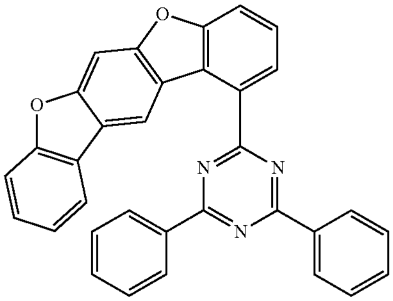
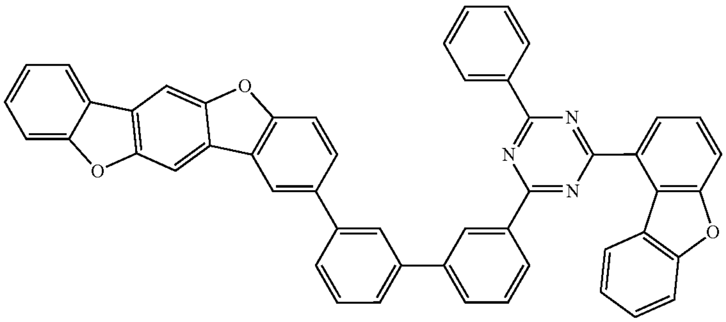
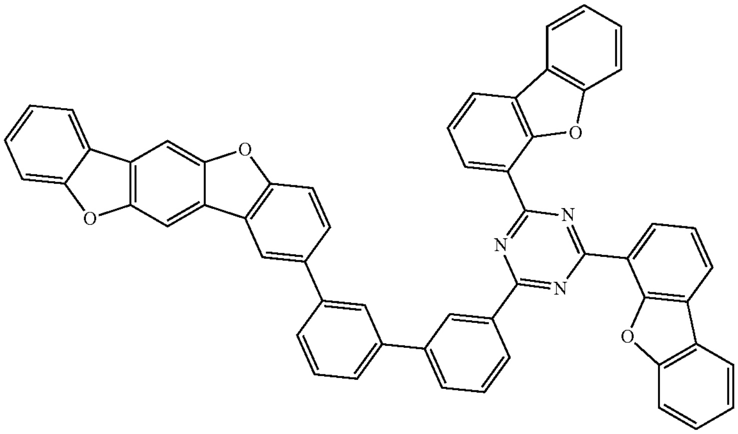

-continued
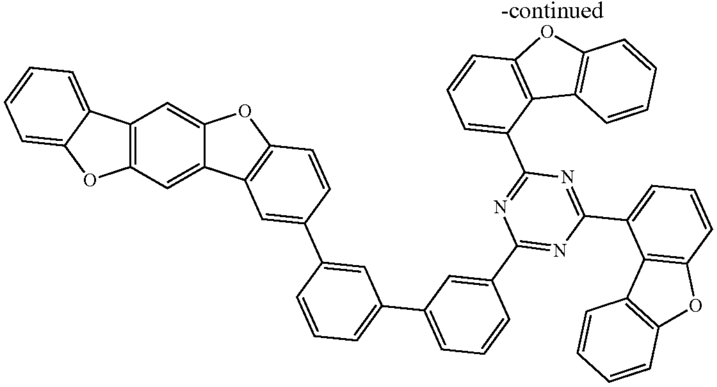
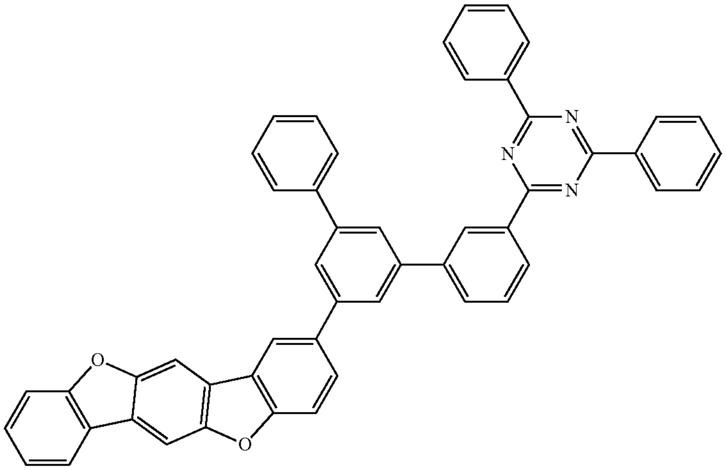
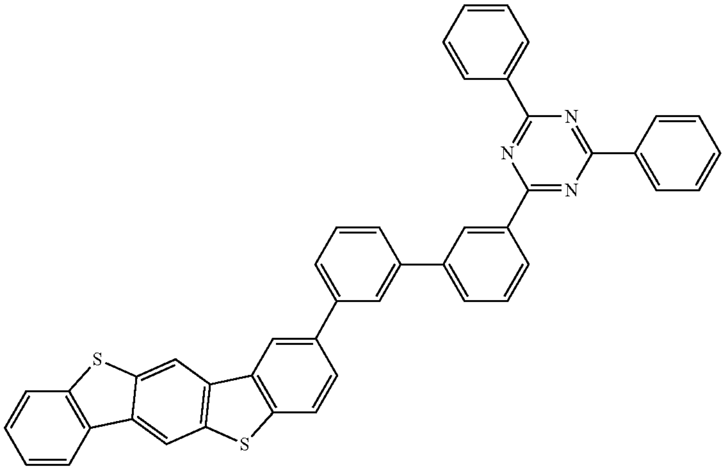

-continued
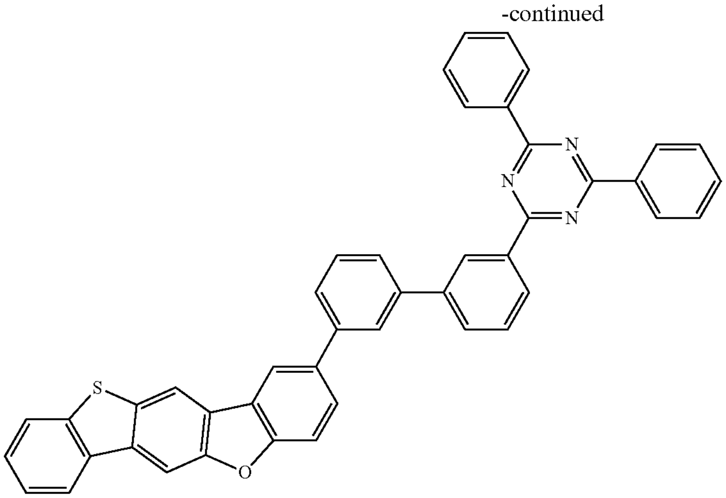
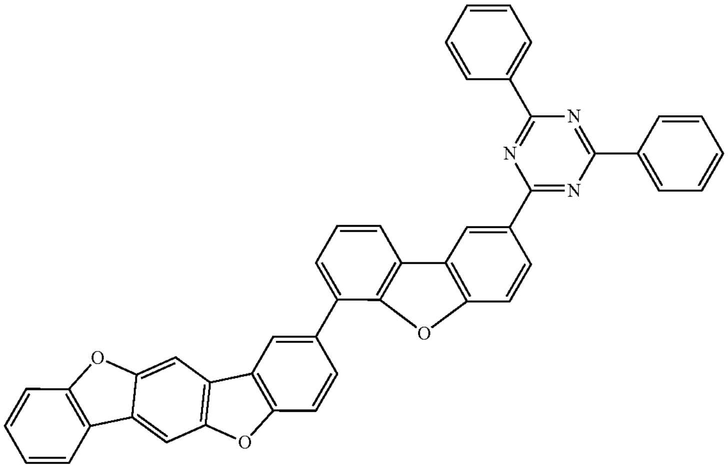
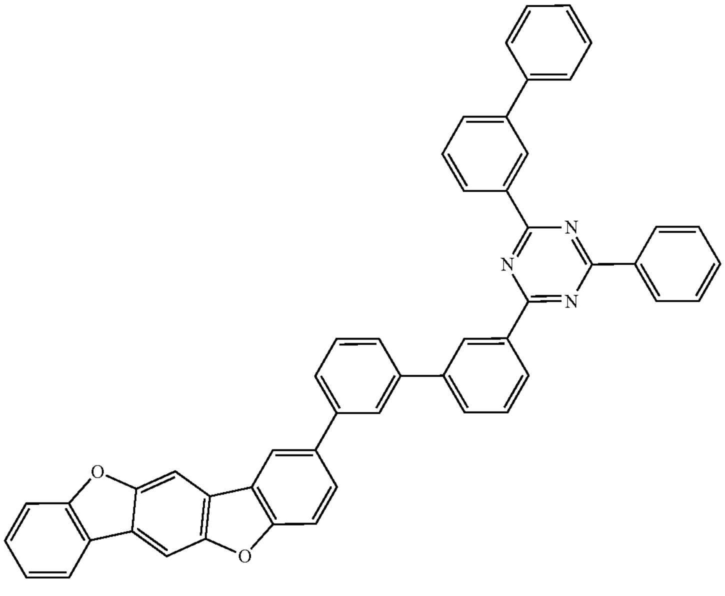

-continued
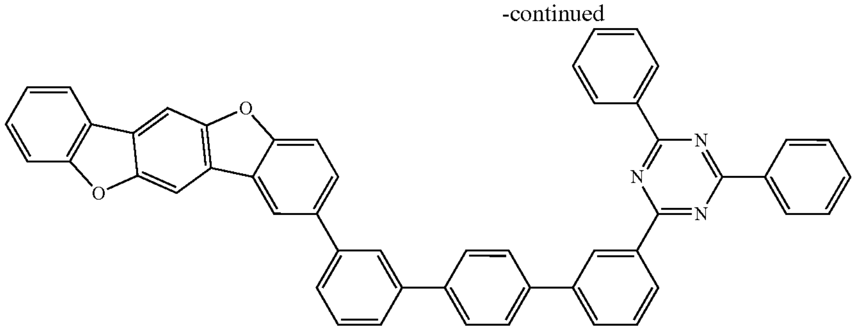
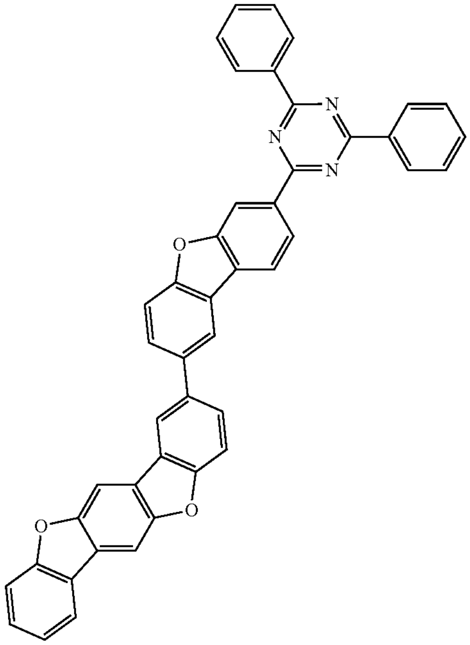
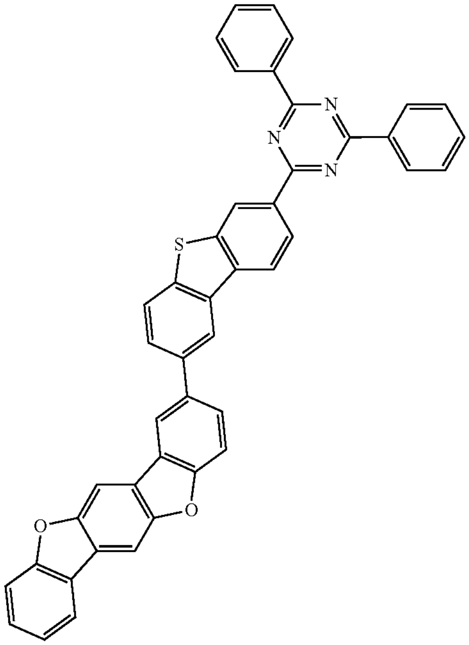
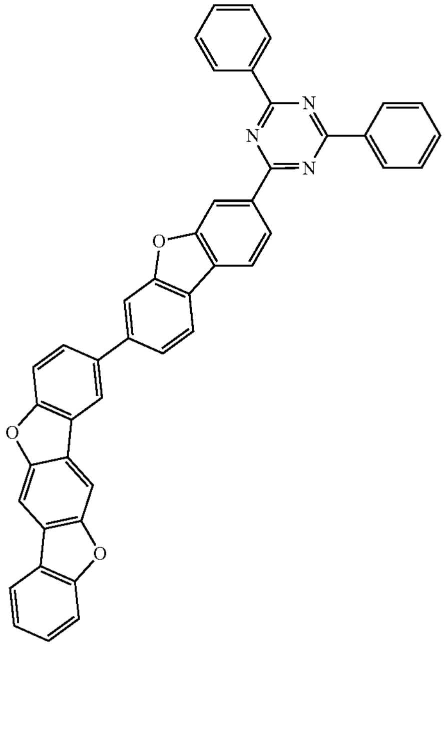
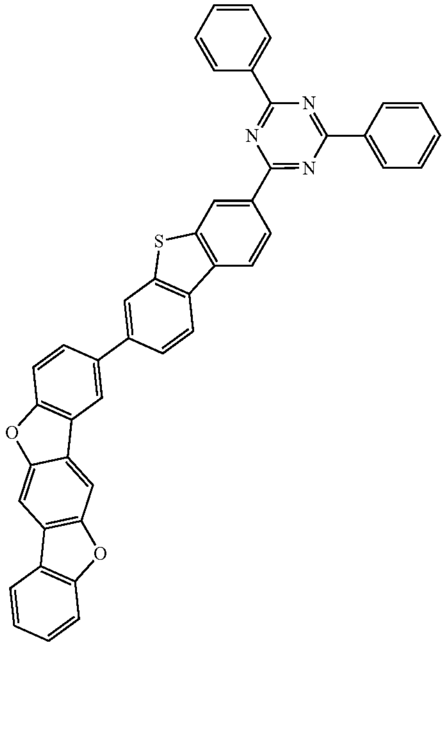

-continued
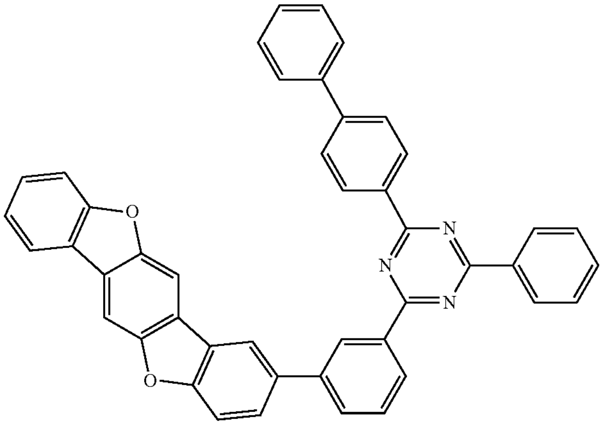
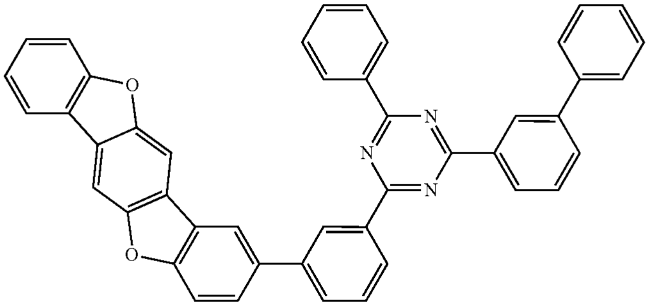
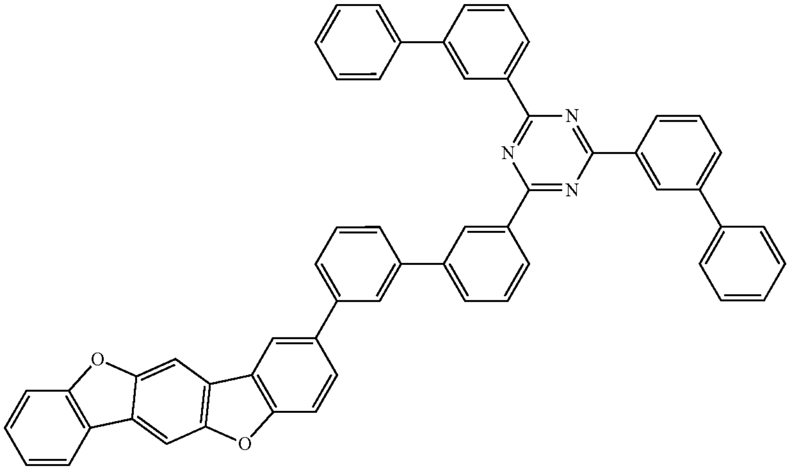
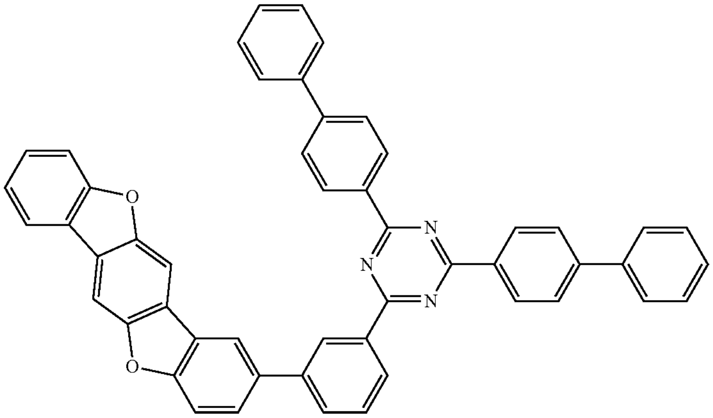

-continued
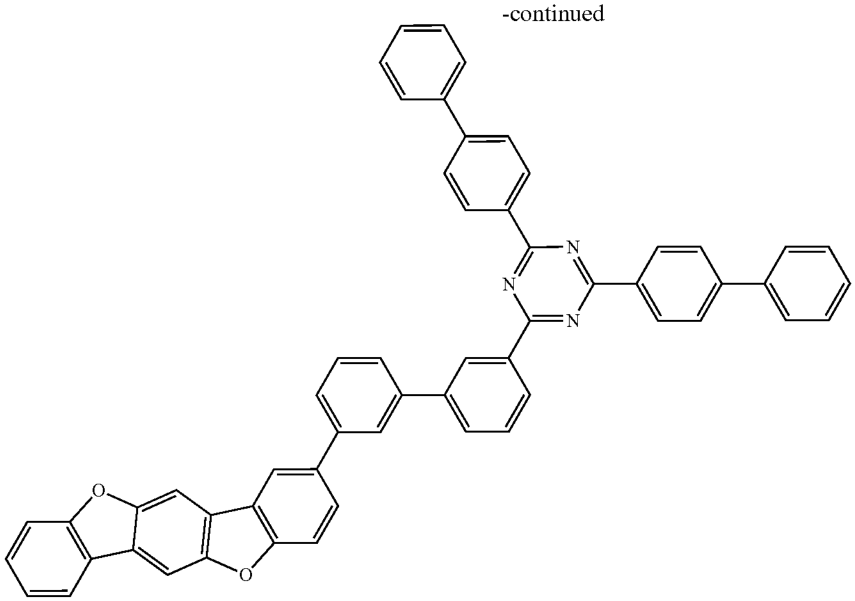
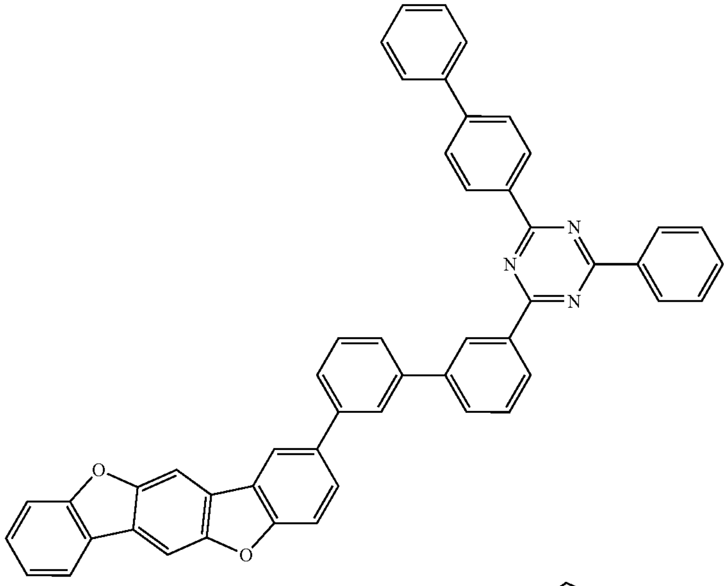
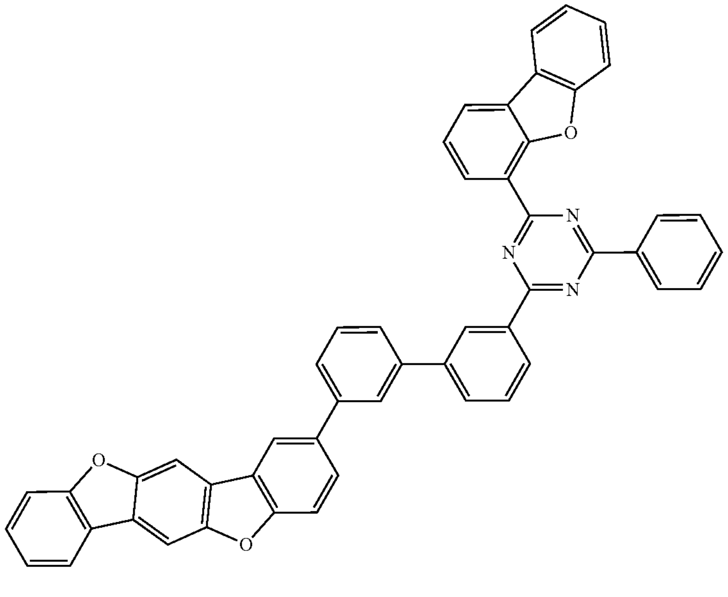

-continued
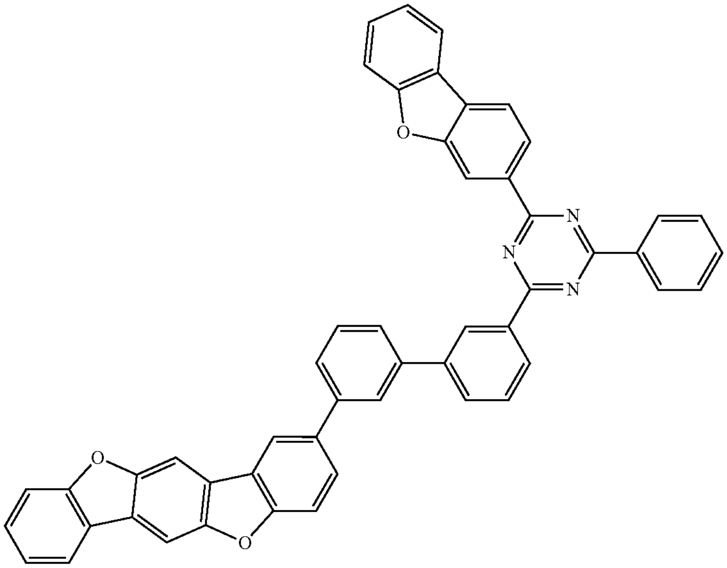
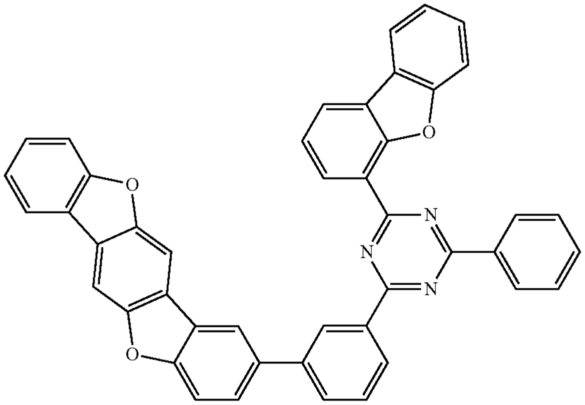
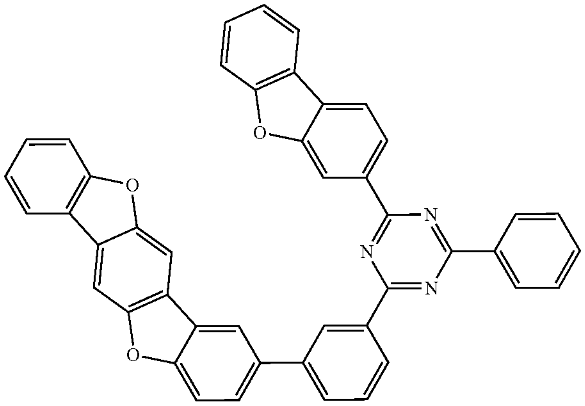

-continued
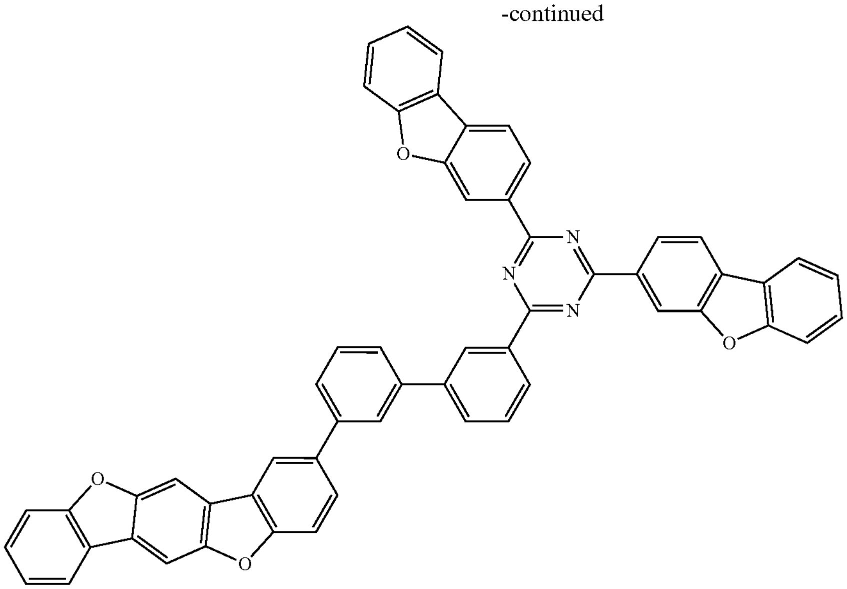
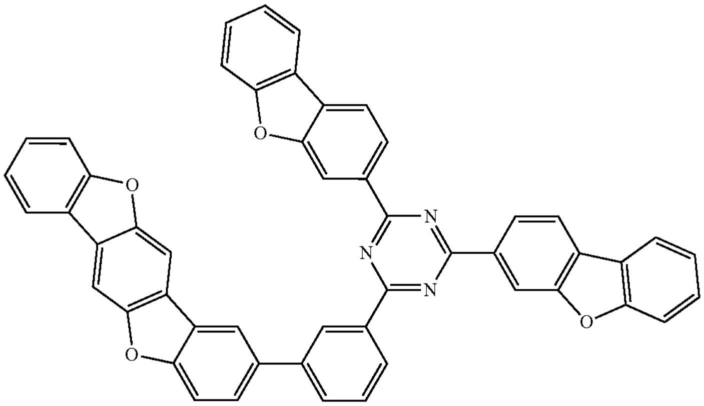
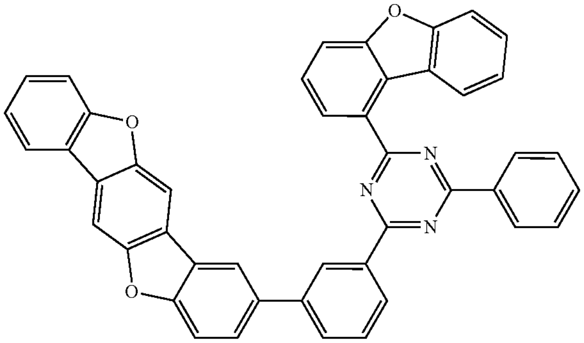
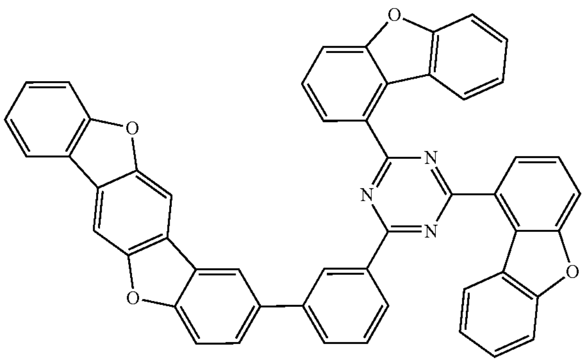

-continued
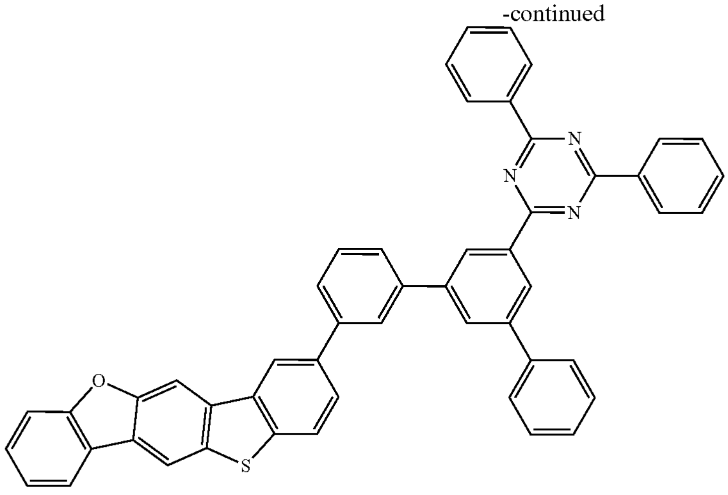
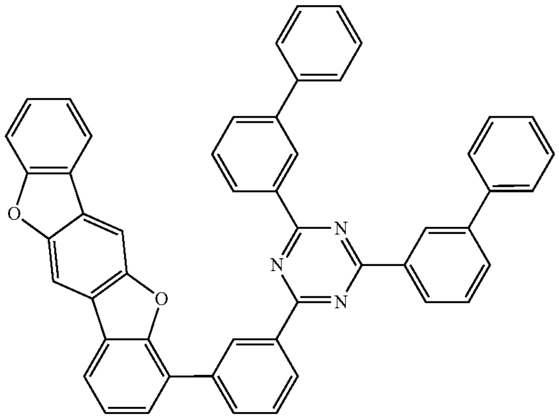
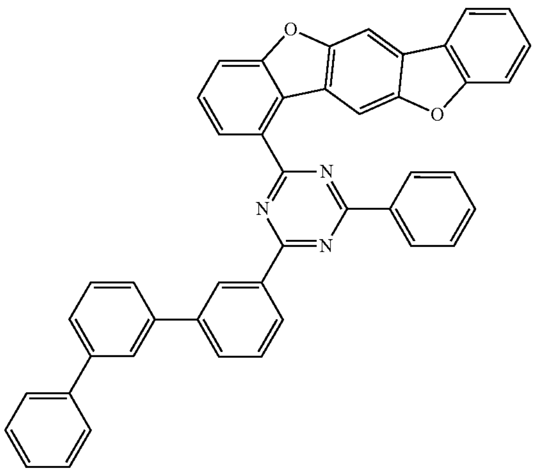
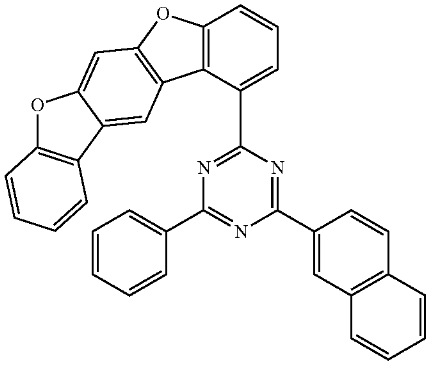

-continued
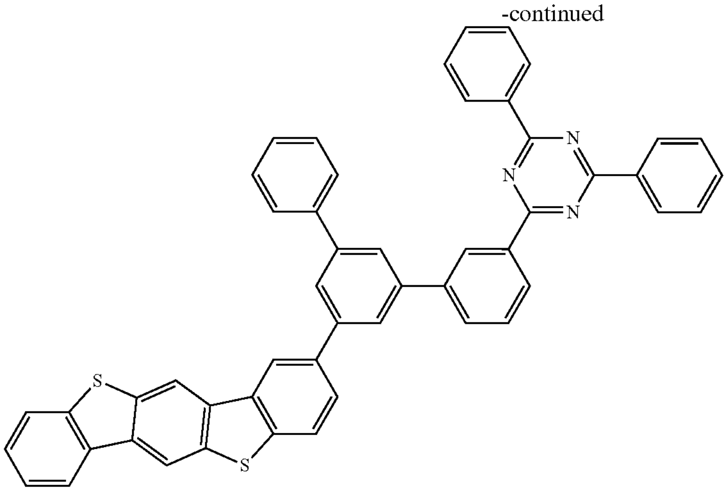
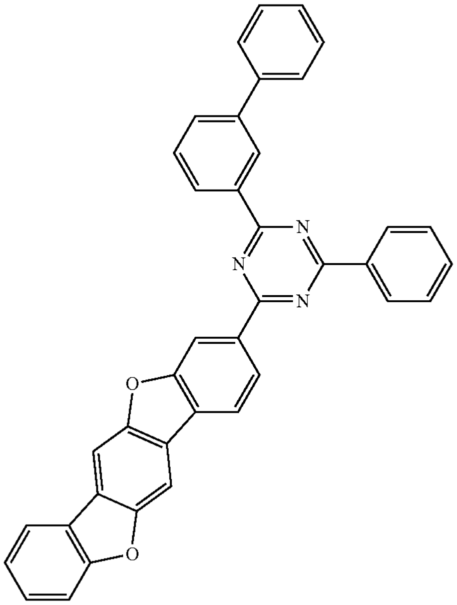
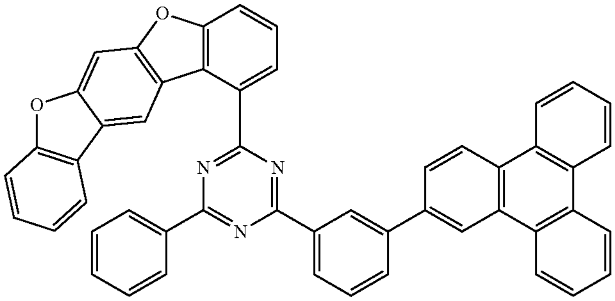
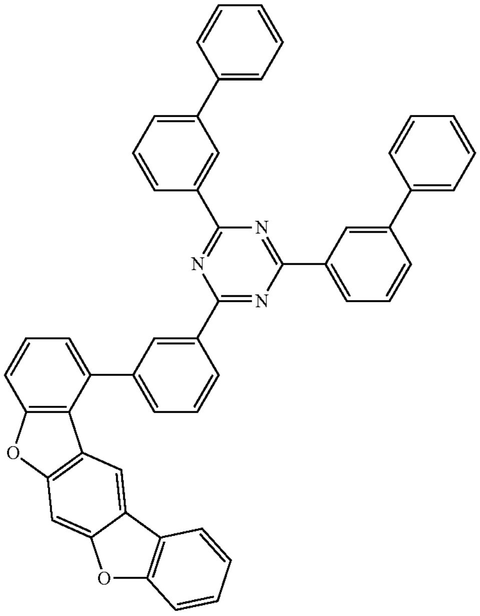
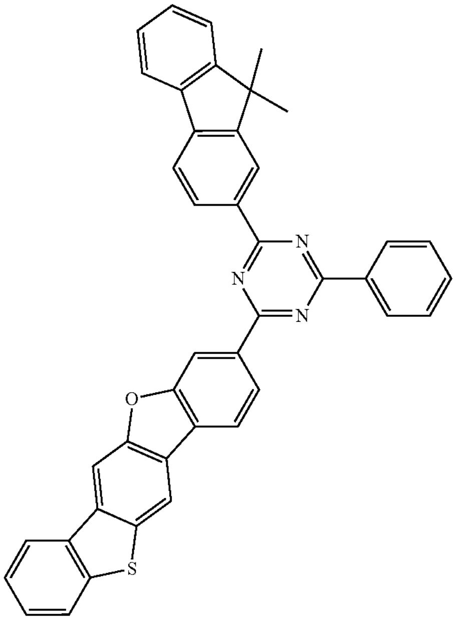

-continued
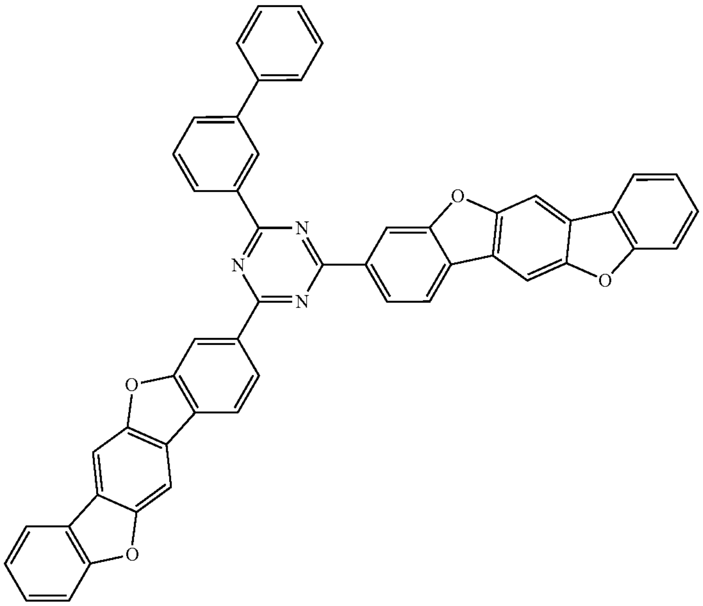
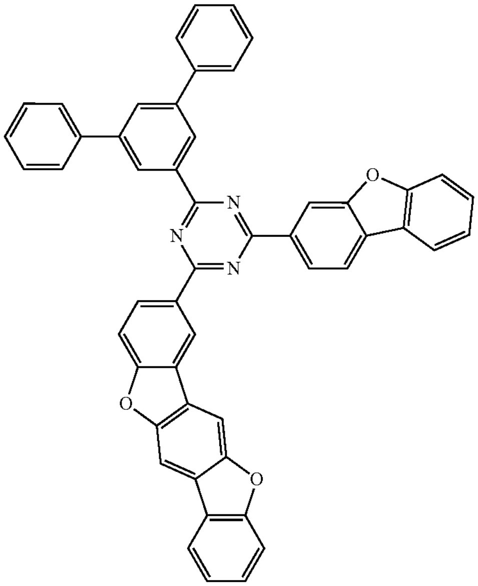
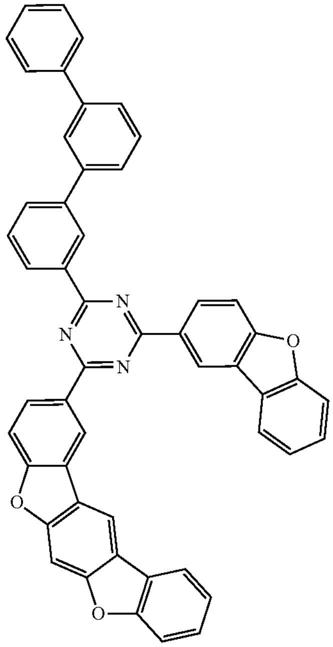
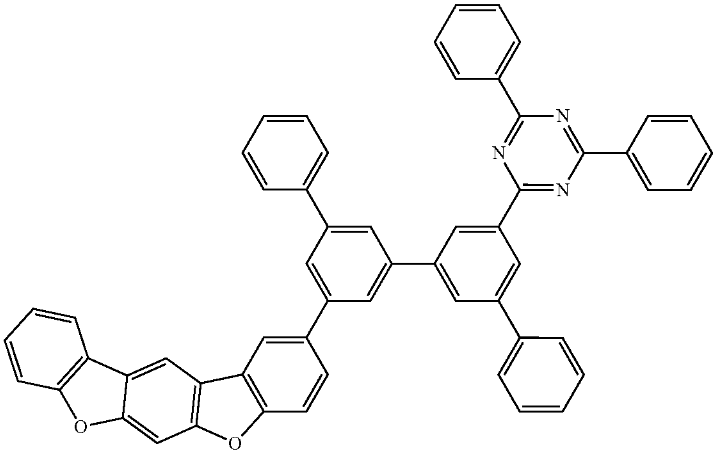

-continued
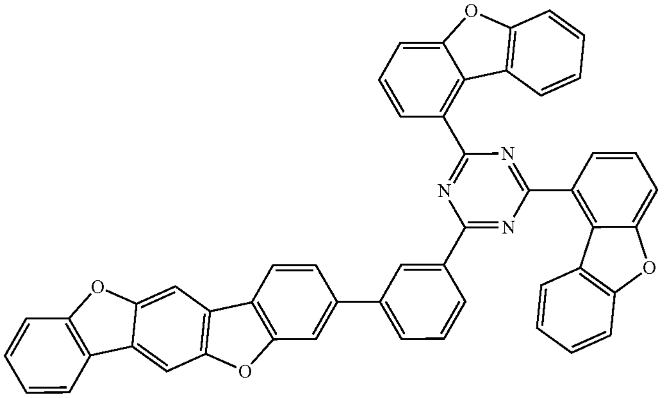
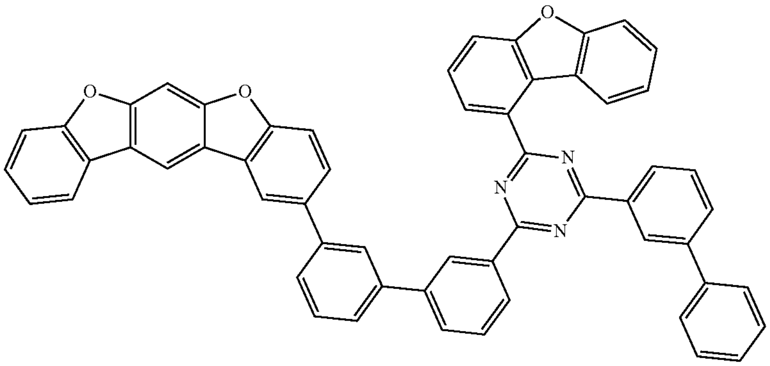
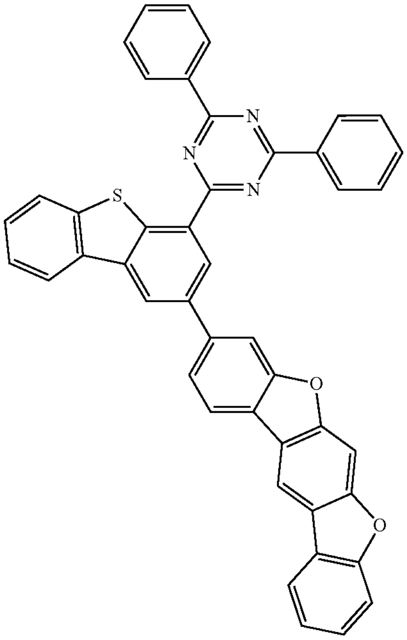
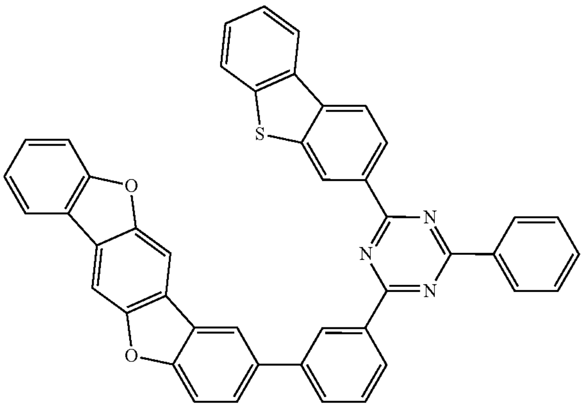

-continued
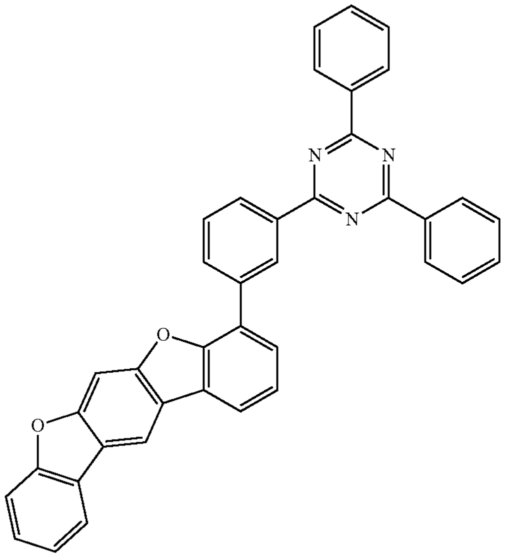
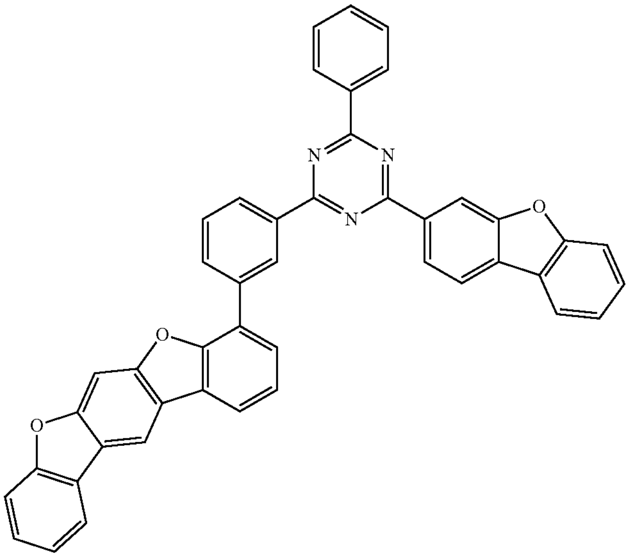
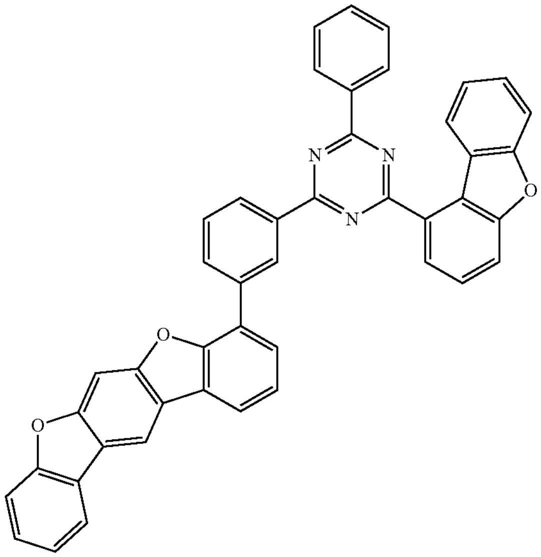
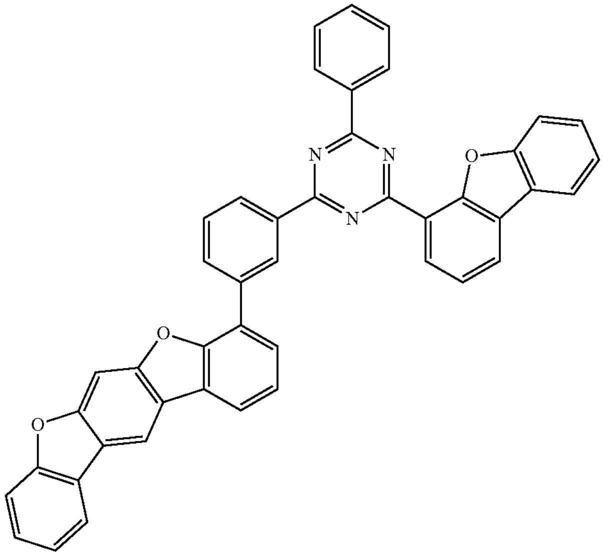

-continued
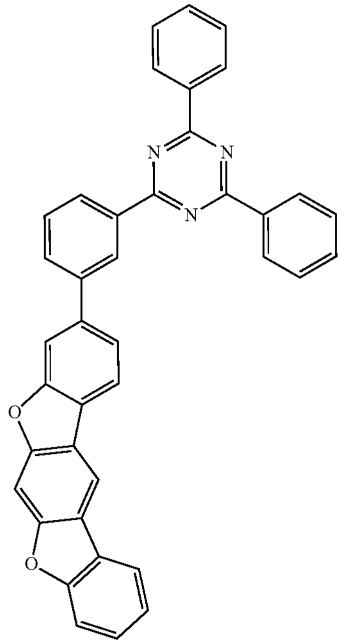
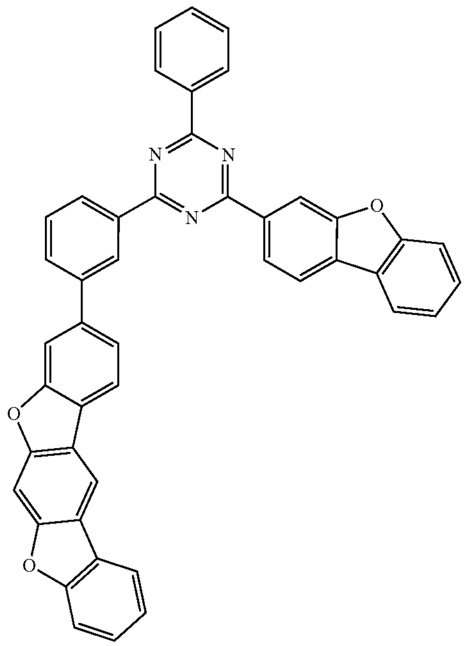
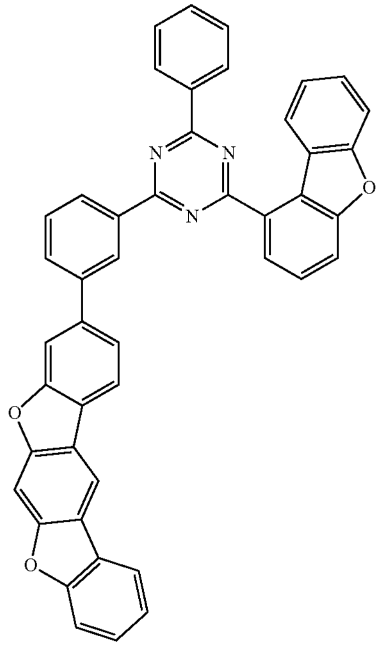
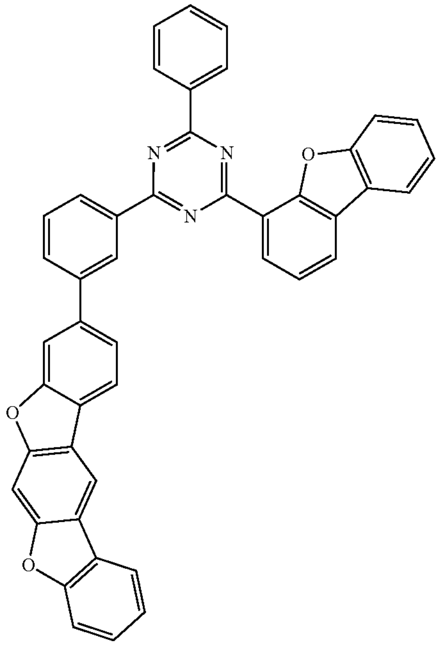

-continued
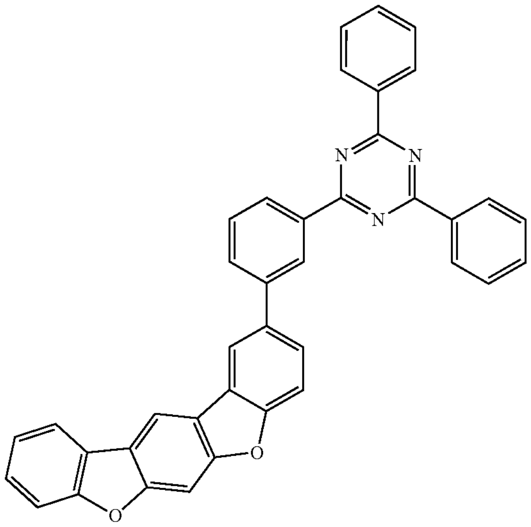
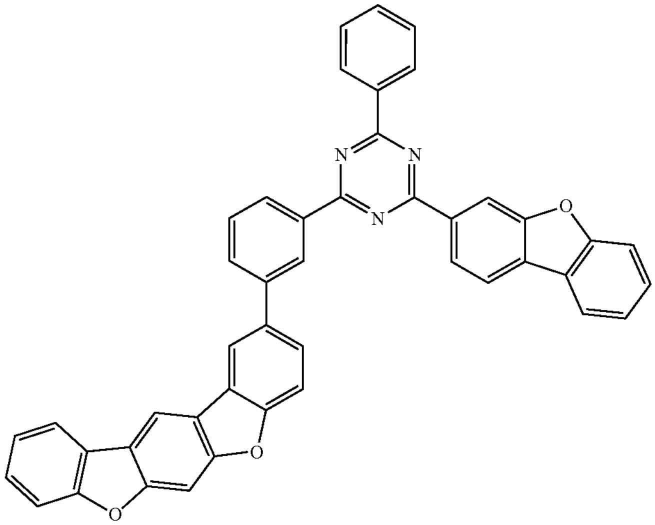
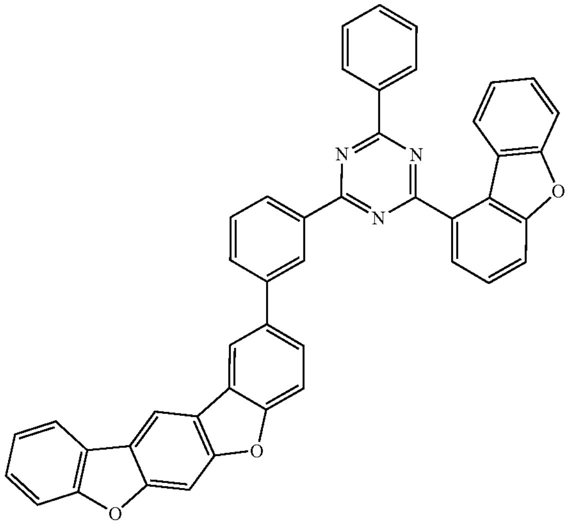

-continued
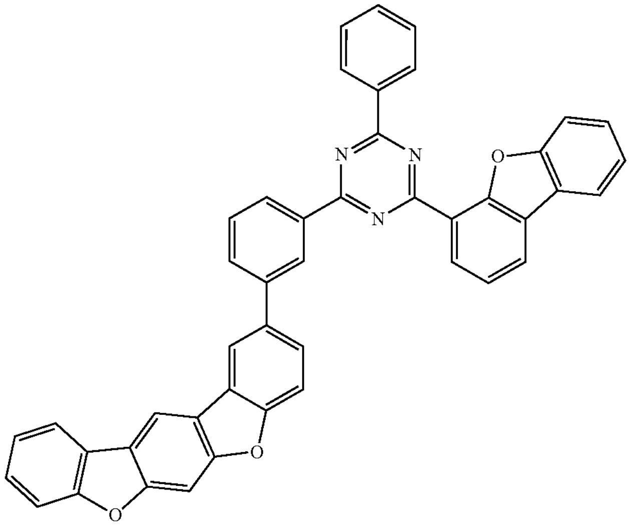
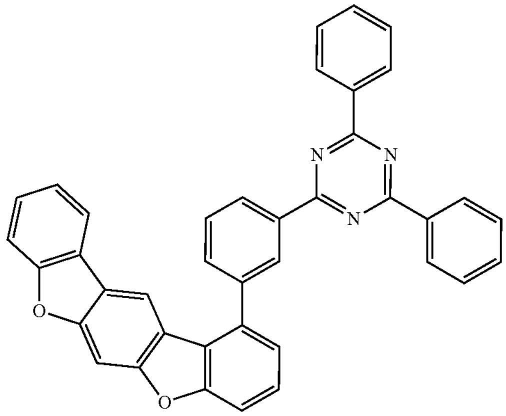
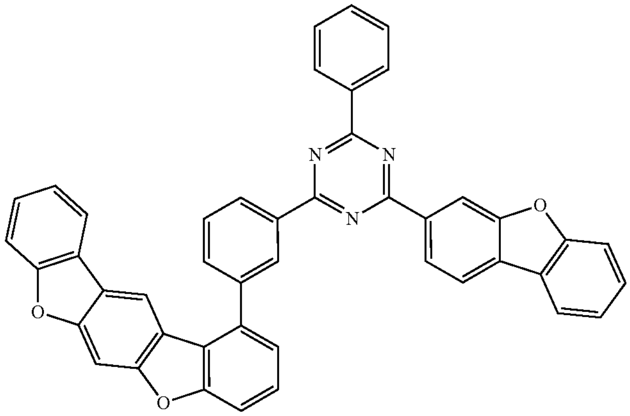
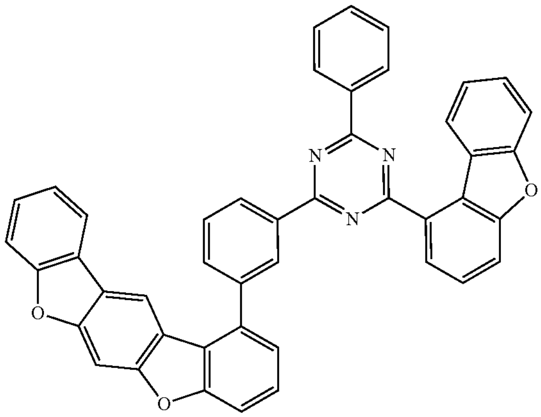

-continued
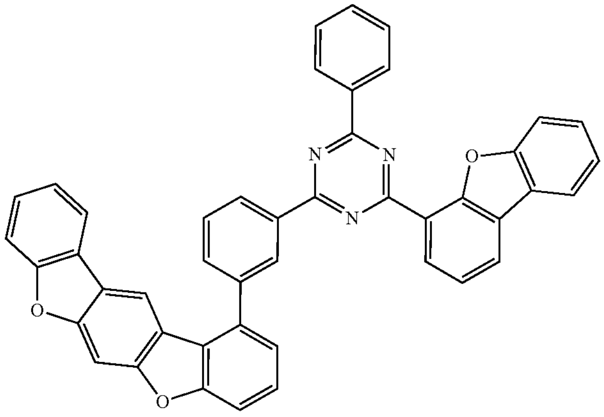
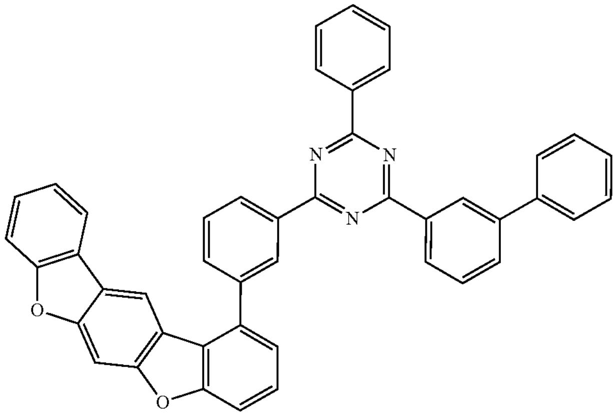
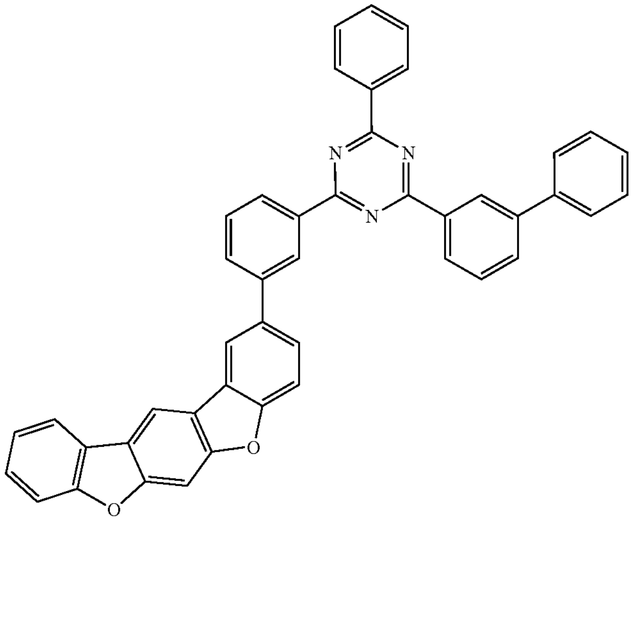
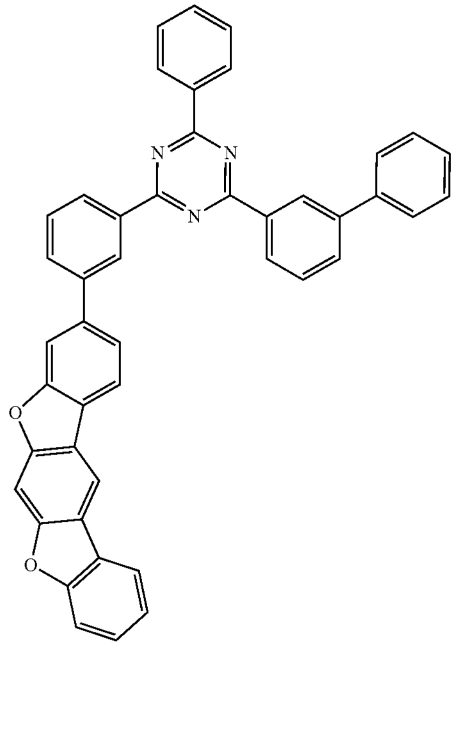

-continued
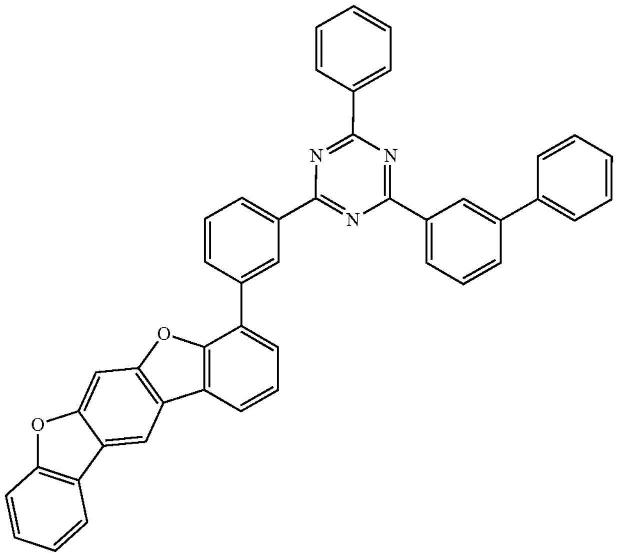
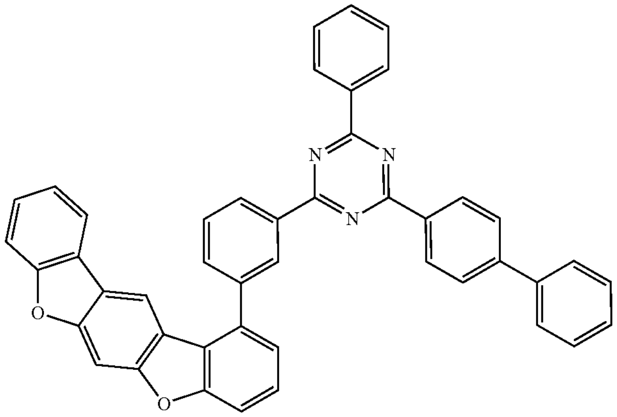
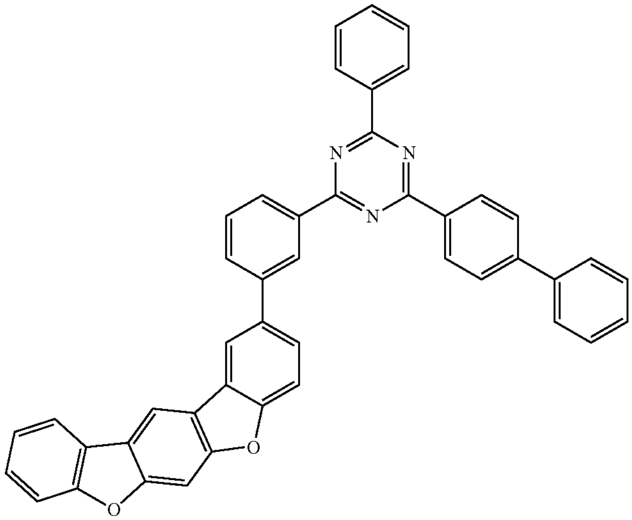
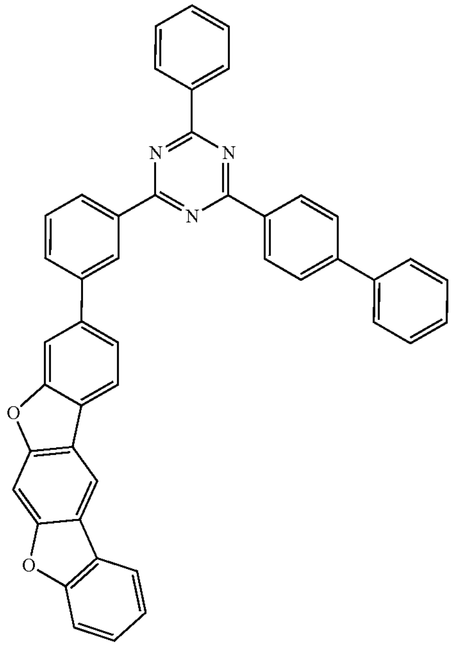

-continued
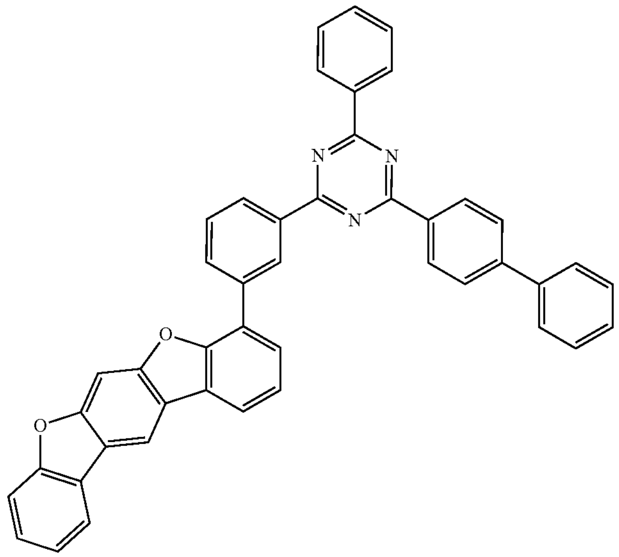
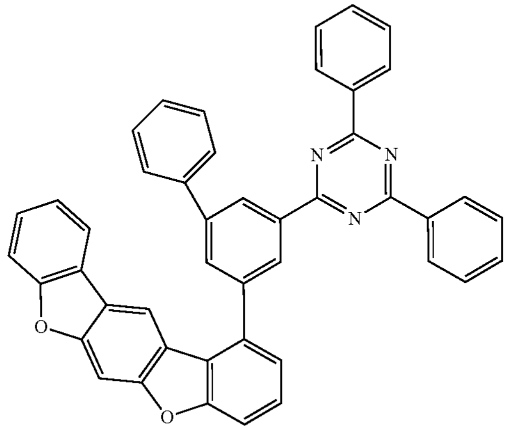
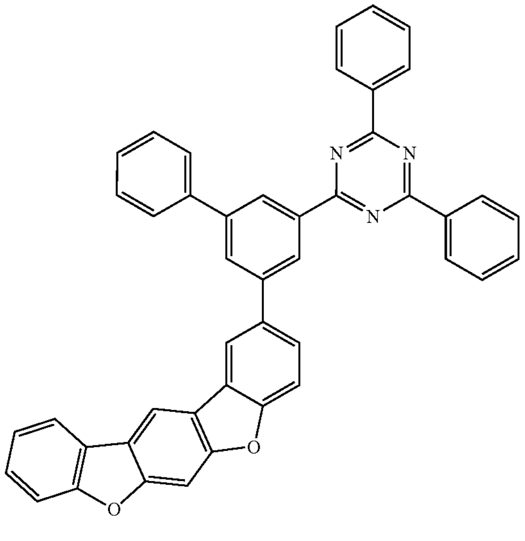
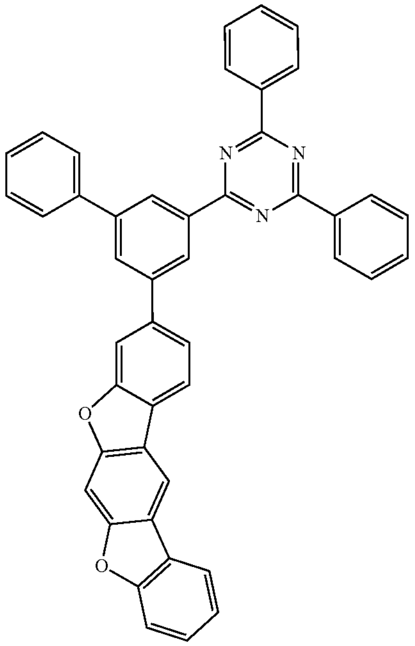

-continued
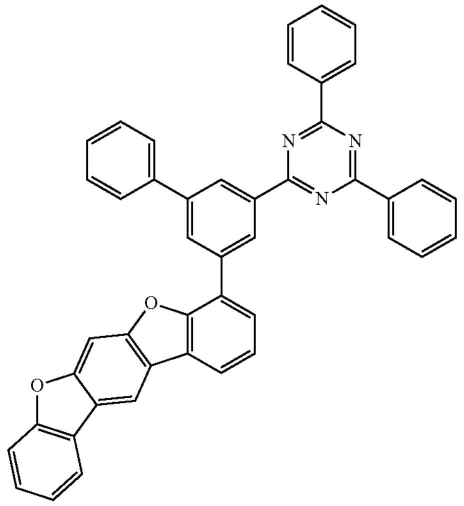
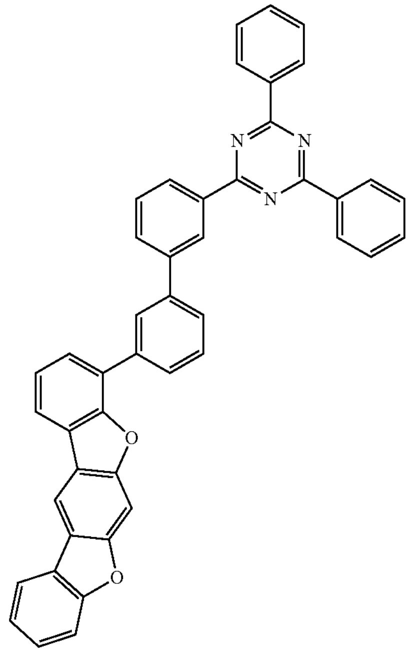
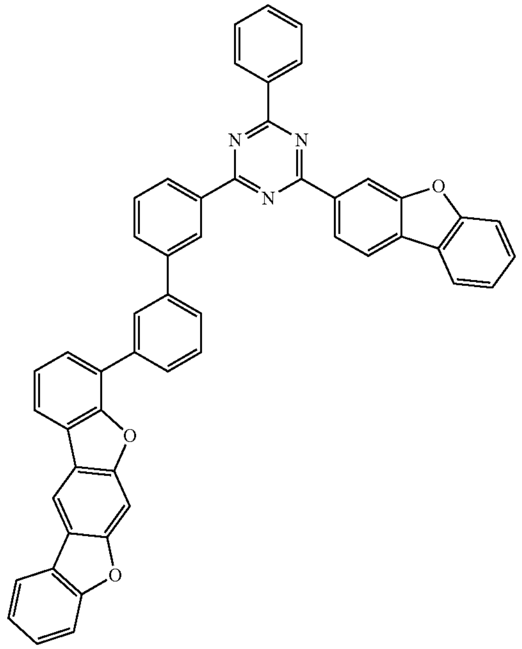
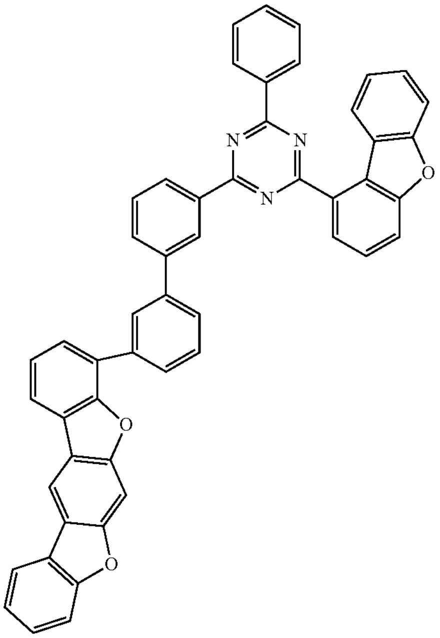

-continued
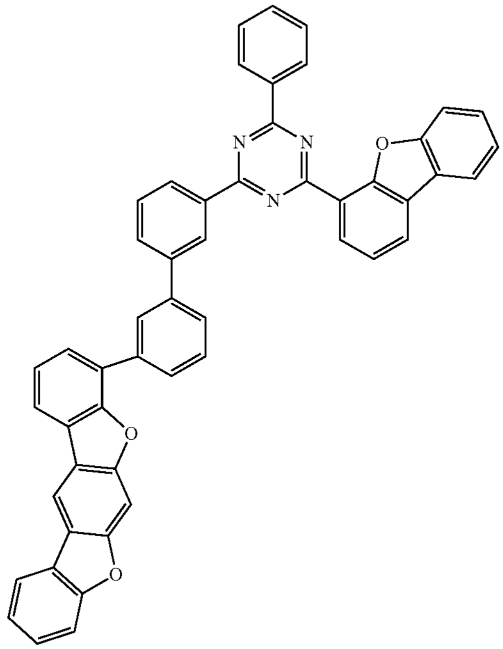
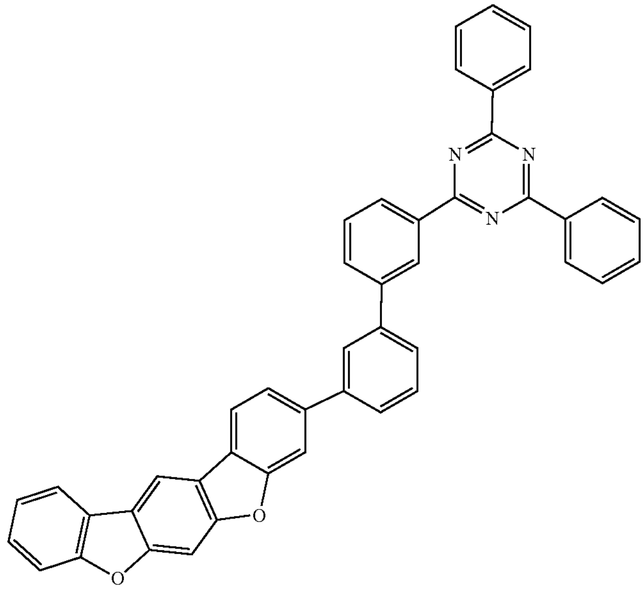

-continued
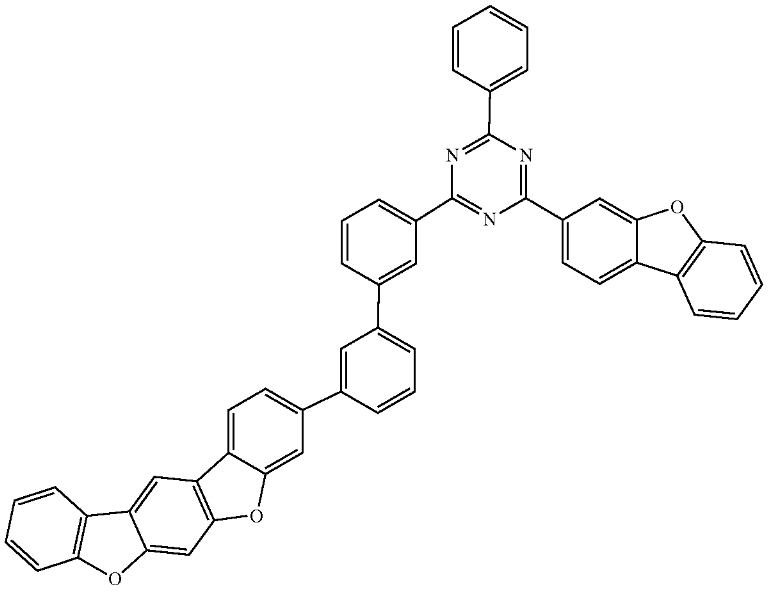
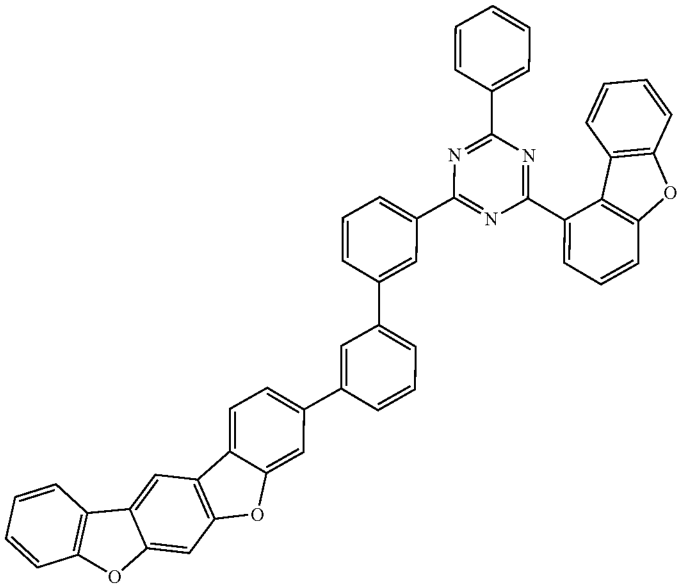

-continued
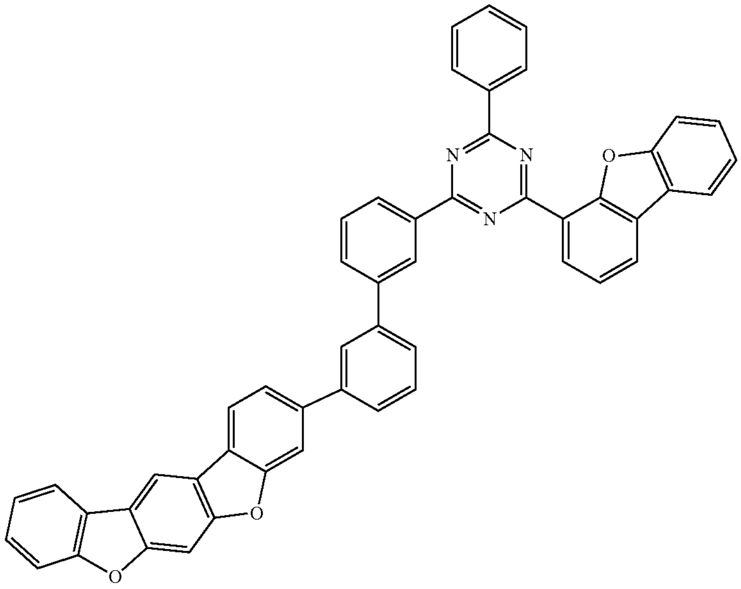
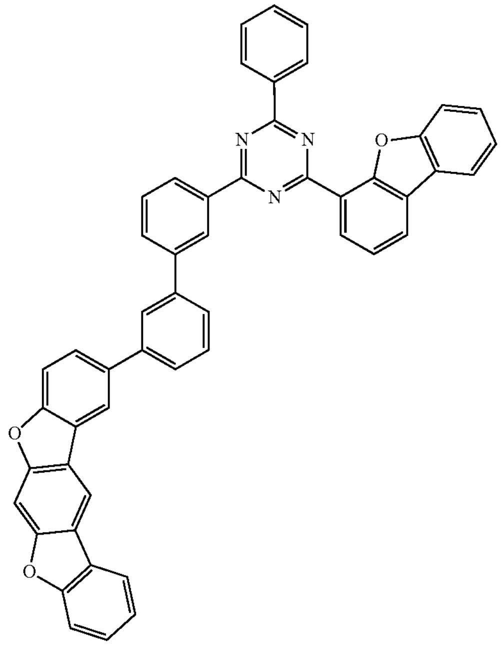
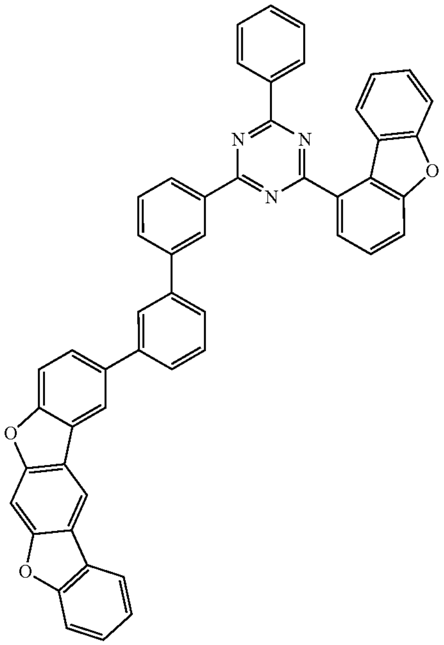

-continued
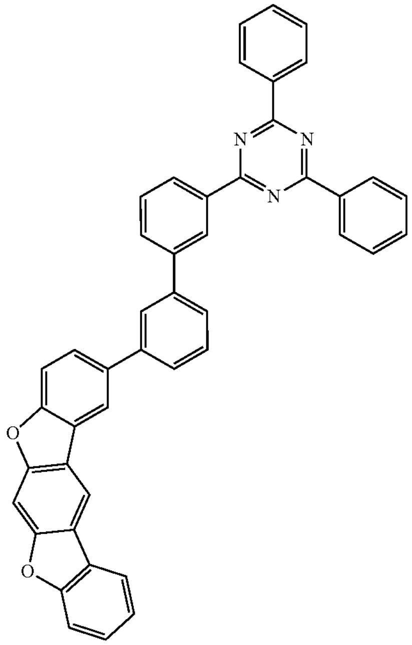
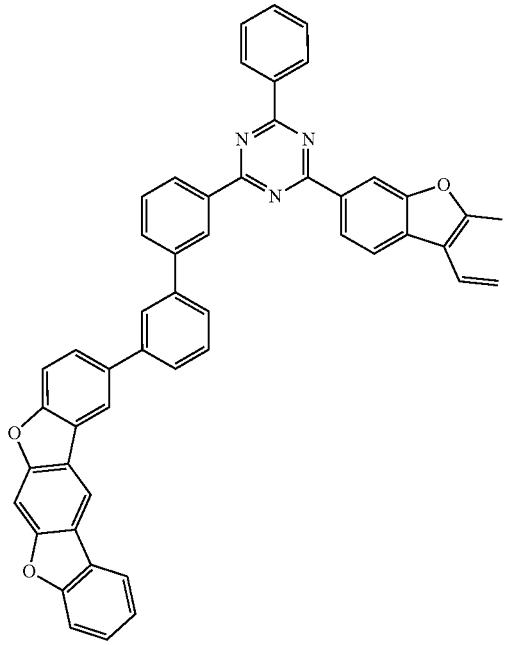
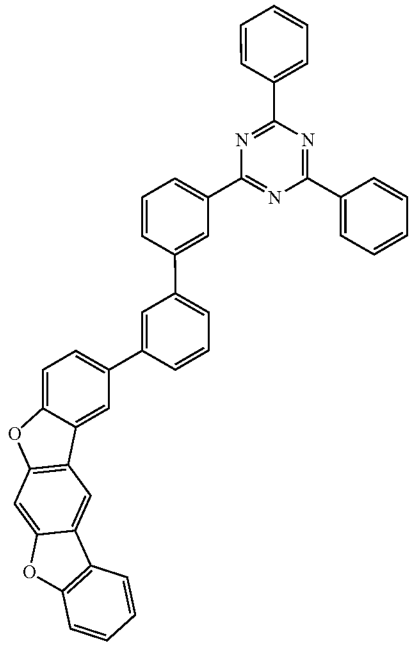
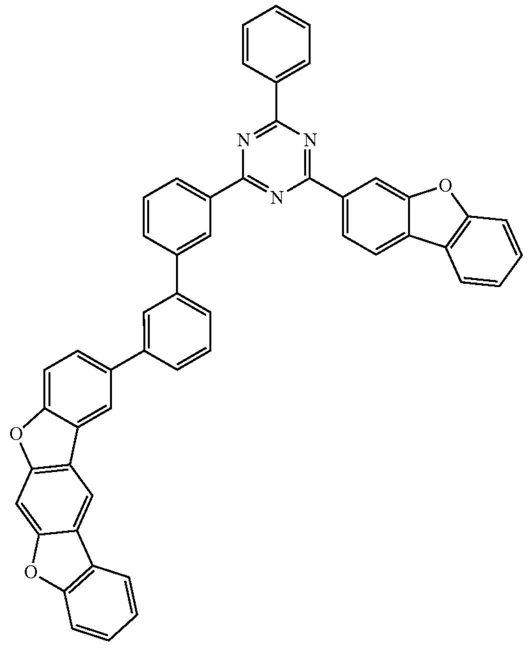

-continued
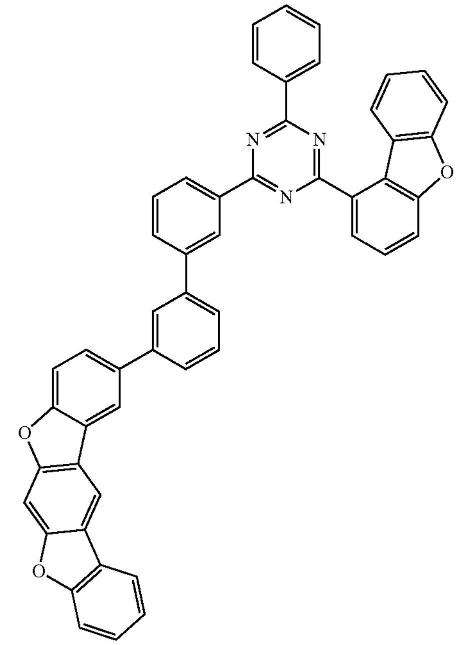
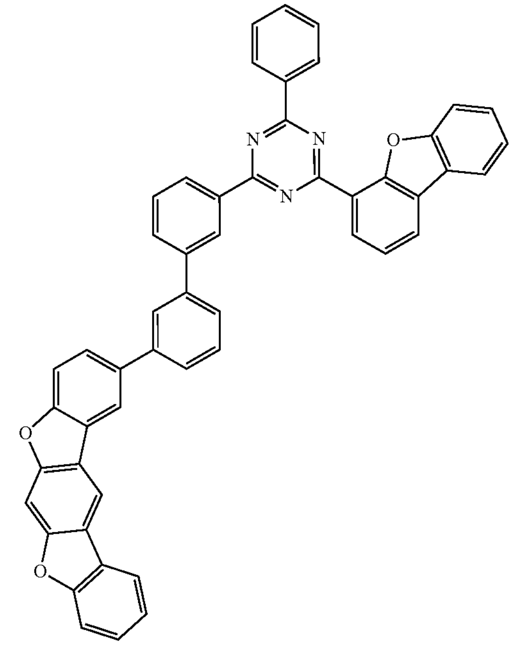
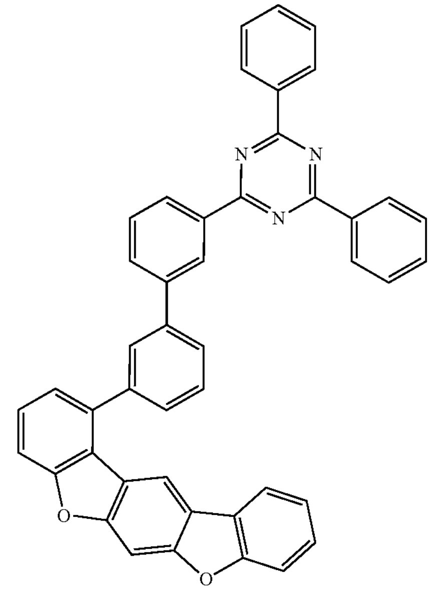
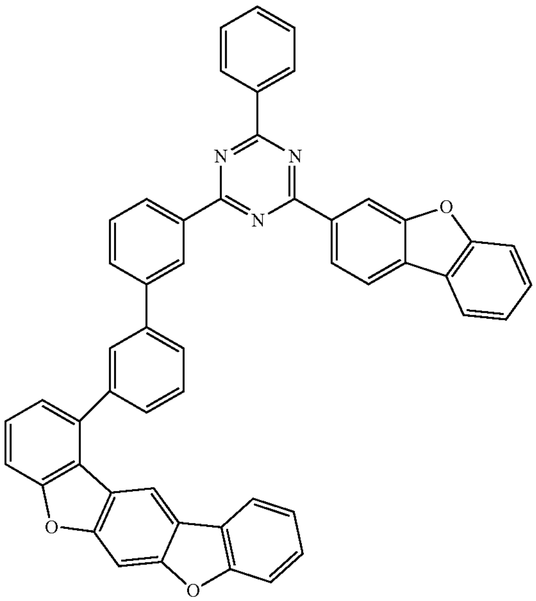

-continued
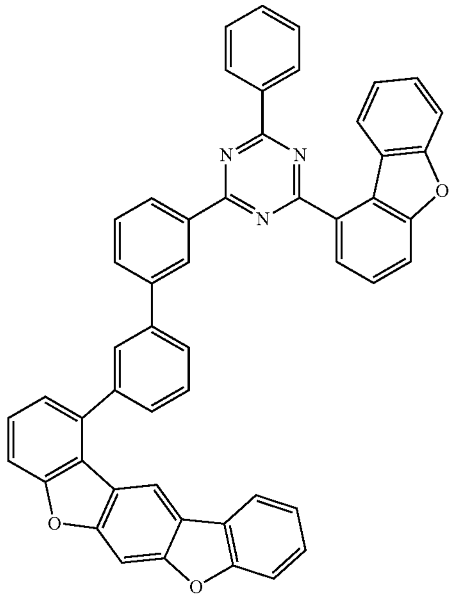
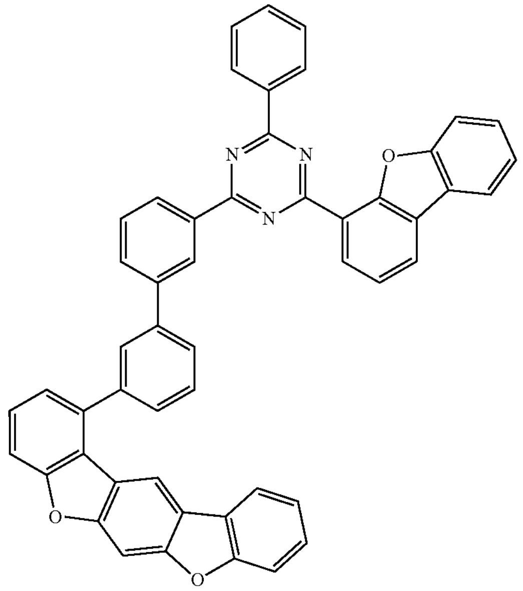
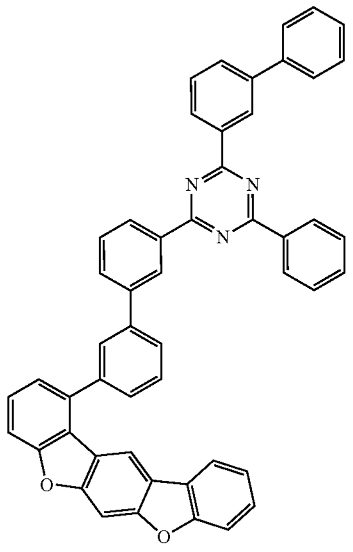
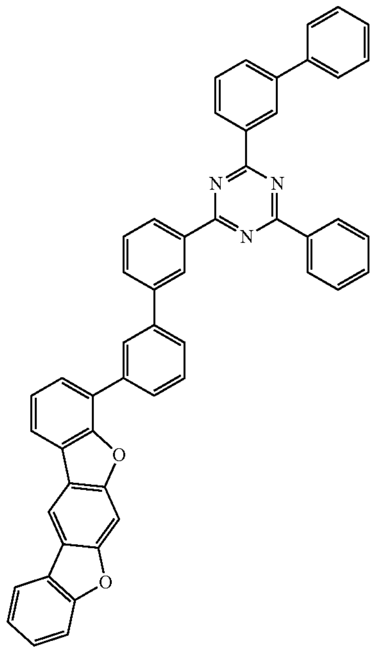

-continued
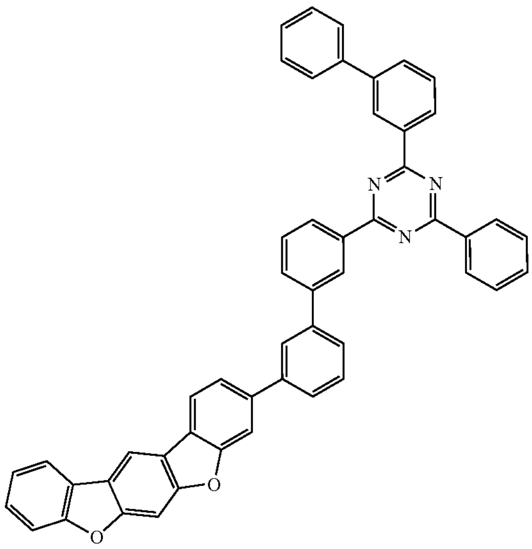
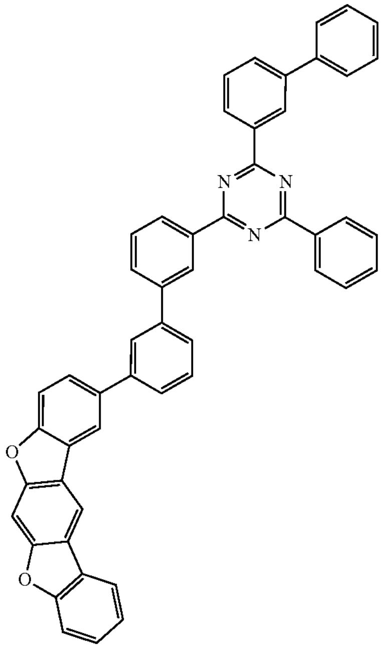
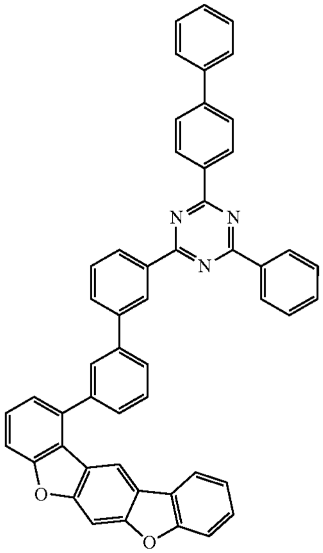
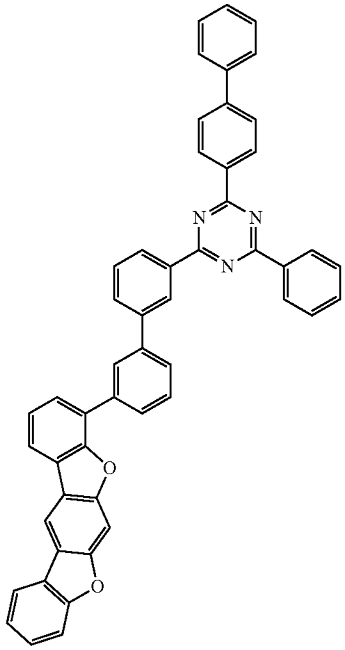

-continued
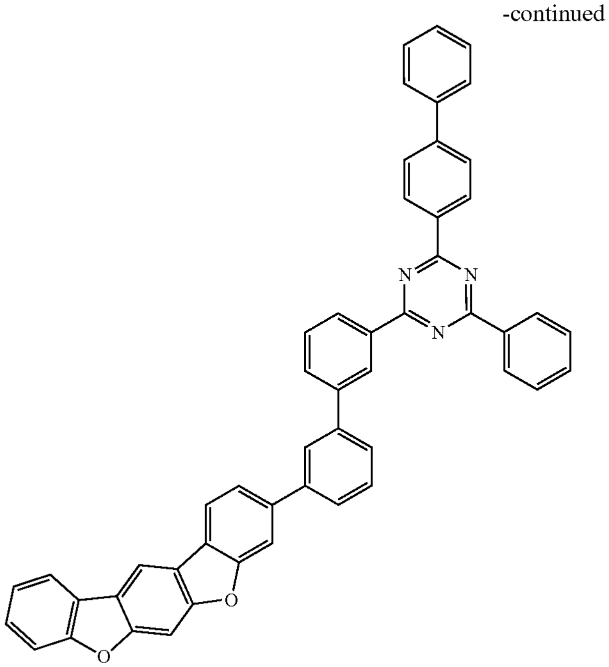
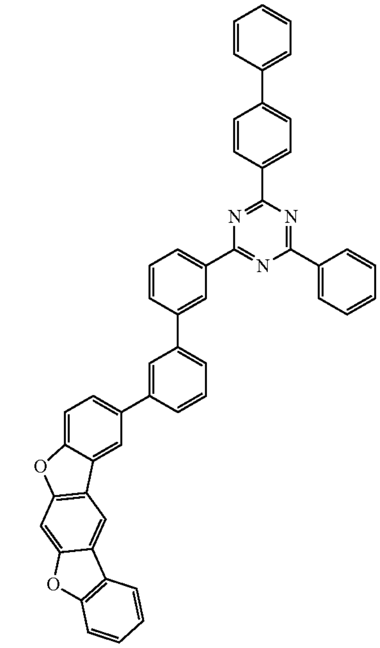
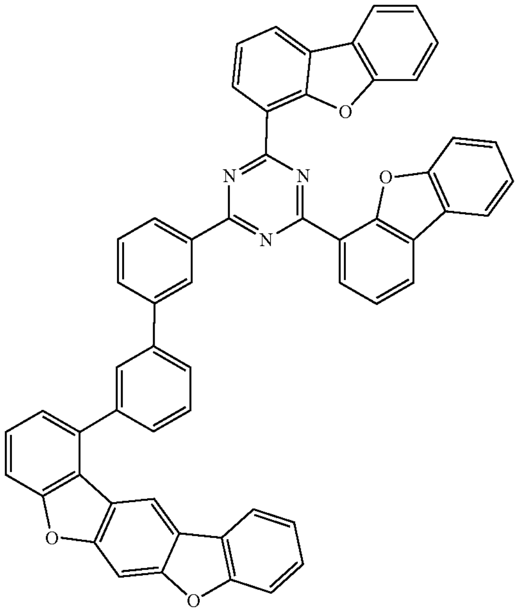
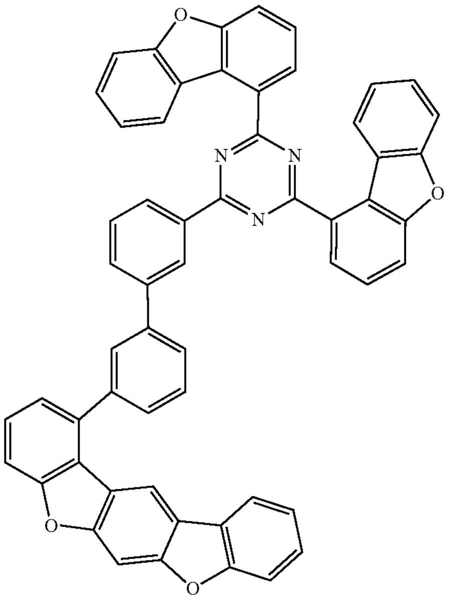

-continued
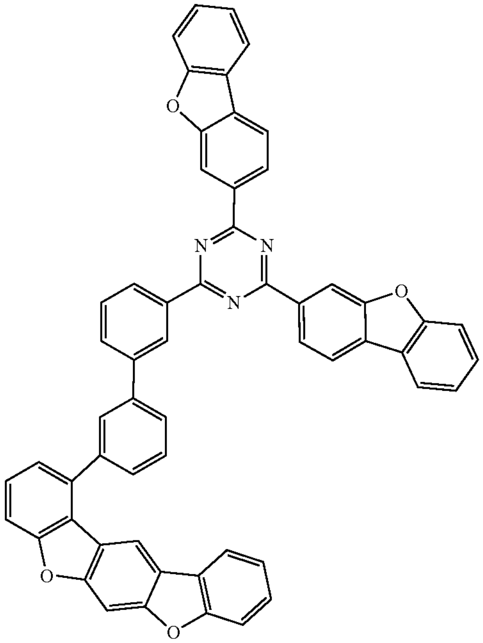
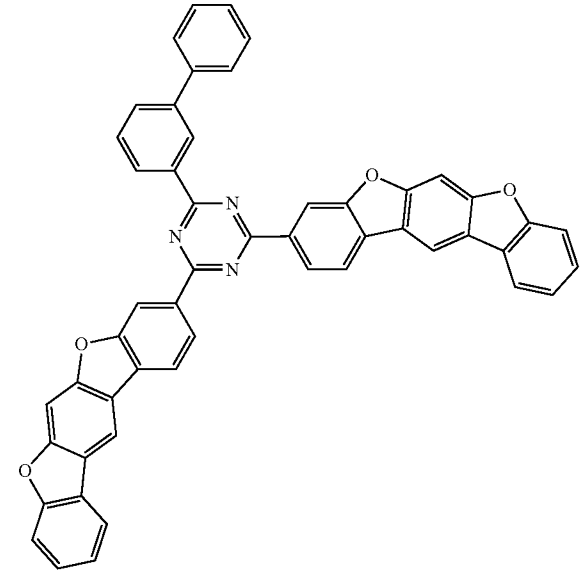
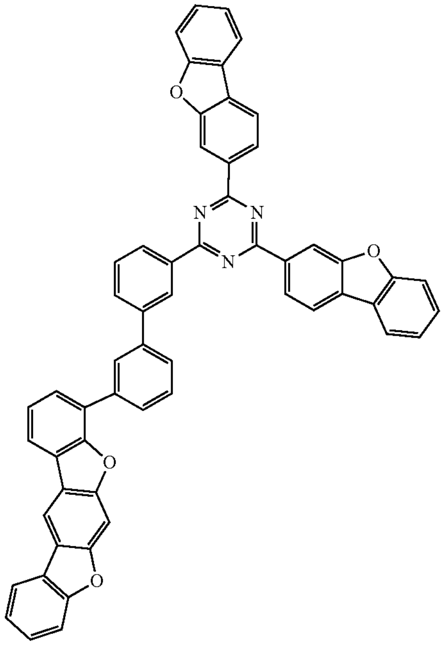
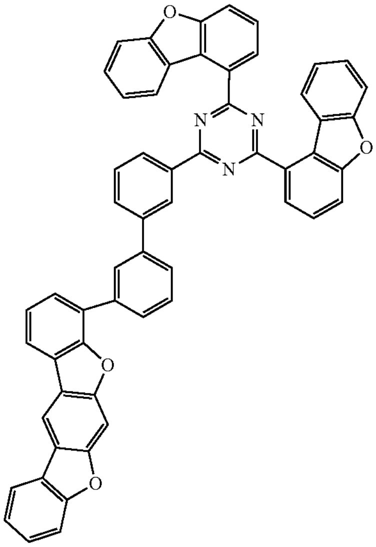

-continued
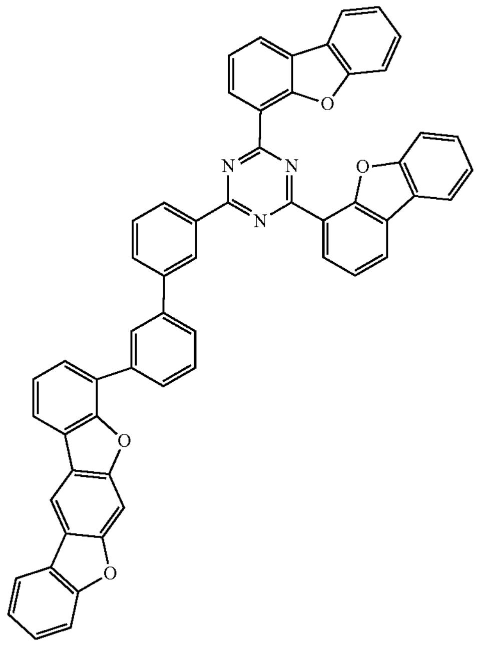
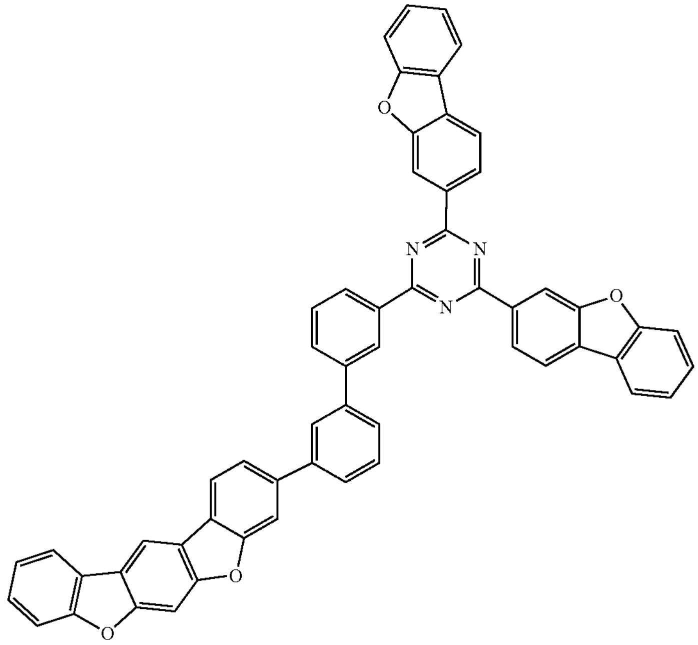

-continued
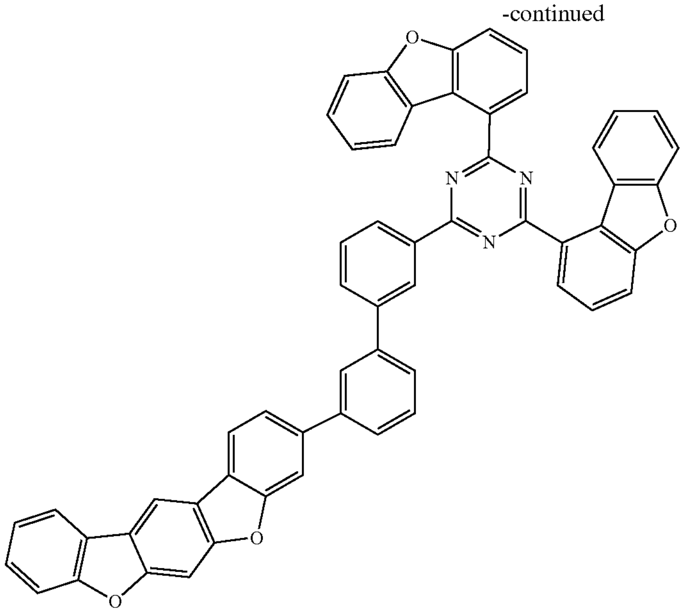
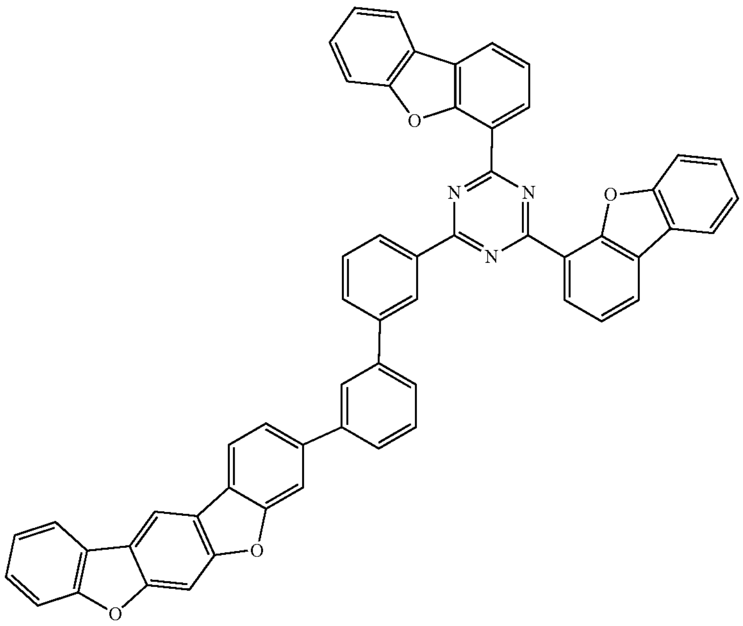

-continued
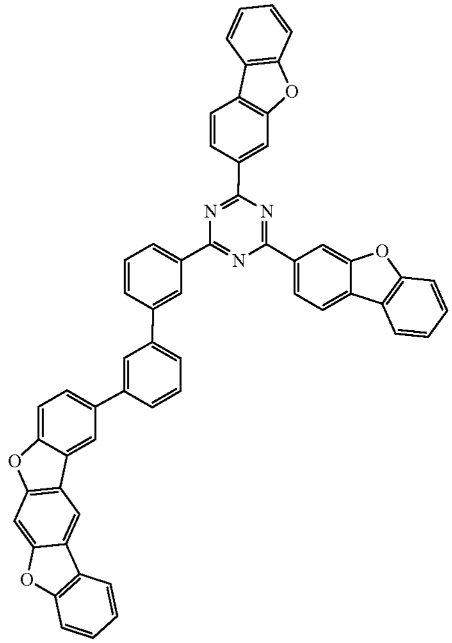 [SMILES: c1cc(-c2cccc(-c3nc(-c4ccc5c(c4)oc4ccccc45)nc(-c4ccc5c(c4)oc4ccccc45)n3)c2)cc(-c2ccc3oc4cc5oc6ccccc6c5cc4c3c2)c1]
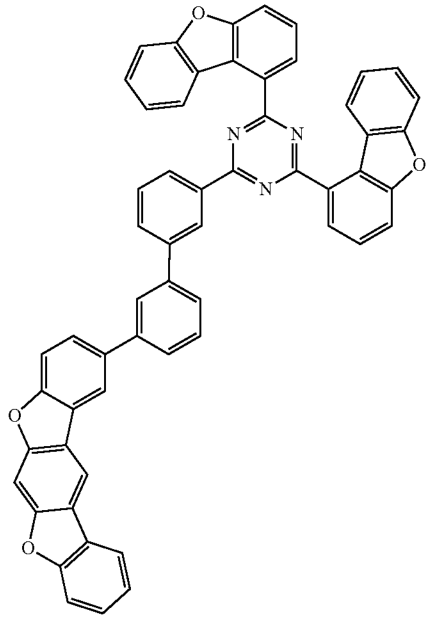
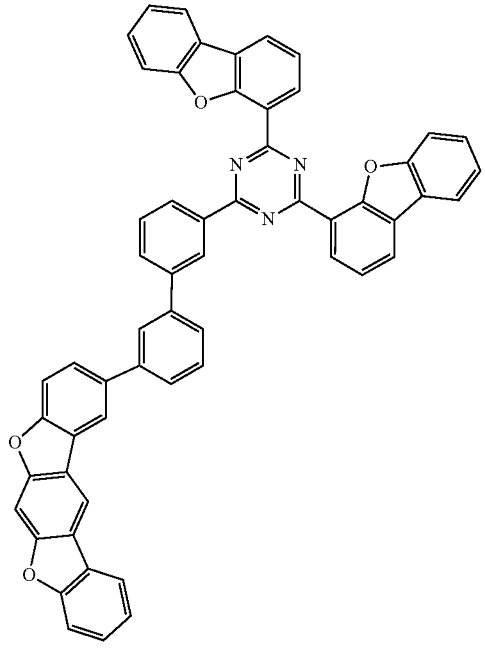

-continued
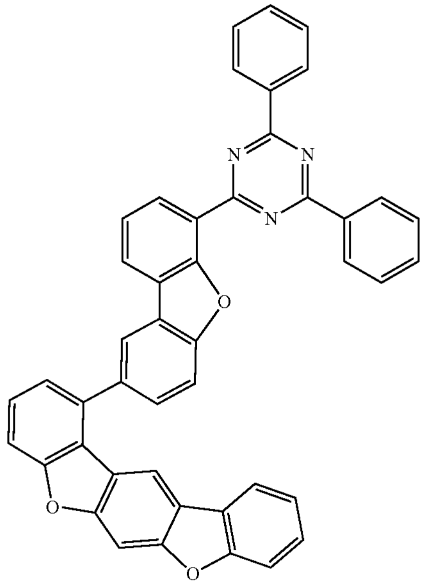
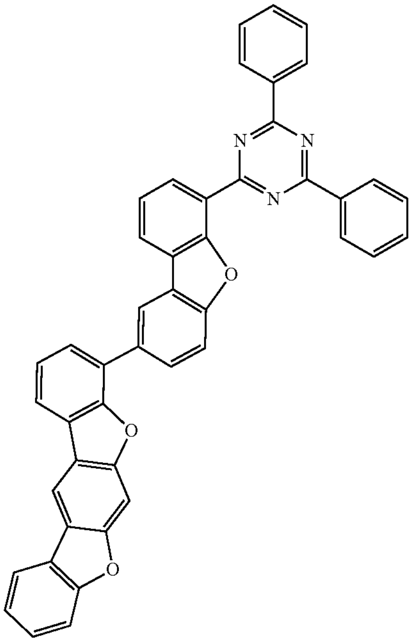
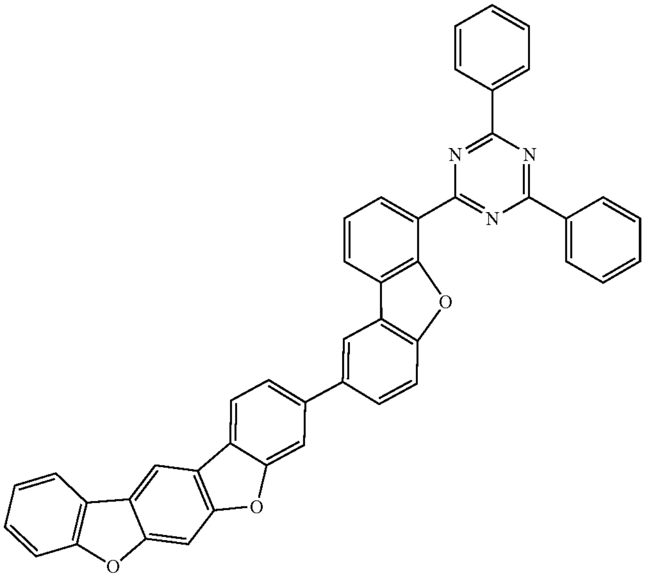

-continued
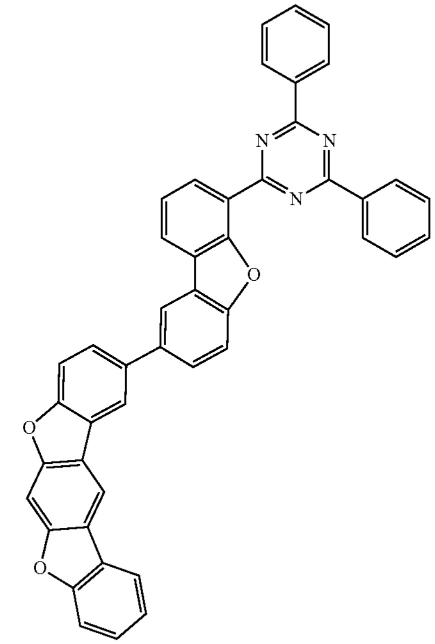
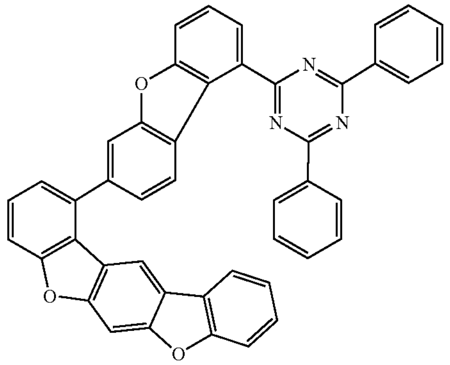
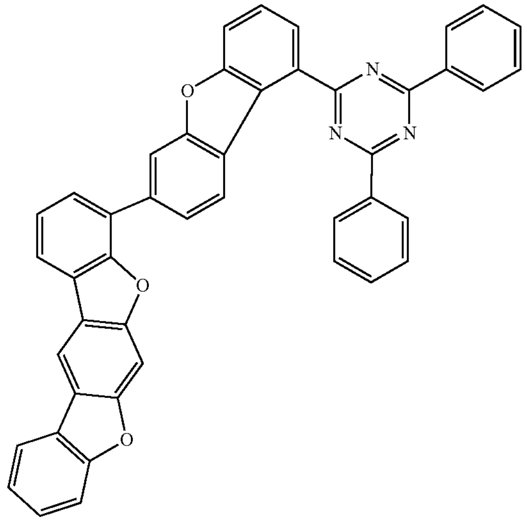
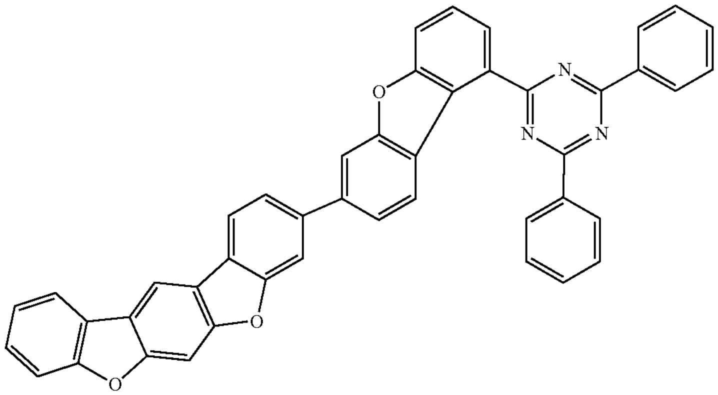

-continued
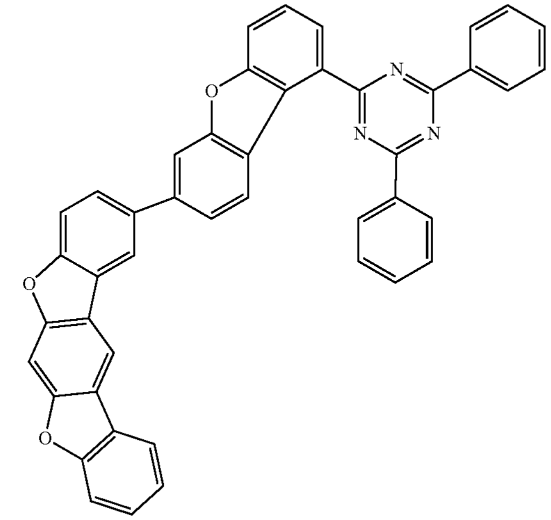
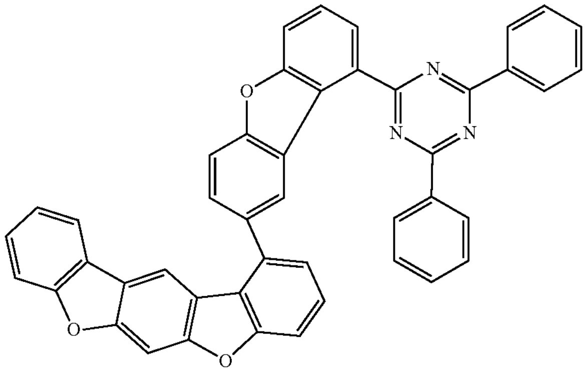
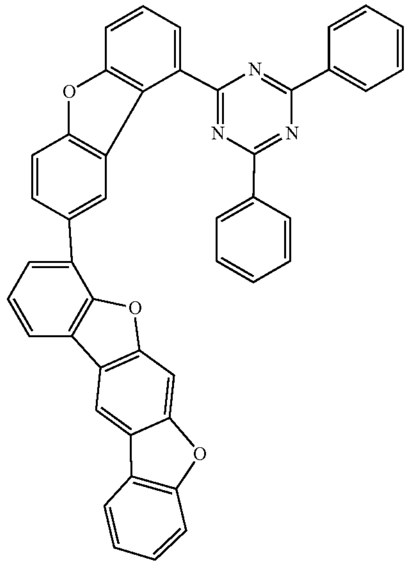
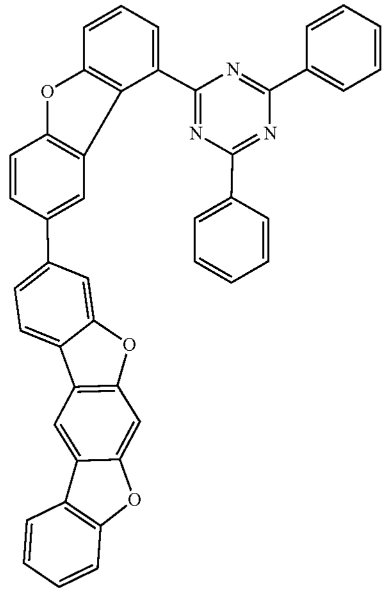
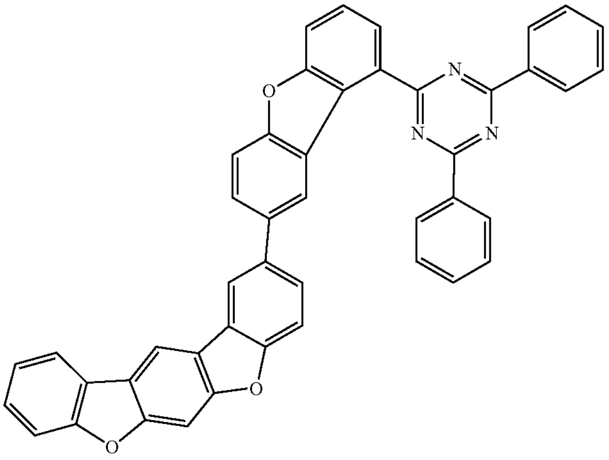

-continued
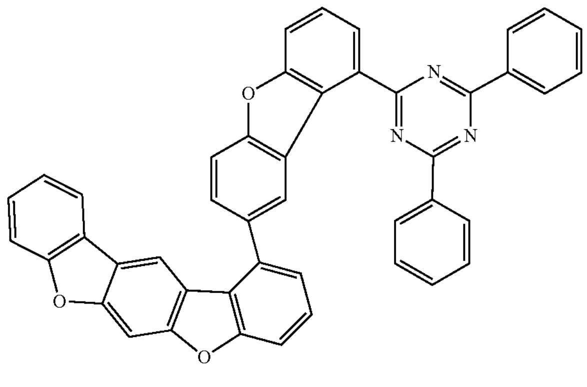
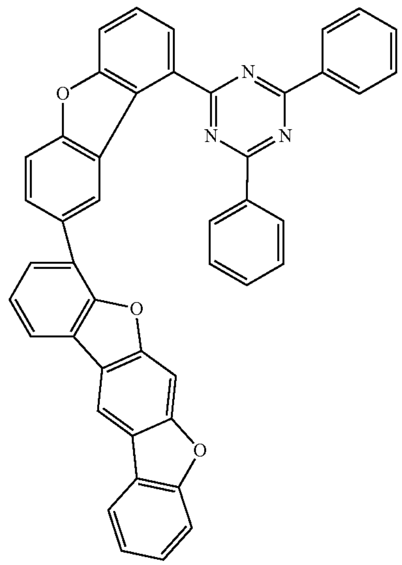
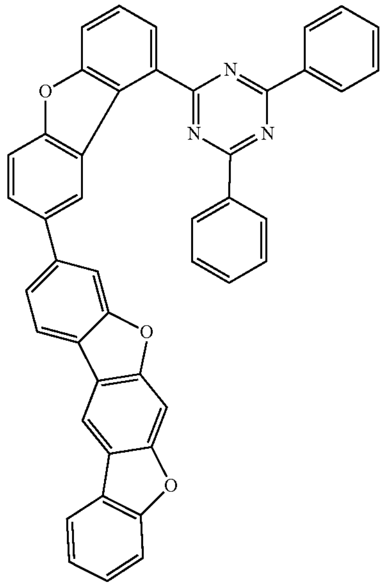
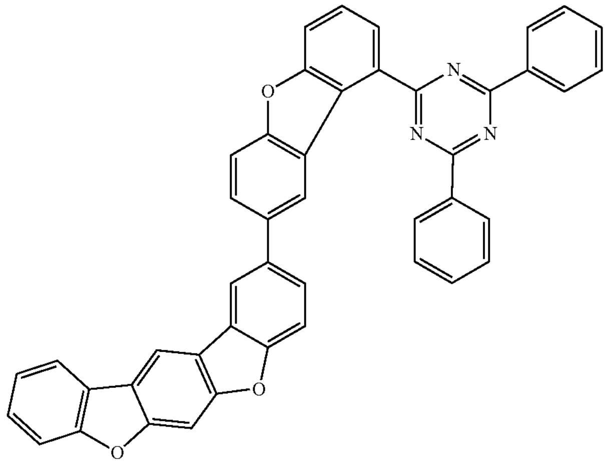
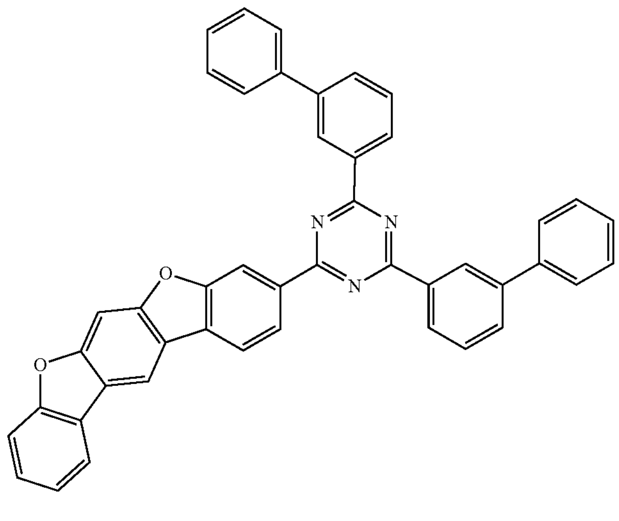
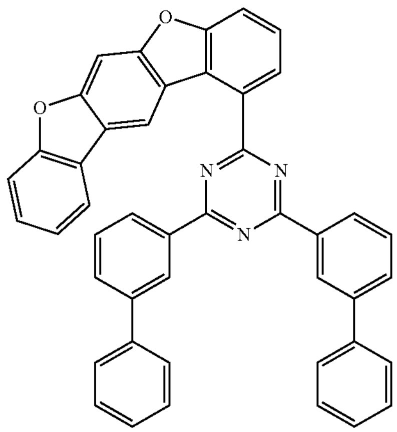

-continued
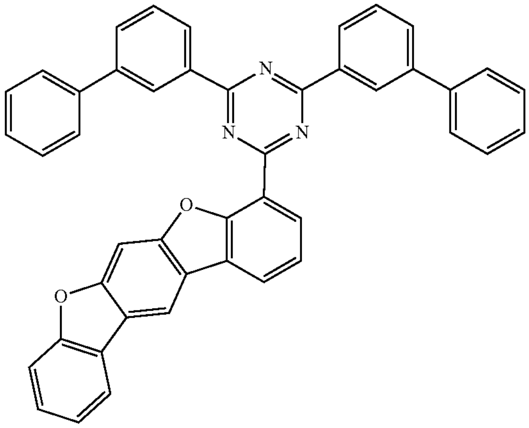
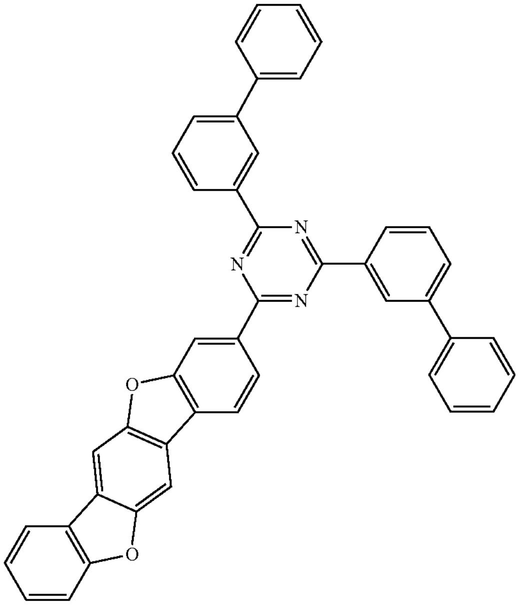
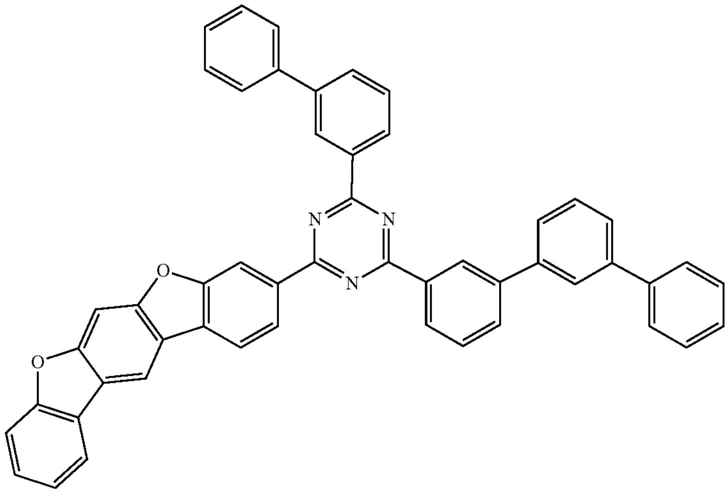
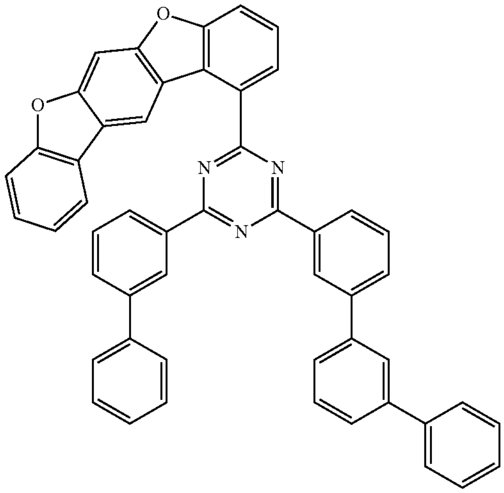
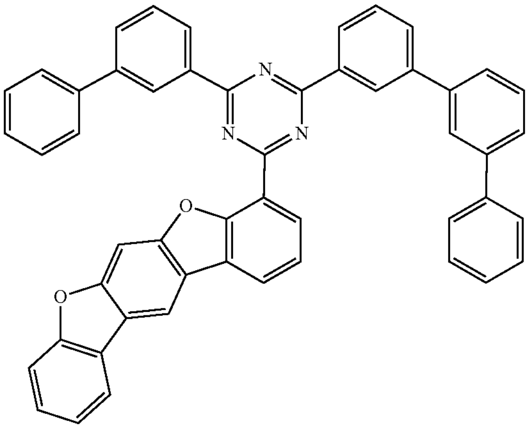

-continued
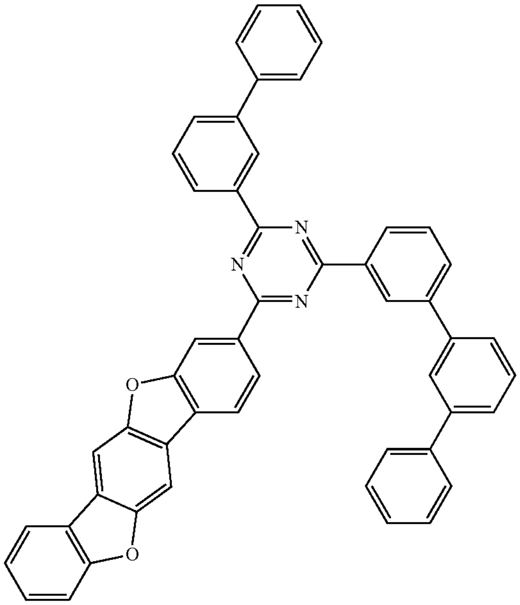
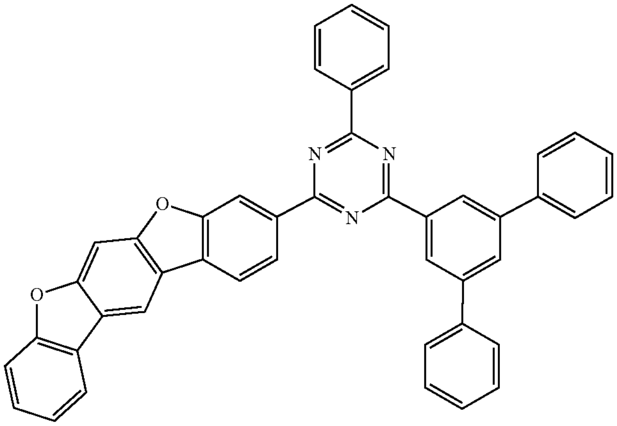
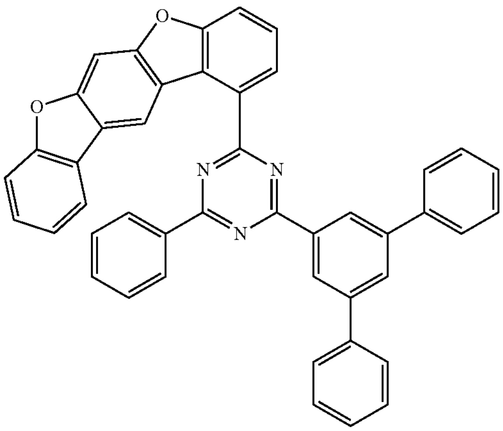
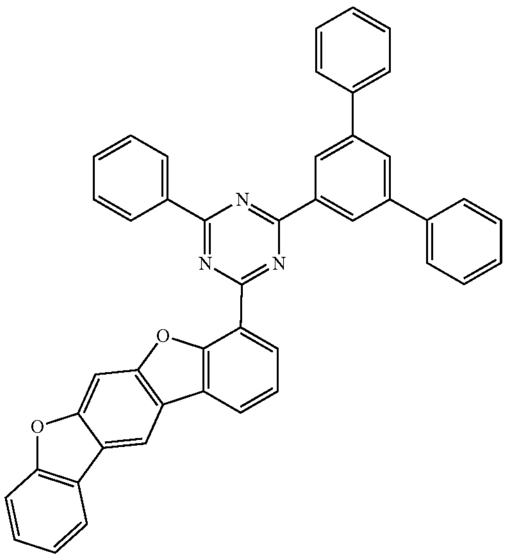

-continued
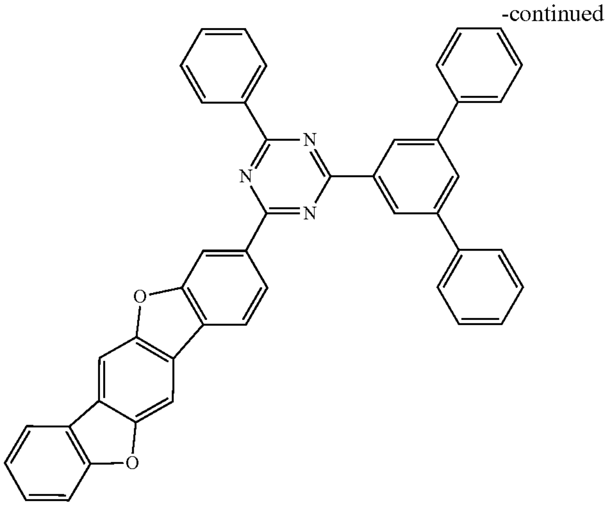
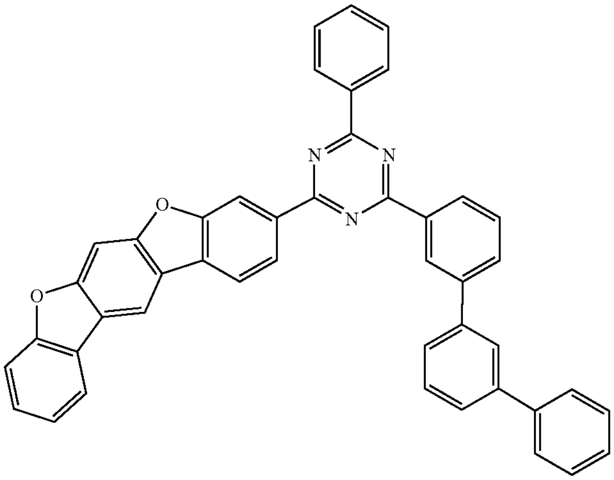
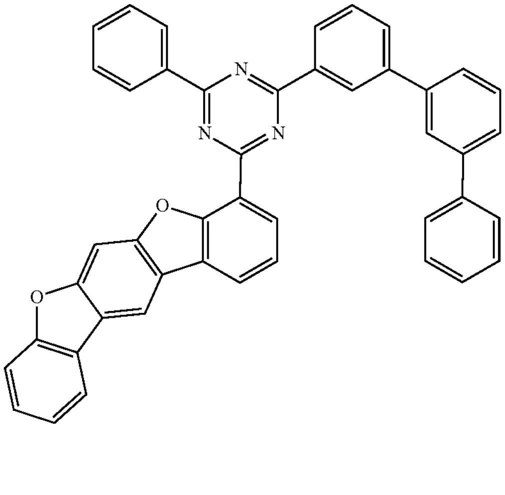
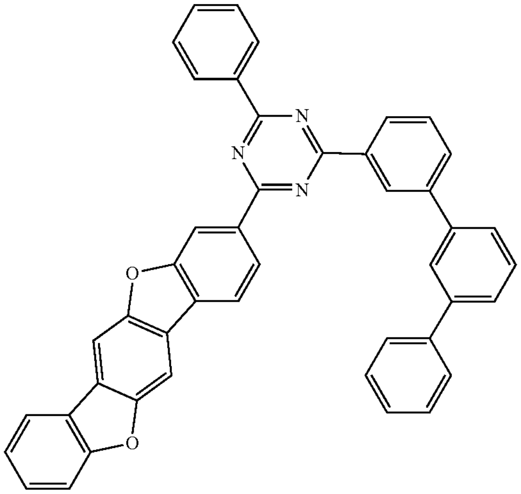

-continued
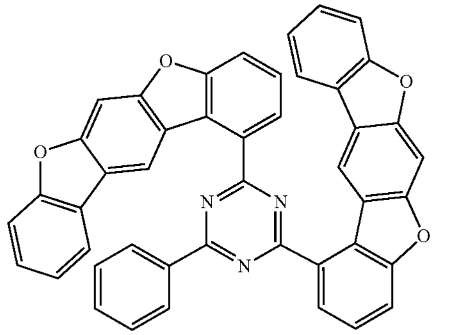
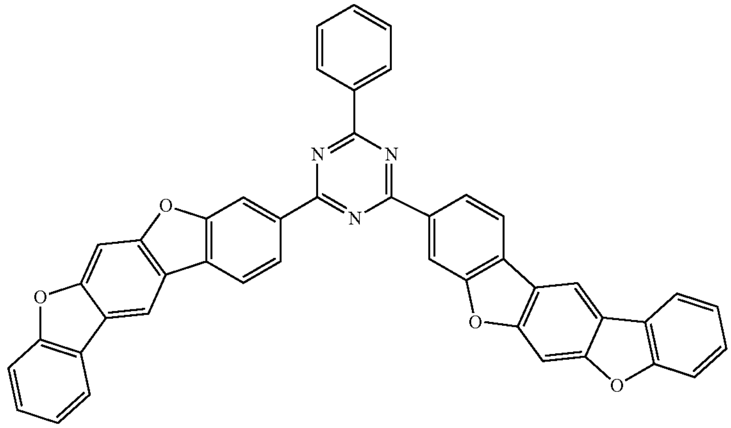
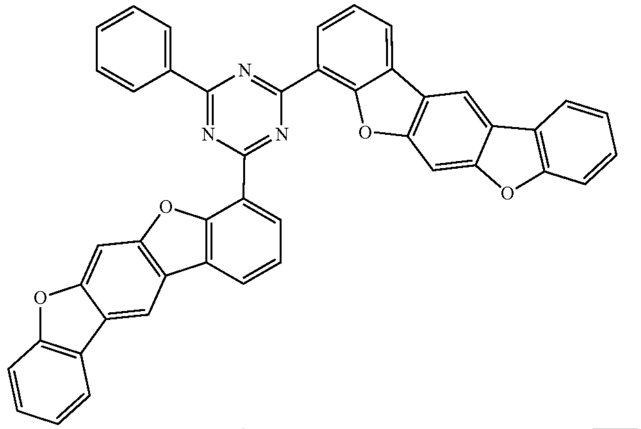
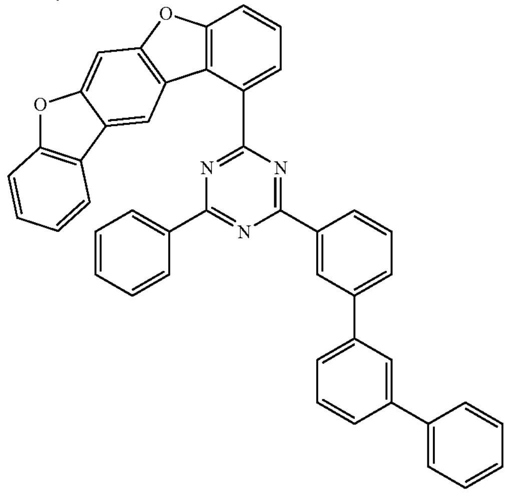
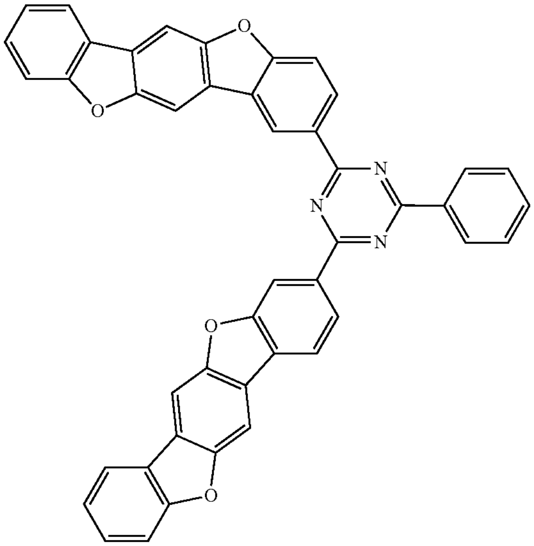

-continued
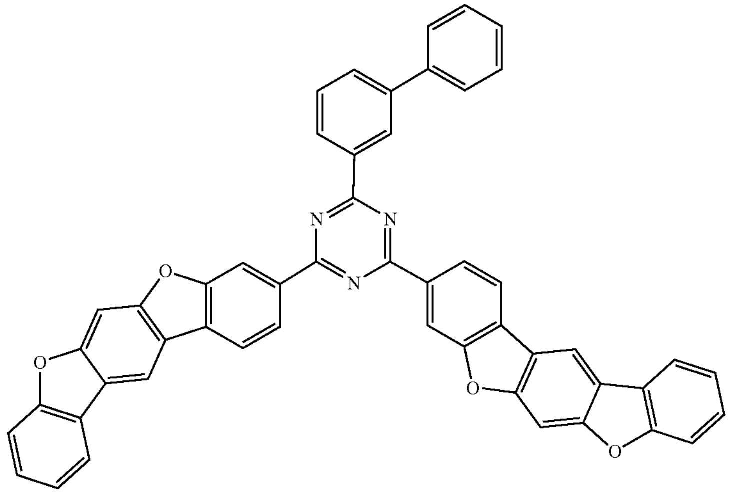
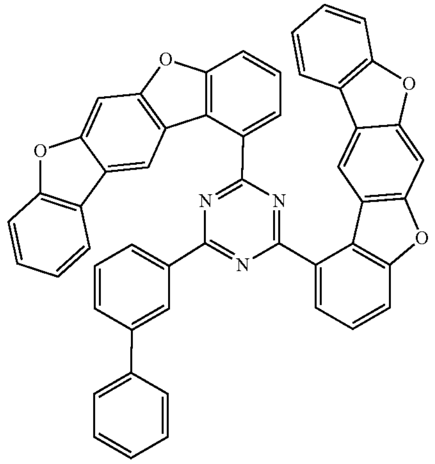
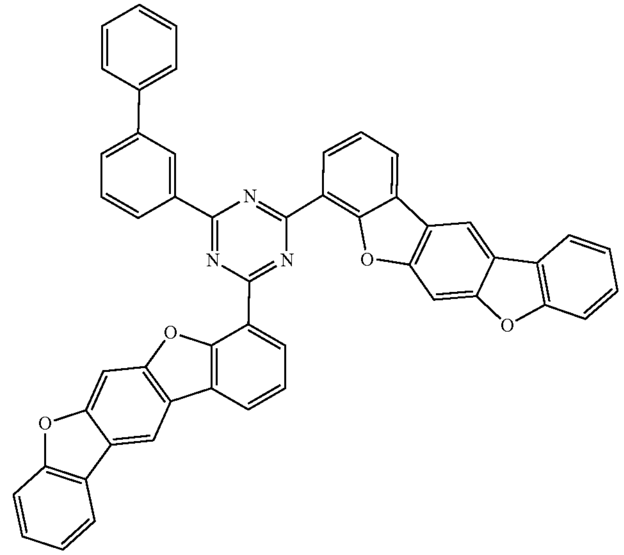
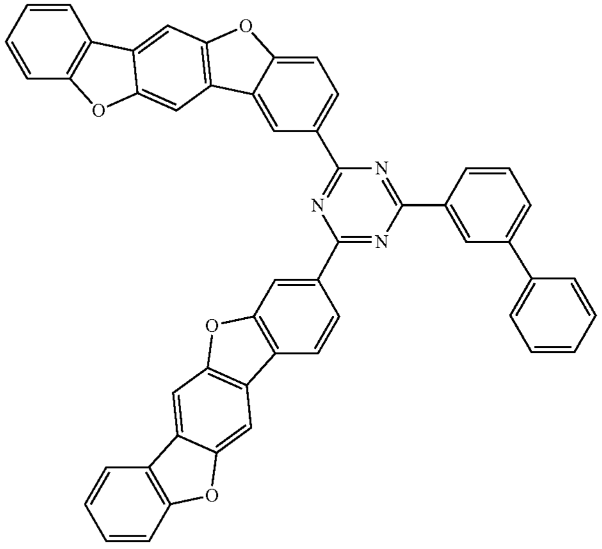
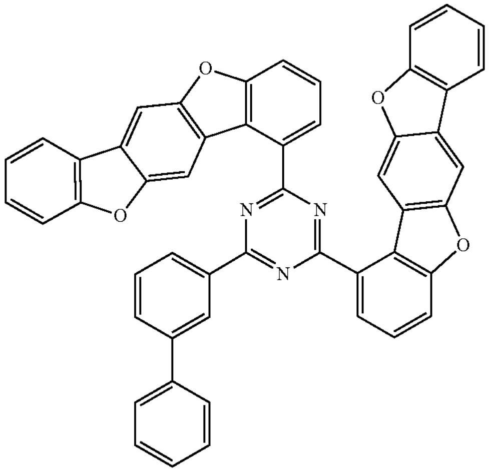

-continued
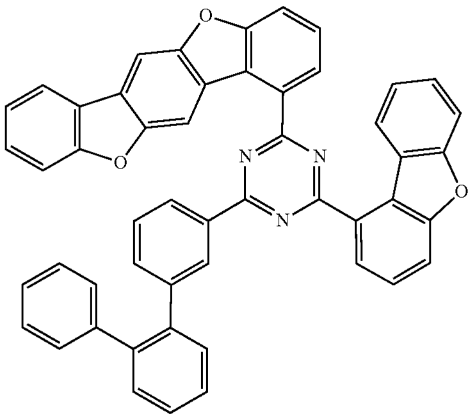
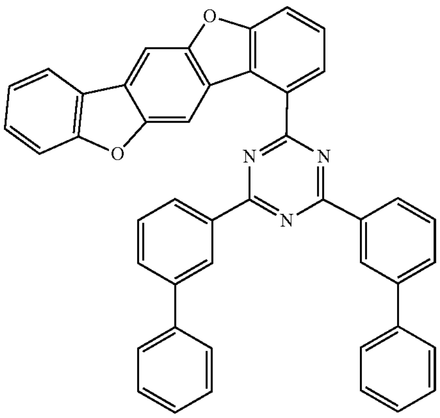
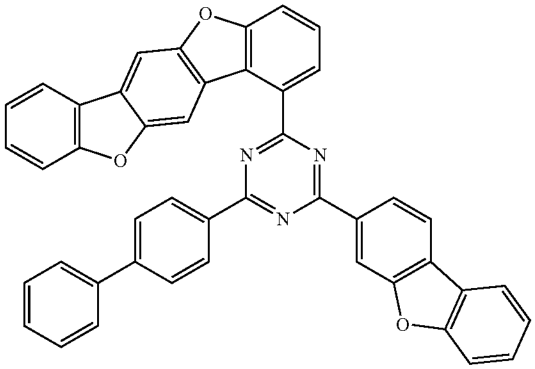
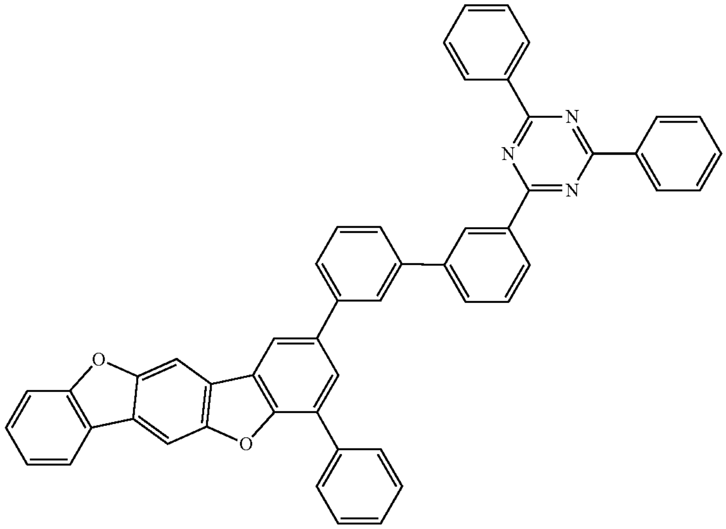

-continued
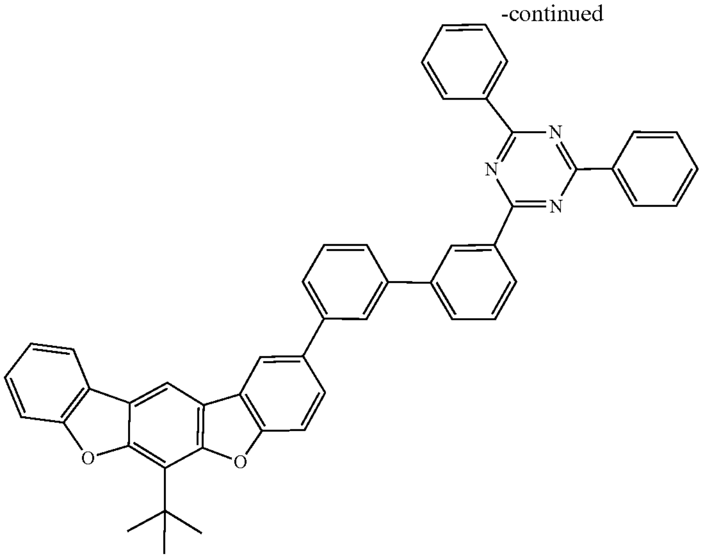
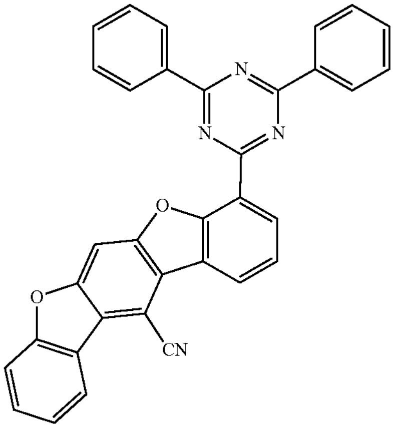
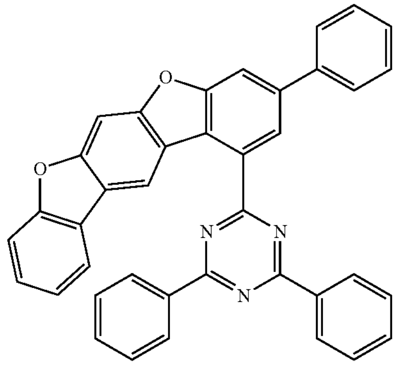
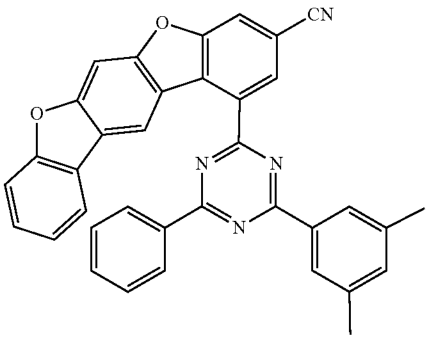
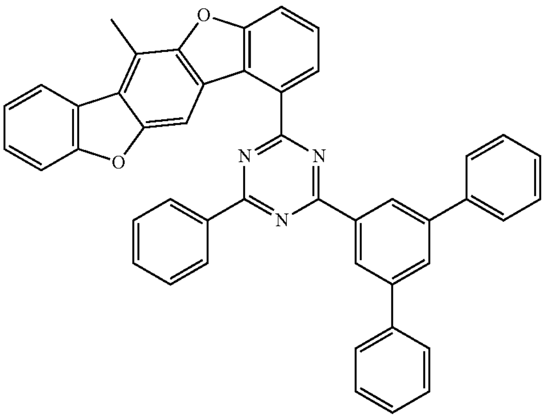

-continued
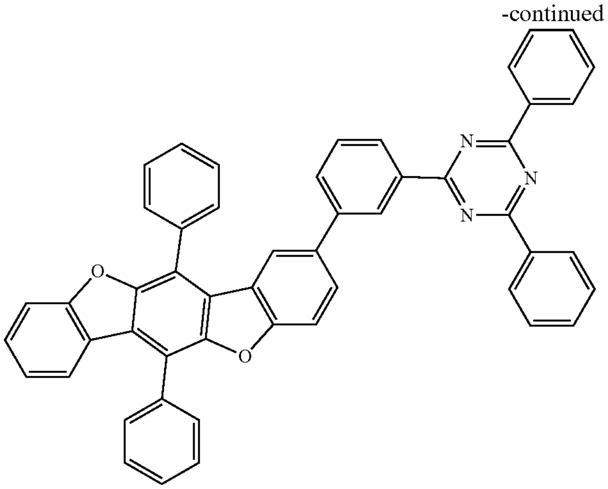
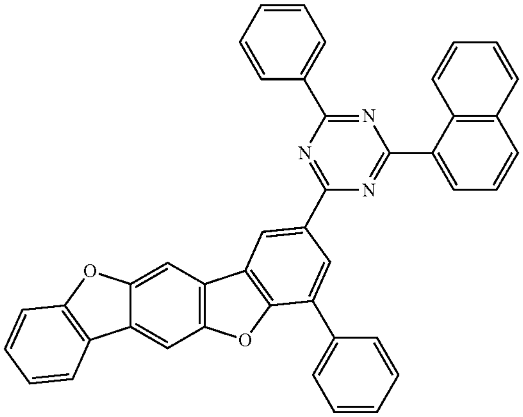
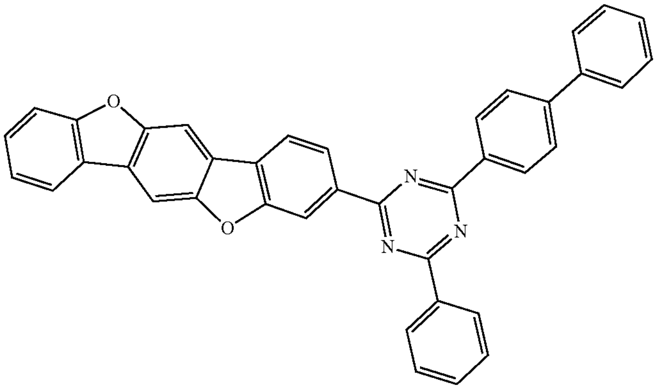
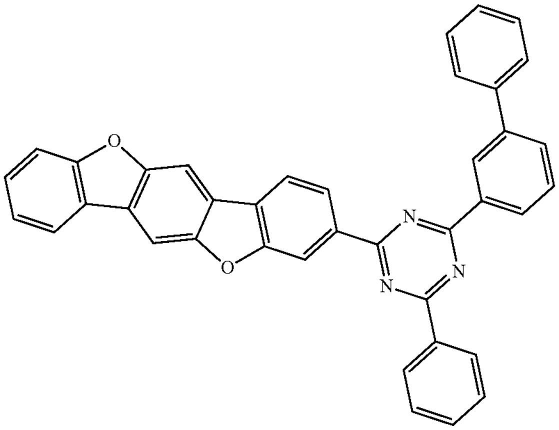

-continued
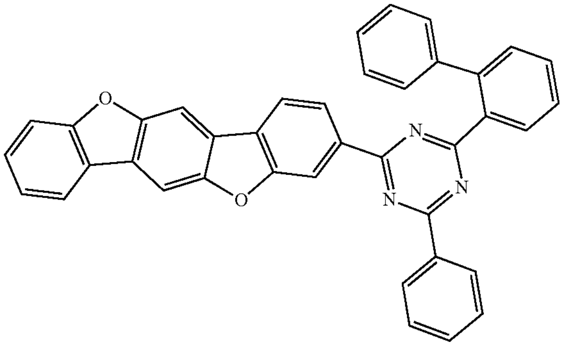
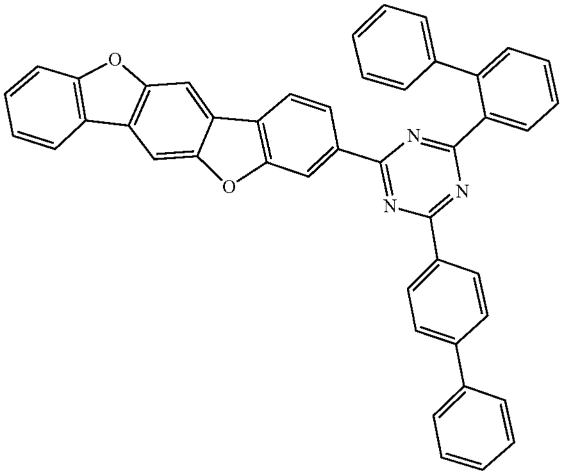
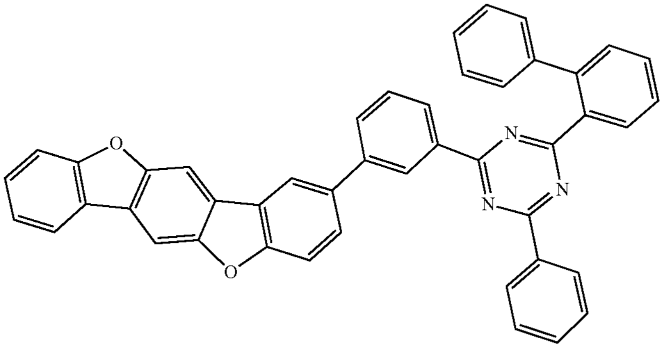
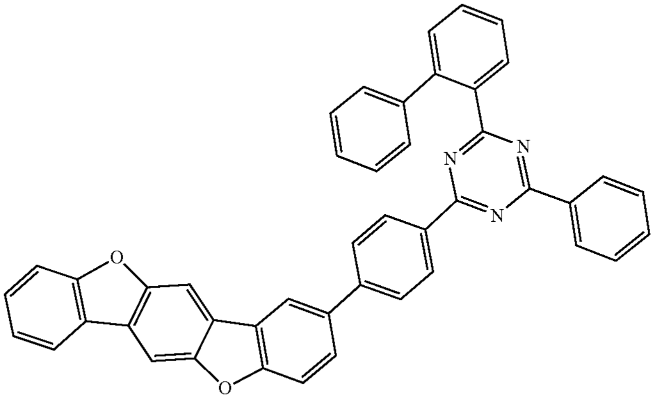

-continued
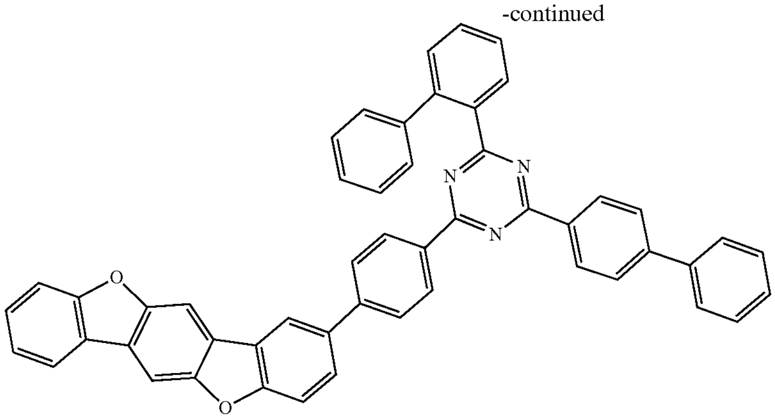
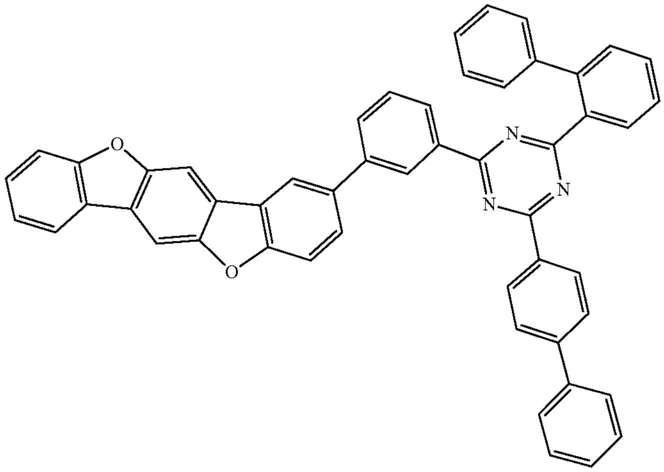
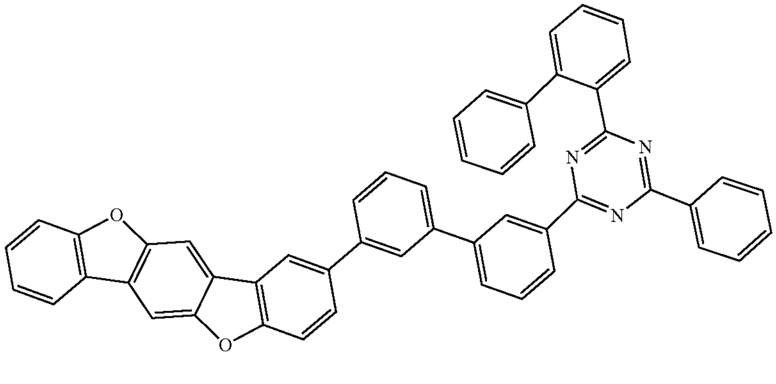
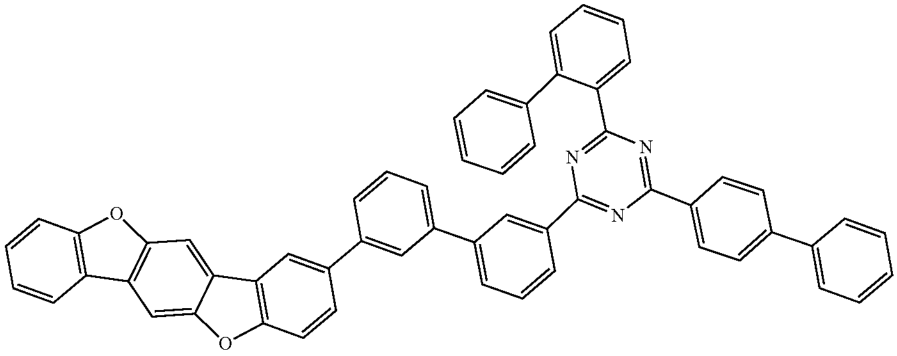

-continued
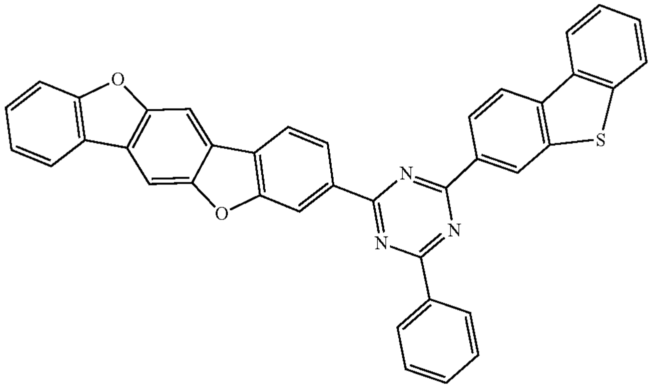
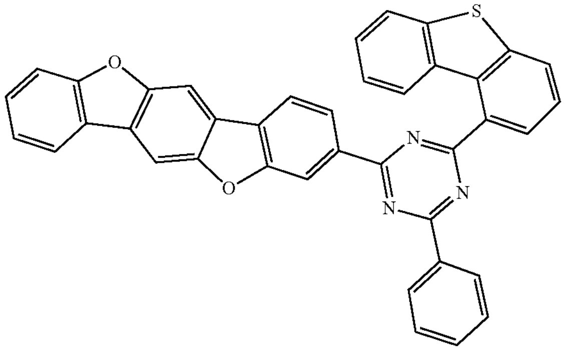
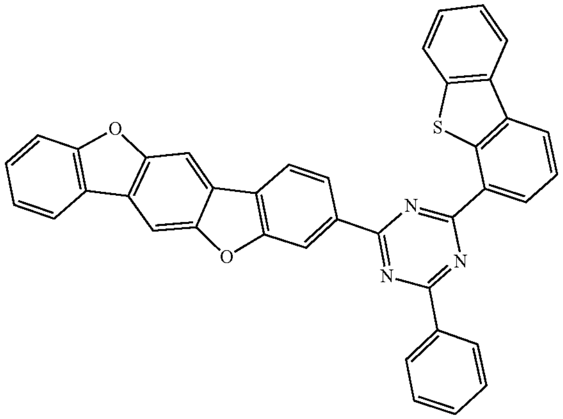
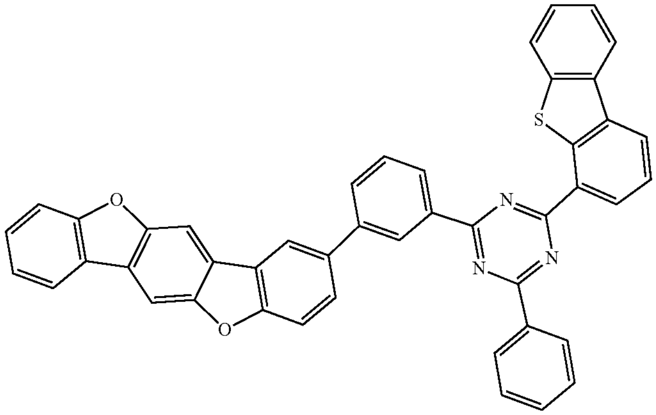

-continued
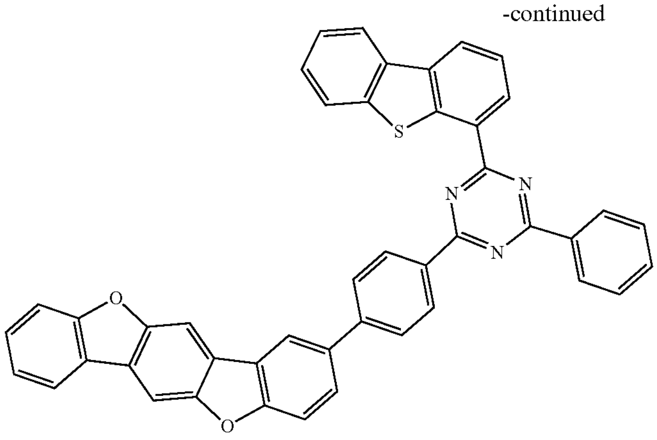
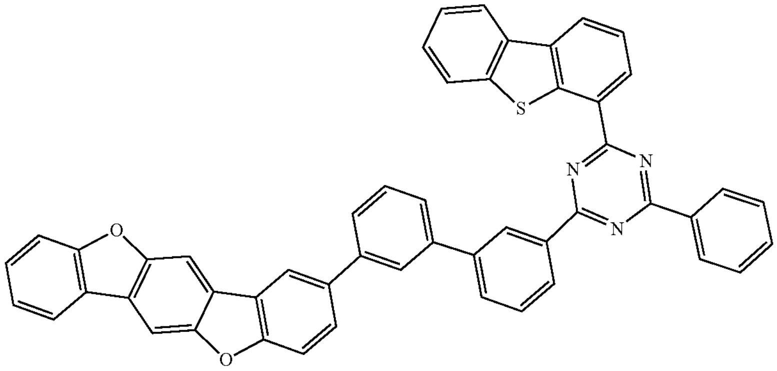
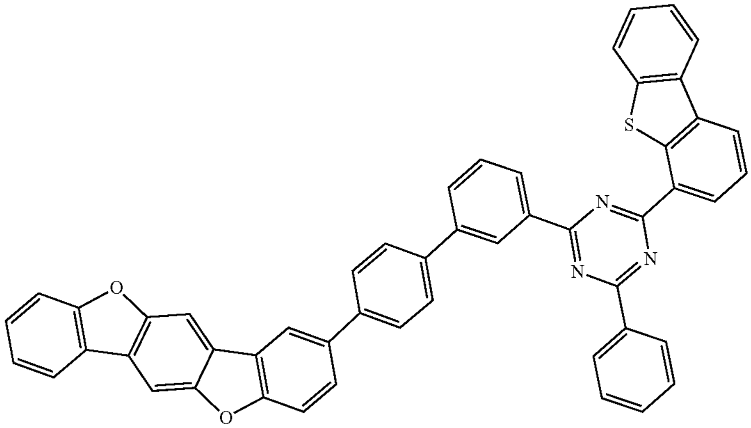
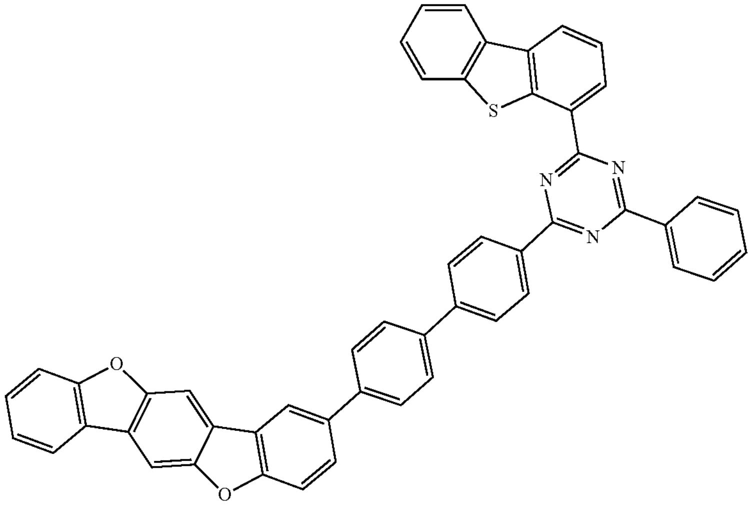

-continued
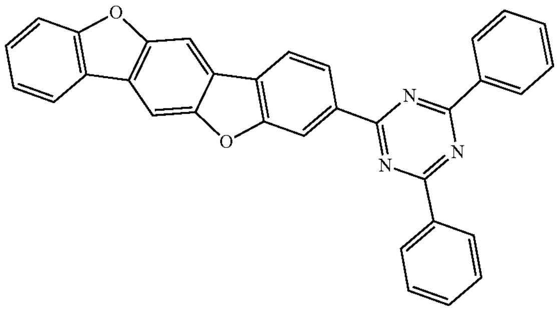
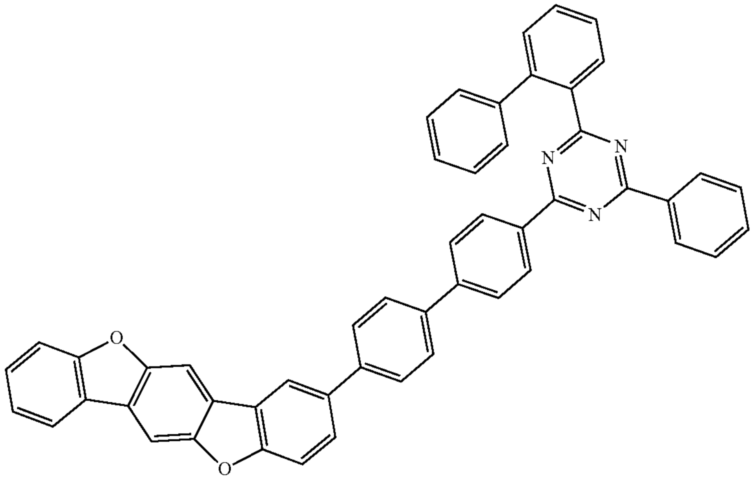
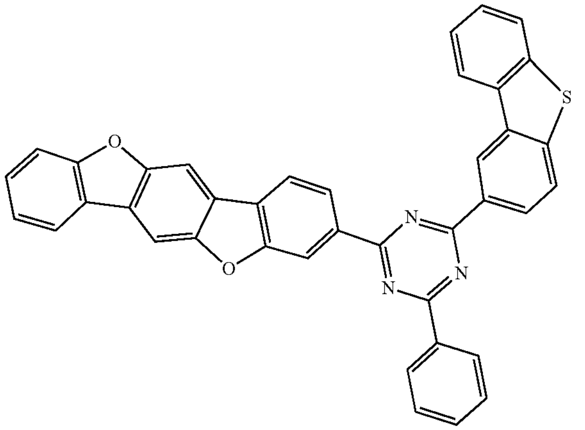
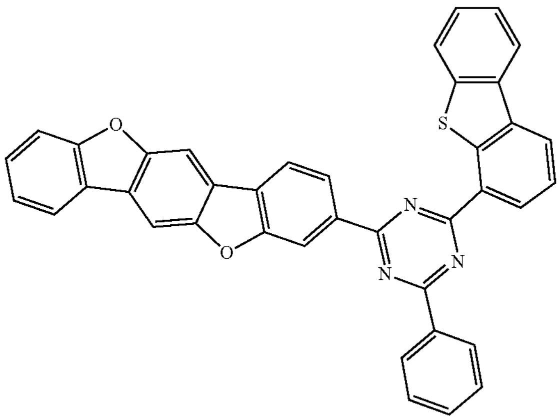

-continued
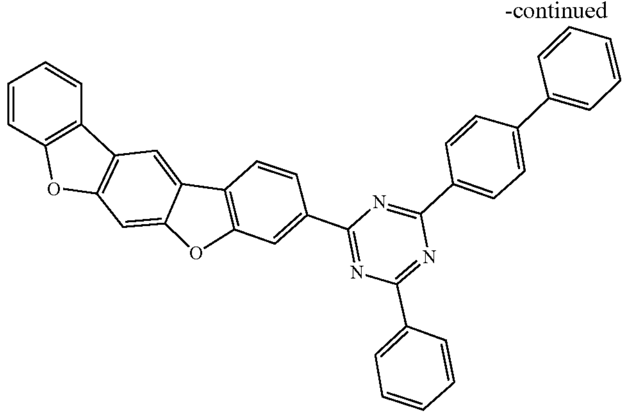
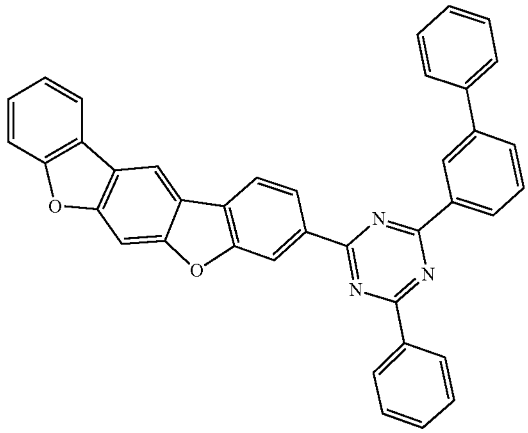
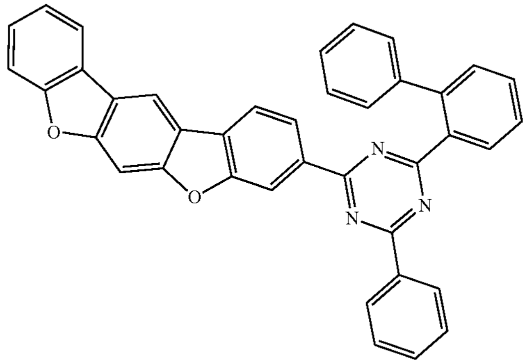
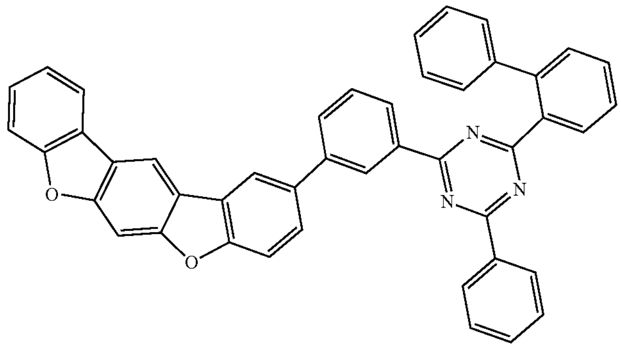

-continued
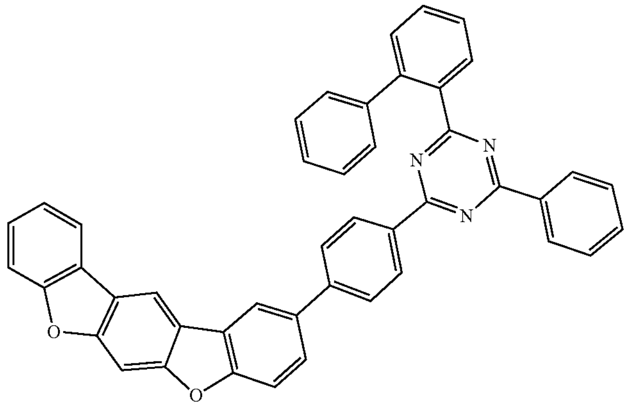
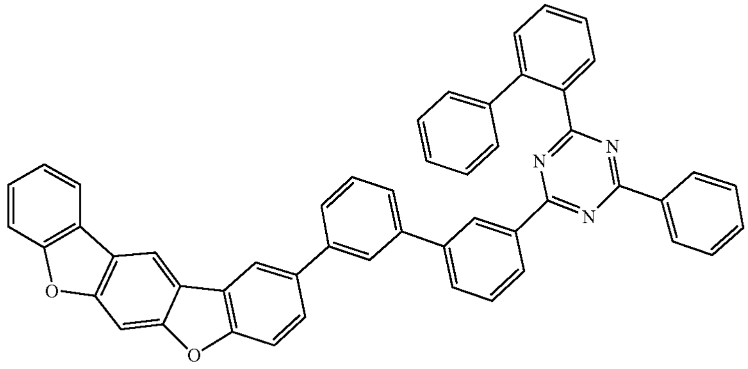
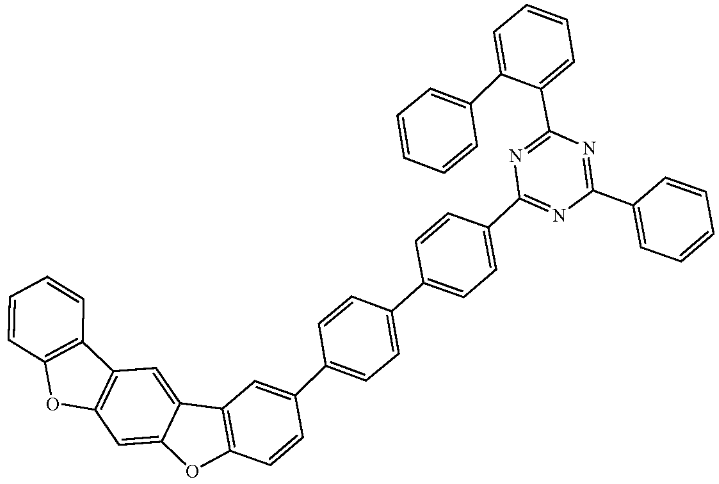 [SMILES: c1ccc(-c2nc(-c3ccc(-c4ccc(-c5ccc6oc7cc8oc9ccccc9c8cc7c6c5)cc4)cc3)nc(-c3ccccc3-c3ccccc3)n2)cc1]
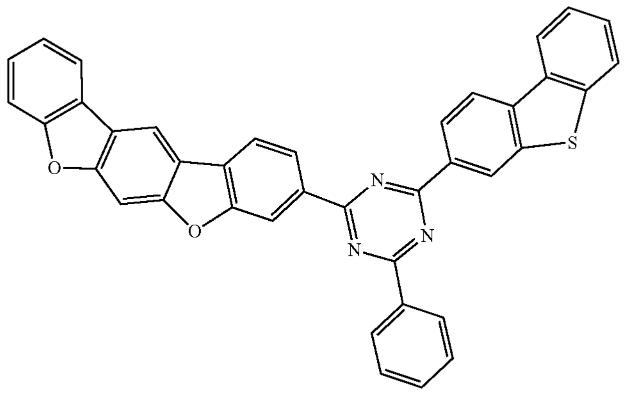

-continued
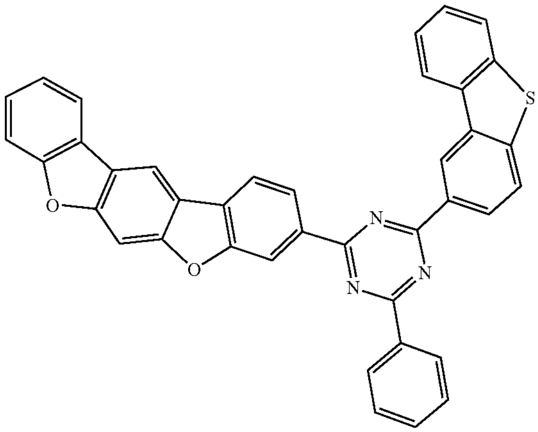
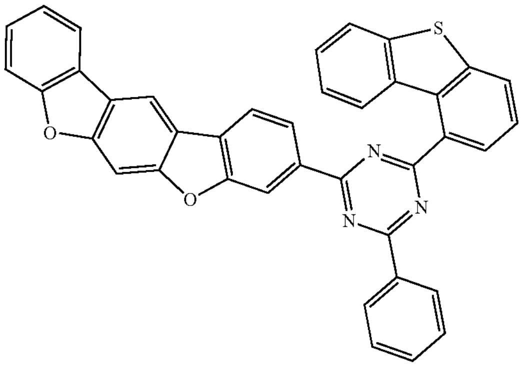
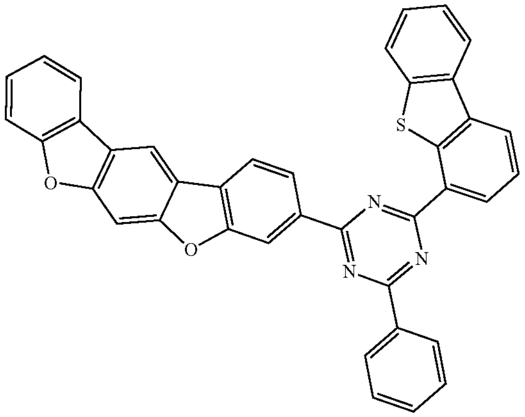
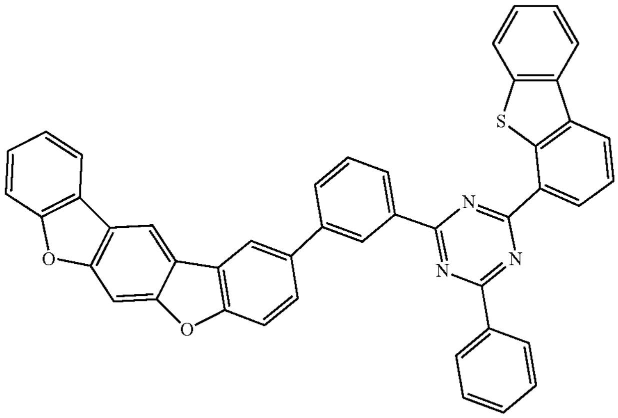
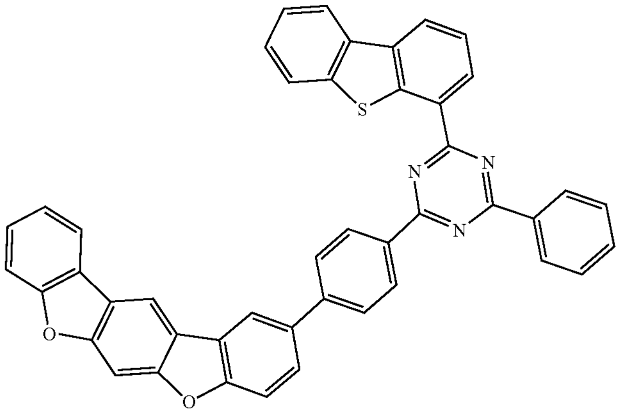

-continued
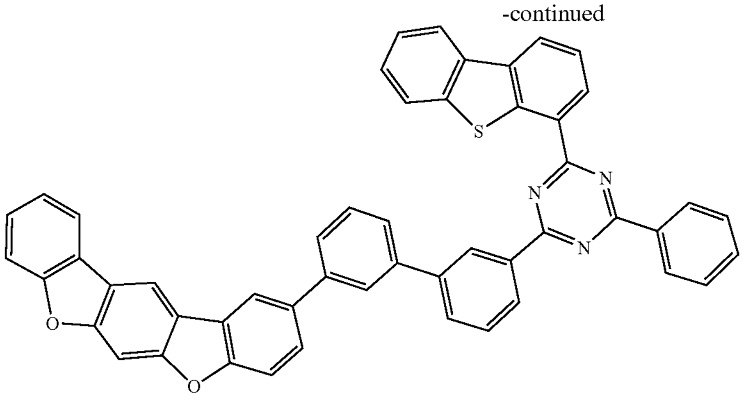
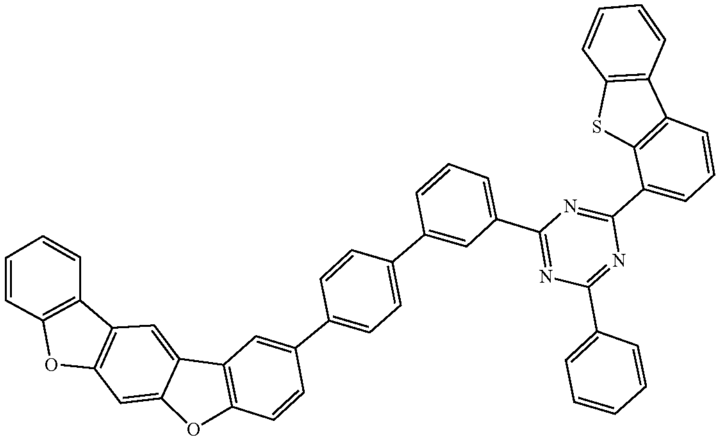
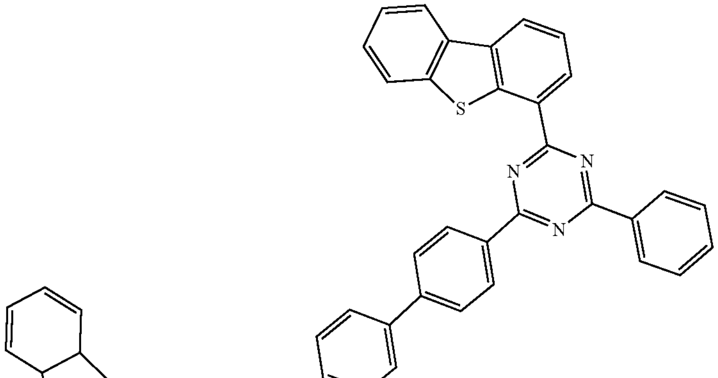
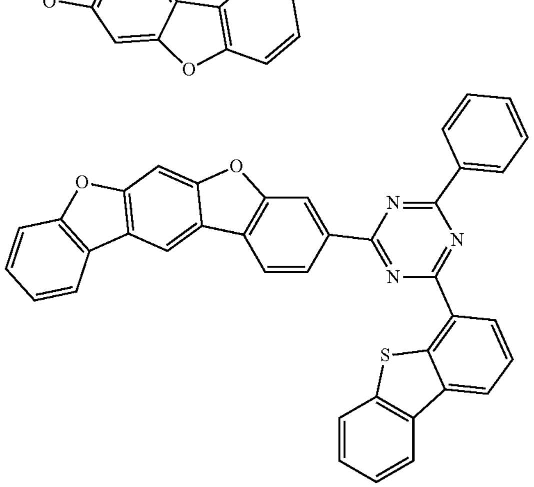
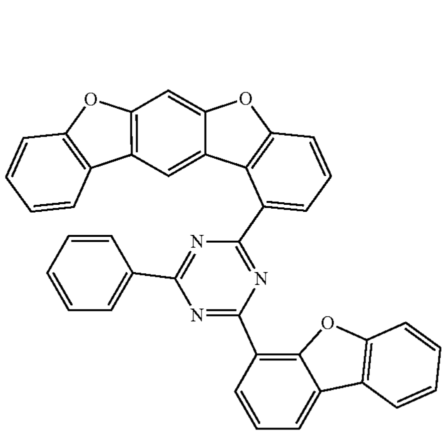

-continued
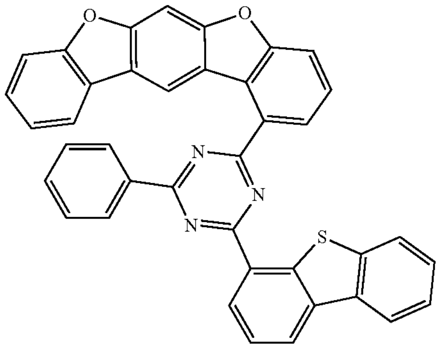
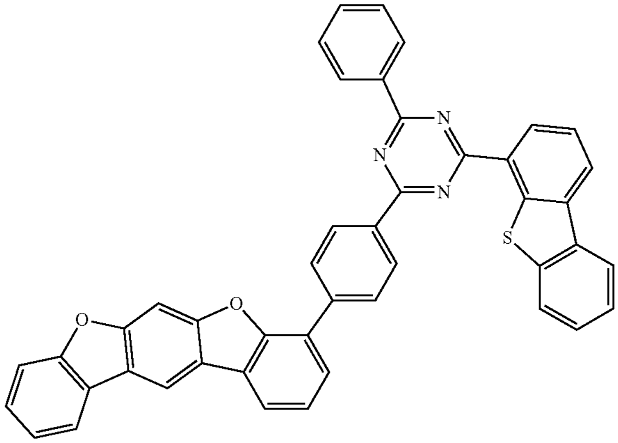
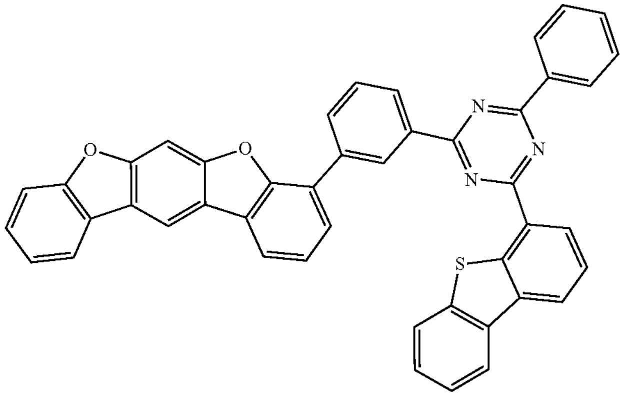
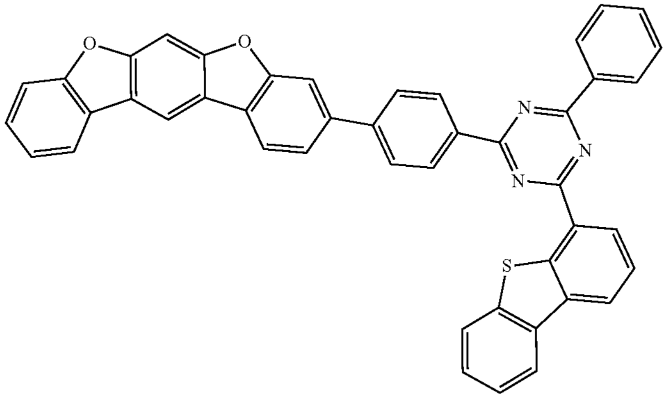

-continued
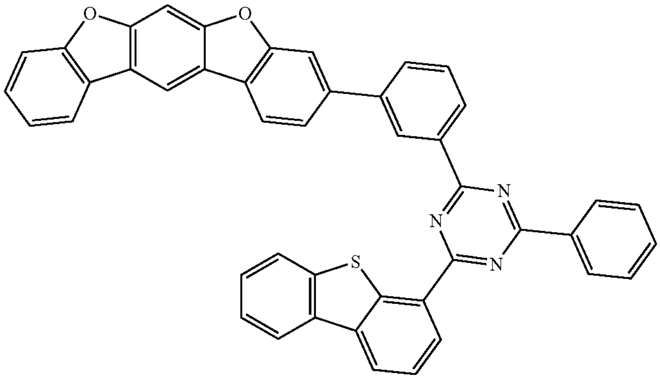
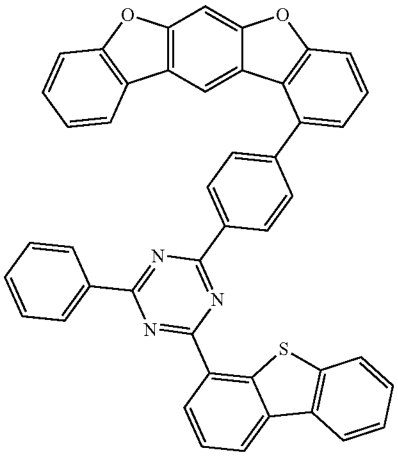
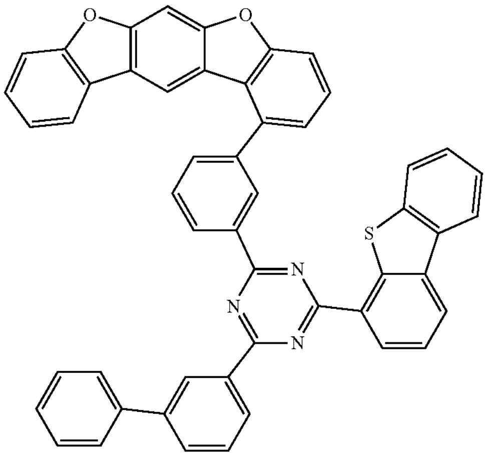
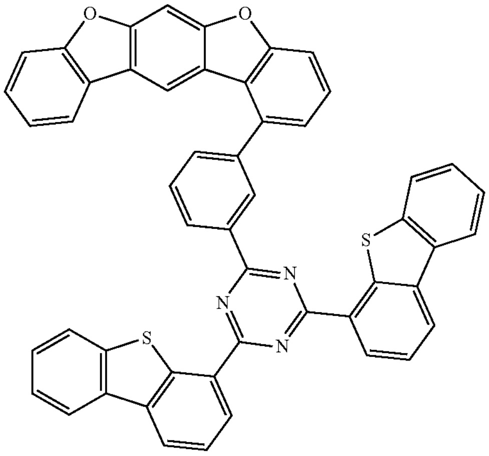
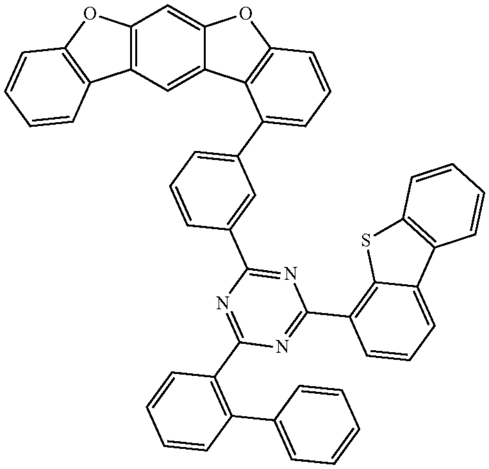
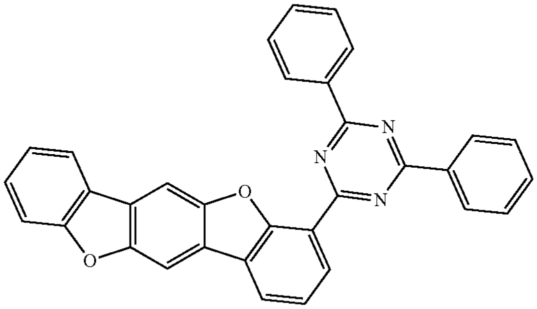

-continued
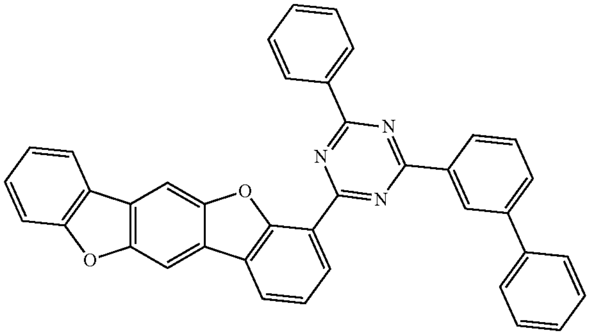
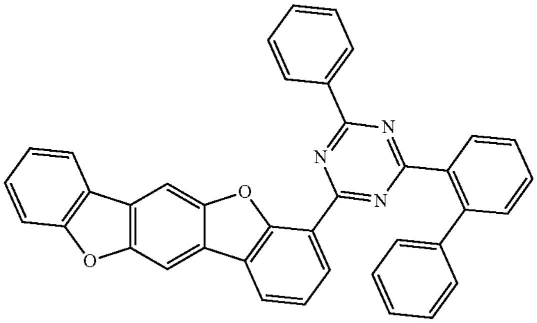
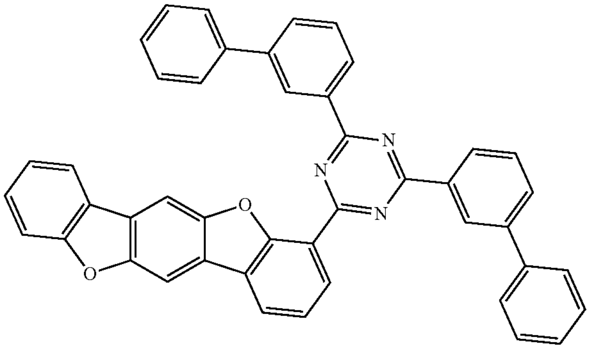
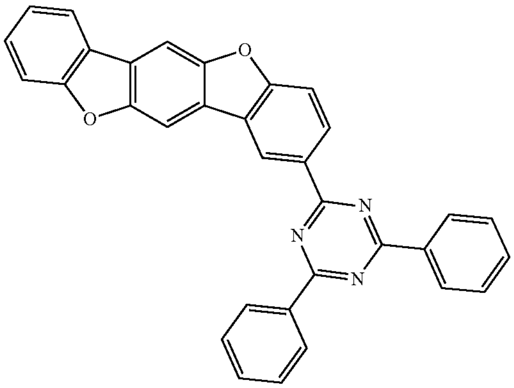

-continued
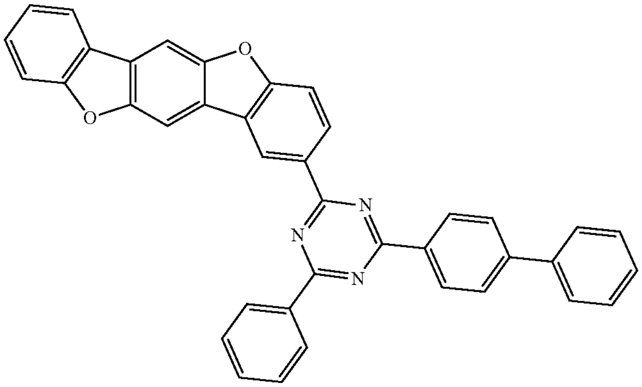
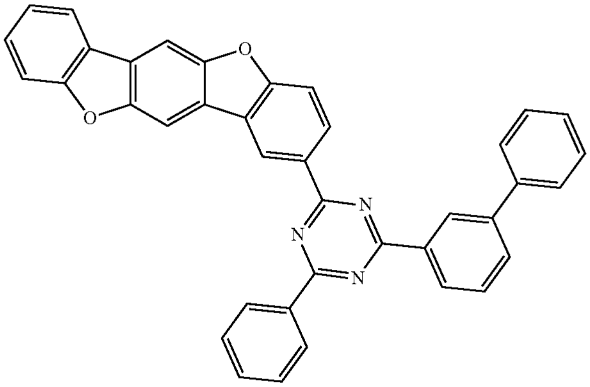
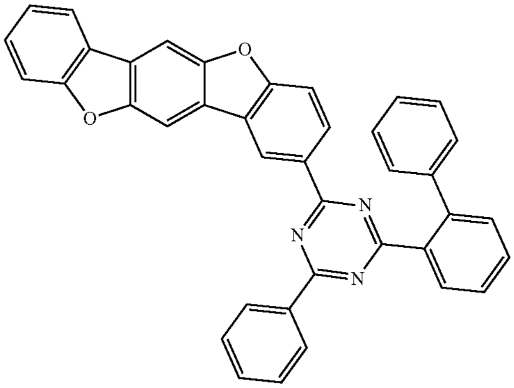
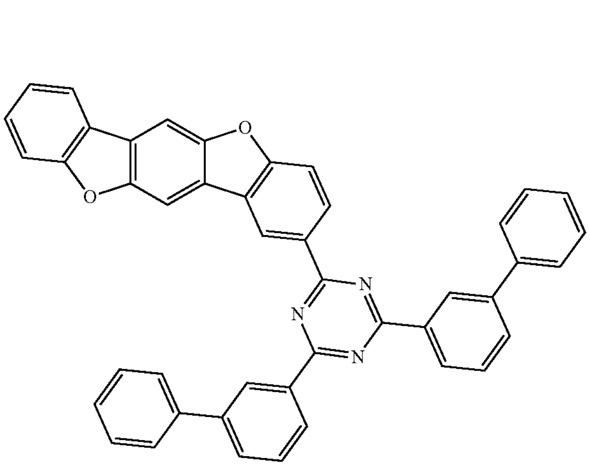

-continued
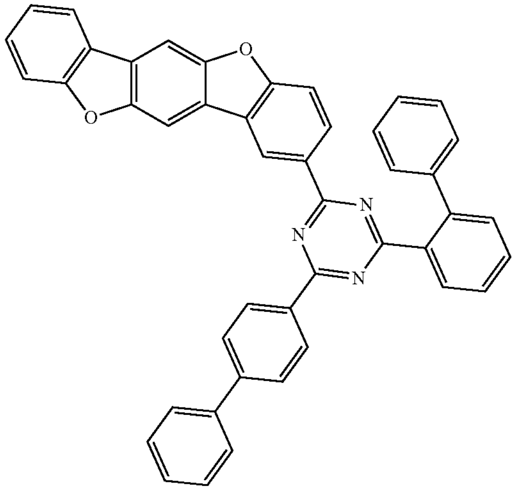
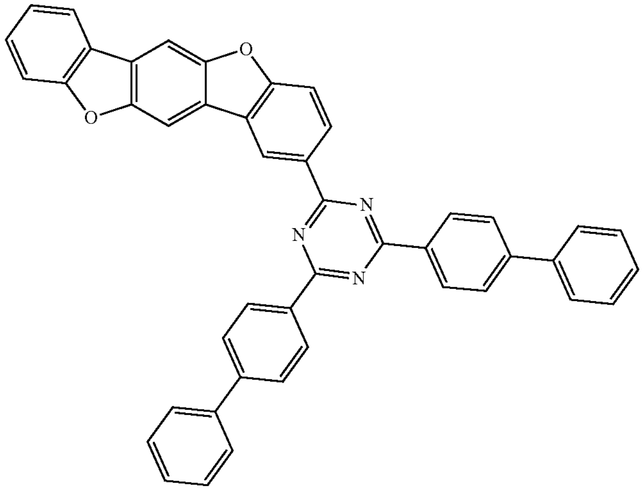
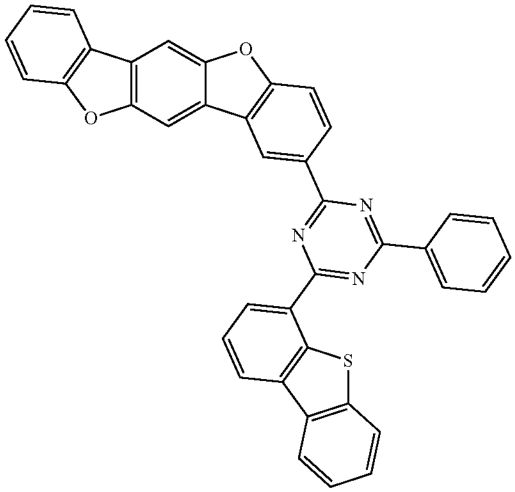

-continued
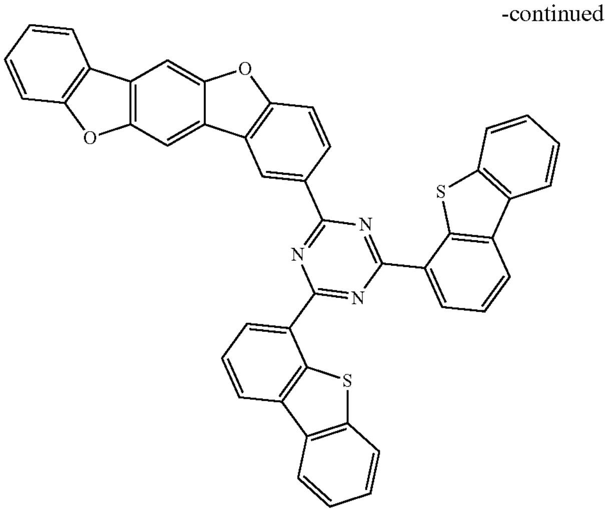
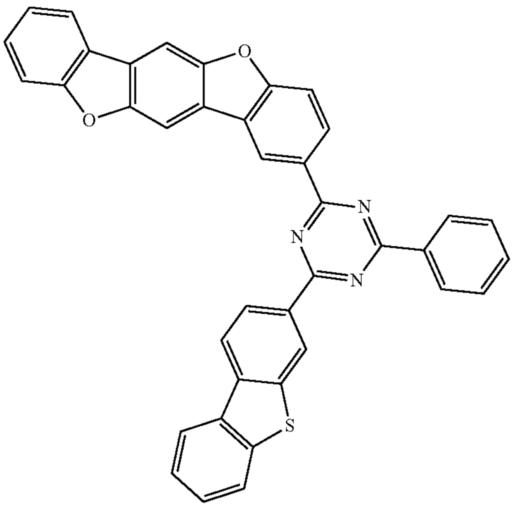
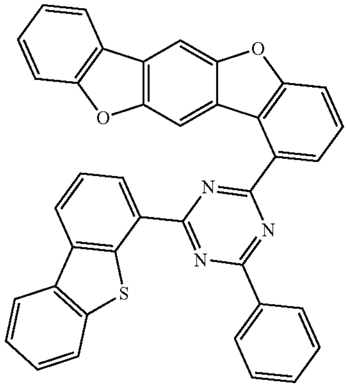
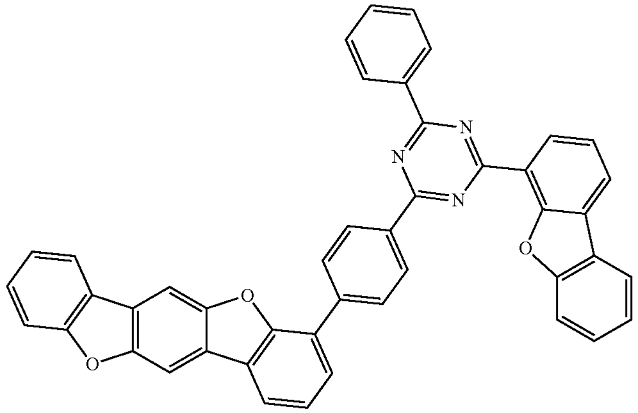
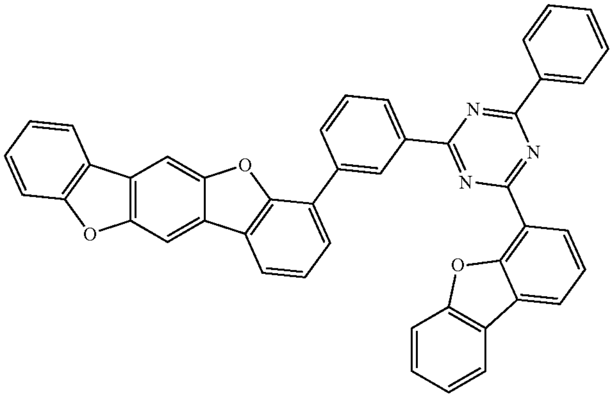
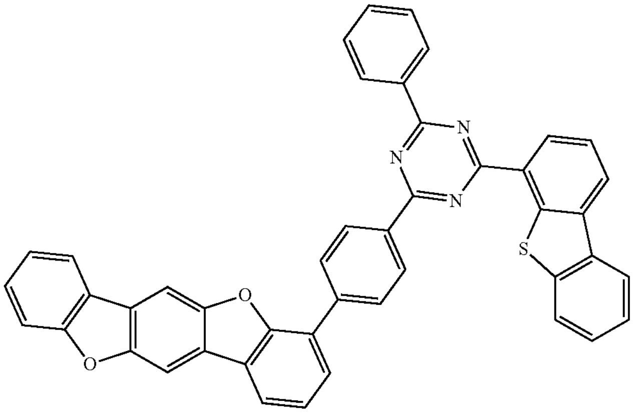

-continued
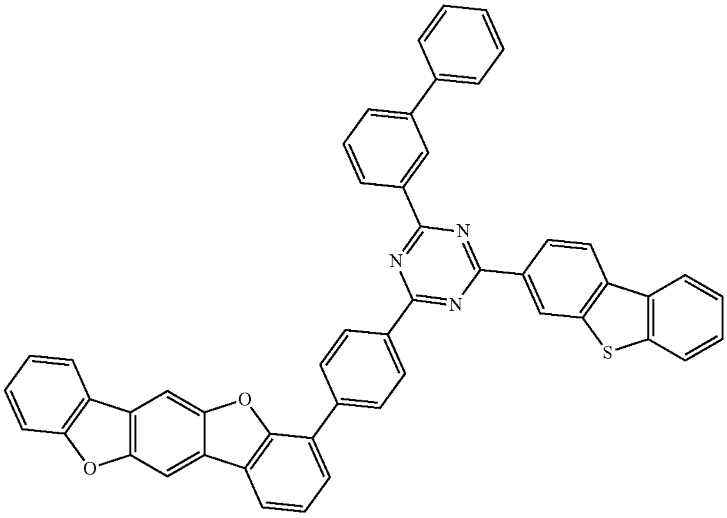
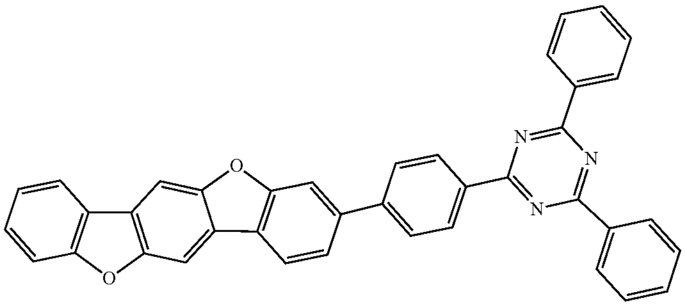
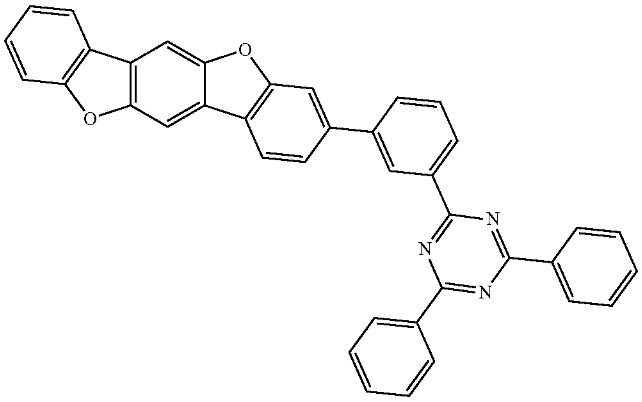
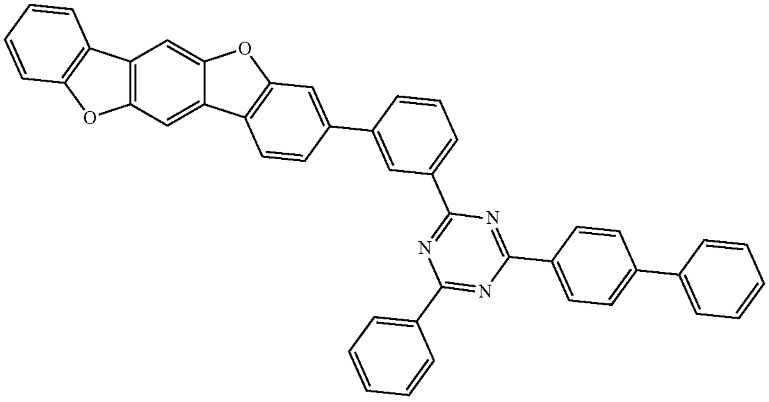

-continued
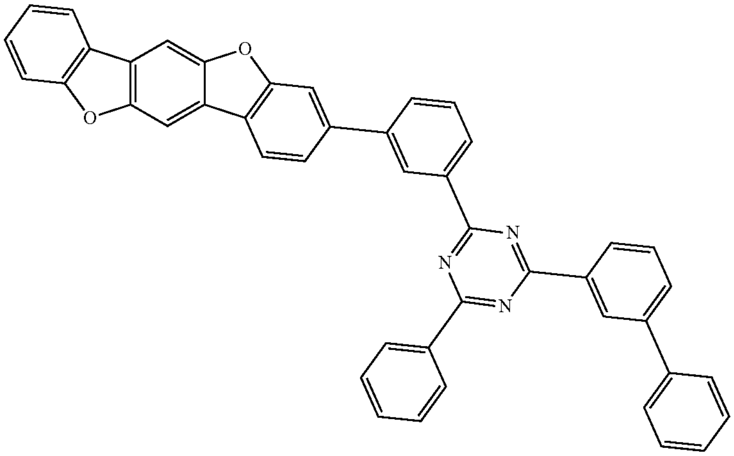
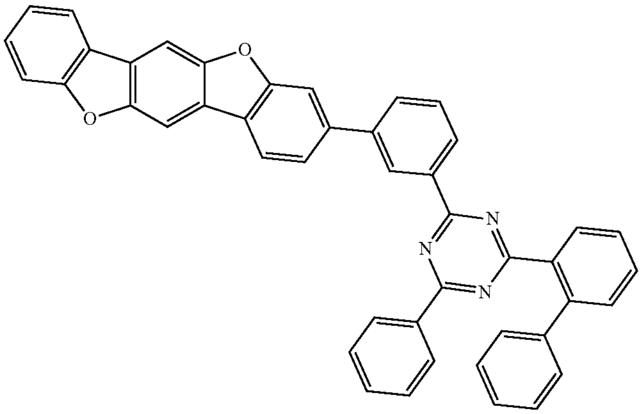
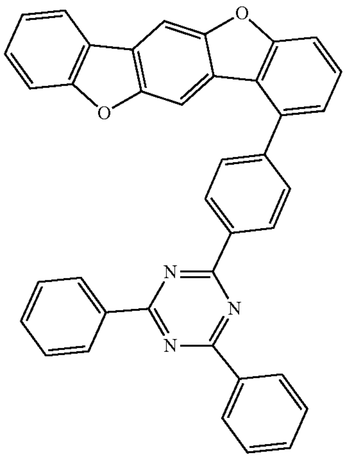

-continued
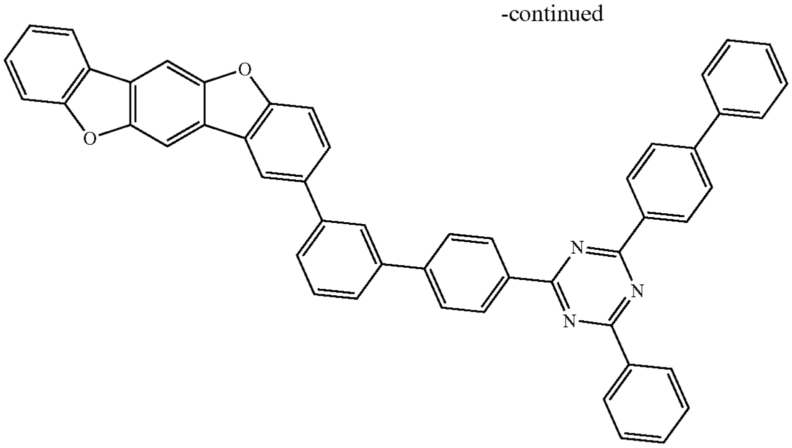
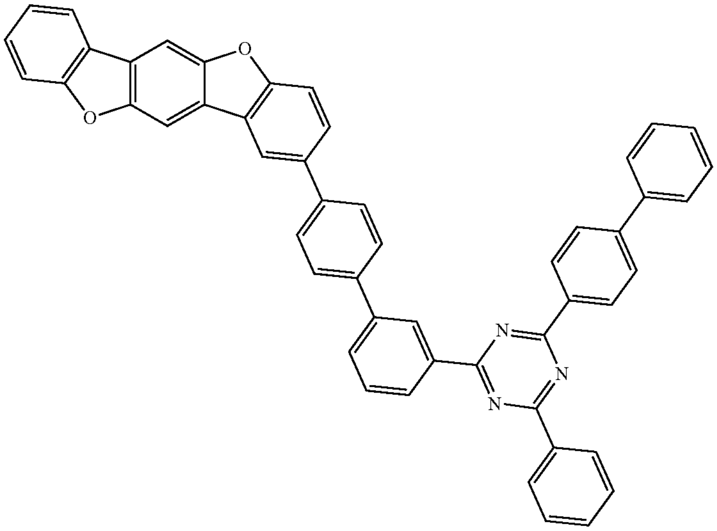
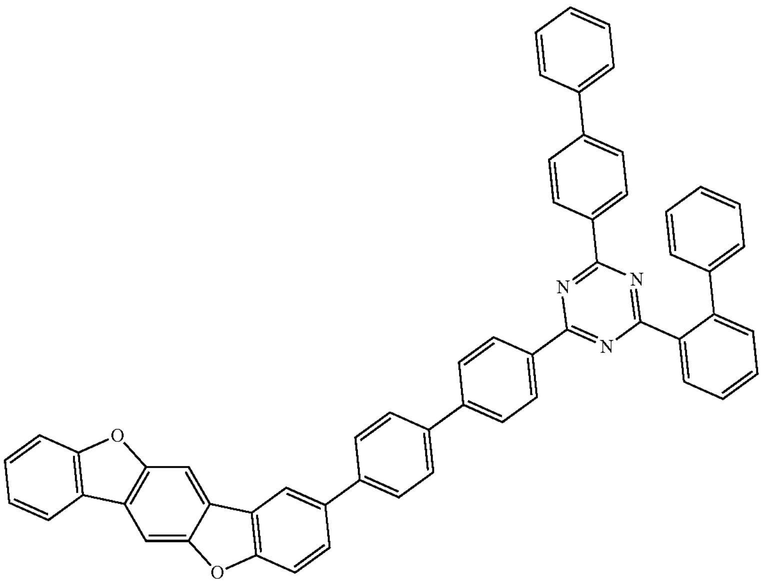

-continued
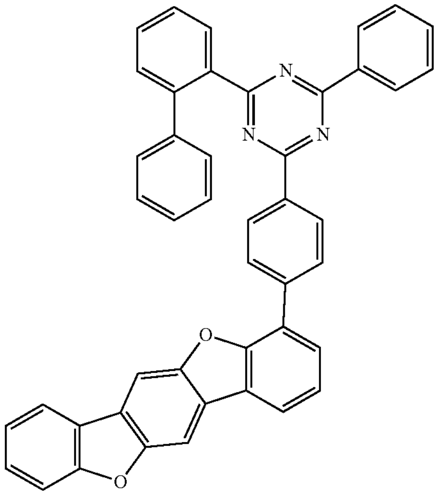
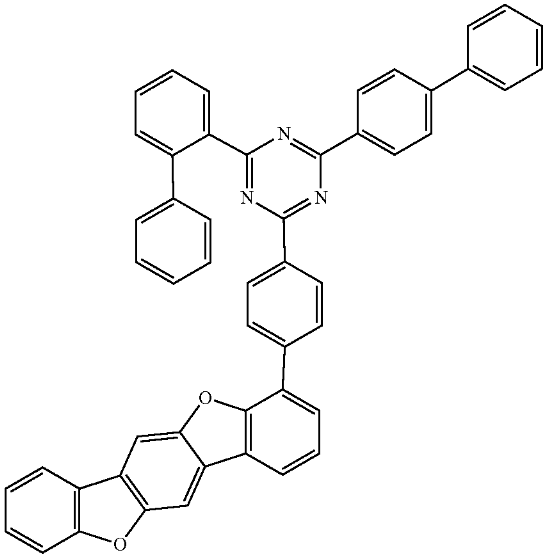
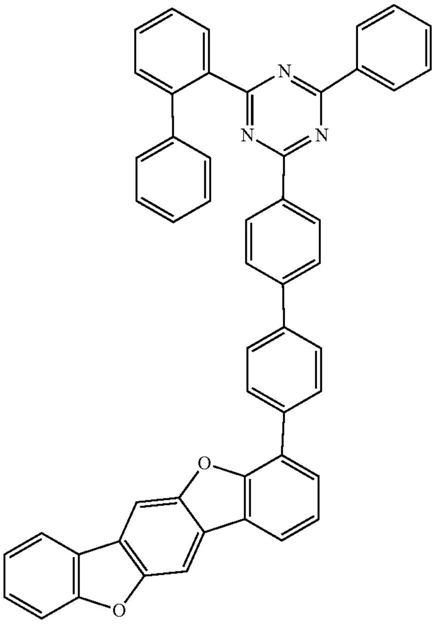
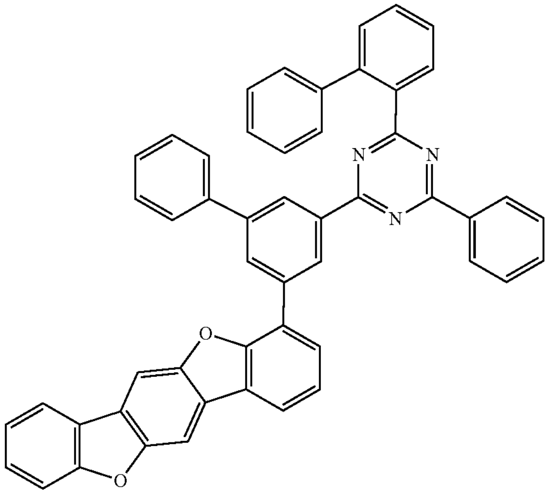
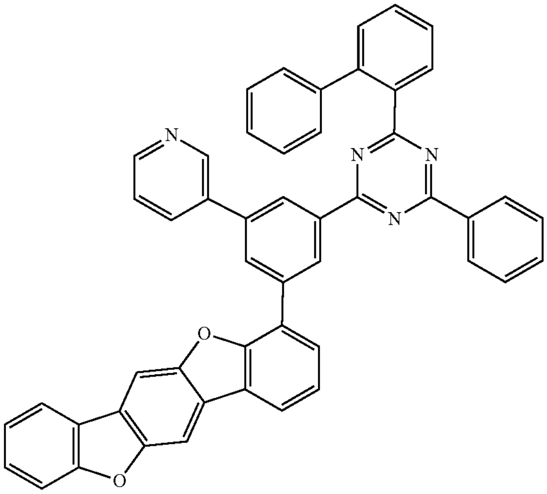

-continued
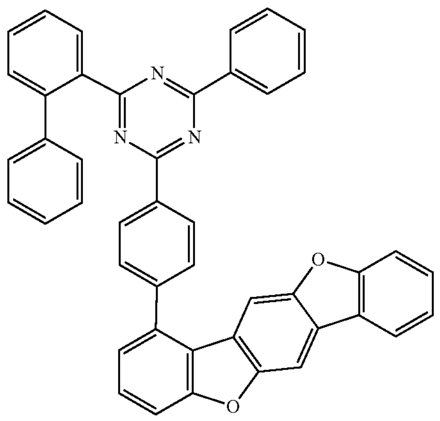
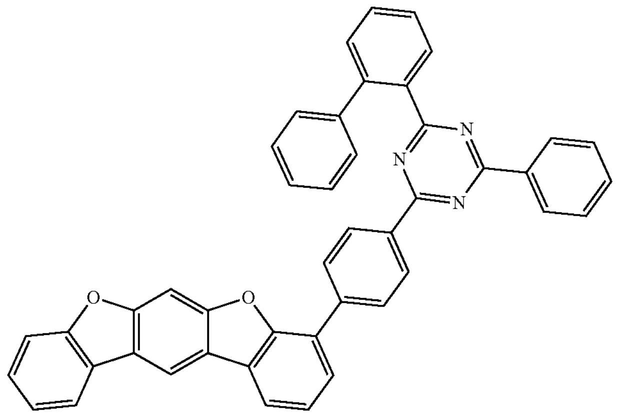
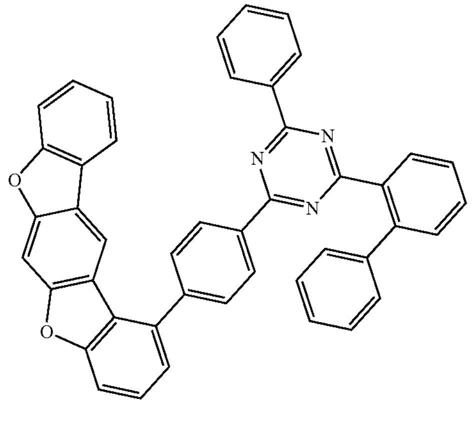

Synthesis of the Compounds of Formula (I)

The compounds of formula (I) are for example prepared by one of the following processes:

(a) Coupling a Compound of Formula (I*)

(I*)

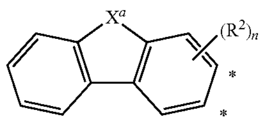

wherein each * is a bonding site to a group of formula (II*)

(II*)

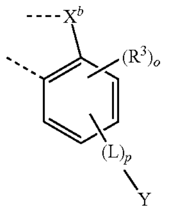

the dotted lines in the group of formula (II*) are bonding sites to the * in the compound of formula (I*);

with a compound of formula (III*)

(III*)

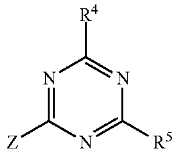

or (b) Coupling a Compound of Formula (I**)

(I**)

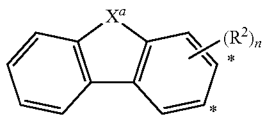

wherein each * is a bonding site to a group of formula (II**)

(II**)

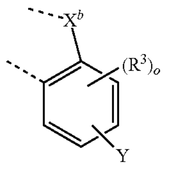

the dotted lines in the group of formula (II**) are bonding sites to the * in the compound of formula (I**);

with a compound of formula (III**)

(III**)

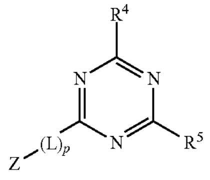

wherein

Y and Z are —$BQ_2$, wherein Q is an unsubstituted alkyl group having 1 to 8 carbon atoms, an unsubstituted cycloalkyl group having 3 to 6 carbon atoms or a cycloalkyl group having 3 to 6 carbon atoms, substituted by one or two unsubstituted alkyl groups having 1 to 8 carbon atoms, a unsubstituted alkoxy group having 1 to 8 carbon atoms, a hydroxyl group, wherein two alkyl groups Q or two alkoxy groups Q together may form a five or six membered ring; halogen or trifluormethansulfonate; or —MgX, wherein X is halogen, preferably bromine.

$X^a$ and $X^b$ are each independently O or S;

L represents a direct bond, divalent unsubstituted or substituted phenyl, divalent unsubstituted or substituted biphenyl, divalent unsubstituted or substituted terphenyl group, divalent unsubstituted or substituted naphthyl, divalent unsubstituted or substituted dibenzothiophenyl or divalent unsubstituted or substituted dibenzofuranyl;

p is 1, 2 or 3;

$R^2$ and $R^3$ each independently represents hydrogen, a halogen atom, a substituted or unsubstituted alkyl group having 1 to 25 carbon atoms, a substituted or unsubstituted alkenyl group having 2 to 25 carbon atoms, a substituted or unsubstituted alkynyl group having 2 to 25 carbon atoms, a substituted or unsubstituted cycloalkyl group having 3 to 25 carbon atoms, a substituted or unsubstituted alkoxy group having 1 to 25 carbon atoms, a substituted or unsubstituted aryl group having 6 to 24 carbon atoms, a substituted or unsubstituted heterocyclic group having 4 to 30 carbon atoms, a substituted or unsubstituted aryloxy group having 6 to 24 carbon atoms, a substituted or unsubstituted alkylthio group having 1 to 25 carbon atoms, a substituted or unsubstituted arylthio group having 6 to 24 carbon atoms, an alkyl and/or aryl substituted silyl group, an alkyl or aryl substituted carbonyl group, or a substituted phosphoryl group;

n is 0, 1 or 2;

o is 0, 1, 2 or 3;

$R^4$ and $R^5$ each independently represents hydrogen, a halogen atom, a substituted or unsubstituted alkyl group having 1 to 25 carbon atoms, a substituted or unsubstituted alkenyl group having 2 to 25 carbon atoms, a substituted or unsubstituted alkynyl group having 2 to 25 carbon atoms, a substituted or unsubstituted cycloalkyl group having 3 to 25 carbon atoms, a substituted or unsubstituted alkoxy group having 1 to 25 carbon atoms, a substituted or unsubstituted aryl group having 6 to 24 carbon atoms, a substituted or unsubstituted heterocyclic group having 4 to 30 carbon atoms, a substituted or unsubstituted aryloxy group having 6 to 24 carbon atoms, a substituted or unsubstituted alkylthio group having 1 to 25 carbon atoms, a substituted or unsubstituted arylthio group having 6 to 24 carbon atoms, an alkyl and/or aryl substituted silyl group, an alkyl or aryl substituted carbonyl group, or a substituted phosphoryl group.

Preferred groups, residues and indices $X^a$, $X^b$, $R^2$, $R^3$, L, A, n, o and p are defined above.

Details of the reaction steps and process conditions are mentioned in the examples of the present application. The production method of the compound of formula (I) according to the present invention is not particularly limited and it is produced according to a known method, for example, by a Suzuki coupling as described in Journal of American Chemistry Society 121 (1999) 9550 to 9561 or Chemical Reviews 95 (1995) 2457 to 2483.

Compounds of Formula (I) in Organic Electronics Applications

It has been found that the compounds of the formula (I) are particularly suitable for use in applications in which charge carrier conductivity is required, especially for use in organic electronics applications, for example selected from switching elements such as organic transistors, e.g. organic FETs and organic TFTs, organic solar cells and organic light-emitting diodes (OLEDs).

The term organic EL device (organic electroluminescence device) is used interchangeably with the term organic light-emitting diode (OLED) in the following; i.e. both terms have the same meaning in the sense of the present application.

The present invention further relates to a material for an organic EL device comprising at least one compound of formula (I).

The organic transistor generally includes a semiconductor layer formed from an organic layer with charge transport capacity; a gate electrode formed from a conductive layer; and an insulating layer introduced between the semiconductor layer and the conductive layer. A source electrode and a drain electrode are mounted on this arrangement in order thus to produce the transistor element. In addition, further layers known to those skilled in the art may be present in the organic transistor. The layers with charge transport capacity may comprise the compounds of formula (I).

The organic solar cell (photoelectric conversion element) generally comprises an organic layer present between two plate-type electrodes arranged in parallel. The organic layer may be configured on a comb-type electrode. There is no particular restriction regarding the site of the organic layer and there is no particular restriction regarding the material of the electrodes. When, however, plate-type electrodes arranged in parallel are used, at least one electrode is preferably formed from a transparent electrode, for example an ITO electrode or a fluorine-doped tin oxide electrode. The organic layer is formed from two sublayers, i.e. a layer with p-type semiconductor properties or hole transport capacity, and a layer formed with n-type semiconductor properties or charge transport capacity. In addition, it is possible for further layers known to those skilled in the art to be present in the organic solar cell. The layers with charge transport capacity may comprise the compounds of formula (I).

The compounds of formula (I) being particularly suitable in OLEDs for use as matrix material (host material) in a light-emitting layer and/or as charge and/or exciton blocker material, i.e. as electron/exciton blocker material or as hole/exciton blocker material, and/or charge transport material, i.e. hole transport material or electron transport material, preferably as matrix material in a light-emitting layer and/or as electron transport material, especially in combination with a phosphorescence emitter.

In the case of use of the inventive compounds of formula (I) in OLEDs, OLEDs having good overall properties, preferably a low driving voltage and/or a long lifetime are obtained. The inventive compounds of formula (I) are suitable especially for use as matrix and/or charge transport, i.e. hole or electron transport, and/or charge blocker material, i.e. hole or electron blocker material. Furthermore, the compounds of the formula (I) can be used as conductor/complementary materials in organic electronic applications selected from switching elements and organic solar cells. (In the sense of the present application, the terms matrix and host are used interchangeable).

Organic EL Device (OLED)

The organic EL device as one embodiment of the invention comprises one or more organic thin film layers including an emitting layer between a cathode and an anode, and at least one layer of the organic thin film layers comprises the compound of formula (I).

As examples of the organic thin film layers that comprise the compound of formula (I), an anode-side organic thin film layer (hole-transporting layer, hole-injecting layer, or the like), an emitting layer, a cathode-side organic thin film layer (electron-transporting layer, electron-injecting layer, or the like) provided between a cathode and an emitting layer, a spacing layer, a barrier layer or the like can be given. The examples are not limited thereto. The compound of formula (I) may be contained in any of the abovementioned layers, and can be used as a host material or a dopant material in the emitting layer of a fluorescent emitting unit, a host material in the emitting layer of a phosphorescent emitting unit, a hole-transporting layer, an electron-transporting layer or the like of an emitting unit.

Preferably, the light emitting layer comprises at least one compound of formula (I) according to the present invention.

Preferably, the compounds of the formula (I) are used as matrix materials (host materials), preferably in an emitting layer of an OLED, more preferably in an emitting layer of an OLED comprising at least one compound of the formula (I) and at least one emitter material, wherein the emitter material is preferably a fluorescent or phosphorescent emitter material, more preferably a blue, green or red fluorescent or phosphorescent emitter material, most preferably a green or red phosphorescent emitter material, further most preferably a green phosphorescent emitter material.

According to another embodiment, the compounds of the formula (I) are preferably used in the electron transporting layer of an OLED.

The present invention therefore further relates to the organic electroluminescence device according to the present invention, wherein an electron transporting layer is provided between the cathode and the light emitting layer, and the electron transporting layer comprises at least one compound of formula (I) according to the present invention.

According to another embodiment, the compounds of the formula (I) are preferably used in the hole blocking layer of an OLED.

The present invention therefore further relates to the organic electroluminescence device according to the present invention, wherein a hole blocking layer is provided between the electron transporting layer and the light emitting layer, and the hole blocking layer comprises at least one compound of formula (I) according to the present invention.

The organic EL device of the invention may be a fluorescent or phosphorescent monochromatic emitting device or may be a fluorescent/phosphorescent hybrid white emitting device. It may be a simple emitting device having a single emitting unit or a tandem emitting device having plural emitting units. Among them, the organic EL device may preferably be a phosphorescent emitting device.

As the representative device structure of a simple type organic EL device, the following device configuration can be given.

(1) Anode/Emitting Unit/Cathode

The emitting unit mentioned above may be a stacked type emitting unit comprising plural phosphorescent emitting layers or plural fluorescent emitting layers. In this case, in order to prevent diffusion of excitons generated in the phosphorescent emitting layer to the fluorescent emitting layer, a spacing layer may be provided between the emitting layers. The representative layer configuration of the emitting unit is given below.

(a) Hole-transporting layer/Emitting layer (/Electron-transporting layer)
(b) Hole-transporting layer/First phosphorescent emitting layer/Second phosphorescent emitting layer (/Electron-transporting layer)
(c) Hole-transporting layer/Phosphorescent emitting layer/Spacing layer/Fluorescent emitting layer (/Electron-transporting layer)
(d) Hole-transporting layer/First phosphorescent emitting layer/Second phosphorescent emitting layer/Spacing layer/Fluorescent emitting layer (/Electron-transporting layer)
(e) Hole-transporting layer/First phosphorescent emitting layer/Spacing layer/Second phosphorescent emitting layer/Spacing layer/Fluorescent emitting layer (/Electron-transporting layer)
(f) Hole-transporting layer/Phosphorescent emitting layer/Spacing layer/First fluorescent emitting layer/Second fluorescent emitting layer (/Electron-transporting layer)
(g) Hole-transporting layer/Electron barrier layer/Emitting layer (/Electron-transporting layer)
(h) Hole-transporting layer/Emitting layer/Hole barrier layer (/Electron-transporting layer)
(i) Hole-transporting layer/Fluorescent emitting layer/Triplet barrier layer (/Electron-transporting layer)

The phosphorescent or fluorescent emitting layer as mentioned above can emit different colors of light. Specifically, in the stacked emitting layer (d), a layer configuration of the hole transporting layer/first phosphorescent emitting layer (red emission)/second phosphorescent emitting layer (green emission)/spacing layer/fluorescent emitting layer (blue emission)/electron transporting layer or the like can be given.

Between each emitting layer and the hole-transporting layer or the spacing layer, an electron barrier layer may be provided appropriately. Between each emitting layer and the electron transporting layer, a hole-barrier layer (a hole blocking layer) may be provided appropriately. Due to provision of an electron-barrier layer or a hole-barrier layer, electrons or holes can be confined within the emitting layer, whereby possibility of recombination of carriers in the emitting layer can be increased, and the life can be improved.

As the represented device configuration of a tandem organic EL device, the following device configuration can be given.

(2) Anode/First Emitting Unit/Intermediate Layer/Second Emitting Unit/Cathode

Here, as the first emitting unit and the second emitting unit, the same emitting units as those mentioned above can independently be given, for example.

In general, the intermediate layer is called an intermediate electrode, an intermediate conductive layer, a carrier-generating layer, an electron-withdrawing layer, and a known material configuration that supplies electrons to the first emitting unit and supplies holes to the second emitting unit can be used.

The FIGURE shows a schematic configuration of one example of the organic EL device of the invention. The organic EL device 1 comprises a substrate 2, an anode 3, a cathode 4 and an emitting unit 10 provided between the anode 3 and the cathode 4. The emitting unit 10 comprises an emitting layer 5 preferably comprising a host material and a dopant. A hole injecting and transporting layer 6 or the like may be provided between the emitting layer 5 and the anode 3 and an electron-injecting layer 8 and an electron transporting layer 7 or the like (electron injecting and transporting unit 11) may be provided between the emitting layer 5 and the cathode 4. An electron-barrier layer may be provided on the anode 3 side of the emitting layer 5 and a hole-barrier layer may be provided on the cathode 4 side of the emitting layer 5. Due to such configuration, electrons or holes can be confined in the emitting layer 5, whereby possibility of generation of excitons in the emitting layer 5 can be improved.

Due to such configuration, electrons or holes can be confined in the emitting layer 5, whereby possibility of generation of excitons in the emitting layer 5 can be improved.

Herein, a host that is combined with a fluorescent dopant is referred to as a fluorescent host and a host that is combined with a phosphorescent dopant is referred to as a phosphorescent host. The fluorescent host and the phosphorescent host are not distinguished only by the molecular structure thereof. That is, the phosphorescent host means a material constituting a phosphorescent emitting layer that contains a phosphorescent dopant and does not mean a material that cannot be used as a material constituting a fluorescent dopant. The same can be applied to a fluorescent host.

Substrate

The organic EL device is usually formed on a transparent substrate. The transparent substrate is a substrate for supporting the organic EL device, and is preferably a flat and smooth substrate having a 400-to-700-nm-visible-light transmittance of 50% or more. Specific examples thereof include glass plates and polymer plates. Examples of the glass plate include those obtained by using as raw materials soda-lime glass, barium/strontium-containing glass, lead glass, aluminosilicate glass, borosilicate glass, barium borosilicate glass, quartz, or the like. Examples of the polymer plate include those obtained by using as raw materials polycarbonate, acrylic polymer, polyethylene terephthalate, polyethersulfide, polysulfone, or the like.

Anode

The anode of the organic EL device plays a role for injecting holes into its hole-transporting layer or emitting layer. It is effective to use one having a work function of 4.5 eV or more. As specific examples of the anode material, indium tin oxide alloy (ITO), tin oxide (NESA), indium zinc oxide, gold, silver, platinum, copper, and the like can be given. The anode can be formed by forming these electrode materials into a thin film by vapor deposition, sputtering or the like. In the case where emission from the emitting layer is taken out through the anode, the transmittance of the anode to the emission is preferably more than 10%. The sheet resistance of the anode is preferably several hundred Ω/□ or less. The film thickness of the anode, which varies depending upon the material thereof, is usually from 10 nm to 1 μm, preferably from 10 to 200 nm.

Cathode

The cathode plays a role for injecting electrons into its electron-injecting layer, electron-transporting layer or emitting layer. The cathode is preferably formed of a material having a small work function. The cathode material is not particularly restricted. As specific examples of the cathode material, indium, aluminum, magnesium, a magnesium-indium alloy, a magnesium-aluminum alloy, an aluminum-lithium alloy, an aluminum-scandium-lithium alloy, a magnesium-silver alloy or the like can be given. As in the case of the anode, the cathode can be formed by forming the materials into a thin film by a deposition method, a sputtering method or the like. If necessary, emission can be outcoupled from the cathode side.

Emitting Layer

The present invention relates—in one embodiment—to an organic electroluminescence device, wherein the light emitting layer comprises at least one compound of formula (I).

The emitting layer is an organic layer having an emitting function, and where a doping system is used, it usually comprises a host material and a dopant material (emitter).

The host material has a function of accelerating recombination of electrons and holes and confining excitons within the emitting layer. The dopant material has a function of emitting efficiently excitons obtained by recombination.

In the case of a phosphorescent device, the host material has a function of confining excitons mainly generated by a dopant within the emitting layer. The host material is preferably a compound of the formula (I) according to the invention.

In one preferred embodiment, in the emitting layer, a double host (also referred to as a host/cohost) that adjusts the carrier balance in the emitting layer may be used by combining an electron-transporting host and a hole-transporting host or by other methods. In said embodiment, the emitting layer comprises a first host material and a second host material and at least one component of the first host material and the second host material is a compound of the formula (I) according to the invention.

Double dopant may be used in which two or more types of dopant materials having a high quantum yield are incorporated, and each dopant emits light. Specifically, by allowing a host, a red dopant and a green dopant to be co-deposited, yellow emission from the common emitting layer, whereby yellow emission is realized.

As for the emitting layer, by allowing plural emitting layers to be a stacked body, electrons and holes are accumulated in the interface of the emitting layers, whereby the recombination region is concentrated in the interface of the emitting layers. As a result, the quantum efficiency is improved.

Easiness in injection of holes to the emitting layer and easiness in injection of electrons to the emitting layer may differ. Further, the hole-transporting performance and the electron transporting performance indicated by the mobility of holes and electrons in the emitting layer may differ from each other.

The emitting layer can be formed by a known method such as a deposition method, a spin coating method, a LB method (Langmuir Blodgett method) or the like, for example. The emitting layer can also be formed by forming a solution obtained by dissolving a binder such as a resin and material compounds in a solvent into a thin film by a spin coating method and the like.

The emitting layer is preferably a molecular deposited film. The "molecular deposited film" means a thin film formed by deposition of a raw material compound in a vapor phase or a film formed by solidification of a raw material compound in a solution state or a liquid phase state. Normally, this molecular deposited film differs from a thin film (molecular accumulated film) formed by a LB method in aggregation structure or high-order structure, or differ in function derived from such difference in structure.

The content of the emitter materials (dopants), preferably the phosphorescent emitter materials, in the light emitting layer is not particularly limited and selected according to the use of the device, and preferably 0.1 to 70% by mass, and more preferably 1 to 30% by mass. If being 0.1% by mass or more, the amount of light emission is sufficient. If being 70% by mass or less, the concentration quenching can be avoided. The further component in the emitting layer is usually one or more host material, which is preferably present in an amount of 30 to 99.9% by mass, more preferably 70 to 99% by mass, wherein the sum of the emitter material(s) and the host material(s) is 100% by mass. Suitable host (matrix) and emitter materials are mentioned below. Preferably, at least one host material is a compound of formula (I) according to the invention.

(1) Phosphorescent Emitting Layer

The phosphorescent emitting layer usually comprises at least one emitter material and at least one host material. The phosphorescent host is a compound which confines the triplet energy of the phosphorescent dopant efficiently in the light emitting layer to cause the phosphorescent dopant to emit light efficiently.

A host material for phosphorescent emitting layer is usually selected from known phosphorescent host materials. Specific examples of the preferable phosphorescent host are, nitrogen-containing heteroaromatics, such as, indole compounds, carbazole compounds, pyridine compounds, pyrimidine compounds, triazine compounds, quinoline compounds, isoquinoline compounds, quinazoline compounds, nitrogenated-dibenzothiophene compounds, nitrogenated-dibenzofuran compounds, imidazole compounds, such as benzimidazole compounds, imidazopyridine compounds, Benzimidazophenanthridine compounds, benzimidzobenzimidazole compounds; oxygen or sulfur containing heteroaromatics, such as thiophene compounds, furan compounds, benzothiophene compounds, benzofuran compounds, dibenzothiophene compounds, dibenzofuran compounds; aryl or heteroaryl substituted amine compounds; metal complexes; aromatic hydrocarbon compounds, such as benzene compounds naphthalene compounds, phenanthrene compounds, triphenylene compounds, fluorene compounds. Most preferably, the host comprises at least one compound of formula (I) according to the present invention.

According to one embodiment, the light-emitting layer comprises at least one emitter material and at least two matrix materials, wherein one of the matrix materials is a compound of the formula (I) and the other matrix material(s) is/are used as co-host(s). Suitable other host materials than the compounds of formula (I) (co-hosts) are mentioned above and below (second host material).

However, it is also possible to use two or more different compounds of formula (I) as host material in the light-emitting layer in an OLED of the present application.

Said second host material is selected from general phosphorescent host materials mentioned above. Specific examples are selected from above mentioned compounds, preferably, nitrogen containing heteroaromatics, more preferably, following general formula (N-1). The present invention therefore further relates to an organic electroluminescence device, wherein the light emitting layer comprises a heterocyclic compound represented by the general formula (N-1) and preferably at least one compound of formula (I).

(N-1)

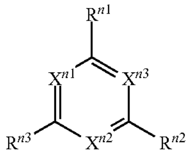

$X^{n1}$ to $X^{n3}$ each independently represents $CR^{n4}$ or N, $R^{n1}$ to $R^{n4}$ each independently represents hydrogen, halogen atom, a substituted or unsubstituted alkyl group having 1 to 25 carbon atoms, a substituted or unsubstituted alkenyl group having 2 to 25 carbon atoms, a substituted or unsubstituted alkynyl group having 2 to 25 carbon atoms, a substituted or unsubstituted cycloalkyl group having 3 to 25 carbon atoms, a substituted or unsubstituted alkoxy group having 1 to 25 carbon atoms, a substituted or unsubstituted aryl group having 6 to 24 carbon atoms, a substituted or unsubstituted heterocyclic group having 5 to 30 cyclic atoms, a substituted or unsubstituted aryloxy group having 6 to 24 carbon atoms, a substituted or unsubstituted alkylthio group having 1 to 25 carbon atoms, a substituted or unsubstituted arylthio group having 6 to 24 carbon atoms, alkyl or aryl substituted silyl group, alkyl or aryl substituted carbonyl group, or a substituted phosphoryl group, in the case of at least one of $X^{n1}$ to $X^{n3}$ represent $CR^{n4}$, two or more substituents selected among $R^{n1}$ to $R^{n4}$ may be bonded to each other to form a ring structure.

In one embodiment of the present invention, preferable heteroaromatics for the second host is specific nitrogen containing heteroaromatics with electron donating nitrogen atom(s), such as pyrrole compounds, indole compounds, carbazole compounds, acridine compounds, phenoxadine compounds, phenothiazine compounds, imidazole compounds, benzimidazole compounds, and benzimidazobenzimidazole compounds, which may have additional substituents and additional fused ring structures, preferably carbazole compounds, more preferably following general formula (P-1).

(P-1)

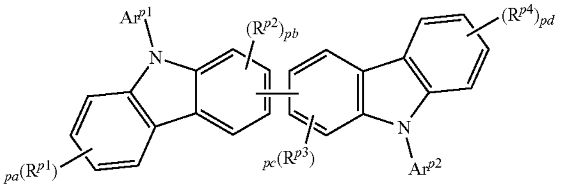

$Ar^{p1}$ and $Ar^{p2}$ each independently represents a substituted or unsubstituted aryl group having 6 to 24 carbon atoms, preferably, phenyl group, biphenyl group, terphenyl group, quarterphenyl group, naphthyl group, phenanthryl group or triphenylenyl group, or a substituted or unsubstituted heterocyclic group having 5 to 30 cyclic atoms, preferably, carbazoryl group, dibenzofuranyl group or dibenzothiophenyl group, or a substituent which consists of substituted or un substituted aryl group and substituted or unsubstituted heteroaryl group, preferably, aryl group and dibenzofuran group, aryl group and dibenzothiophene group or aryl group and carbazole group.

$R^{p1}$ to $R^{p4}$ each independently represents halogen atom, a substituted or unsubstituted alkyl group having 1 to 25 carbon atoms, a substituted or unsubstituted alkenyl group having 2 to 25 carbon atoms, a substituted or unsubstituted alkynyl group having 2 to 25 carbon atoms, a substituted or unsubstituted cycloalkyl group having 3 to 25 carbon atoms, a substituted or unsubstituted alkoxy group having 1 to 25 carbon atoms, a substituted or unsubstituted aryl group having 6 to 24 carbon atoms, a substituted or unsubstituted heterocyclic group having 5 to 30 cyclic atoms, a substituted or unsubstituted aryloxy group having 6 to 24 carbon atoms, a substituted or unsubstituted alkylthio group having 1 to 25 carbon atoms, a substituted or unsubstituted arylthio group having 6 to 24 carbon atoms, alkyl or aryl substituted silyl group, alkyl or aryl substituted carbonyl group, a substituted phosphoryl group or a cyano group, or $R^{50}$ and $R^{51}$ may be bonded to each other to form a substituted or unsubstituted aryl group having 6 to 24 carbon atoms.

pa and pd each independently represents 0 to 4.

pb and pc each independently represents 0 to 3.

In one embodiment of the present invention, aryl or heteroaryl substituted amine compounds can be preferably used for the second host material. Latter mentioned materials for hole transporting layer can be preferably used as a second host material.

In one embodiment of the present invention, fused aryl compounds or fused heteroaryl compounds are preferable for the second host material.

According to another embodiment, the light-emitting layer comprises at least one emitter material and at least two matrix materials (host materials), wherein one of the matrix materials is a material selected from the above mentioned known host materials and the other matrix material(s) is/are used as co-host(s). Suitable other host material(s) is/are selected from before mentioned general host materials.

In said embodiment, the light-emitting layer is formed from 0.1 to 70% by weight, preferably 1 to 30% by weight, of the at least one emitter material and 30 to 99.9% by weight, preferably 70 to 99% by weight, of a first host and the further matrix material, where the sum total of the at least one emitter material, the further matrix materials adds up to 100% by weight. The content ratio of the compound of the first host material and the second matrix material as co-host in the light emitting layer is not particularly limited and may be selected accordingly, and the ratio of first host material: second host material is preferably 1:99 to 99:1, more preferably 10:90 to 90:10, each based on mass.

A phosphorescent dopant (phosphorescent emitting material) that forms the emitting layer is a compound that can emit light from triplet excited state. The phosphorescent dopant is not limited as long as it can emit from triplet excited state. The phosphorescent dopant is preferably an organic metal complex containing at least one metal selected from Ir, Pt, Os, Au, Cu, Re and Ru and a ligand. It is preferred that the ligand have an ortho-metalated bond. In respect of a high phosphorescent quantum yield and capability of improving external quantum yield of an emitting device, the phosphorescent dopant is preferably a compound having a metal atom selected from Ir, Os and Pt. Further preferable is a metal complex such as an iridium complex, an osmium complex and a platinum complex, with an ortho-metalated complex being more preferable.

The present invention therefore further relates to the organic electroluminescence device according to the present invention, wherein the light emitting layer comprises a phosphorescent material, which is an ortho-metallated complex comprising a metal atom selected from iridium (Ir), osmium (Os) and platinum (Pt).

Among them, an iridium complex and a platinum complex are more preferable, and an ortho-metalated iridium complex is particularly preferable.

The phosphorescent host is a compound having a function of allowing a phosphorescent dopant to emit light efficiently by efficiently confining the triplet energy of the phosphorescent dopant in the emitting layer. The material for an organic EL device according to the invention is preferable as the phosphorescent host. The emitting layer may comprise one kind of the material for an organic EL device according to the invention or may comprise two or more kinds of the material for an organic EL device according to the invention.

When the material for an organic EL device according to the invention is used as a host material of the emitting layer, the emission wavelength of the phosphorescent dopant contained in the emitting layer is not particularly restricted. It is preferred that at least one kind of the phosphorescent dopant materials contained in the emitting layer have a peak of an emission wavelength of 490 nm or more and 700 nm or less, more preferably 490 nm or more and 650 nm or less. As for the emission color of the emitting layer, red, yellow and green are preferable, for example. By using the compound according to the invention as the host material and by forming an emitting layer by doping the phosphorescent dopant having such an emission wavelength, it is possible to obtain a long-lived organic EL device.

In the organic EL device according to the invention, other compounds than the material for an organic EL device according to the invention can appropriately be selected as the phosphorescent host according to the above-mentioned purpose.

The material for an organic EL device according to the invention and other compounds may be used in combination as the phosphorescent host material in the same emitting layer. When plural emitting layers are present, as the phosphorescent host material for one of these emitting layers, the material for an organic EL device according to the invention is used, and as the phosphorescent host material for one of other emitting layers, other compounds than the material for an organic EL device according to the invention may be used. The material for an organic EL device according to the invention can be used in an organic layer other than the emitting layer. In that case, as the phosphorescent host of the emitting layer, other compounds than the material for an organic EL device according to the invention may be used.

Suitable metal complexes (dopants, especially phosphorescent dopants) for use in the inventive OLEDs, preferably as emitter material, are described as following general formula (E-1).

(E-1)

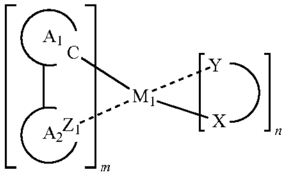

Wherein $M_1$ is a metal having an atomic weight greater than 40, preferably, Ir, Pt, Pd, Rh, Re, Ru, Os, Tl, Pb, Bi, In, Sn, Sb, Te, Au, or Ag, more preferably Ir, Pt, or Os, most preferably Ir, $A_1$ represents aryl group having 6 to 24 carbon atoms or heterocyclic group having 3 to 24 cyclic atoms, preferably above mentioned substituents which may have additional substituents, $A_2$ represents nitrogen containing heterocyclic group having 3 to 24 cyclic atoms, preferably above mentioned substituents which may have additional substituents, $Z_1$ represents C or N, preferably N, (X—Y) is an ancillary ligand, preferably acetylacetonate compounds, picolinate compounds, more preferably acetylacetonate compounds, m is a value from 1 to the maximum number of ligands that may be attached to the metal;

and m+n is the maximum number of ligands that may be attached to the metal.

If m or n is more than 2, two or more ligands may be the same or different in each occurrence.

According to one embodiment, a metal complex represented by the following general formula (E-2) is more preferable especially for green and yellow emitter, (E-2)

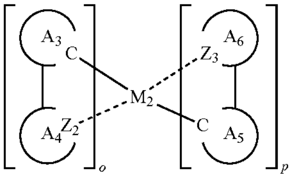

Wherein $M_2$ is a metal having an atomic weight greater than 40, preferably, Ir, Pt, Pd, Rh, Re, Ru, Os, Tl, Pb, Bi, In, Sn, Sb, Te, Au, or Ag, more preferably Ir, Pt, or Os, most preferably Ir, $A_3$, $A_5$ each independently represents aryl group having 6 to 24 carbon atoms or heterocyclic group having 3 to 24 cyclic atoms, preferably above mentioned substituents which may have additional substituents, $A_4$, $A_6$ each independently represents nitrogen containing heterocyclic group having 3 to 24 cyclic atoms, preferably above mentioned substituents which may have additional substituents, $Z_2$, $Z_3$ each independently represents C or N, preferably N, o is a value from 1 to the maximum number of ligands that may be attached to the metal; and o+p is the maximum number of ligands that may be attached to the metal.

If o or p is more than 2, two or more ligands may be the same or different in each occurrence.

A metal complex represented by the following general formula (T) or (β) is more preferable.

(T)

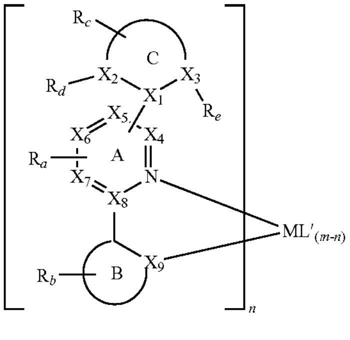

M represents the above mentioned metal atom,

B, C each independently represents aryl group having 6 to 24 carbon atoms or heteroaryl group having 3 to 24 cyclic atoms, preferably phenyl group, dibenzofuran group, dibenzothiophene group, aza-dibenzofuran group, aza-dibenzothiophene group, which may have additional substituents, A represents a nitrogen containing 6 membered ring structure which may have additional substituents, preferably pyridine, pyrimidine, more preferably pyridine, X4 to X8 each represents C or N, preferably C, m represents oxidation state of the metal M, n is 1 or greater than 1, L' represents following chemical structure, (L')

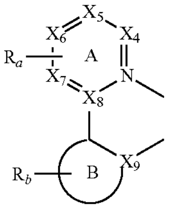

wherein A represents nitrogen containing 6 membered ring structure which may have additional substituents, preferably pyridine, pyrimidine, more preferably pyridine, B represents aryl group having 6 to 24 carbon atoms or heteroaryl group having 3 to 24 cyclic atoms, preferably phenyl group, dibenzofuran group, dibenzothiophene group, aza-dibenzofuran group, aza-dibenzothiophene group, which may have additional substituents, X9 represents C or N, preferably, N.

Ra, Rb, Rc or Rd each independently represents hydrogen, a substituted or unsubstituted alkyl group having 1 to 25 carbon atoms, a substituted or unsubstituted alkoxy group having 1 to 25 carbon atoms, a substituted or unsubstituted amino group, a substituted or unsubstituted alkenyl group having 2 to 25 carbon atoms, a substituted or unsubstituted alkynyl group having 2 to 25 carbon atoms, a substituted or unsubstituted aralkyl group having 7 to 24 carbon atoms, a substituted or unsubstituted aryl group having 6 to 24 carbon atoms or a substituted or unsubstituted heterocyclic group having 5 to 30 cyclic atoms, (β)

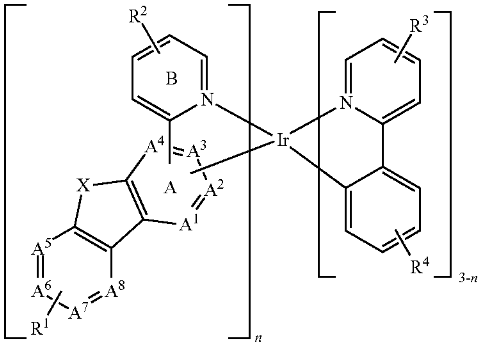

Wherein X represents NR, oxygen atom, sulfur atom, BR or Selenium atom,

R represents hydrogen atom, a substituted or unsubstituted alkyl group having 1 to 25 carbon atoms, $A^1$ to $A^8$ independently represents CH, $CR^5$ or N, preferably CH or $CR^5$, $R^1$ to $R^5$ each independently represents a substituted or unsubstituted alkyl group having 1 to 25 carbon atoms, a substituted or unsubstituted aryl group having 6 to 24 ring carbon atoms, n is 1, 2 or 3, preferably 1.

In another embodiment, a metal complex represented by any one of the following general formula (V), (X), (Y), (Z) can be used.

(V)

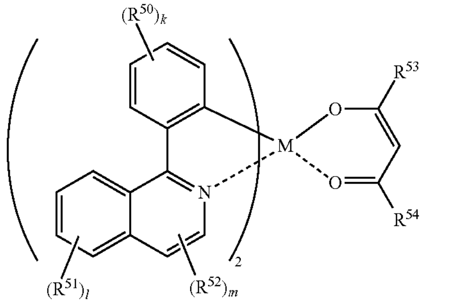

(X)

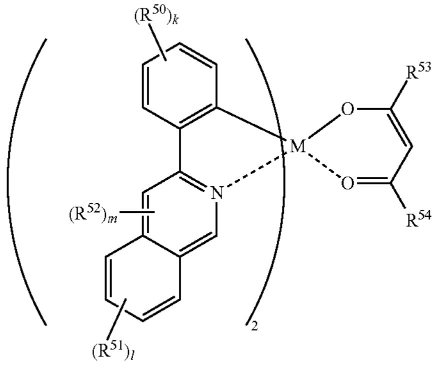

(Y)

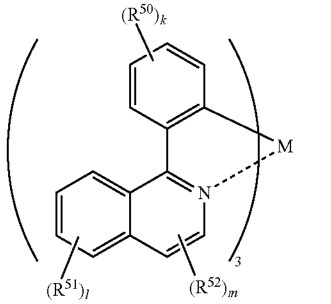

(Z)

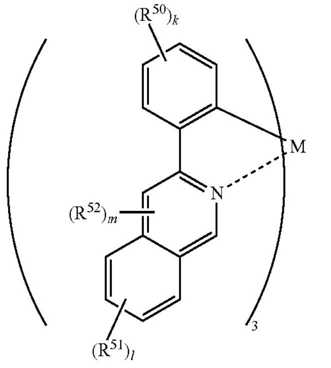

Wherein $R^{50}$ to $R^{52}$ each represents a substituted or unsubstituted alkyl group having 1 to 25 carbon atoms, a substituted or unsubstituted aryl group having 6 to 24 ring carbon atoms, k is 0, 1, 2, 3 or 4, m is 0, 1 or 2, l is 0, 1, 2, 3 or 4, M represents iridium atom (Ir), osmium atom (Os) or platinum atom (Pt).

Formula (V) is preferably represented by formula (V-1). Formula (X) is preferably represented by formula (X-1) or (X-2).

(V-1)

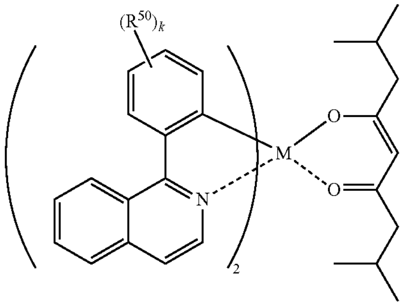

(X-1)

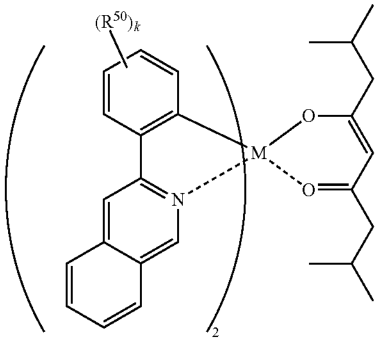

(X-2)

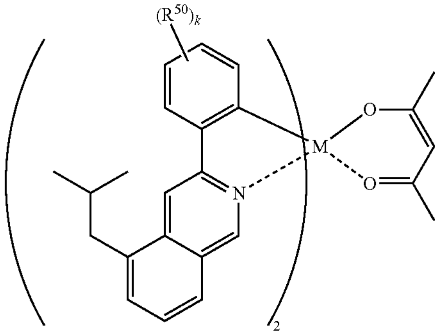

Wherein $R^{50}$, M and k are as defined in formula (V) and (X).

(2) Fluorescent Emitting Layer

The fluorescent emitting layer usually comprises at least one emitter material and at least one host material.

A host material for fluorescent emitting layer is usually selected from general host materials, which preferably have wider band-gap than the emitter material to get highly efficient light emission from the emitter through energy transfer mechanism from the excited host to the emitter. Specific examples of the preferable fluorescent host are, substituted or unsubstituted above mentioned heterocyclic compound; or substituted or unsubstituted aromatic hydrocarbon compound, such as oligo-phenylene compounds, naphthalene compounds, fluorene compounds, fluoranthene compounds, anthracene compounds, phenanthrene compounds, pyrene compounds, triphenylene compounds, benzanthracene compounds, chrysene compounds, benzphenanthrene compounds, naphthacene derivatives, benzochrysene compounds, preferably anthracene compounds, pyrene compounds and naphthacene compounds, more preferably, anthracene compounds represented by following general formula (X) especially for fluorescent blue or green device.

(X)

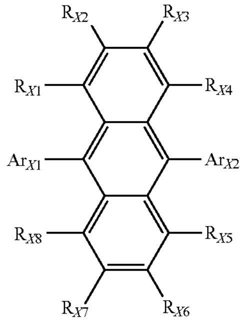

$Ar_{X1}$ and $Ar_{X2}$ are independently a substituted or unsubstituted aryl group including 6 to 50 ring carbon atoms, preferably phenyl group, biphenyl group, naphthyl group, phenanthryl group, fluorenyl group, fluoranthenyl group, anthryl group, pyrenyl group, benzophenanthryl group, triphenylenyl group, benzanthryl group, benzochrysenyl group, or a heterocyclic group including 5 to 50 ring atoms, preferably, benzofuranyl group, benzothiophenyl group, indolyl group, dibenzothiophenyl group, dibenzofuranyl group, carbazolyl group, benzocarbazoryl group, dibenzocarbazoryl group, indolophenanthryl group, naphthobenzofuranyl group, naphthobenzothiophenyl group, dinaphthofuranyl group, dinaphthothiophenyl group, benzophenanthlofuranyl group, benzophenanthlothiophenyl group, benzofurodibenzofuranyl group, benzothiodibenzothiophenyl group, benzofurodibenzotihiophenyl group, benzothiodibenzofuranyl group, more preferably oxygen or sulfur containing heteroaromatics, such as furan or thiophene containing heteroaromatics in one of the part of the heteroaromatics.

$R_{X1}$ to $R_{X8}$ are independently a hydrogen atom, a substituted or unsubstituted aryl group including 6 to 50 ring carbon atoms, a substituted or unsubstituted heterocyclic group including 5 to 50 ring atoms, an alkyl group including 1 to 50 carbon atoms, a substituted or unsubstituted alkoxy group including 1 to 50 carbon atoms, a substituted or unsubstituted aralkyl group including 7 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted alkoxycarbonyl group including 2 to 50 carbon atoms, a substituted or unsubstituted silyl group, a carboxy group, a halogen atom, a cyano group, a nitro group or a hydroxyl group.

An emitter material for fluorescent emitting layer is usually selected from general emitter materials or fluorescent dyes, which preferably have high absorption co-efficiency and high quantum efficiency to get highly efficient light emission from the emitter. Specific examples of the preferable fluorescent emitter are, aromatic hydrocarbon compounds, such as oligo-phenylene compounds, naphthalene compounds, fluorene compounds, fluoranthenyl group, fused fluoranthenyl group, anthracene compounds, phenanthrene compounds, pyrene compounds, triphenylene compounds, benzanthracene compounds, chrysene compounds, benzphenanthrene compounds, naphthacene derivstives, benzochrysene compounds; aromatic or heterocyclic amine compounds represented by following general formula (Y); organic boron compounds represented by general formula (Z), (Y)

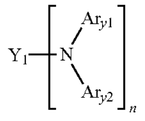

$Y_1$ is a substituted or unsubstituted aromatic hydrocarbon group including 6 to 50 ring carbon atoms, preferably fused aromatic hydrocarbon group, or substituted or unsubstituted heterocyclic group having 5 to 50 cyclic atoms.

$Ar_{y1}$ and $Ar_{y2}$ are independently a substituted or unsubstituted aryl group including 6 to 50 ring carbon atoms or a substituted or unsubstituted heterocyclic ring group including 5 to 50 ring atoms, preferably, oxygen or sulfur containing heterocyclic group.

Specific examples of $Y_1$ include the above-mentioned fused aryl group. $Y_1$ is preferably a substituted or unsubstituted anthryl group; a substituted or unsubstituted pyrenyl group; a substituted or unsubstituted chrysenyl group; substituted or unsubstituted fluorenyl group, especially substituted or unsubstituted mono-, di-, or tri-benzofuro-fused fluorene, or substituted or unsubstituted mono-, di-, or tri-benzothio-fused fluorene; substituted or unsubstituted dibenzofuran containing heterocyclic group; substituted or unsubstituted dibenzothiophene containing heterocyclic group.

n is an integer of 1 to 4, preferably 1 or 2.

Electron-Transporting Layer

The electron-transporting layer is an organic layer that is formed between the emitting layer and the cathode and has a function of transporting electrons from the cathode to the emitting layer. When the electron-transporting layer is formed of plural layers, an organic layer that is nearer to the cathode is often defined as the electron-injecting layer. The electron-injecting layer has a function of injecting electrons from the cathode efficiently to the organic layer unit.

According to one embodiment, it is preferred that an electron-transporting layer further comprises one or more layer(s) like an electron injection layer to enhance efficiency and lifetime of the device, a hole blocking layer, an exciton blocking layer or a triplet blocking layer.

In one embodiment of the present invention, the compound of the formula (I) is present in the electron transporting layer, as an electron transporting material, an electron-injecting material, a hole blocking material, a exciton blocking material and/or a triplet blocking material.

According to one embodiment, it is preferred that an electron-donating dopant be contained in the interfacial region between the cathode and the emitting unit. Due to such a configuration, the organic EL device can have an increased luminance or a long life. Here, the electron-donating dopant means one having a metal with a work function of 3.8 eV or less. As specific examples thereof, at least one selected from an alkali metal, an alkali metal complex, an alkali metal compound, an alkaline earth metal, an alkaline earth metal complex, an alkaline earth metal compound, a rare earth metal, a rare earth metal complex and a rare earth metal compound or the like can be mentioned.

As the alkali metal, Na (work function: 2.36 eV), K (work function: 2.28 eV), Rb (work function: 2.16 eV), Cs (work function: 1.95 eV) and the like can be given. One having a work function of 2.9 eV or less is particularly preferable. Among them, K, Rb and Cs are preferable. Rb or Cs is further preferable. Cs is most preferable. As the alkaline earth metal, Ca (work function: 2.9 eV), Sr (work function: 2.0 eV to 2.5 eV), Ba (work function: 2.52 eV) and the like can be given. One having a work function of 2.9 eV or less is particularly preferable. As the rare-earth metal, Sc, Y, Ce, Tb, Yb and the like can be given. One having a work function of 2.9 eV or less is particularly preferable.

Examples of the alkali metal compound include an alkali oxide such as $Li_2O$, $Cs_2O$ or $K_2O$, and an alkali halide such as LiF, NaF, CsF and KF. Among them, LiF, $Li_2O$ and NaF are preferable. Examples of the alkaline earth metal compound include BaO, SrO, CaO, and mixtures thereof such as $Ba_xSr_{1-x}O$ ($0<x<1$) and $Ba_xCa_{1-x}O$ ($0<x<1$). Among them, BaO, SrO and CaO are preferable. Examples of the rare earth metal compound include $YbF_3$, $ScF_3$, $ScO_3$, $Y_2O_3$, $Ce_2O_3$, $GdF_3$ and $TbF_3$. Among these, $YbF_3$, $ScF_3$ and $TbF_3$ are preferable.

The alkali metal complexes, the alkaline earth metal complexes and the rare earth metal complexes are not particularly limited as long as they contain, as a metal ion, at least one of alkali metal ions, alkaline earth metal ions, and rare earth metal ions. Meanwhile, preferred examples of the ligand include, but are not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfluborane, bipyridyl, phenanthroline, phthalocyanine, porphyrin, cyclopentadiene, β-diketones, and azomethines.

Regarding the addition form of the electron-donating dopant, it is preferred that the electron-donating dopant be formed in a shape of a layer or an island in the interfacial region. A preferred method for the formation is a method in which an organic compound (a light emitting material or an electron-injecting material) for forming the interfacial region is deposited simultaneously with deposition of the electron-donating dopant by a resistant heating deposition method, thereby dispersing the electron-donating dopant in the organic compound. The dispersion concentration of the organic compound: the electron-donating dopant (molar ratio) is 100:1 to 1:100, preferably 5:1 to 1:5.

In a case where the electron-donating dopant is formed into the shape of a layer, the light-emitting material or electron-injecting material which serves as an organic layer in the interface is formed into the shape of a layer. After that, a reductive dopant is solely deposited by the resistant heating deposition method to form a layer preferably having a thickness of from 0.1 nm to 15 nm. In a case where the electron-donating dopant is formed into the shape of an island, the emitting material or the electron-injecting material which serves as an organic layer in the interface is formed into the shape of an island. After that, the electron-donating dopant is solely deposited by the resistant heating deposition method to form an island preferably having a thickness of from 0.05 nm to 1 nm.

The ratio of the main component and the electron-donating dopant in the organic EL device according to the invention is main component:electron-donating dopant=5:1 to 1:5 in terms of molar ratio, more preferably 2:1 to 1:2.

As the electron-transporting material used in the electron-transporting layer other than a compound of the formula (I), an aromatic heterocyclic compound having one or more hetero atoms in the molecule may preferably be used. In particular, a nitrogen containing heterocyclic compound is preferable.

According to one embodiment, it is preferable that the electron-transporting layer comprises a nitrogen containing heterocyclics metal chelate, such as 8-hydroxyquinolinolato aluminum, which is generally called as $Alq_3$.

According to the other embodiment, it is preferable that the electron-transporting layer comprising substituted or unsubstituted nitrogen containing heterocyclic compound. Specific examples of the preferable heterocyclic compound for the elecrtron-transporting layer are, 6-membered azine compounds; such as pyridine compounds, pyrimidine compounds, triazine compounds, pyrazine compounds, preferably pyrimidine compounds or triazine compounds; 6-membered fused azine compounds, such as quinolone compounds, isoquinoline compounds, quinoxaline compounds, quinazoline compounds, phenanthroline compounds, benzoquinoline compounds, benzoisoquinoline compounds, dibenzoquinoxaline compounds, preferably quinolone compounds, isoquinoline compounds, phenanthroline compounds; 5-membered heterocyclic compounds, such as imidazole compounds, oxazole compounds, oxadiazole compounds, triazole compounds, thiazole compounds, thiadiazole compounds; fused imidazole compounds, such as benzimidazole compounds, imidazopyridine compounds, naphthoimidazole compounds, benzimidazophenanthridine compounds, benzimidzobenzimidazole compounds, preferably benzimidazole compounds, imidazopyridine compounds or benzimidazophenanthridine compounds.

According to the other embodiment, it is preferable the electron-transporting layer comprises phosphine oxide compound represented as $Ar_{p1}Ar_{p2}Ar_{p3}P{=}O$.

$Ar_{p1}$ to $Ar_{p3}$ are the substituents of phosphor atom and each independently represents substituted or unsubstituted above mentioned aryl group or substituted or unsubstituted above mentioned heterocyclic group.

According to the other embodiment, it is preferable that the electron-transporting layer comprises aromatic hydrocarbon compounds.

Specific examples of the preferable aromatic hydrocarbon compounds for the electron-transporting layer are, oligophenylene compounds, naphthalene compounds, fluorene compounds, fluoranthenyl group, anthracene compounds, phenanthrene compounds, pyrene compounds, triphenylene compounds, benzanthracene compounds, chrysene compounds, benzphenanthrene compounds, naphthacene derivstives, and benzochrysene compounds, preferably anthracene compounds, pyrene compounds and fluoranthene compounds.

The present invention therefore relates to an organic electroluminescence device, wherein an electron transporting layer is provided between the cathode and the light emitting layer, and the electron transporting layer comprises at least one compound of formula (I).

The present invention therefore further relates to an organic electroluminescence device, wherein a hole blocking layer is provided between the electron transporting layer and the light emitting layer, and the hole blocking layer comprises at least one compound of formula (I).

According to one embodiment, it is preferred that the other electron transporting region is further comprised between the hole blocking layer comprising the compound of general formula (I) and cathode. Said electron transporting region generally comprises one or more electron transporting layer(s).

Above mentioned electron injection materials, such as alkali metal compound or alkali metal complex, preferably comprising as one of electron transporting layer at the interface of cathode. Second electron transporting layer preferably comprises between hole blocking layer and said electron transporting layer comprising electron injection material.

Above mentioned heterocyclic compounds or fused aromatic compounds are preferably used for second electron transporting layer, more preferably heterocyclic compounds represented by general formulae (ET-1), (ET-2), (ET-3) or (ET-4).

(ET-1)

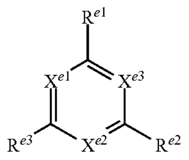

$X^{e1}$ to $X^{e3}$ each independently represents $CR^{e4}$ or N, preferably more than two of $X^{e1}$ to $X^{e3}$ are N, $R^{e1}$ to $R^{e4}$ each independently represents hydrogen, halogen atom, a substituted or unsubstituted alkyl group having 1 to 25 carbon atoms, a substituted or unsubstituted alkenyl group having 2 to 25 carbon atoms, a substituted or unsubstituted alkynyl group having 2 to 25 carbon atoms, a substituted or unsubstituted cycloalkyl group having 3 to 25 carbon atoms, a substituted or unsubstituted alkoxy group having 1 to 25 carbon atoms, a substituted or unsubstituted aryl group having 6 to 24 carbon atoms, a substituted or unsubstituted heterocyclic group having 5 to 30 cyclic atoms, a substituted or unsubstituted aryloxy group having 6 to 24 carbon atoms, a substituted or unsubstituted alkylthio group having 1 to 25 carbon atoms, a substituted or unsubstituted arylthio group having 6 to 24 carbon atoms, alkyl or aryl substituted silyl group, alkyl or aryl substituted carbonyl group, or a substituted phosphoryl group, in the case of at least one of $X^{e1}$ to $X^{e3}$ represent $CR^{e4}$, two or more substituents selected among $R^{e1}$ to $R^{e4}$ may be bonded to each other to form a ring structure.

(ET-2)

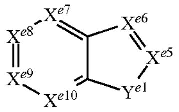

$X^{e6}$ to $X^{e10}$ each independently represents $CR^{e5}$ or N, preferably at least $X^{e6}$ is N, $Y^{e1}$ represents oxygen atom, sulfur atom, $CR^{e6}R^{e7}$ or $NR^{e7}$, $R^{e5}$ to $R^{e8}$ each independently represents hydrogen, halogen atom, a substituted or unsubstituted alkyl group having 1 to 25 carbon atoms, a substituted or unsubstituted alkenyl group having 2 to 25 carbon atoms, a substituted or unsubstituted alkynyl group having 2 to 25 carbon atoms, a substituted or unsubstituted cycloalkyl group having 3 to 25 carbon atoms, a substituted or unsubstituted alkoxy group having 1 to 25 carbon atoms, a substituted or unsubstituted aryl group having 6 to 24 carbon atoms, a substituted or unsubstituted heterocyclic group having 5 to 30 cyclic atoms, a substituted or unsubstituted aryloxy group having 6 to 24 carbon atoms, a substituted or unsubstituted alkylthio group having 1 to 25 carbon atoms, a substituted or unsubstituted arylthio group having 6 to 24 carbon atoms, alkyl or aryl substituted silyl group, alkyl or aryl substituted carbonyl group, or a substituted phosphoryl group, two or more substituents selected among $R^{e5}$ to $R^{e8}$ may be bonded to each other to form a ring structure.

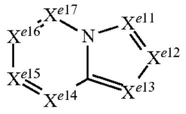

(ET-3)

$X^{e11}$ to $X^{e17}$ each independently represents $CR^{e9}$ or N, preferably at least one selected from $X^{e11}$, $X^{e12}$ and $X^{e13}$ is N, $R^{e9}$ each independently represents hydrogen, halogen atom, a substituted or unsubstituted alkyl group having 1 to 25 carbon atoms, a substituted or unsubstituted alkenyl group having 2 to 25 carbon atoms, a substituted or unsubstituted alkynyl group having 2 to 25 carbon atoms, a substituted or unsubstituted cycloalkyl group having 3 to 25 carbon atoms, a substituted or unsubstituted alkoxy group having 1 to 25 carbon atoms, a substituted or unsubstituted aryl group having 6 to 24 carbon atoms, a substituted or unsubstituted heterocyclic group having 5 to 30 cyclic atoms, a substituted or unsubstituted aryloxy group having 6 to 24 carbon atoms, a substituted or unsubstituted alkylthio group having 1 to 25 carbon atoms, a substituted or unsubstituted arylthio group having 6 to 24 carbon atoms, alkyl or aryl substituted silyl group, alkyl or aryl substituted carbonyl group, or a substituted phosphoryl group, two or more substituents selected among $R^{e9}$ may be bonded to each other to form a ring structure.

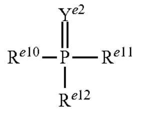

(ET-4)

$R^{e10}$ to $R^{e12}$ each independently represents a substituted or unsubstituted aryl group having 6 to 24 carbon atoms, a substituted or unsubstituted heterocyclic group having 5 to 30 cyclic atoms, two or more substituents selected among $R^{e10}$ to $R^{e12}$ may be bonded to each other to form a ring structure, preferably at least one of $R^{e10}$ to $R^{e12}$ have additional substituted or unsubstituted aryl group having 6 to 24 carbon atoms, or substituted or unsubstituted heterocyclic group having 5 to 30 cyclic atoms, $Y^{e2}$ represents oxygen atom or sulfur atom.

Hole-Transporting Layer

The hole-transporting layer is an organic layer that is formed between the emitting layer and the anode, and has a function of transporting holes from the anode to the emitting layer. If the hole-transporting layer is composed of plural layers, an organic layer that is nearer to the anode may often be defined as the hole-injecting layer. The hole-injecting layer has a function of injecting holes efficiently to the organic layer unit from the anode.

Said hole injection layer is generally used for stabilizing hole injection from anode to hole transporting layer which is generally consist of organic materials.

Organic material having good contact with anode or organic material with p-type doping is preferably used for the hole injection layer.

Acceptor materials, or fused aromatic hydrocarbon materials or fused heterocycles which have high planarity, are preferably used, acceptor materials are more preferably used for the hole injection layer.

Specific examples for acceptor materials are, the quinone compounds with one or more electron withdrawing groups, such as $F_4TCNQ$(2,3,5,6-tetrafluoro-7,7,8,8-tetracyanoquinodimethane), and 1,2,3-tris[(cyano)(4-cyano-2,3,5,6-tetrafluorophenyl)methylene]cyclopropane; hexa-azatriphenylene compounds with one or more electron withdrawing groups, such as hexa-azatriphenylene-hexanitrile; aromatic hydrocarbon compounds with one or more electron withdrawing groups; and aryl boron compounds with one or more electron withdrawing groups.

p-doping is usually consist of one or more p-dopant materials and one or more matrix materials. Matrix materials preferably have shallower HOMO level and p-dopant preferably have deeper LUMO level to enhance the carrier density of the layer. Aryl or heteroaryl amine compounds are preferably used as the matrix materials. Specific examples for the matrix material are the same as that for hole transporting layer which is explained at the later part. Specific examples for p-dopant are the above mentioned acceptor materials, preferably the quinone compounds with one or more electron withdrawing groups, such as $F_4TCNQ$, 1,2,3-Tris[(cyano)(4-cyano-2,3,5,6-tetrafluorophenyl)methylene]cyclopropane.

The ratio of the p-type dopant is preferably less than 20% of molar ratio, more preferably less than 10%, such as 1%, 3%, or 5%.

Hole transporting layer is generally used for injecting and transporting holes efficiently, and aromatic or heterocyclic amine compounds are preferably used.

Specific examples for hole transporting layer are represented as general formula (H),

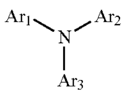

(H)

$Ar_1$ to $Ar_3$ each independently represents substituted or unsubstituted aryl group having 5 to 50 carbon atoms or substituted or unsubstituted heterocyclic group having 5 to 50 cyclic atoms, preferably phenyl group, biphenyl group, terphenyl group, naphthyl group, phenanthryl group, triphenylenyl group, fluorenyl group, spirobifluorenyl group, indenofluorenyl group, carbazolyl group, dibenzofuranyl group, dibenzothiophenyl group, carbazole substituted aryl group, dibenzofuran substituted aryl group or dibenzothiophene substituted aryl group; two or more substituents selected among $Ar^1$ to $Ar^3$ may be bonded to each other to form a ring structure, such as a carbazole ring structure, or a acridane ring structure.

According to one embodiment, it is preferable that at least one of $Ar_1$ to $Ar_3$ have additional one aryl or heterocyclic amine substituent, more preferably $Ar_1$ has an additional aryl amino substituent, at the case of that it is preferable that $Ar_1$ represents substituted or unsubstituted biphenylene group, substituted or unsubstituted fluorenylene group.

A second hole transporting layer is preferably inserted between the first hole transporting layer and the emitting layer to enhance device performance by blocking excess electrons or excitons.

Specific examples for second hole transporting layer is the same as the first hole transporting layer. It is preferably that second hole transporting layer have higher triplet energy to block triplet exciton especially for phosphorescent green device, such as bicarbazole compounds, biphenylamine compounds, triphenylenyl amine compounds, fluorenyl amine compounds, carbazole substituted arylamine compounds, dibenzofuran substituted arylamine compounds, and dibenzothiophene substituted arylamine compounds.

Spacing Layer

The spacing layer is a layer provided between the fluorescent emitting layer and the phosphorescent emitting layer when the fluorescent emitting layer and the phosphorescent emitting layer are stacked in order to prevent diffusion of excitons generated in the phosphorescent emitting layer to the fluorescent emitting layer or in order to adjust the carrier balance. Further, the spacing layer can be provided between the plural phosphorescent emitting layers.

Since the spacing layer is provided between the emitting layers, the material for the spacing layer is preferably a material having both electron-transporting properties and hole-transporting properties. In order to prevent diffusion of the triplet energy in adjacent phosphorescent emitting layers, it is preferred that the spacing layer have a triplet energy of 2.6 eV or more. As the material used for the spacing layer, the same material as those used in the above-mentioned hole-transporting layer can be given.

Barrier Layer

It is preferred that the organic EL device according to the invention have a barrier layer such as an electron-barrier layer, a hole-barrier layer and a triplet barrier layer in a part that is adjacent to the emitting layer. Here, the electron-barrier layer is a layer that serves to prevent leakage of electrons from the emitting layer to the hole-transporting layer, and the hole-barrier layer is a layer that serves to prevent leakage of holes from the emitting layer to the electron-transporting layer.

The triplet barrier layer prevents diffusion of triplet excitons generated in the emitting layer to the surrounding layers, and has a function of preventing energy deactivation of triplet excitons on molecules in the electron-transporting layer other than the emitting dopant by confining the triplet excitons within the emitting layer.

When the triplet barrier layer is provided, in the phosphorescent emitting device, the following is considered. The triplet energy of the phosphorescent emitting dopant is taken as $E^T_d$ and the triplet energy of the compound used as the triplet barrier layer is taken as $E^T_{TB}$. If the energy relationship $E^T_d<E^T_{TB}$ is satisfied, in respect of energy, the triplet excitons of the phosphorescent emitting dopant is confined (i.e. the triplet excitons cannot be moved to other molecules), whereby the energy deactivation route other than emission on the dopant is cut off, leading to efficient emission. However, even when the relationship $E^T_d<E^T_{TB}$ is established, if the energy difference $\Delta E^T=E^T_{TB}-E^T_d$ is small, it is thought that, in an environment at around room temperature where the device is actually driven, due to thermal energy of the surrounding area, the triplet excitons can move to other molecules by endothermically overcoming this energy difference $\Delta E^T$. In particular, in the case of phosphorescent emission that has a longer exciton life as compared with fluorescent emission, effects of the endothermic move of excitons relatively tend to appear. Relative to the thermal energy at room temperature, a larger energy difference $\Delta E^T$ is preferable. The energy difference $\Delta E^T$ is further preferably 0.1 eV or more, and particularly preferably 0.2 eV or more. On the other hand, in a fluorescent device, as the triplet barrier layer of the TTF device configuration disclosed in WO2010/134350A1, the inventive compounds of formula (I) can be used.

The electron mobility of the material constituting the triplet barrier layer is desirably $10^{-6}$ $cm^2/Vs$ or more in a field intensity range of 0.04 to 0.5 MV/cm. As the method for measuring the electron mobility of an organic material, several methods that include the Time of Flight method are known. Here, the electron mobility means an electron mobility that is determined by the impedance spectroscopy.

The electron mobility of the electron-injecting layer is desirably $10^{-6}$ $cm^2/Vs$ or more in a field intensity range of 0.04 to 0.5 MV/cm. The reason is that, by this electron mobility, injection of electrons from the cathode to the electron-transporting layer is promoted, and as a result, injection of electrons to adjacent barrier layer and emitting layer is promoted, enabling the device to be driven at a lower voltage.

The present invention further relates to an electronic equipment comprising the organic electroluminescence device according to the present invention.

The organic EL device using the inventive compounds of formula (I) can be used as an emitting device in a panel module used in various displays.

The organic EL device using the inventive compounds of formula (I) can be used as a display element of a TV, a mobile phone and a PC; or an electronic apparatus such as lightings or the like.

The OLEDs (organic EL devices) can be used in all apparatus in which electroluminescence is useful. Suitable devices (electronic equipment) are preferably selected from stationary and mobile visual display units and illumination units. Stationary visual display units are, for example, visual display units of computers, televisions, visual display units in printers, kitchen appliances and advertising panels, illuminations and information panels. Mobile visual display units are, for example, visual display units in cellphones, tablet PCs, laptops, digital cameras, MP3 players, vehicles and destination displays on buses and trains. Further devices in which the inventive OLEDs can be used are, for example, keyboards; items of clothing; furniture; wallpaper. In addition, the present invention relates to a device selected from the group consisting of stationary visual display units such as visual display units of computers, televisions, visual display units in printers, kitchen appliances and advertising panels, illuminations, information panels, and mobile visual display units such as visual display units in cellphones, tablet PCs, laptops, digital cameras, MP3 players, vehicles and destination displays on buses and trains; illumination units; keyboards; items of clothing; furniture; wallpaper, comprising at least one inventive organic light-emitting diode or at least one inventive light-emitting layer.

The following examples are included for illustrative purposes only and do not limit the scope of the claims. Unless otherwise stated, all parts and percentages are by weight.

EXAMPLES

I Preparation Examples

Synthesis Example 1-1

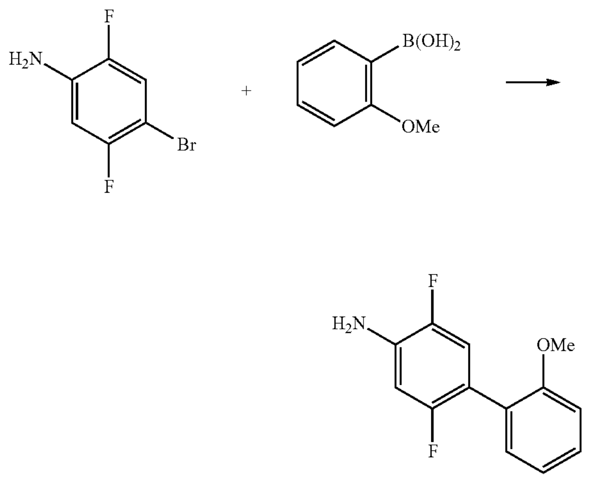

Intermediate 1

In a nitrogen flushed 1000 ml three-necked round-bottomed flask 4-bromo-2,5-difluoroaniline (20.5 g, 99 mmol) and 2-methoxyphenylboronic acid (17.97 g, 118 mmol) were dissolved in dimethoxyethane (200 ml) under nitrogen. 2M-sodium carbonate solution (99 ml, 197 mmol) and tetrakis(triphenylphosphine)palladium(0) (5.69 g, 4.93 mmol) were added to the reaction mixture. The reaction mixture was heated in an oil bath at 100° C. for 7 hours. Water was added to the reaction mixture followed by extraction with toluene. The combined organic layers were concentrated. The crude product was added to a silica gel column and was eluted with dichloromethane and hexane to give 25 g of a white solid (quantitative yield, Intermediate 1). The identification of the Intermediate 1 was made by FD-MS (field desorption mass spectrometry) analysis.

Synthesis Example 1-2

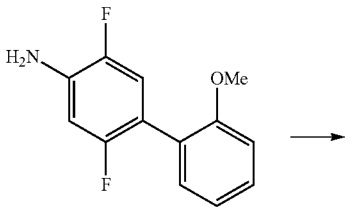

Intermediate 1

-continued

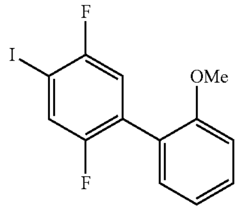

Intermediate 2

In a 1000 ml three-necked round-bottomed flask Intermediate 1 (19.4 g, 82.4 mmol) was dissolved in acetone 164 ml. Hydrochloric acid (80 ml, 494 mmol) was added to the reaction mixture dropwise. Sodium nitrite (6.8 g, 99 mmol), as a solution in water (16 ml), was added to the reaction mixture dropwise. Potassium iodide (20.5 g, 124 mmol), as a solution in water (80 ml), was added to the reaction mixture dropwise. Water was added to the reaction mixture followed by extraction with toluene and then washed with 5% sodium sulfite solution. The combined organic layers were concentrated. The crude product was added to a silica gel column and was eluted with dichloromethane and hexane to give 14.4 g of white solid (86% yield, Intermediate 2). The identification of the Intermediate 2 was made by FD-MS (field desorption mass spectrometry) analysis.

Synthesis Example 1-3

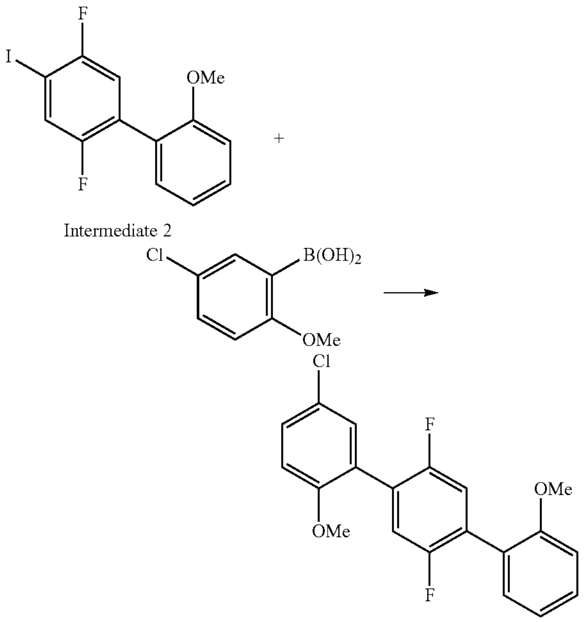

Intermediate 2

Intermediate 3

In a dried 200 ml three-necked round-bottomed flask Intermediate 2 (8.9 g, 25.7 mmol) and (5-chloro-2-methoxyphenyl)boronic acid (5.75 g, 30.9 mmol) were dissolved in dimethoxyethane (52 ml). Tetrakis(triphenylphosphine)palladium(0) (0.594 g, 0.514 mmol) and 2M-sodium carbonate solution (25.7 ml, 51.4 mmol), were added to the reaction mixture. The reaction mixture was heated in an oil bath at 100° C. for 7 hours. Water was added to the reaction mixture followed by extraction with toluene and then washed with water. The combined organic layers were concentrated. The crude product was added to a silica gel column and was eluted with toluene. The crude material was crystallized from ethyl acetate to give 5.3 g of white solid (57% yield, Intermediate 3). The identification of the Intermediate 3 was made by FD-MS (field desorption mass spectrometry) analysis.

Synthesis Example 1-4

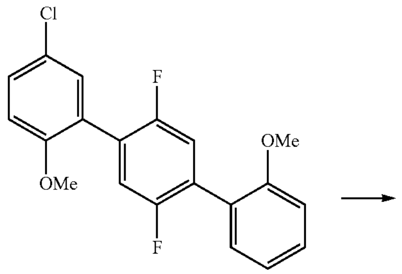

Intermediate 3

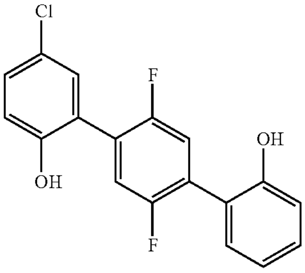

Intermediate 4

In a nitrogen flushed 100 ml three-necked round-bottomed flask Intermediate 3 (4.70 g, 13.03 mmol) was dissolved in dichloromethane under nitrogen. The reaction mixture was cooled to 0° C. with an ice/water bath. 1M-tribromoborane in dichloromethane (52.1 ml, 52.1 mmol) was added to the reaction mixture dropwise. The reaction mixture was heated to room temperature for 2 hours. The reaction mixture was cooled to 0° C. with an ice/water bath. Ice was added to the reaction mixture. The reaction mixture was filtered through a glass fiber paper and the filter cake was rinsed with water and dried to give 4.1 g of white solid (95% yield, Intermediate 4). The identification of the Intermediate 4 was made by FD-MS (field desorption mass spectrometry) analysis.

Synthesis Example 1-5

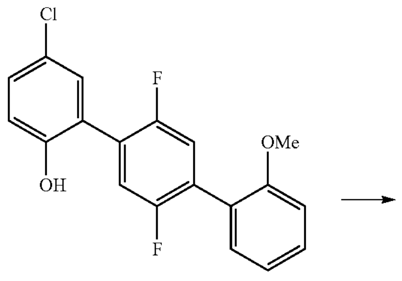

Intermediate 4

-continued

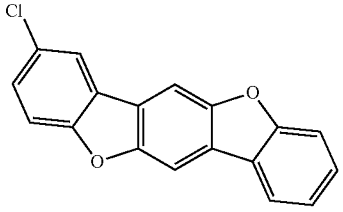

Intermediate 5

In a dried 200 ml three-necked round-bottomed flask Intermediate 4 (2.78 g, 8.36 mmol) and potassium carbonate (3.46 g, 25.1 mmol) were dissolved in N-methyl-2-pyrrolidone (84 ml) under nitrogen. The reaction mixture was heated to 130° C. with an oil bath for 24 hours. The reaction mixture was added to water. The precipitate was rinsed with water and methanol and dried to give 2.0 g of white solid (82% yield, Intermediate 5). The identification of the Intermediate 5 was made by FD-MS (field desorption mass spectrometry) analysis.

Synthesis Example 1-6

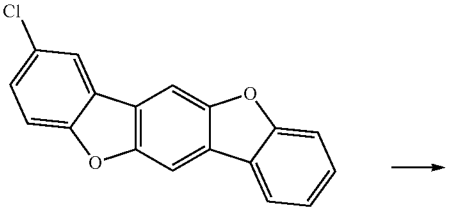

Intermediate 5

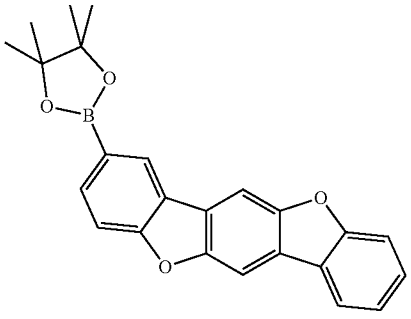

Intermediate 6

In a nitrogen flushed 750 ml three-necked round-bottomed flask Intermediate 5 (4.30 g, 14.7 mmol), bis(pinacolato)diboron (7.47 g, 29.4 mmol), tris(dibenzylideneacetone)dipalladium(0) (0.538 g, 0.588 mmol), dicyclohexylphosphino-2', 4', 6'-triisopropylbiphenyl (1.121 g, 2.352 mmol), potassium acetate (4.33 g, 44.1 mmol) were dissolved in 1,4-dioxane (290 ml) under nitrogen. The reaction mixture was heated to 85° C. with an oil bath for 20 hours. The reaction mixture cooled down, precipitated salts filtrated and dioxane evaporated. Solid residue was added to a silica gel column and was eluted with toluene and heptane (1:1) to give 3.96 g of white solid (70% yield, Intermediate 6). The identification of the Intermediate 6 was made by FD-MS (field desorption mass spectrometry) analysis.

Synthesis Example 1-7

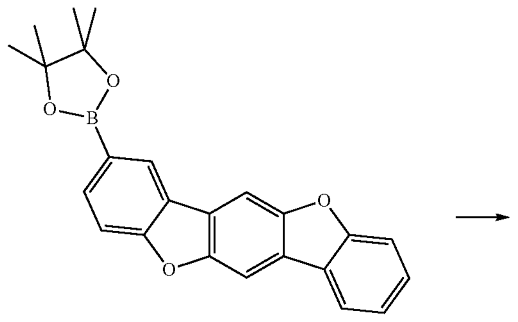

Intermediate 6

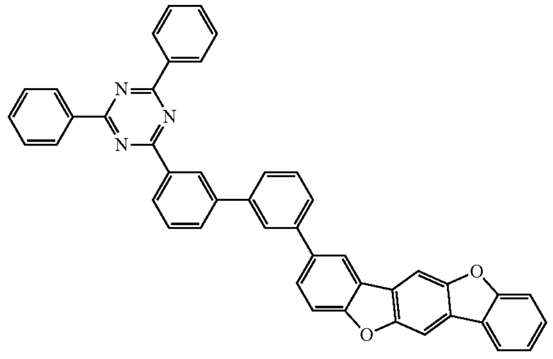

Compound 1

The procedure of the synthesis of Intermediate 1 was repeated except for using Intermediate 6 in place of 2-methoxyphenylboronic acid and using 2-(3'-bromo[biphenyl]-3-yl)-4,6-diphenyl-1,3,5-triazine in place of 4-bromo-2,5-difluoroaniline. The obtained Compound 1 was characterized by FD-MS (field desorption mass spectrometry), maximum ultraviolet absorption wavelength (UV(PhMe) λmax) in toluene, and maximum fluorescence wavelength (FL(PhMe, λex=350 nm) λmax) in toluene. The results are shown below.

FD-MS: calcd. for $C45H27N3O2$=641, found m/z=641 (M+)

UV(PhMe) λmax: 341 nm

FL(PhMe, λex=350 nm) λmax: 461 nm

Synthesis Example 2-1

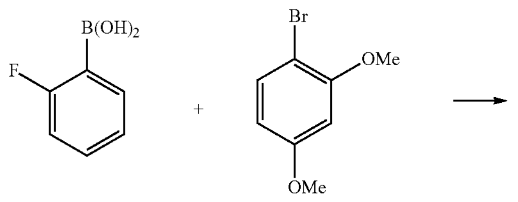

-continued

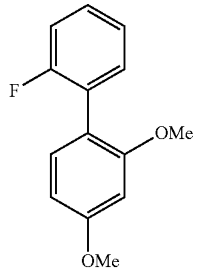

Intermediate 7

The procedure of the synthesis of Intermediate 1 was repeated except for using 1-bromo-2,4-dimethoxybenzene in place of 4-bromo-2,5-difluoroaniline and using 2-fluorophenylboronic acid in place of 2-methoxyphenylboronic acid. The identification of the Intermediate 7 was made by FD-MS (field desorption mass spectrometry) analysis.

Synthesis Example 2-2

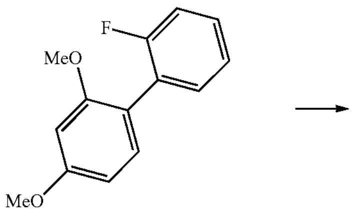

Intermediate 7

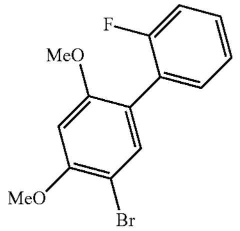

Intermediate 8

In a nitrogen flushed 300 ml three-necked round-bottomed flask Intermediate 7 (15.0 g, 64.5 mmol) was dissolved in DMF (30 ml) under nitrogen. The reaction mixture was cooled to 0° C. with an ice/water bath. N-bromosuccinimide (11.2 g, 62.9 mmol), as a solution in DMF (30 ml), was added to the reaction mixture dropwise. The reaction mixture was heated to room temperature for 20 hours. Water was added to the reaction mixture followed by extraction with toluene. The combined organic layers were dried sodium sulfate, filtered and concentrated. The crude material was crystallized from acetone and methanol to give 14.8 g of white solid (73% yield, Intermediate 8). The identification of the Intermediate 8 was made by FD-MS (field desorption mass spectrometry) analysis.

Synthesis Example 2-3

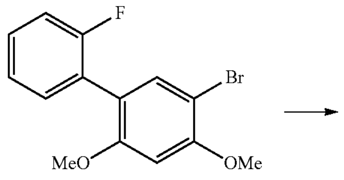

Intermediate 8

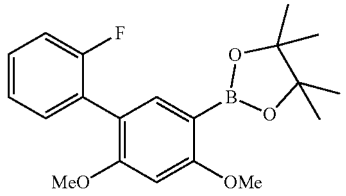

Intermediate 9

In a nitrogen flushed 500 ml three-necked round-bottomed flask Intermediate 8 (14.8 g, 47.6 mmol), bis(pinacolato)diboron (24.2 g, 95 mmol), [1,1'-bis(diphenylphosphino)ferrocene]dichloropalladium(II) complex with dichloromethane (1.5 g, 3 mol %) and potassium acetate (14.0 g, 143 mmol) were dissolved in 1,4-dioxane (200 ml) under nitrogen. The reaction mixture was heated to 70° C. with an oil bath for 20 hours. Toluene was added to the reaction mixture followed by vacuum concentration. The crude product was added to a silica gel column and was eluted with toluene to give 11.7 g of white solid (66% yield). The identification of the Intermediate 9 was made by FD-MS (field desorption mass spectrometry) analysis.

Synthesis Example 2-4

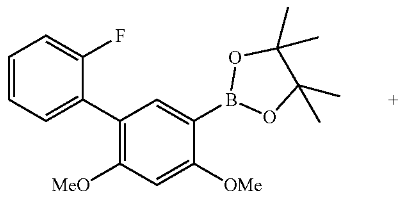

Intermediate 9

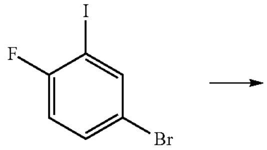

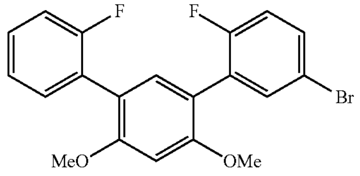

Intermediate 10

The procedure of the synthesis of Intermediate 1 was repeated except for using 4-bromo-1-fluoro-2-iodobenzene in place of 4-bromo-2,5-difluoroaniline and using Intermediate 9 in place of 2-methoxyphenylboronic acid. The identification of the Intermediate 10 was made by FD-MS (field desorption mass spectrometry) analysis.

Synthesis Example 2-5

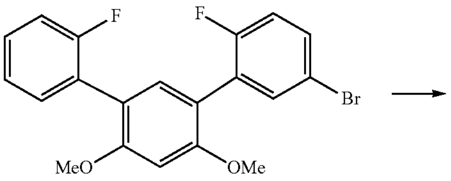

Intermediate 10

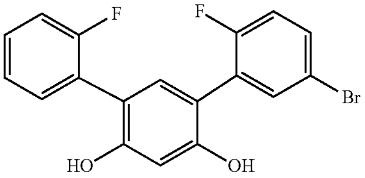

Intermediate 11

The procedure of the synthesis of Intermediate 4 was repeated except for using Intermediate 10 in place of Intermediate 3. The identification of the Intermediate 11 was made by FD-MS (field desorption mass spectrometry) analysis.

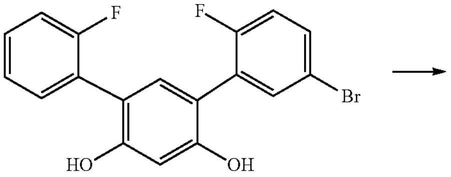

Intermediate 11

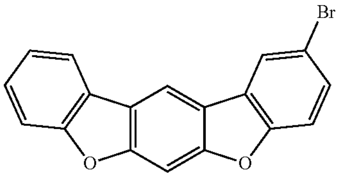

Intermediate 12

Synthesis Example 2-6

The procedure of the synthesis of Intermediate 5 was repeated except for using Intermediate 11 in place of Intermediate 4. The identification of the Intermediate 12 was made by FD-MS (field desorption mass spectrometry) analysis.

Synthesis Example 2-7

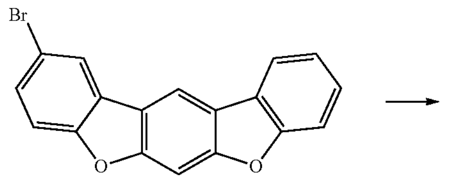

Intermediate 12

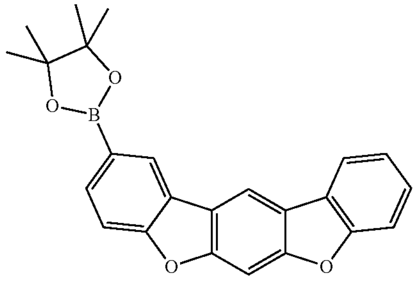

Intermediate 13

The procedure of the synthesis of Intermediate 6 was repeated except for using Intermediate 12 in place of Intermediate 5. The identification of the Intermediate 13 was made by FD-MS (field desorption mass spectrometry) analysis.

Synthesis Example 2-8

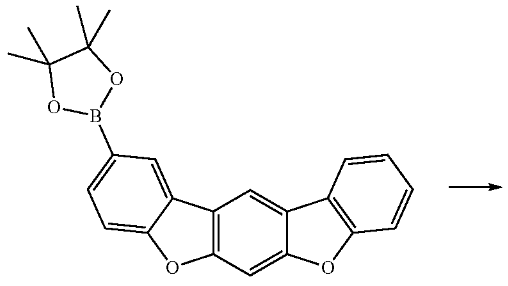

Intermediate 13

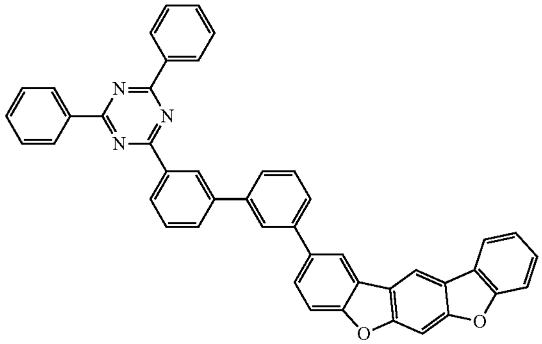

Compound 2

The procedure of the synthesis of Intermediate 1 was repeated except for using Intermediate 13 in place of 2-methoxyphenylboronic acid and using 2-(3'-bromo[biphenyl]-3-yl)-4,6-diphenyl-1,3,5-triazine in place of 4-bromo- 2,5-difluoroaniline. The obtained Compound 2 was characterized by FD-MS (field desorption mass spectrometry), maximum ultraviolet absorption wavelength (UV(PhMe) λmax) in toluene, and maximum fluorescence wavelength (FL(PhMe, λex=350 nm) λmax) in toluene. The results are shown below.

FD-MS: calcd. for C45H27N3O2=641, found m/z=641 (M+)

UV(PhMe) λmax: 335 nm

FL(PhMe, λex=350 nm) λmax: 410 nm

Synthesis Example 3-1

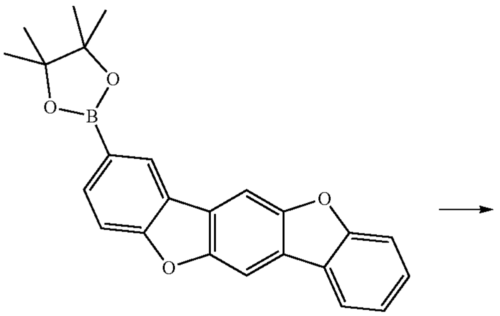

Intermediate 6

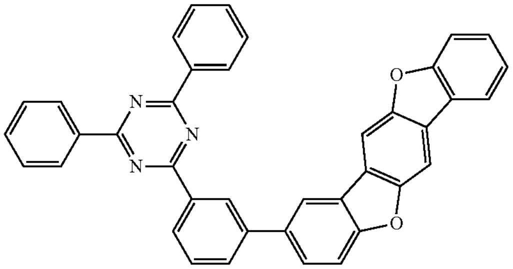

Compound 3

The procedure of the synthesis of Intermediate 1 was repeated except for using Intermediate 6 in place of 2-methoxyphenylboronic acid and using 2-(3-bromophenyl)-4,6-diphenyl-1,3,5-triazine in place of 4-bromo-2,5-difluoroaniline. The obtained Compound 3 was characterized by FD-MS (field desorption mass spectrometry), maximum ultraviolet absorption wavelength (UV(PhMe) λmax) in toluene, and maximum fluorescence wavelength (FL(PhMe, λex=350 nm) λmax) in toluene. The results are shown below.

FD-MS: calcd. for C39H23N3O2=565, found m/z=565 (M+)

UV(PhMe) λmax: 341 nm

FL(PhMe, λex=350 nm) λmax: 447 nm

Synthesis Example 4-1

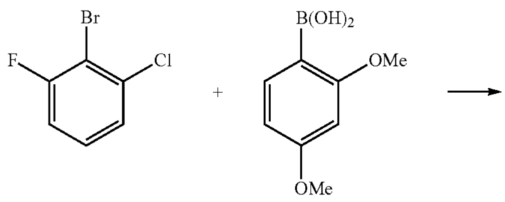

-continued

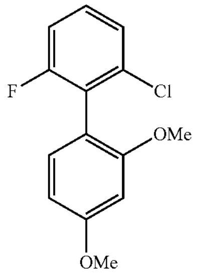

Intermediate 14

The procedure of the synthesis of Intermediate 1 was repeated except for using (2,4-dimethoxyphenyl)boronic acid in place of 2-methoxyphenylboronic acid and using 2-bromo-1-chloro-3-fluorobenzene in place of 4-bromo-2,5-difluoroaniline. The identification of the Intermediate 14 was made by FD-MS (field desorption mass spectrometry) analysis.

Synthesis Example 4-2

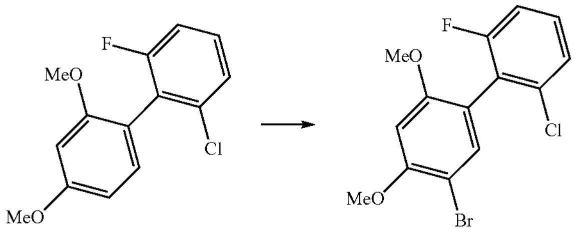

Intermediate 14 Intermediate 15

The procedure of the synthesis of Intermediate 8 was repeated except for using intermediate 14 in place of Intermediate 7. The identification of the intermediate 15 was made by FD-MS (field desorption mass spectrometry) analysis.

Synthesis Example 4-3

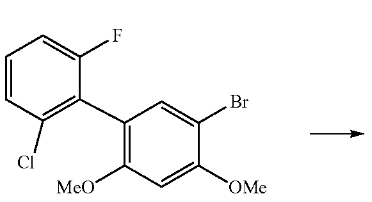

Intermediate 15

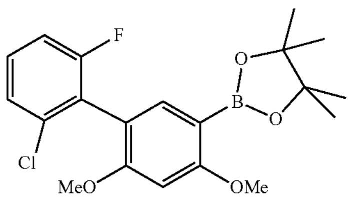

Intermediate 16

The procedure of the synthesis of Intermediate 9 was repeated except for using Intermediate 15 in place of intermediate 8. The identification of the Intermediate 16 was made by FD-MS (field desorption mass spectrometry) analysis.

Synthesis Example 4-4

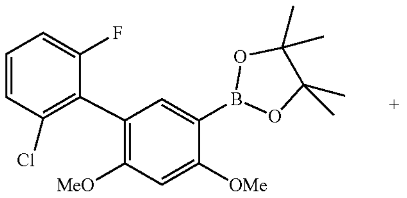

Intermediate 16

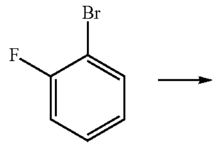

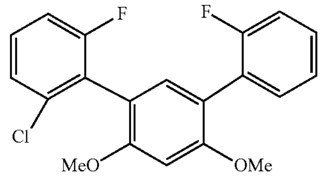

Intermediate 17

The procedure of the synthesis of Intermediate 1 was repeated except for using Intermediate 16 in place of 2-methoxyphenylboronic acid and using 1-bromo-2-fluorobenzene instead of 4-bromo-2,5-difluoroaniline. The identification of the Intermediate 17 was made by FD-MS (field desorption mass spectrometry) analysis.

Synthesis Example 4-5

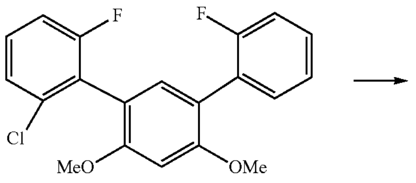

Intermediate 17

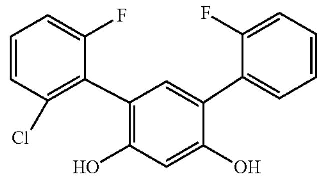

Intermediate 18

The procedure of the synthesis of Intermediate 4 was repeated except for using Intermediate 17 in place of Intermediate 3. The identification of the Intermediate 18 was made by FD-MS (field desorption mass spectrometry) analysis.

Synthesis Example 4-6

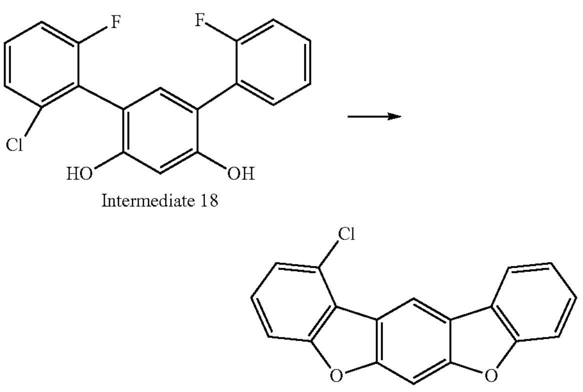

Intermediate 18

Intermediate 19

The procedure of the synthesis of Intermediate 5 was repeated except for using Intermediate 18 in place of Intermediate 4. The identification of the intermediate 19 was made by FD-MS (field desorption mass spectrometry) analysis.

Synthesis Example 4-7

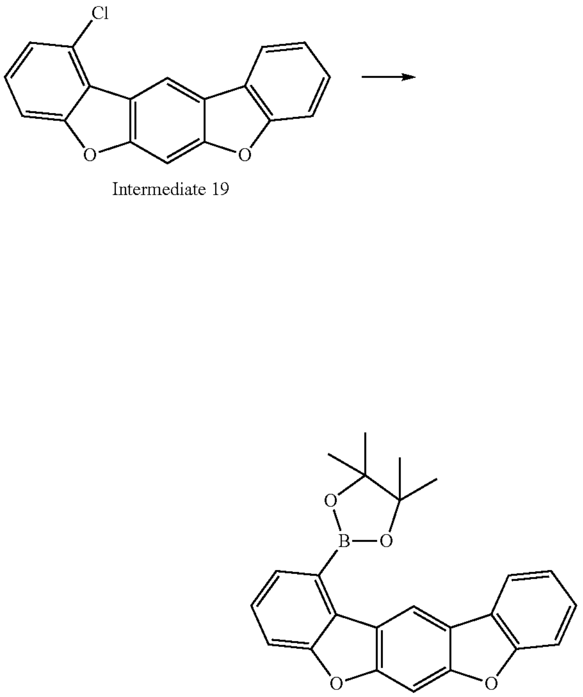

Intermediate 19

Intermediate 20

The procedure of the synthesis of Intermediate 6 was repeated except for using Intermediate 19 in place of Intermediate 5. The identification of the Intermediate 20 was made by FD-MS (field desorption mass spectrometry) analysis.

Synthesis Example 4-8

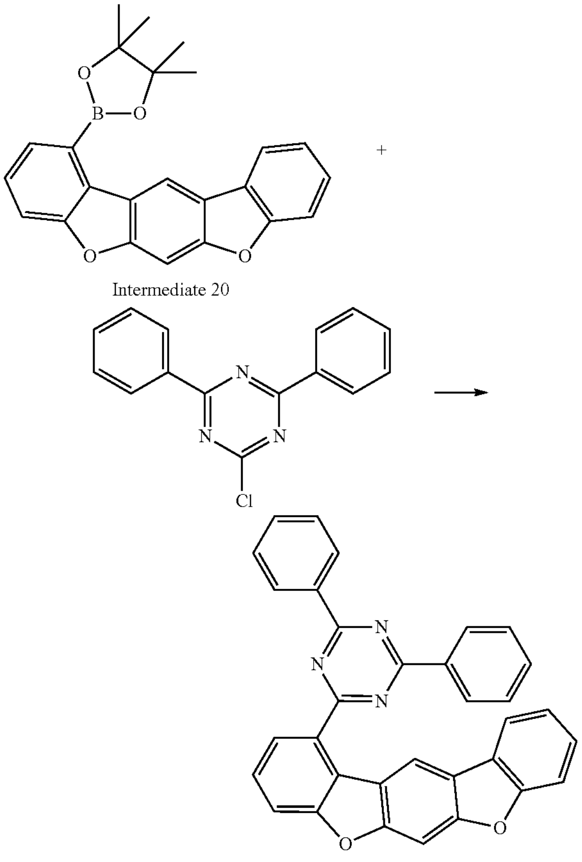

Intermediate 20

Compound 4

The procedure of the synthesis of Intermediate 1 was repeated except for using Intermediate 20 in place of 2-methoxyphenylboronic acid and using 2-chloro-4,6-diphenyl-1,3,5-triazine in place of 4-bromo-2,5-difluoroaniline. The obtained Compound 4 was characterized by FD-MS (field desorption mass spectrometry), maximum ultraviolet absorption wavelength (UV(PhMe) λmax) in toluene, and maximum fluorescence wavelength (FL(PhMe, λex=350 nm) λmax) in toluene. The results are shown below.

FDMS: calcd. for $C_{33}H_{19}N_3O_2$=489, found m/z=489 (M+)

UV(PhMe) λmax: 354 nm

FL(PhMe, λex=350 nm) λmax: 422 nm

Synthesis Example 5-1

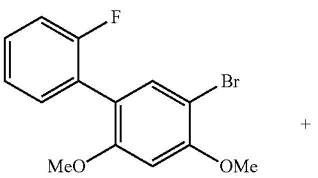

Intermediate 8

-continued

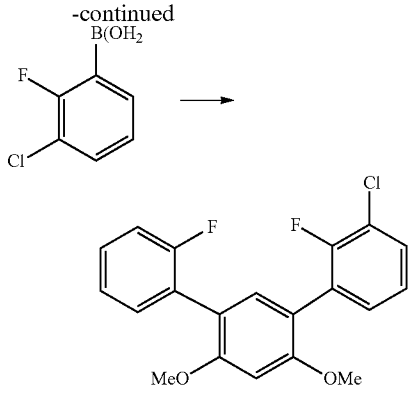

Intermediate 21

The procedure of the synthesis of Intermediate 1 was repeated except for using Intermediate 8 in place of 4-bromo-2,5-difluoroaniline and using (3-chloro-2-fluorophenyl)boronic acid in place of 2-methoxyphenylboronic acid. The identification of the Intermediate 21 was made by FD-MS (field desorption mass spectrometry) analysis.

Synthesis Example 5-2

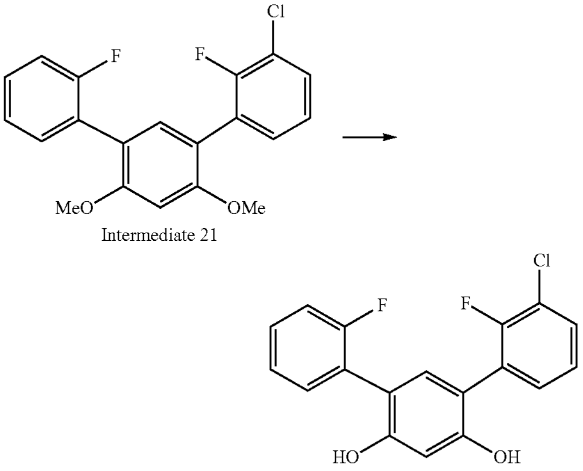

Intermediate 21

Intermediate 22

The procedure of the synthesis of Intermediate 4 was repeated except for using Intermediate 21 in place of Intermediate 3. The identification of the Intermediate 22 was made by FD-MS (field desorption mass spectrometry) analysis Synthesis Example 5-3

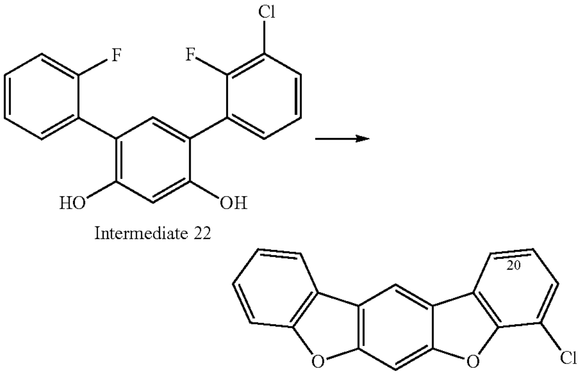

Intermediate 22

Intermediate 23

The procedure of the synthesis of Intermediate 5 was repeated except for using Intermediate 22 in place of Intermediate 4. The identification of the Intermediate 23 was made by FD-MS (field desorption mass spectrometry) analysis.

Synthesis Example 5-4

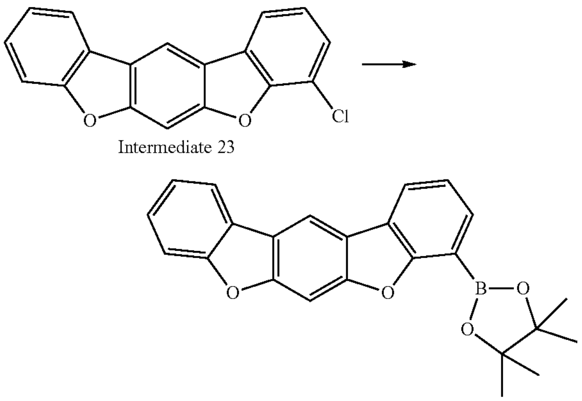

Intermediate 23

Intermediate 24

The procedure of the synthesis of Intermediate 6 was repeated except for using Intermediate 23 in place of Intermediate 5. The identification of the Intermediate 24 was made by FD-MS (field desorption mass spectrometry) analysis.

Synthesis Example 5-5

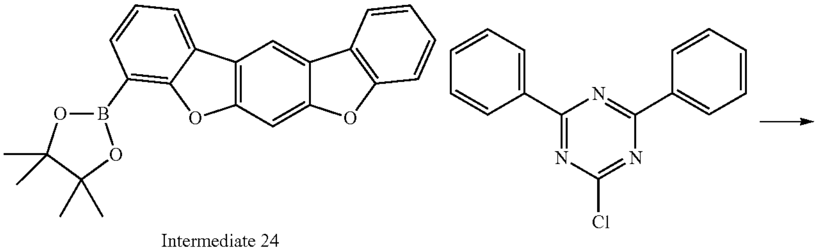

Intermediate 24

-continued

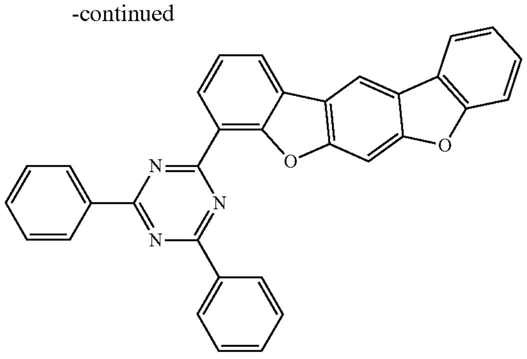

Compound 5

The procedure of the synthesis of Intermediate 1 was repeated except for using Intermediate 24 in place of 2-methoxyphenylboronic acid and using 2-chloro-4,6-diphenyl-1,3,5-triazine in place of 4-bromo-2,5-difluoroaniline. The obtained Compound 5 was characterized by FD-MS (field desorption mass spectrometry), maximum ultraviolet absorption wavelength (UV(PhMe) λmax) in toluene, and maximum fluorescence wavelength (FL(PhMe, λex=350 nm) λmax) in toluene. The results are shown below.

FDMS: calcd. for C33H19N3O2=489, found m/z=489 (M+)

UV(PhMe) λmax: 336 nm

FL(PhMe, λex=350 nm) λmax: 392 nm

Synthesis Example 6

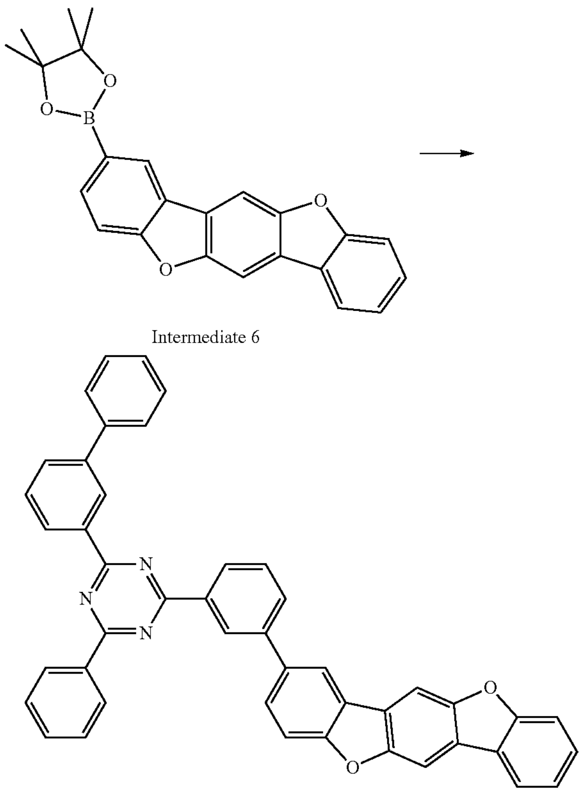

Intermediate 6

Compound 6

The procedure of the synthesis of Intermediate 1 was repeated except for using Intermediate 6 in place of 2-methoxyphenylboronic acid and using 2-([1,1'-biphenyl]-3-yl)-4-(3-bromophenyl)-6-phenyl-1,3,5-triazine in place of 4-bromo-2,5-difluoroaniline. The obtained Compound 6 was characterized by FD-MS (field desorption mass spectrometry), maximum ultraviolet absorption wavelength (UV (PhMe) λmax) in toluene, and maximum fluorescence wavelength (FL(PhMe, λex=330 nm) λmax) in toluene. The results are shown below.

FD-MS: calcd. for C45H27N3O2=641, found m/z=641 (M+)

UV(PhMe) λmax: 342 nm

FL(PhMe, λex=330 nm) λmax: 341 nm

Synthesis Example 7

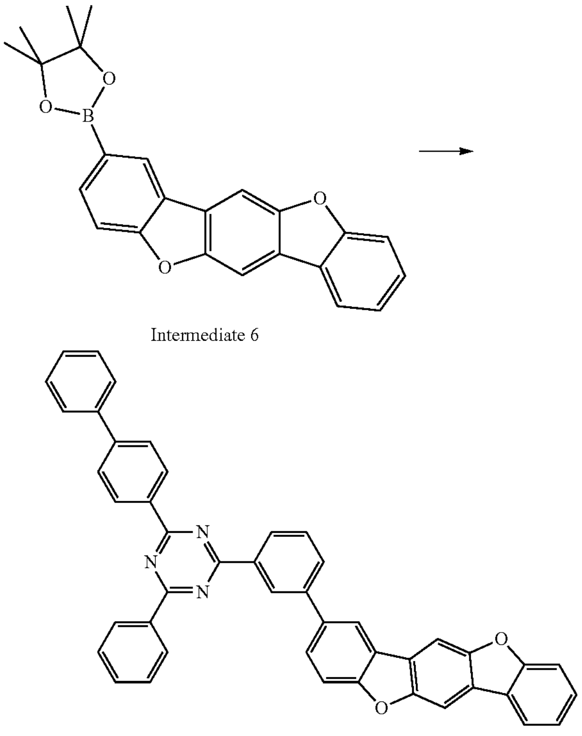

Intermediate 6

Compound 7

The procedure of the synthesis of Intermediate 1 was repeated except for using Intermediate 6 in place of 2-methoxyphenylboronic acid and using 2-([1,1'-biphenyl]-4-yl)-4-(3-bromophenyl)-6-phenyl-1,3,5-triazine in place of 4-bromo-2,5-difluoroaniline. The obtained Compound 7 was characterized by FD-MS (field desorption mass spectrometry), maximum ultraviolet absorption wavelength (UV (PhMe) λmax) in toluene, and maximum fluorescence wavelength (FL(PhMe, λex=320 nm) λmax) in toluene. The results are shown below.

FD-MS: calcd. for C45H27N3O2=641, found m/z=641 (M+)

UV(PhMe) λmax: 325 nm

FL(PhMe, λex=320 nm) λmax: 367 nm

Synthesis Example 8

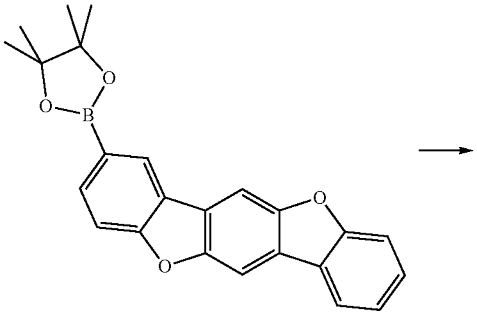

Intermediate 6

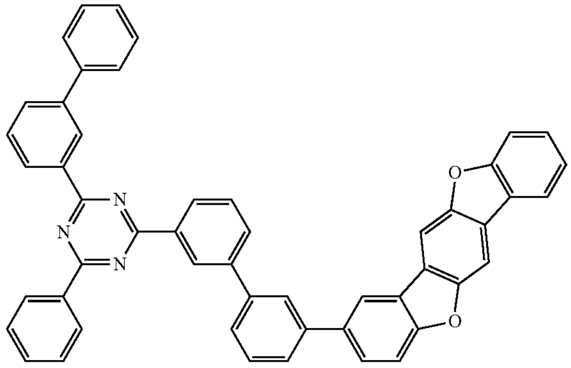

Compound 8

The procedure of the synthesis of Intermediate 1 was repeated except for using Intermediate 6 in place of 2-methoxyphenylboronic acid and using 2-([1,1'-biphenyl]-3-yl)-4-(3'-bromo-[1,1'-]-3-yl)-6-phenyl-1,3,5-triazine in place of 4-bromo-2,5-difluoroaniline. The obtained Compound 8 was characterized by FD-MS (field desorption mass spectrometry), maximum ultraviolet absorption wavelength (UV(PhMe) λmax) in toluene, and maximum fluorescence wavelength (FL(PhMe, λex=320 nm) λmax) in toluene. The results are shown below.

FD-MS: calcd. for C51H31N3O2=718, found m/z=718 (M+)

UV(PhMe) λmax: 340 nm

FL(PhMe, λex=320 nm) λmax: 357 nm

Synthesis Example 9

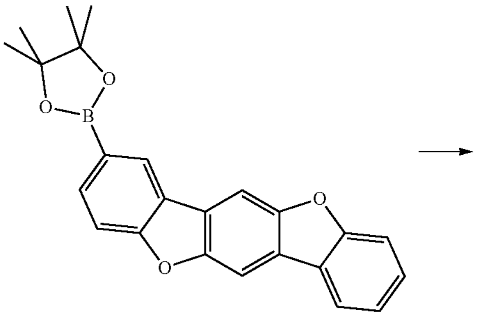

Intermediate 6

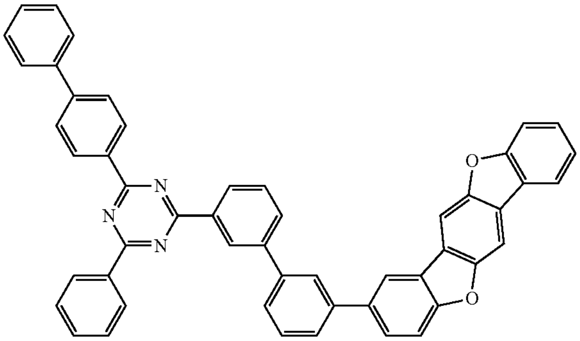

Compound 9

The procedure of the synthesis of Intermediate 1 was repeated except for using Intermediate 6 in place of 2-methoxyphenylboronic acid and using 2-([1,1'-biphenyl]-4-yl)-4-(3'-bromo-[1,1'-biphenyl]-3-yl)-6-phenyl-1,3,5-triazine in place of 4-bromo-2,5-difluoroaniline. The obtained Compound 9 was characterized by FD-MS (field desorption mass spectrometry), maximum ultraviolet absorption wavelength (UV(PhMe) λmax) in toluene, and maximum fluorescence wavelength (FL(PhMe, λex=330 nm) λmax) in toluene. The results are shown below.

FD-MS: calcd. for C51H31N3O2=718, found m/z=718 (M+)

UV(PhMe) λmax: 325 nm

FL(PhMe, λex=330 nm) λmax: 366 nm

Synthesis Example 10

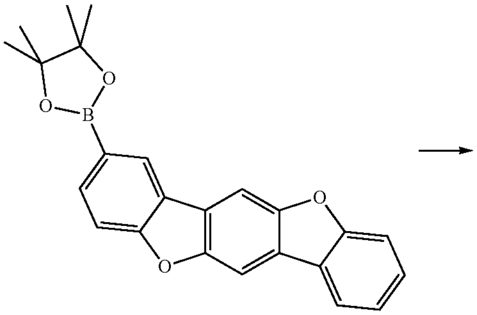

Intermediate 6

-continued

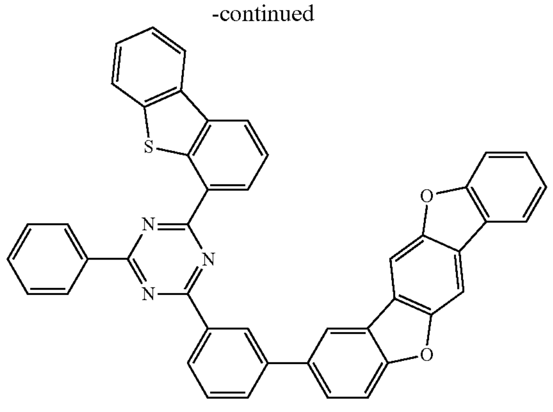

Compound 10

The procedure of the synthesis of Intermediate 1 was repeated except for using Intermediate 6 in place of 2-methoxyphenylboronic acid and using 2-(3-bromophenyl)-4-(dibenzo[b,d]thiophen-4-yl)-6-phenyl-1,3,5-triazine in place of 4-bromo-2,5-difluoroaniline. The obtained Compound 10 was characterized by FD-MS (field desorption mass spectrometry), maximum ultraviolet absorption wavelength (UV(PhMe) λmax) in toluene, and maximum fluorescence wavelength (FL(PhMe, λex=350 nm) λmax) in toluene. The results are shown below.

FD-MS: calcd. for C45H25N3O2S=672, found m/z=672 (M+)

UV(PhMe) λmax: 341 nm

FL(PhMe, λex=350 nm) λmax: 413 nm

Synthesis Example 11

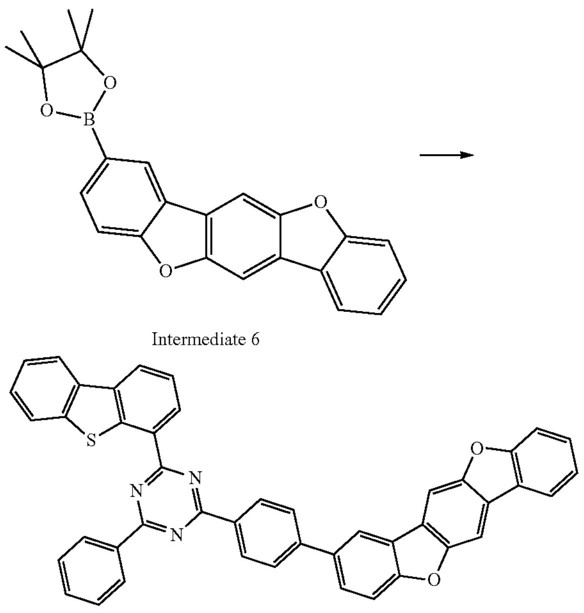

Intermediate 6

Compound 11

The procedure of the synthesis of Intermediate 1 was repeated except for using Intermediate 6 in place of 2-methoxyphenylboronic acid and using 2-(4-bromophenyl)-4-(dibenzo[b,d]thiophen-4-yl)-6-phenyl-1,3,5-triazine in place of 4-bromo-2,5-difluoroaniline. The obtained Compound 11 was characterized by FD-MS (field desorption mass spectrometry), maximum ultraviolet absorption wavelength (UV(PhMe) λmax) in toluene, and maximum fluorescence wavelength (FL(PhMe, λex=350 nm) λmax) in toluene. The results are shown below.

FD-MS: calcd. for C45H25N3O2S=672, found m/z=672 (M+)

UV(PhMe) λmax: 337 nm

FL(PhMe, λex=350 nm) λmax: 415 nm

Synthesis Example 12

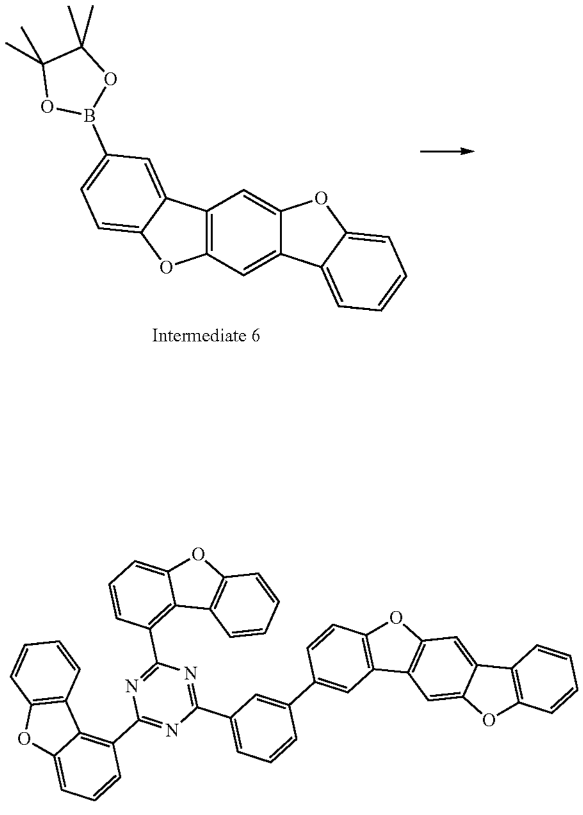

Intermediate 6

Compound 12

The procedure of the synthesis of Intermediate 1 was repeated except for using Intermediate 6 in place of 2-methoxyphenylboronic acid and using 2-(3-chlorophenyl)-4,6-bis(dibenzo[b,d]furan-1-yl)-1,3,5-triazine in place of 4-bromo-2,5-difluoroaniline and $Pd(OAc)_2$ and XPhos in place of tetrakis(triphenylphosphine)palladium. The obtained Compound 12 was characterized by FD-MS (field desorption mass spectrometry), maximum ultraviolet absorption wavelength (UV(PhMe) λmax) in toluene, and maximum fluorescence wavelength (FL(PhMe, λex=350 nm) λmax) in toluene. The results are shown below.

FD-MS: calcd. for C51H27N3O4=746, found m/z=746 (M+)

UV(PhMe) λmax: 342 nm

FL(PhMe, λex=320 nm) λmax: 397 nm

Synthesis Example 13

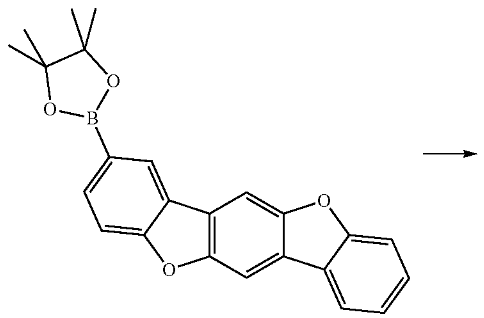

Intermediate 6

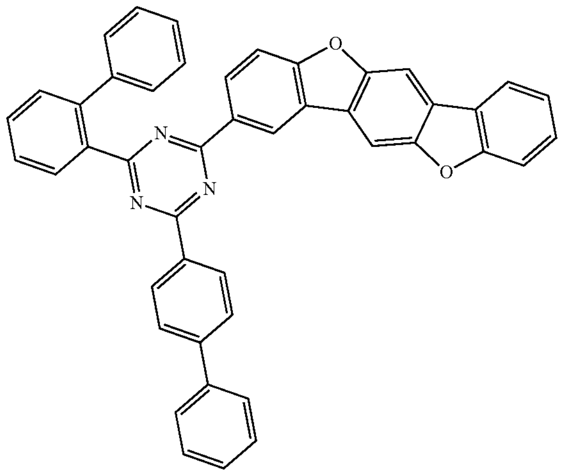

Compound 13

The procedure of the synthesis of Intermediate 1 was repeated except for using Intermediate 6 in place of 2-methoxyphenylboronic acid and using 2-([1,1'-biphenyl]-2-yl)-4-([1,1'-biphenyl]-4-yl)-6-chloro-1,3,5-triazine in place of 4-bromo-2,5-difluoroaniline. The obtained Compound 13 was characterized by FD-MS (field desorption mass spectrometry), maximum ultraviolet absorption wavelength (UV(PhMe) λmax) in toluene, and maximum fluorescence wavelength (FL(PhMe, λex=350 nm) λmax) in toluene. The results are shown below.

FD-MS: calcd. for C45H27N3O2=642, found m/z 642 (M+)

UV(PhMe) λmax: 330 nm

FL(PhMe, λex=320 nm) λmax: 392 nm

Synthesis Example 14

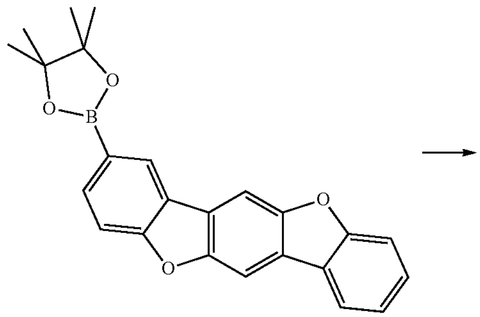

Intermediate 6

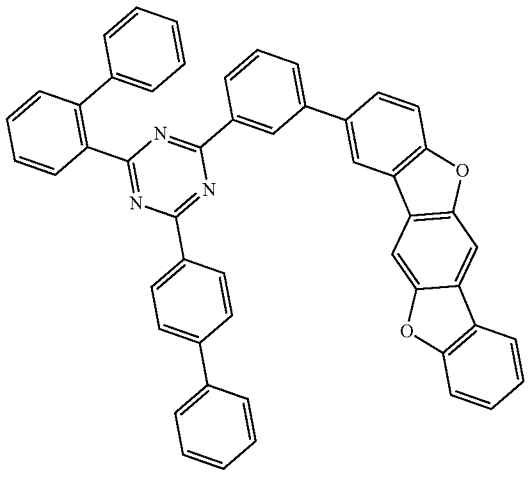

Compound 14

The procedure of the synthesis of Intermediate 1 was repeated except for using Intermediate 6 in place of 2-methoxyphenylboronic acid and using 2-([1,1'-biphenyl]-2-yl)-4-([1,1'-biphenyl]-4-yl)-6-(3-chlorophenyl)-1,3,5-triazine in place of 4-bromo-2,5-difluoroaniline and $Pd(OAc)_2$ and 2-Dicyclohexylphosphino-2',4',6'-triisopropylbiphenyl in place of tetrakis(triphenylphosphine)palladium. The obtained Compound 14 was characterized by FD-MS (field desorption mass spectrometry), maximum ultraviolet absorption wavelength (UV(PhMe) λmax) in toluene, and maximum fluorescence wavelength (FL(PhMe, λex=350 nm) λmax) in toluene. The results are shown below.

FD-MS: calcd. for C51H31N3O2=718, found m/z=718 (M+)

UV(PhMe) λmax: 342 nm

FL(PhMe, λex=320 nm) λmax: 388 nm

Synthesis Example 15

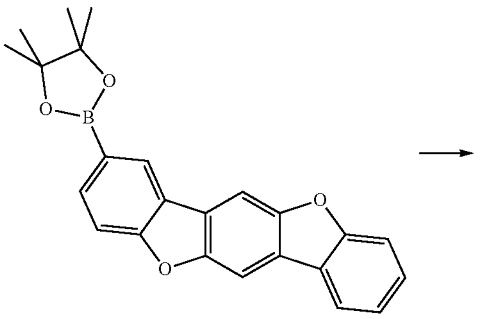

Intermediate 6

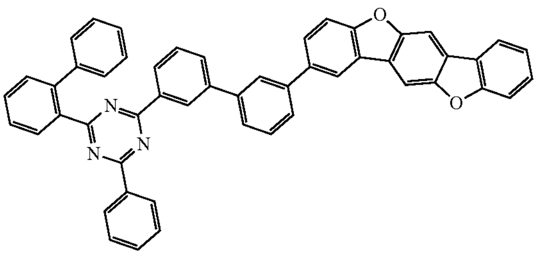

Compound 15

The procedure of the synthesis of Intermediate 1 was repeated except for using Intermediate 6 in place of 2-methoxyphenylboronic acid and using 2-([1,1'-biphenyl]-2-yl)-4-(3'-bromo-[1,1'-biphenyl]-3-yl)-6-phenyl-1,3,5-triazine in place of 4-bromo-2,5-difluoroaniline. The obtained Compound 15 was characterized by FD-MS (field desorption mass spectrometry), maximum ultraviolet absorption wavelength (UV(PhMe) λmax) in toluene, and maximum fluorescence wavelength (FL(PhMe, λex=350 nm) λmax) in toluene. The results are shown below.

FD-MS: calcd. for C51H31N3O2=718, found m/z=718 (M+)

UV(PhMe) λmax: 342 nm

FL(PhMe, λex=320 nm) λmax: 354 nm

Synthesis Example 16

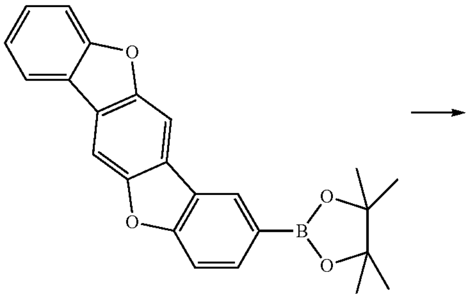

Intermediate 6

-continued

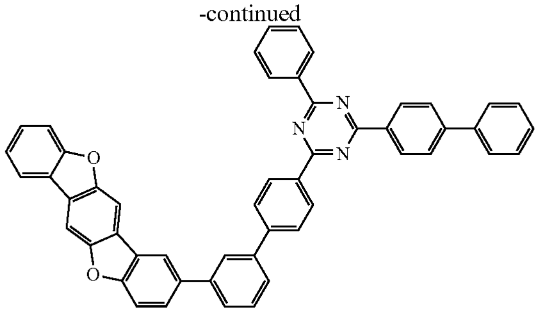

Compound 16

The procedure of the synthesis of Intermediate 1 was repeated except for using Intermediate 6 in place of 2-methoxyphenylboronic acid and using 2-([1,1'-biphenyl]-4-yl)-4-(3'-chloro-[1,1'-biphenyl]-4-yl)-6-phenyl-1,3,5-triazine in place of 4-bromo-2,5-difluoroaniline and $Pd(OAc)_2$ and XPhos in place of tetrakis(triphenylphosphine)palladium. The obtained Compound 16 was characterized by FD-MS (field desorption mass spectrometry), maximum ultraviolet absorption wavelength (UV(PhMe) λmax) in toluene, and maximum fluorescence wavelength (FL(PhMe, λex=350 nm) λmax) in toluene. The results are shown below.

FD-MS: calcd. for C51H31N3O2=718, found m/z=718 (M+)

UV(PhMe) λmax: 327 nm

FL(PhMe, λex=320 nm) λmax: 367 nm

Synthesis Example 17

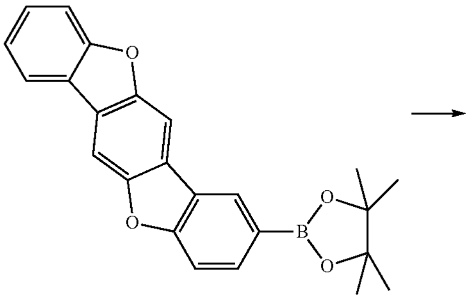

Intermediate 6

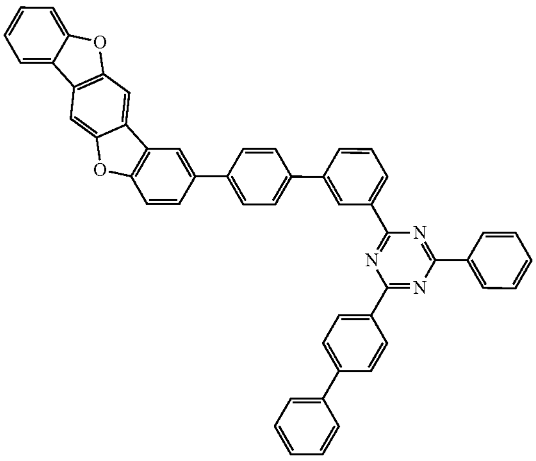

Compound 17

The procedure of the synthesis of Intermediate 1 was repeated except for using Intermediate 6 in place of 2-methoxyphenylboronic acid and using 2-([1,1'-biphenyl]-4-yl)-4-(4'-chloro-[1,1'-biphenyl]-3-yl)-6-phenyl-1,3,5-triazine in place of 4-bromo-2,5-difluoroaniline and $Pd(OAc)_2$ and XPhos in place of tetrakis(triphenylphosphine)palladium. The obtained Compound 17 was characterized by FD-MS (field desorption mass spectrometry), maximum ultraviolet absorption wavelength (UV(PhMe) λmax) in toluene, and maximum fluorescence wavelength (FL(PhMe, λex=350 nm) λmax) in toluene. The results are shown below.

FD-MS: calcd. for C51H31N3O2=718, found m/z=718 (M+)

UV(PhMe) λmax: 364 nm

FL(PhMe, λex=320 nm) λmax: 383 nm

II Application Examples

Application Example 1

A glass substrate with 120 nm-thick indium-tin-oxide (ITO) transparent electrode (manufactured by Geomatec Co., Ltd.) used as an anode was first cleaned with isopropanol in an ultrasonic bath for 10 min. To eliminate any possible organic residues, the substrate was exposed to an ultraviolet light and ozone for further 30 min. This treatment also improves the hole injection properties of the ITO. The cleaned substrate was mounted on a substrate holder and loaded into a vacuum chamber. Thereafter, the organic materials specified below were applied by vapor deposition to the ITO substrate at a rate of approx. 0.2-1 Å/sec at about $10^{-6}$-$10^{-8}$ mbar. As a hole injection layer, 5 nm-thick of compound HI was applied. Then 100 nm-thick of compound HT1 and 60 nm-thick compound HT2 were applied as hole transporting layer 1 and hole transporting layer 2, respectively.

Subsequently, a mixture of 5% by weight of an emitter compound PGD1, 95% by weight of a host (compound 1) were applied to form a 40 nm-thick phosphorescent-emitting layer. On the emitting layer, 30 nm-thick compound ET was applied as an electron transport layer. Finally, 1 nm-thick LiF was deposited as an electron injection layer and 80 nm-thick Al was then deposited as a cathode to complete the device. The device was sealed with a glass lid and a getter in an inert nitrogen atmosphere with less than 1 ppm of water and oxygen. To characterize the OLED, electroluminescence spectra are recorded at various currents and voltages. Driving voltage (Voltage) and electroluminescence spectra were given at a current density of 10 $mA/cm^2$. The device results were shown in Table 1.

Compound HI

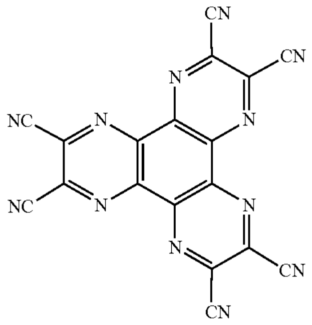

-continued

Compound HT1

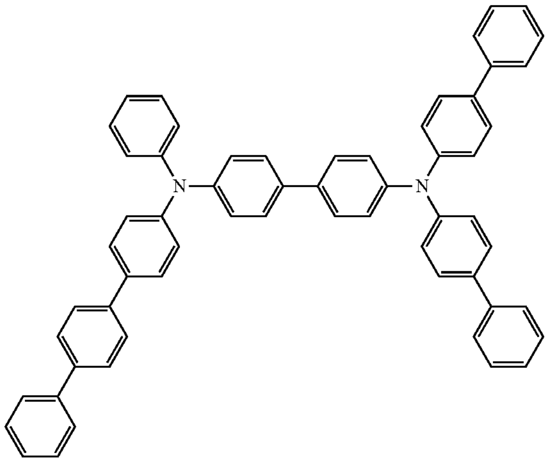

Compound HT2

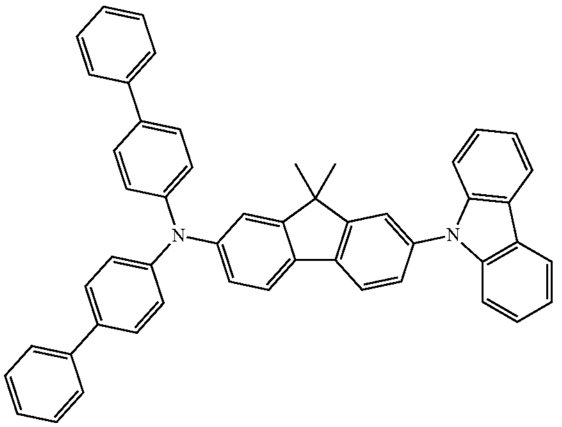

PGD 1

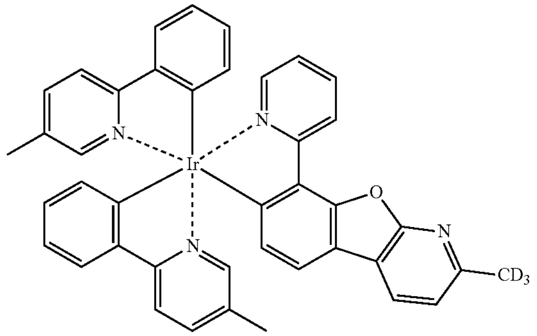

-continued

Compound 1

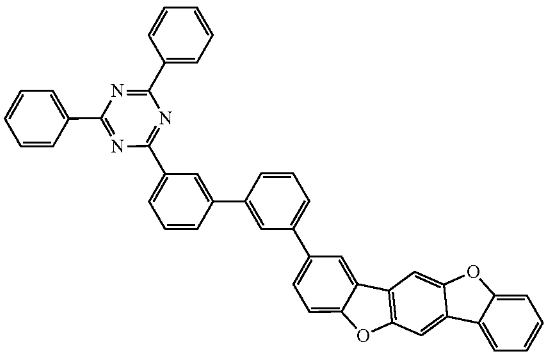

Compound ET

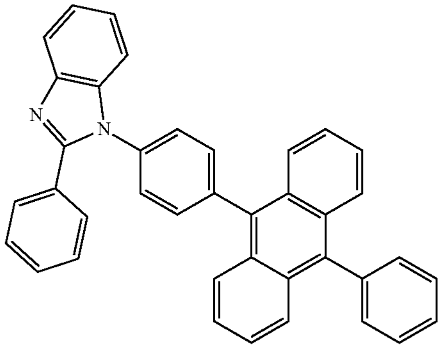

Application Example 2 and Comparative Application Examples 1 and 2 and 3

Application Example 1 was repeated except for using each compound shown in Table 1 in place of the host (compound 1). The device results were shown in Table 1.

TABLE 1

| Appl. Ex. | Host | Voltage [V] | electro-luminescence spectra peak (nm) |
|---|---|---|---|
| Appl. Ex. 1 | Compound 1 | 4.7 | 527 |
| Appl. Ex. 2 | Compound 2 | 4.6 | 527 |
| Comp. Appl. Ex. 1 | Comparative Compound 1 | 5.1 | 527 |
| Comp. Appl. Ex. 2 | Comparative Compound 2 | 5.1 | 528 |
| Comp. Appl. Ex. 3 | Comparative Compound 3 | 5.0 | 527 |

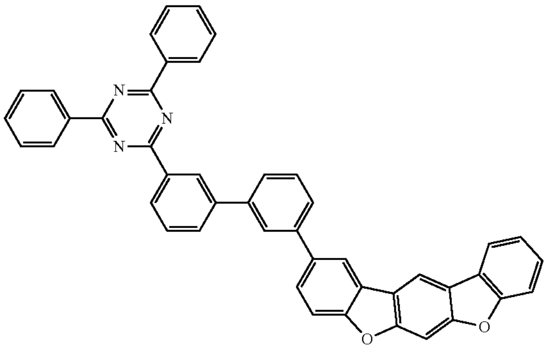

Compound 2

TABLE 1-continued

| Appl. Ex. | Host | Voltage [V] | electro-luminescence spectra peak (nm) |
|---|---|---|---|
| | 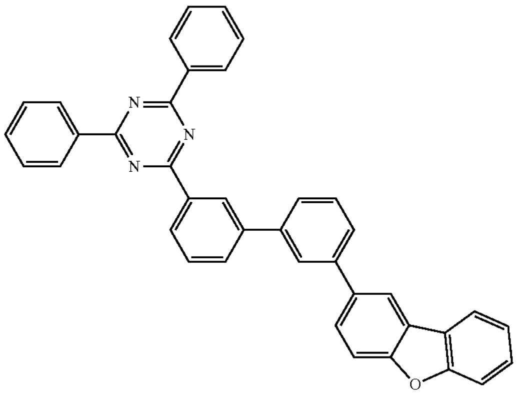 Comparative Compound 1 | | |
| | 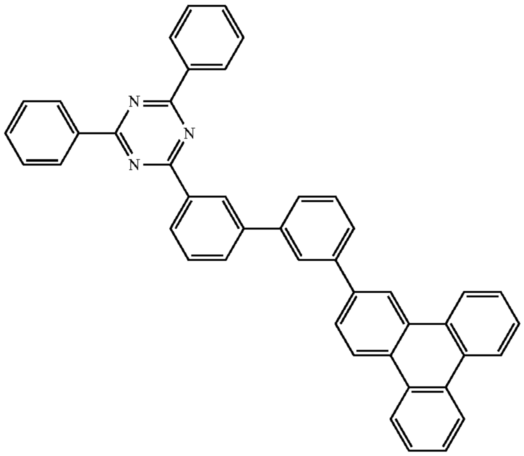 Comparative Compound 2 | | |
| | 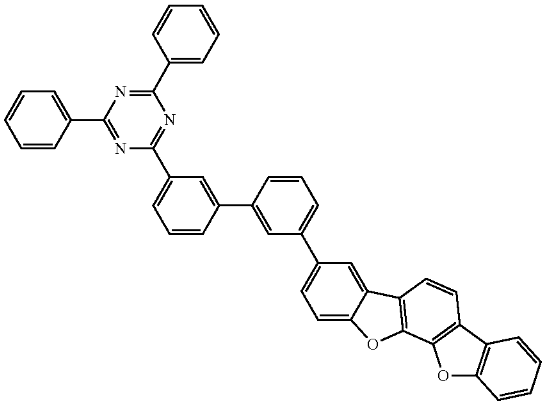 Comparative Compound 3 | | |

The results shown in Table 1 demonstrate that the voltage was improved in the case that the inventive Compound 1 or 2 was used as green hosts.

Application Example 3

A glass substrate with 120 nm-thick indium-tin-oxide (ITO) transparent electrode (manufactured by Geomatec Co., Ltd.) used as an anode was first cleaned with isopropanol in an ultrasonic bath for 10 min. To eliminate any possible organic residues, the substrate was exposed to an ultraviolet light and ozone for further 30 min. This treatment also improves the hole injection properties of the ITO. The cleaned substrate was mounted on a substrate holder and loaded into a vacuum chamber. Thereafter, the organic materials specified below were applied by vapor deposition to the ITO substrate at a rate of approx. 0.2-1 Å/sec at about $10^{-6}$-$10^{-8}$ mbar. As a hole injection layer, 5 nm-thick of compound HI was applied. Then 155 nm-thick of compound HT3 and 5 nm-thick compound HT4 were applied as hole transporting layer 1 and hole transporting layer 2, respectively.

Subsequently, a mixture of 5% by weight of an emitter PGD1, 31.7% by weight of a host 1 (compound 1) and 63.3% by weight of a host 2 (compound PH1) were applied to form a 40 nm-thick phosphorescent-emitting layer. On the emitting layer, 5 nm of hole blocking material HBL1 was deposited followed by 20 nm-thick compound ET as an electron transport layer. Finally, 1 nm-thick LiF was deposited as an electron injection layer and 80 nm-thick Al was then deposited as a cathode to complete the device. The device was sealed with a glass lid and a getter in an inert nitrogen atmosphere with less than 1 ppm of water and oxygen. To characterize the OLED, electroluminescence spectra were recorded at various currents and voltages. Driving voltage (Voltage) was given at a current density of 10 mA/cm$^2$, and 95% lifetime (LT95), the time spent until the initial luminance at 50 mA/cm$^2$ was reduced to 95%, was recorded. The device results were shown in Table 2.

Compound HT3

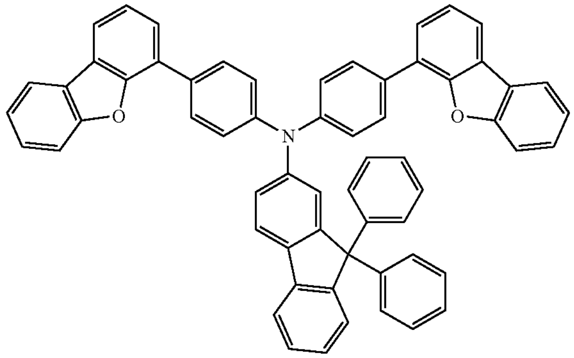

-continued

Compound HT4

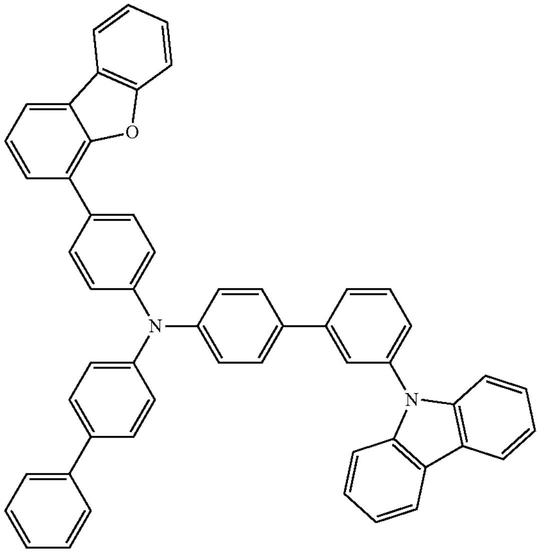

Compound HBL1

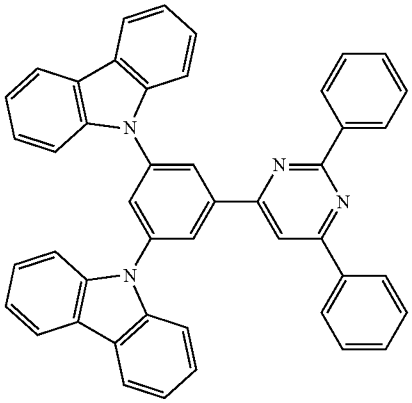

Compound PH1

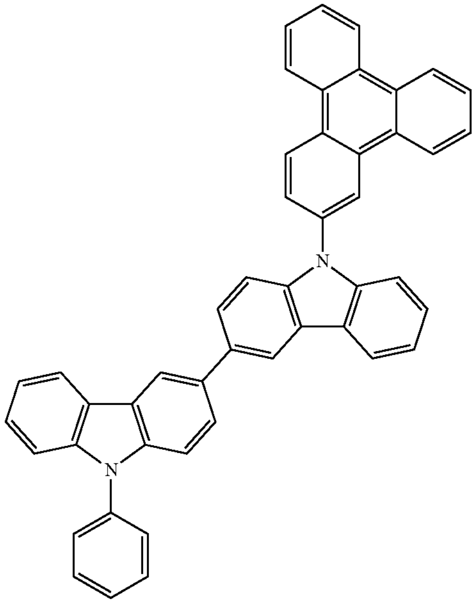

Application Examples 4-12, Comparative Application Examples 4-5

Application Example 3 was repeated except for using the compounds shown in place of the host 1. The device results were shown in Table 2.

TABLE 2

| Appl. Ex. | Host 1 | Voltage [V] | LT95 [hrs] |
|---|---|---|---|
| Appl. Ex. 3 | Compound 1 | 4.08 | 90 |
| Appl. Ex. 4 | Compound 6 | 4.08 | 76 |
| Appl. Ex. 5 | Compound 7 | 3.97 | 97 |
| Appl. Ex. 6 | Compound 8 | 3.91 | 84 |
| Appl. Ex. 7 | Compound 9 | 3.95 | 111 |
| Appl. Ex. 8 | Compound 10 | 3.95 | 55 |
| Appl. Ex. 9 | Compound 11 | 3.96 | 73 |
| Appl. Ex. 10 | Compound 12 | 3.88 | 46 |
| Appl. Ex. 11 | Compound 16 | 3.93 | 76 |
| Appl. Ex. 12 | Compound 17 | 4.11 | 93 |
| Comp. Appl. Ex. 4 | Comparative Compound 1 | 4.37 | 40 |
| Comp. Appl. Ex. 5 | Comparative Compound 3 | 4.34 | 21 |

The results shown in Table 2 demonstrated that the lifetime and voltage were improved in the case that the compounds according to the present invention were used as an phosphorescent green host as compared with Comparative Compound 1 and Comparative Compound 3.

Application Example 13

A glass substrate with 130 nm-thick indium-tin-oxide (ITO) transparent electrode (manufactured by Geomatec Co., Ltd.) used as an anode was first cleaned with isopropanol in an ultrasonic bath for 10 min. To eliminate any possible organic residues, the substrate was exposed to an ultraviolet light and ozone for further 30 min. This treatment also improves the hole injection properties of the ITO. The cleaned substrate was mounted on a substrate holder and loaded into a vacuum chamber. Thereafter, the organic materials specified below were applied by vapor deposition to the ITO substrate at a rate of approx. 0.2-1 Å/sec at about $10^{-6}$-$10^{-8}$ mbar. As a hole injection layer, 5 nm-thick of compound HI was applied. Then 80 nm-thick of compound HT5 and 10 nm-thick compound HT6 were applied as hole transporting layer 1 and hole transporting layer 2, respectively.

Subsequently, a mixture of 4% by weight of an emitter compound BD1, 96% by weight of a host (compound BH1) were applied to form a 25 nm-thick fluorescent layer-emitting layer. On the emitting layer, 10 nm-thick compound 1 was applied as an electron transport layer (ET). Finally, Compound ET1 co-evaporated with Li metal were deposited as a 15 nm thick layer and an 80 nm-thick Al was then deposited as a cathode to complete the device. The device was sealed with a glass lid and a getter in an inert nitrogen atmosphere with less than 1 ppm of water and oxygen. To characterize the OLED, electroluminescence spectra are recorded at various currents and voltages. Driving voltage (Voltage) and efficiency (EQE) and electroluminescence spectra were given at a current density of 10 $mA/cm^2$. The device results were shown in Table 3.

Compound HT5

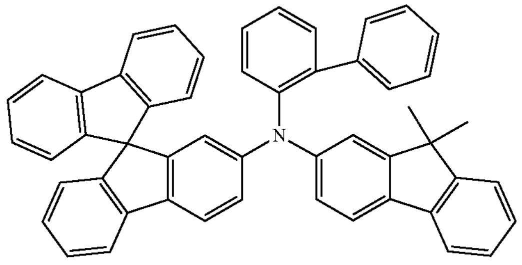

Compound HT6

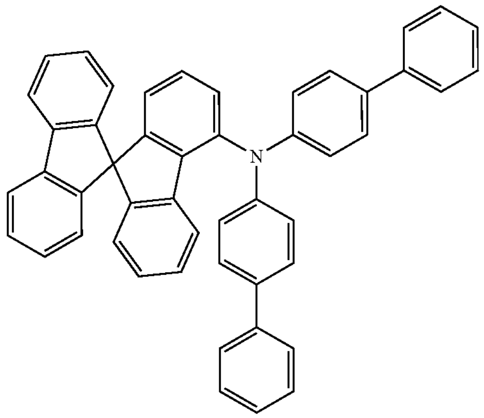

Compound BD1

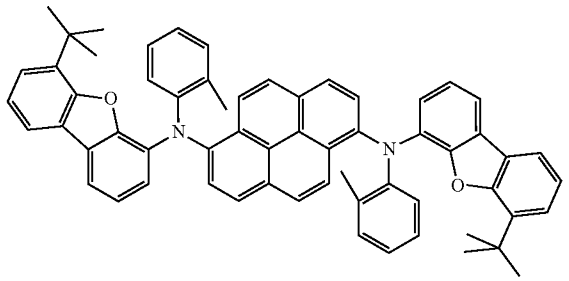

Compound BH1

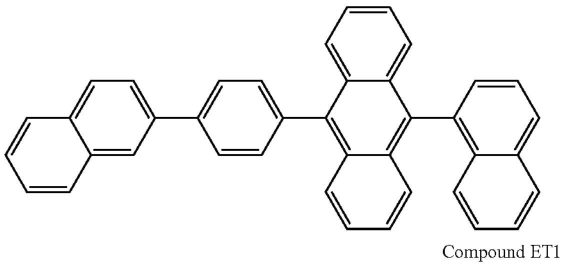

Compound ET1

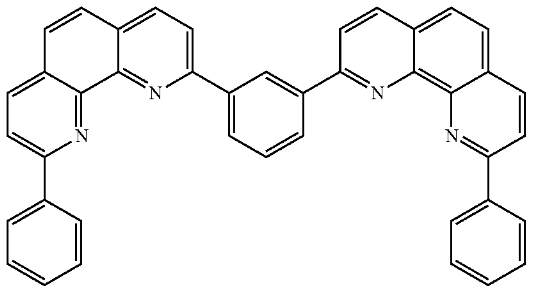

Application Examples 14-21, Comparative Application Example 6

Application Example 13 was repeated except for using each compound shown in Table 3 in place of the ET (compound 1). The device results were shown in Table 3.

TABLE 3

| Appl. Ex. | ET | Voltage [V] | EQE (%) | electro-luminescence spectra peak(nm) |
|---|---|---|---|---|
| Appl. Ex. 13 | Compound 1 | 4.12 | 10.1 | 455 |
| Appl. Ex. 14 | Compound 2 | 4.39 | 9.2 | 455 |
| Appl. Ex. 15 | Compound 6 | 4.21 | 9.8 | 455 |
| Appl. Ex. 16 | Compound 7 | 4.08 | 10.2 | 455 |
| Appl. Ex. 17 | Compound 9 | 4.10 | 9.9 | 455 |
| Appl. Ex. 18 | Compound 11 | 4.35 | 9.4 | 455 |
| Appl. Ex. 19 | Compound 13 | 4.21 | 9.5 | 455 |
| Appl. Ex. 20 | Compound 14 | 4.19 | 9.8 | 455 |
| Appl. Ex. 21 | Compound 15 | 4.15 | 9.8 | 455 |
| Comp. Appl. Ex. 6 | Comparative Compound 3 | 4.50 | 8.9 | 455 |

The electroluminescence peak values showed that the electroluminescence was originated from the blue emitter compound BD1. The devices wherein compounds according to the present invention were used as an electron transporting material exhibited decreased driving voltage and higher EQE as compared with Comparative Compound 3.

Application Example 22

A glass substrate with 120 nm-thick indium-tin-oxide (ITO) transparent electrode (manufactured by Geomatec Co., Ltd.) used as an anode was first cleaned with isopropanol in an ultrasonic bath for 10 min. To eliminate any possible organic residues, the substrate was exposed to an ultraviolet light and ozone for further 30 min. This treatment also improves the hole injection properties of the ITO. The cleaned substrate was mounted on a substrate holder and loaded into a vacuum chamber. Thereafter, the organic materials specified below were applied by vapor deposition to the ITO substrate at a rate of approx. 0.2-1 Å/sec at about $10^{-6}$-$10^{-8}$ mbar. As a hole injection layer, 5 nm-thick of compound HI was applied. Then 80 nm-thick of compound HT7 and 5 nm-thick of compound HT6 were applied as hole transporting layer 1 and hole transporting layer 2, respectively.

Subsequently, a mixture of 4% by weight of an emitter compound BD1, 96% by weight of a host (compound BH1) were applied to form a 25 nm-thick fluorescent layer-emitting layer. On the emitting layer, 5 nm-thick compound 1 was applied as an hole blocking layer (HBL). Then, 20 nm-thick compound ET was applied as an electron transport layer. Finally, 1 nm-thick LiF was deposited as an electron injection layer and 80 nm-thick Al was then deposited as a cathode to complete the device. The device was sealed with a glass lid and a getter in an inert nitrogen atmosphere with less than 1 ppm of water and oxygen. To characterize the OLED, electroluminescence spectra are recorded at various currents and voltages. Driving voltage (Voltage) and efficiency (EQE) and electroluminescence spectra were given at a current density of 10 mA/$cm^2$. The device results were shown in Table 4.

Compound HT7

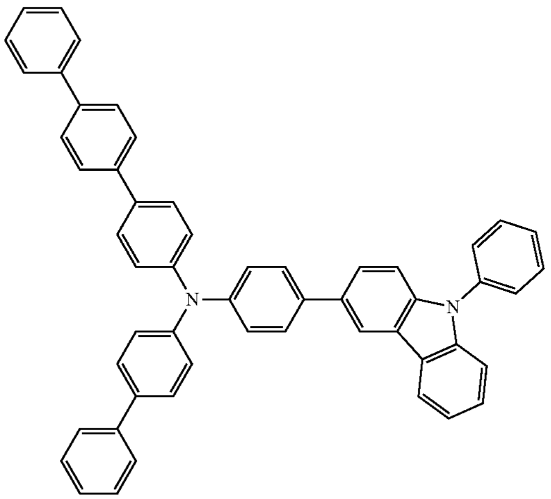

Application Examples 23-30, Comparative Application Example 7

Application Example 22 was repeated except for using each compound shown in Table 4 in place of the HBL (compound 1). The device results were shown in Table 4.

TABLE 4

| Appl. Ex. | HBL | Voltage [V] | EQE (%) | electro-luminescence spectra peak(nm) |
|---|---|---|---|---|
| Appl. Ex. 22 | Compound 1 | 3.78 | 10.1 | 455 |
| Appl. Ex. 23 | Compound 2 | 3.94 | 9.7 | 455 |
| Appl. Ex. 24 | Compound 6 | 3.85 | 9.8 | 455 |
| Appl. Ex. 25 | Compound 7 | 3.92 | 9.6 | 455 |
| Appl. Ex. 26 | Compound 9 | 3.80 | 10.0 | 455 |
| Appl. Ex. 27 | Compound 12 | 3.90 | 9.6 | 455 |
| Appl. Ex. 28 | Compound 13 | 3.81 | 9.9 | 455 |
| Appl. Ex. 29 | Compound 14 | 3.92 | 9.8 | 455 |
| Appl. Ex. 30 | Compound 15 | 3.96 | 9.8 | 455 |
| Comp. Appl. Ex. 7 | Comparative Compound 3 | 4.06 | 9.2 | 455 |

The electroluminescence peak values showed that the electroluminescence was originated from the blue emitter compound BD1. The devices wherein compounds according to the present invention were used as a hole blocking layer exhibited higher EQE and reduced driving voltage as compared with Comparative Compound 3.

The invention claimed is:

1. An organic electroluminescence device, comprising:

a cathode;

an anode; and an organic thin film between the cathode and the anode, wherein the organic thin film comprises a light emitting layer, and at least one other layer, the at least one other layer of the organic thin film comprises an electron transporting layer between the cathode and the light emitting layer or a hole blocking layer and an electron layer is between the electron transporting layer and the light emitting layer, the at least one other layer comprises a layer is between the electron transporting layer, the at least one other layer comprises a compound, and the light emitting layer does not comprise the compound, wherein the compound is selected from the group consisting of Compounds 1, 3, and 6 to 17:
Compound 1
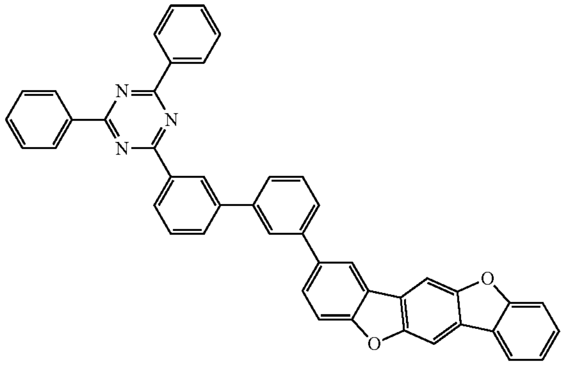
,
Compound 3
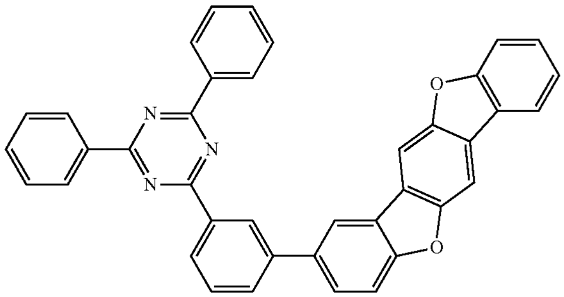
,
Compound 6
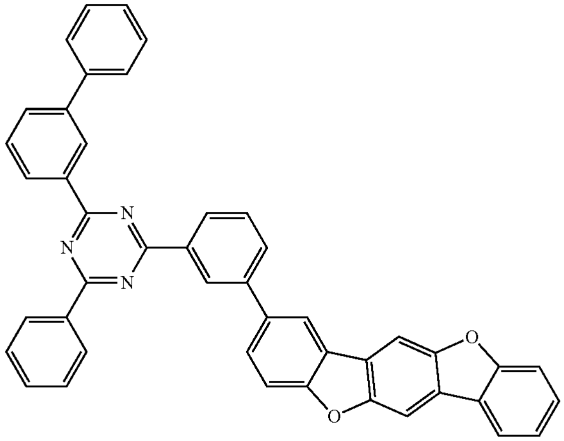
,
-continued
Compound 7
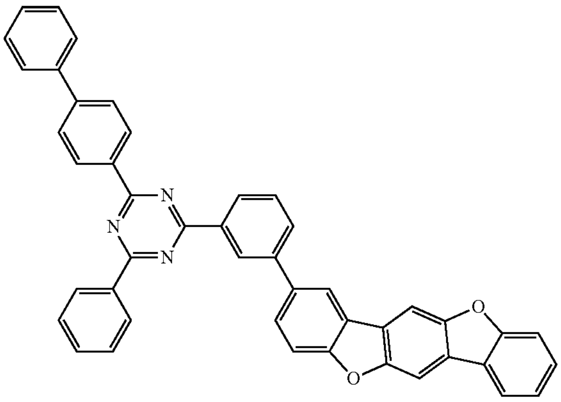
,
Compound 8
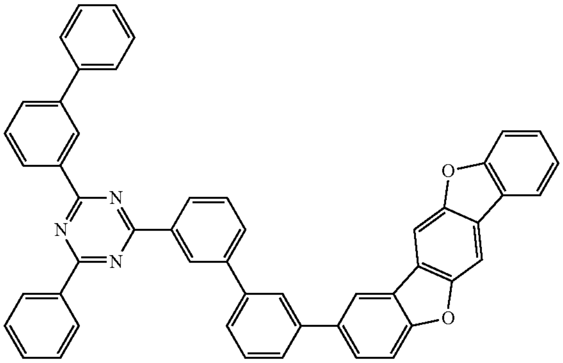
,
Compound 9
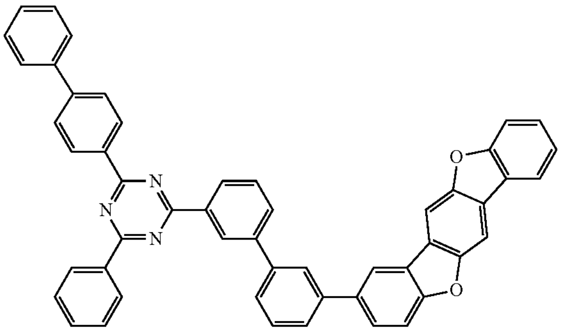
,
Compound 10
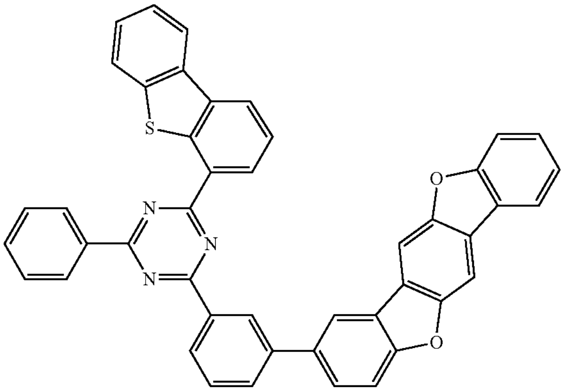
, -continued Compound 11

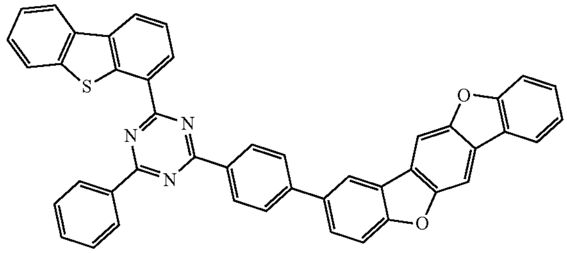

,

Compound 12

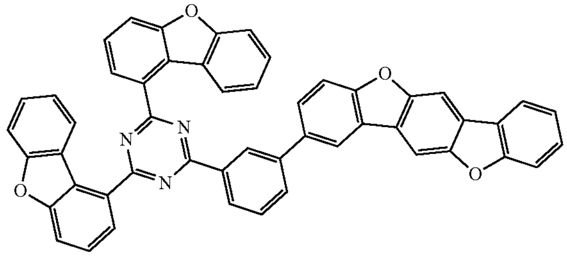

,

Compound 13

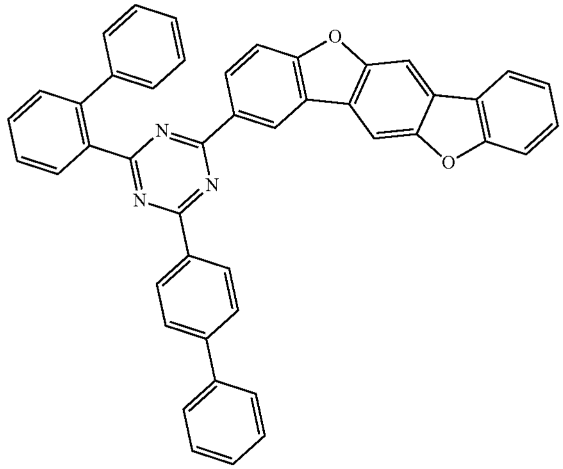

,

Compound 14

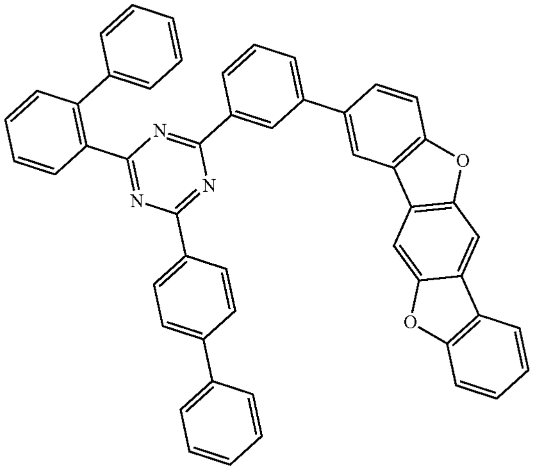

,

-continued

Compound 15

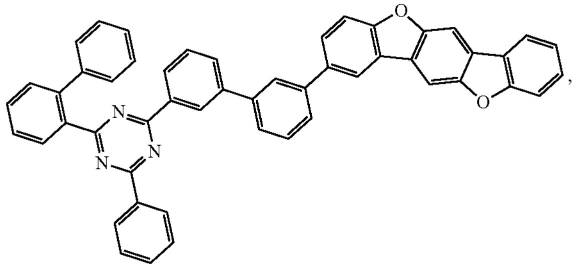

,

Compound 16

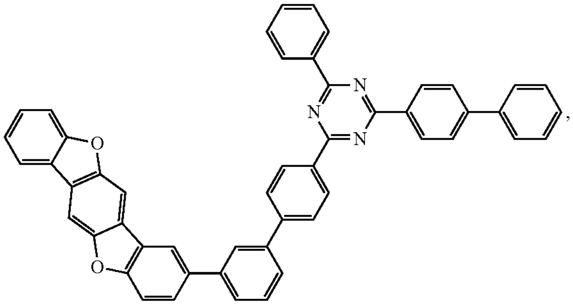

, and

Compound 17

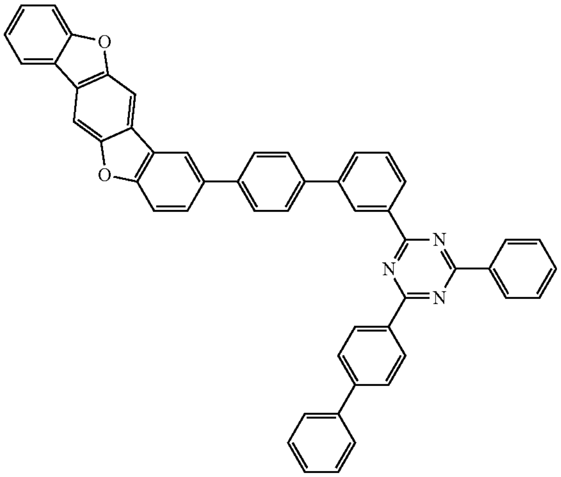

,

2. The organic electroluminescence device according to claim 1, wherein the at least one other layer of the organic thin film comprises an electron transporting layer between the cathode and the light emitting layer and the electron transporting layer comprises the compound.

3. The organic electroluminescence device according to claim 1, wherein the at least one other layer of the organic thin film comprises a hole blocking layer and an electron transporting layer between the cathode and the light emitting layer, where the hole-blocking layer is between the electron transporting layer and the light emitting layer, and the hole blocking layer comprises the compound.

* * * * *